US008618302B2

(12) United States Patent
Errico et al.

(10) Patent No.: US 8,618,302 B2
(45) Date of Patent: Dec. 31, 2013

(54) METHODS AND COMPOSITIONS OF TARGETED DRUG DEVELOPMENT

(75) Inventors: Joseph P. Errico, Green Brook, NJ (US); Benjamin Mugrage, Cranbury, NJ (US); Ignatius Turchi, Yardley, PA (US); Matthew Sills, Berkeley Heights, NJ (US); Jane Ong, Franklin Park, NJ (US); John Allocco, Staten Island, NY (US); Pam Wines, Manalapan, NJ (US)

(73) Assignee: Joseph P. Errico, Warren, NJ (US)

( * ) Notice: Subject to any disclaimer, the term of this patent is extended or adjusted under 35 U.S.C. 154(b) by 0 days.

(21) Appl. No.: 12/986,146

(22) Filed: Jan. 6, 2011

(65) Prior Publication Data

US 2011/0301193 A1 Dec. 8, 2011

Related U.S. Application Data

(60) Provisional application No. 61/292,776, filed on Jan. 6, 2010.

(51) Int. Cl.
| | | |
|---|---|---|
| *C07D 213/73* | (2006.01) | |
| *C07D 215/28* | (2006.01) | |
| *C07D 215/38* | (2006.01) | |
| *C07D 401/12* | (2006.01) | |
| *C07D 409/10* | (2006.01) | |

(52) U.S. Cl.
USPC ............................ 546/175; 546/177; 546/311

(58) Field of Classification Search
None
See application file for complete search history.

(56) References Cited

U.S. PATENT DOCUMENTS

| | | | |
|---|---|---|---|
| 6,465,448 B1 | 10/2002 | Gerson et al. | |
| 6,664,288 B1 | 12/2003 | Pardee et al. | |
| 6,916,455 B2 | 7/2005 | Segelke et al. | |
| 6,931,325 B2 | 8/2005 | Wall et al. | |
| 7,514,240 B2 | 4/2009 | Yokoyama et al. | |
| 8,119,656 B2 * | 2/2012 | Roth et al. ................. | 514/296 |
| 8,138,356 B2 * | 3/2012 | Chaudhary et al. ........... | 549/49 |
| 2007/0004750 A1 | 1/2007 | Lorsbach et al. | |
| 2008/0269213 A1 | 10/2008 | Bursavich et al. | |
| 2008/0305041 A1 | 12/2008 | Manivet et al. | |
| 2009/0029949 A1 | 1/2009 | Parrill-Baker et al. | |
| 2009/0088420 A1 * | 4/2009 | Neamati et al. ......... | 514/217.07 |
| 2009/0163545 A1 * | 6/2009 | Goldfarb ...................... | 514/312 |
| 2009/0233905 A1 | 9/2009 | Burke et al. | |
| 2011/0224207 A1 * | 9/2011 | Padmanabhan et al. ... | 514/235.2 |
| 2011/0294848 A1 * | 12/2011 | Roxas-Duncan et al. .... | 514/314 |

FOREIGN PATENT DOCUMENTS

| | | |
|---|---|---|
| WO | WO-2007002433 | 1/2007 |
| WO | WO 2009/051801 | 4/2009 |
| WO | WO 2009/117484 | 9/2009 |
| WO | WO 2009/151972 | 12/2009 |

OTHER PUBLICATIONS

Phillips et al., The Reaction of Anils with 8-Quinolinol, 19 JOC 907-9 (1954) (CAS Abstract).*
Sen et al., Reaction of Aldehydes & Amines with 8-Hydroxyquinaldine & 8-Quinolinol. II, 37 J. Indian Chem. Soc. 640-2 (1960) (CAS Abstract).*
Phillips et al., The Betti Reaction, 24(3-4) Trans. Kent. Aca. Science, 95-100 (1964) (CAS Abstract).*
Sergiev et al., Plant Growth Regulating Activity of Some Novel N-(6-methylpyrid-2-yl)-alpha-(8-hydroxy-quinolin-7-yl)-substituted benzylamines, 51(5-6) Dokladi Na Bulgarskata Akademiya Na Naukite 67-70 (1998) (CAS Abstract).*
Berkson et al., Pilot Screening Programme for Small Molecule Activators of p53, 115(5) Intn'l J Cancer 701-710 (2005) (CAS Abstract).*
Ma et al., A Small-Molecule E2F Inhibitor Blocks Growth in a Melanoma Culture Model, 68(15) Cancer Research 6292-6299 (2008) (CAS Abstract).*
Moy et al., High-Throughput Screen for Novel Antimicrobials Using a Whole Animal Infection Model, 4(7) ACS Chem. Bio. 527-533 (2009) (CAS Abstract).*
Roxas-Duncan et al., Identification and Biochemical Characterization of Small-Molecule Inhibitors of *Clostridium botulinum* Neurotoxin Serotype A, 53(8) Antimicrobial Agents & Chemotherapy 3

(56) References Cited

OTHER PUBLICATIONS

De La Motte Rouge et al., A Novel Epidermal Growth Factor Receptor Inhibitor Promotes Apoptosis in Non-Small Cell Lung Cancer Cells Resistant to Erlotinib, Cancer Res., 2007, pp. 6253-6262, vol. 67, No. 13.

Dickson et al., Tyrosine kinase receptor—nuclear protooncogene interactions in breast cancer (Chapter 13), Cancer Treatment Res., Genes, Oncogenes and Hormones, 1992, pp. 249-273, vol. 61, Kluwer Academic Publishers, ISBN: 0792317483, Abstract only, 1 page.

Duh et al., Epidermal Growth Factor Receptors and Adenylate Cyclase Activity in Human Thyroid Tissues, World J. Surgery, 1990, pp. 410-418, vol. 14.

Duke et al., IL-2 addictions: withdrawal of growth factor activates a suicide program in dependent T cells, Lymphokine Res., 1986, pp. 289-299, vol. 5, No. 4, Abstract only, 1 page.

Duvall et al., Death and the cell, Immunol. Today, 1986, pp. 115-119, vol. 7, No. 4.

Elhai et al., Conjugal Transfer of DNA to Cyanobacteria, Methods in Enzymology, 1988, pp. 747-754, vol. 167.

Farfan et al., Multiplexing Homogeneous Cell-Based Assays, Cell Notes, 2004, pp. 15-18, Issue 10.

Ferguson et al., EGF Activates its Receptor by Removing Interactions that Autoinhibit Ectodomain Dimerization, Mol. Cell, 2003, pp. 507-517, vol. 11.

Garcia-Calvo et al., Purification and catalytic properties of human caspase family members, Cell Death Differ., 1999, pp. 362-369, vol. 6.

Gopalakrishnan et al., Application of micro arrayed compound screening (pcARCS) to identify inhibitors of caspase-3, J. Biomol. Screening, 2002, pp. 317-323, vol. 7.

Herbst et al., Monoclonal Antibodies to Target Epidermal Growth Factor Receptor—Positive Tumors A New Paradigm for Cancer Therapy, Cancer, 2002, pp. 1593-1611, vol. 94, No. 5.

Hotz et al., Flow Cytometric Detection of Apoptosis: Comparison of the Assays of In Situ DNA Degradation and Chromatin Changes, Cytometry, 1994, pp. 237-244, vol. 15.

International Search Report and Written Opinion in related PCT Application No. PCT/US11/20414 dated May 26, 2011, 11 pages.

International Search Report in related PCT Application No. PCT/US11/20418 dated Jul. 7, 2011, 2 pages.

Irwin et al., ZINC—A Free Database of Commercially Available Compounds for Virtual Screening, J. Chem. Inf. Model, 2005, pp. 177-182, vol. 45, No. 1.

Karvinen et al., Homogeneous Time-Resolved Fluorescence Quenching assay (LANCE) for Capsase-3, J. Biomol. Screen, 2002, pp. 223-231, vol. 7.

Korc et al., Overexpression of the Epidermal Growth Factor Receptor in Human Pancreatic Cancer is Associated with Concomitant Increases in the Levels of Epidermal Growth Factor and Transforming Growth Factor Alpha, J. Clin. Invest., 1992, pp. 1352-1360, vol. 90.

Kumabe et al., Amplification of alpha-platelet-derived growth factor receptor gene lacking an exon coding for a portion of the extracellular region in a primary brain tumor of glial origin, Oncogene, 1992, pp. 627-633, vol. 7, No. 4, Abstract only, 1 page.

Larson et al., Perform Multiplexed Cell-Based Assays on Automated Platforms, Cell Notes, 2005, pp. 13-16, No. 12.

Le et al., Caspase activation and neuroprotection in caspase-3-deficient mice after in vivo cerebral ischemia and in vitro oxygen glucose deprivation, Proc. Natl. Acad. Sci, 2002, pp. 15188-15193, vol. 99, No. 23.

Lee et al., Intracellular retention of membrane-anchored v-sis protein abrogates autocrine signal-transduction, J. Cell. Biol., 1992, pp. 1057-1070, vol. 118, No. 5.

Lipinski, Drug-like properties and the causes of poor solubility and poor permeability, J. Pharm. Tox. Methods, 2000, pp. 235-249, vol. 44.

Lokeshwar et al., Protamine Enhances Epidermal Growth Factor (EGF)-stimulated Mitogenesis by Increasing Cell Surface EGF Receptor Number, J. Biol. Chem., 1989, 19318-19326, vol. 264, No. 32.

Magesh et al., *Ocimum sanctum* Induces Apoptosis in A549 Lung Cancer Cells and Suppresses the In Vivo Growth of Lewis Lung Carcinoma Cells, 2009, Phytother. Res., 2009, pp. 1385-1391, vol. 23.

Modjtahedi et al., Phase I trial and tumour localisation of the anti-EGFR monoclonal antibody ICR62 in head and neck or lung cancer, Br. J. Cancer, 1996, pp. 228-235, vol. 73.

Mooney et al., Apoptotic mechanisms in T47D and MCF-7 human breast cancer cells, Br. J. Cancer, 2002, pp. 909-917, vol. 87.

Mukku, Regulation of Epidermal Growth Factor Receptor Levels by Thyroid Hormone*, J. Biol. Chem., 1984, pp. 6543-6546, vol. 259, No. 10.

Naumov et al., Combined Vascular Endothelial Growth Factor Receptor and Epidermal Growth Factor Receptor (EGFR) Blockade Inhibits Tumor Growth in Xenograft Models of EGFR Inhibitor Resistance, Clin. Cancer Res., 2009, pp. 3484-3494, vol. 15, No. 10.

Nicholson et al., Caspases: killer proteases, Trends Biochem. Sci., 1997, pp. 299-306, vol. 22.

Oehm et al., Purification and Molecular Cloning of the APO-1 Cell Surface Antigen, a Member of the Tumor Necrosis Factor/Nerve Growth Factor Receptor Superfamily, J. Biol. Chem., 1992, pp. 10709-10715, vol. 267, No. 15.

Preaudat et al., A Homogeneous Caspase-3 Activity Assay Using HTRF Technology, J. Biomol. Screening, 2002, pp. 267-274, vol. 7, No. 3.

Reddy et al., Novel Coumarin-3-(N-aryl)carboxamides arrest breast cancer cell growth by inhibiting ErbB-2 and ERK1, Bioorganic and Medicinal Chemistry Letters, 2005, pp. 3141-3147, vol. 13.

Sanderson, The Mechanism of Lymphocyte-Mediated Cytotoxicity, Biol. Rev., 1981, 153-197, vol. 56.

Scanlon et al., Cytolysis by tumor necrosis factor is preceded by a rapid and specific dissolution of microfilaments, Proc. Natl. Acad. Sci. USA, 1989, pp. 182-186, vol. 86.

Schlegel et al., CPP32/Apopain Is a Key Interleukin 1β Converting Enzyme-like Protease Involved in Fas-mediated Apoptosis*, J. Biol. Chem., 1996, pp. 1841-1844, vol. 271, No. 4.

Slamon et al., Studies of the HER-2-neu proto-oncogene in human breast and ovarian cancer, Science, 1989, pp. 707-712, vol. 244.

Stach et al., Biological Activity of the β Nerve Growth Factor: The Effects of Various Added Proteins, J. Neurochem., 1979, pp. 257-261, vol. 33.

Studier, Protein production by auto-induction in high-density shaking cultures, Protein Expr. Purif., 2005, pp. 207-234, vol. 41, No. 1.

Tang et al., Synergistic effect of triptolide combined with 5-fluorouracil on colon carcinoma, Postgrad. Med. J., 2007, pp. 338-343, vol. 83.

Tang et al., Dual MET-EGFR combinatorial inhibition against T790M-EGFR-mediated erlotinib-resistant lung cancer, Br. J. Cancer, 2008, pp. 911-922, vol. 99.

Teague et al., The design of leadlike combinatorial libraries, Angewandte Chemie Int. Ed., 1999, pp. 3743-3748, vol. 38, No. 24.

Telford et al., Comparative Evaluation of Several DNA Binding Dyes in the Detection of Apoptosis-Associated Chromatin Degradation by Flow Cytometry, Cytometry, 1992, pp. 137-143, vol. 13.

Thornberry et al., A Combinatorial Approach Defines Specificities of Members of the Caspase Family and Granzyme B, J. Biol. Chem., 1997, pp. 17907-17911, vol. 272, No. 29.

Thornberry et al., Caspases: Enemies Within, Science, 1998, pp. 1312-1316, vol. 281.

Tomlinson et al., A Chemical Genomic Approach Identifies Matrix Metalloproteinases as Playing an Essential and Specific Role in *Xenopus* Melanophore Migration, Chemistry & Biology, 2009, pp. 93-104, vol. 16.

Torp et al., Expression of the epidermal growth factor receptor gene in human brain metastases, APMIS, 1992, pp. 713-719, vol. 100.

Trauth et al., Monoclonal Antibody-Mediated Tumor Regression by Induction of Apoptosis, Science, 1989, pp. 301-305, vol. 245.

Tuzi et al., Expression of growth factor receptors in human brain tumours, Br. J. Cancer, 1991, pp. 227-233, vol. 63.

(56) References Cited

OTHER PUBLICATIONS

Vermes et al., A novel assay for apoptosis Flow cytometric detection of phosphatidylserine expression on early apoptotic cells using fluorescein labelled Annexin V, J. Immun. Meth., 1995, pp. 39-51, vol. 184.

Weis et al., Cellular Events in Fas/APO-1-Mediated Apoptosis in JURKAT T Lymphocytes, Exp. Cell Res., 1995, pp. 699-708, vol. 219.

Wyllie et al., Cell Death: The Significance of Apoptosis, Int. Rev. of Cytol., 1980, pp. 251-306, vol. 68.

Yamada et al., Radiation-induced interphase death of rat thymocytes is internally programmed (apoptosis), Int. J. Radiat. Biol., 1988, pp. 65-75, vol. 53, No. 1.

Yonehara et al., A Cell-Killing Monoclonal Antibody (Anti-Fas) to a Cell Surface Antigen Co-Downregulated with the Receptor of Tumor Necrosis Factor, J. Exp. Med., 1989, pp. 1747-1756, vol. 169.

Zhang et al., A Simple Statistical Parameter for Use in Evaluation and Validation of High Throughput Screening Assays, J. Biomol. Screening, 1999, pp. 67-73, vol. 4.

Zhang et al., Apoptosis of human colon carcinoma HT-29 cells induced by Ceramide, 2006, Worl. J. Gastroenterol., pp. 3581-3584, vol. 12, No. 22.

Ahrendt et al., Rapid p53 sequence analysis in primary lung cancer using an oligonucleotide probe array, Proc. Natl. Acad. Sci., USA, Genetics, 1999, pp. 7382-7387, vol. 96.

Chene, Inhibiting the p53-MDM2 Interaction: An Important Target for Cancer Therapy, Nature Reviews, Cancer, 2003, pp. 102-109, vol. 3.

Ding et al., Structure-Based Design of Potent Non-Peptide MDM2 Inhibitors, J. Am. Chem. Soc., 2005, pp. 10130-10131, vol. 127, No. 29.

Ding et al., Structure-Based Design of Spiro-oxindoles as Potent, Specific Small-Molecule Inhibitors of the MDM2-p53 Interaction, J. Med. Chem., 2006, pp. 3432-3435, vol. 49, No. 12.

Fotouhi et al., Small Molecule Inhibitors of p53/MDM2 Interaction, Curr. Top. Med. Chem., 2005, pp. 159-165, vol. 5, Issue 2.

Grasberger et al., Discovery and Cocrystal Structure of Benzodiazepinedione HDM2 Antagonists That Activate p53 in Cells, J. Med. Chem., 2005, pp. 909-912, vol. 48, No. 4.

Issaeva et al. Small molecule RITA binds to p53, blocks p53—HDM-2 interaction and activates p53 function in tumors, Nature Med., 2004, pp. 1321-1328, vol. 10, No. 4.

Lawrence et al., Identification of a Disruptor of the MDM2-p53 Protein-Protein Interaction Facilitated by High-throughput in Silico Docking, Bioorg. Med. Chem. Lett., 2009, pp. 3756-375919, vol. 19, No. 14.

Lu et al., Discovery of a Nanomolar Inhibitor of the Human Murine Double Minute 2 (MDM2)-p53 Interaction through an Integrated, Virtual Database Screening Strategy, J. Med. Chem., 2006, pp. 3759-3762, vol. 49.

Olive, Quantitative methods for the analysis of protein phosphorylation in drug development, Expert Rev. Proteomics, 2004, pp. 327-341, vol. 1, No. 3.

Vassilev, p53 Activation by Small Molecules: Application in Oncology, J. Med. Chem. 2005, pp. 4491-4499, vol. 48, No. 14.

Vassilev, MDM2 inhibitors for cancer therapy, Trends in Molecular Medicine, 2006, pp. 23-31, vol. 13, No. 1.

Hamman et al., Synthesis and Biological Activity of a Novel Series of Nonsteroidal, Peripherally Selective Androgen Receptor Antagonists Derived from 1,2-Dihydropyridono[5,6-g]quinolines, J. Med. Chem., 1998, pp. 623-639, vol. 41, No. 4.

Li et al., Structural basis for inhibition of the epidermal growth factor receptor by cetuximab, Cancer Cell, 2005, pp. 301-311, vol. 7.

Shikhaliev et al., 2-Quinazolylguanidines in Heterocyclization Reactions. 3.* Synthesis of 2-[(6-R-4-Methyl-2-quinazolyl)amino]pyrimidine-(1H)-ones, Chem. Het. Compounds, 2002, pp. 1368-1370, vol. 38, No. 11.

Sporn et al., Proliferative Diseases, Am. J. Med, 1981, pp. 1231-1236, vol. 70, No. 6, abstract only.

Webb et al., Quinazolines as Adenosine Receptor Antagonists: SAR and Selectivity for $A_{2B}$ Receptors, 2003, pp. 77-85, Bioorg. Med. Chem. vol. 11, No. 1.

Written Opinion in related International Application No. PCT/US11/20418 dated Jul. 7, 2011, 5 pages.

Chemical Abstracts Service, accession No. 690650-87-4, 2004, 1 page.

Extended European Search Report dated Jul. 29, 2013 in related European Application No. EP 11732160.4, 9 pages.

Extended European Search Report dated Jul. 19, 2013 in related European Application No. EP 11732163.8, 7 pages.

\* cited by examiner

METHODS AND COMPOSITIONS OF TARGETED DRUG DEVELOPMENT

CROSS-REFERENCE TO RELATED APPLICATIONS

This application claims priority from U.S. Provisional Application Ser. No. 61/292,776, filed on Jan. 6, 2010, which is incorporated herein by reference in its entirety.

INCORPORATION-BY-REFERENCE OF SEQUENCE LISTING

The Sequence Listing, which is a part of the present disclosure, includes a computer readable form comprising nucleotide and/or amino acid sequences of the present invention. The subject matter of the Sequence Listing is incorporated herein by reference in its entirety.

FIELD OF THE INVENTION

The present invention generally relates to novel chemical compounds for use in the treatment of disease, methods of manufacture of such compounds and intermediates thereof, and methods of identifying lead molecules for use in quasi-rational drug design.

BACKGROUND OF THE INVENTION

Rational drug development is a process of developing lead molecules, not by randomly screening thousands of molecules in the blind hope of finding one that shows the desired activity, but rather by deducing the active site of the target and devising a chemical that interacts with that site in the appropriate manner.

Epidermal Growth Factor Receptor (EGFR) is a member of the ErbB (HER) family receptor tyrosine kinase (RTKs), which regulate cell growth and differentiation and are implicated in many human cancers. EGFR activation and dimerization is discussed in, for example, Burgess et al. (2003) Molecular Cell 12, 541-552 and Ferguson et al. (2003) Molecular Cell 11, 507-517.

EGF activates its receptor by inducing dimerization of the extracellular region of EGFR. The activation of EGFR has been described through results of disulfide bond mapping as well as X-ray crystal structures. The crystal structures of ligand-bound sEGFR showed that dimerization is receptor mediated, with two individual ligand molecules present in the dimer. The dimerization interface of activated EGFR is completely occluded by intramolecular interactions, and is an autoinhibited configuration. To activate the receptor, a large domain rearrangement that exposes this occluded interface must accompany EGF binding where EGF does not contribute to the EGFR dimer interface. The EGFR mechanism is in sharp contrast to most other receptor tyrosine kinase activation mechanisms in which the bound ligand contributes directly to the receptor dimerization interface and does not dramatically alter the conformation of the extracellular region of the receptor tyrosine kinase.

EGFR contains four subdomain I, II, III, and IV. Almost all receptor/receptor contacts observed in the crystal structures of EGFR are mediated by domain II. At the center of the dimer interface is a prominent loop (residues 242-259 of EGFR) that extends from the second C1 module (module 5) of each domain II and reaches across the interface to interact primarily with domain II of its dimerization partner. This domain II loop, which is specific to ErbB receptors, is the "dimerization arm". The dimerization arm of domain II is completely occluded by intramolecular interactions with domain IV (i.e., an autoinhibited configuration). There are two smaller interaction sites in the dimer that involve side chains from the second and the sixth disulfide-bonded modules of domain II. And the dimer interface may extend into domain IV. While the two receptor molecules approach one another very closely toward the C terminus of domain IV, a well-defined, tight interface is not observed.

Although EGF and TGF-α clearly do not span the dimer interface, each ligand simultaneously contacts two separate binding surfaces in the same EGFR molecule. The bound EGF or TGF-α molecule resembles a wedge between domains I and III. The relationship between domains I and II is essentially identical to that seen in IGF-1R and in the activated sEGFR dimer, implying that ligand binding does not greatly influence the relative orientation of these two domains. But the relationship between domains II and III differs dramatically in the activated and unactivated structures. A direct intramolecular interaction between cysteine-rich domains II and IV restrains the domain II/III relationship that characterizes the unactivated configuration. This interdomain "tether" is stabilized by essentially identical interactions between the two cysteine rich domains (II and IV) in inactive sErbB3 and sEGFR.

The intramolecular domain II/IV tether precisely buries the dimerization arm of domain II against domain IV, so that the tethered configurations of sErbB3 and sEGFR cannot dimerize and thus appear to be autoinhibited. Moreover, the two ligand binding surfaces on domain I and III are too far apart in the tethered configuration for a single ligand to bind to both simultaneously. Consequently, the tethered configuration can only form low-affinity interactions with ligand, using just one of its ligand binding surfaces at a time.

Switching between the unactivated and activated configurations of sEGFR requires domains I and III to be drawn toward one another through a 130° rotation of the rigid domain I/II pair in one plane and a 20° rotation in another. Only this extended configuration of sEGFR is capable of both high-affinity ligand binding and efficient dimerization.

Based upon energetic calculations, it is currently thought that at any given time, about 95% of sEGFR molecules will be tethered and the remaining 5% will not. The presence of ligand and subsequent binding to domains I and III of the non-tethered form will drive the equilibrium toward the non-tethered form, trapping receptor molecules in the extended state that can dimerize.

Exposure of the dimerization arm is not sufficient alone to drive EGFR dimerization. Also required is additional contact sites in modules 2 and 6 of domain III. These two additional contact sites and the dimerization arm cooperate at the dimer interface.

Known strategies of EGFR inhibition are directed to antibody binding of domain III to provide steric hindrance of the required configuration change (e.g., Erbitux). Other conventional strategies are directed to antibody binding of domain II, specifically the dimerization arm, so as to prevent dimerization (e.g., pertuzumab). Still other conventional strategies are directed to antibody binding of domain IV residues that participate in the intramolecular tether (e.g., trastuzumab, Herceptin). But no existing strategies are directed to the tethering mechanism of activation.

SUMMARY OF THE INVENTION

Described herein are compounds and compositions having an anti-proliferative effect, along with methods of therapeutic treatment with such compounds. Also provided are methods of discovery of such compounds. An approach described herein identifies modulators of the activity of multi-domain proteins comprising a dimerization arm and interdomain tether, such as EGFR, where an untethered, extended conformation is the active state and a tethered conformation is the inactive state, resulting in an autoinhibited configuration.

One aspect of the invention provides small molecule compounds, including those of Formula 2. In some embodiments, the small molecule compound substantially conforms to the pharmacophore of Scheme I.

Another aspect provides for treating a proliferative disease, disorder, or condition with compounds and compositions described herein. In some embodiments, the method includes administering to a subject in need thereof a composition comprising a therapeutically effective amount of a compound of Formula 1 or a compound AD4-1505, a stereoisomer or pharmaceutically acceptable salt thereof; and a pharmaceutically acceptable carrier or excipient. In some embodiments, the proliferative disease, disorder, or condition is associated with EGFR. In some embodiments, the proliferative disease, disorder, or condition is selected from the group consisting of: cancer; a blood vessel proliferative disorder; a fibrotic disorder; a mesangial cell proliferative disorder; psoriasis; actinic keratoses; seborrheic keratoses; warts; keloid scars; eczema; and hyperproliferative diseases caused by a viral infection.

Another aspect provides a method for identifying an epidermal growth factor receptor (EGFR) inhibitor. In some embodiments, the method includes providing a pharmacophore comprising Scheme I as input to a 3-dimensional database; comparing a three dimensional structure of a candidate compound to the three dimensional structure of the pharmacophore; selecting a candidate compound with a three dimensional structure that substantially aligns with six or more functional groups of Scheme I (ADS-1505-like); wherein, similarity between the three-dimensional structure of the candidate compound and the three-dimensional structure of the pharmacophore is indicative of an ability of the candidate compound to inhibit EGFR by substantially maintaining a tethered inactive configuration of EGFR or substantially preventing stabilization of the untethered active configuration of EGFR.

Another aspect provides a method for forming a compound described herein, such as a compound of Formula 2. In some embodiments, the method includes combining an amino pyridine intermediate compound, an aldehyde intermediate compound, and a hydroxyquinoline intermediate compound in ethanol under conditions sufficient to form the compound. In some embodiments, the amino pyridine intermediate compound comprises $R^2$—CHO, where $R^2$ is as defined for Formula 2; the aldehyde intermediate compound comprises $R^1$—NH$_2$, where $R^1$ is as defined for Formula 2; and the hydroxyquinoline intermediate compound comprises 8-hydroxyquinoline, optionally substituted with X, where X is as defined for Formula 2.

Another aspect provides a method for forming an aminopyridine compound. In some embodiments, the reaction includes combining a substituted or unsubstituted 2-aminopyridine and N-chlorosuccinimide in a solvent comprising ethylacetate or dimethylformamide under conditions sufficient to form a 2-amino-5-chloropyridine derivative. In some embodiments, the reaction includes combining acetic anhydride in glacial acetic acid and a 2-aminopyridine substituted at 3-position and 5-position with fluoro, chloro, or bromo to form a corresponding acetamide derivative; combining the acetamide derivative and diisopropyl amine and butyllithium in tetrahydrofuran at about −70° C. to deprotonate the acetamide derivative; combining the deprotonated acetamide derivative and a lower alkyl halide to alkylate the 4-position of the acetamide derivative; combining the alkylated acetamide derivative and a concentrated hydrochloric acid in a methanol solvent at about 50° C. to remove the acetamide group and form a 2-amino-3,5-dihalo-4-alkylaminopridine.

Another aspect provides amino pyridine compounds selected from the group consisting of 2-Amino-3-fluoro-4-methyl-5-chloropyridine; 2-Amino-3-ethyl-5-chloropyridine; 2-Amino-3-fluoro-4-ethyl-5-chloropyridine; and 2-Amino-4-methyl-3,5-difluoropyridine.

Other objects and features will be in part apparent and in part pointed out hereinafter.

BRIEF DESCRIPTION OF THE DRAWINGS

Those of skill in the art will understand that the drawings, described below, are for illustrative purposes only. The drawings are not intended to limit the scope of the present teachings in any way.

FIG. 7A shows EGFR as a tethered monomer. FIG. 7B shows EGFR as an untethered monomer. FIG. 7C shows EGFR in a ligand stabilized extended conformation. FIG. 7D shows EGFR as a ligand induced activated dimer.

FIG. 9 is a series of scatter and line plots showing MTT cell proliferation assay for A549 cells.

FIG. 10 shows Abs 560 nm as a function of LogM (µM) for compound AD4-10460. Further information regarding methodology is provided in Example 7.

FIG. 11 shows average percent inhibition (Ave % Inhibition) as a function of Log concentration (M) of Tykerb and Tarceva, with $IC_{50}$ values calculated as 2.7 µM and 12 µM, respectively. Further information regarding methodology is provided in Example 7.

FIG. 16 is a dot plot and a bar graph showing Annexin V Assay.

DETAILED DESCRIPTION OF THE PRESENTLY PREFERRED EMBODIMENTS

Figure 1:
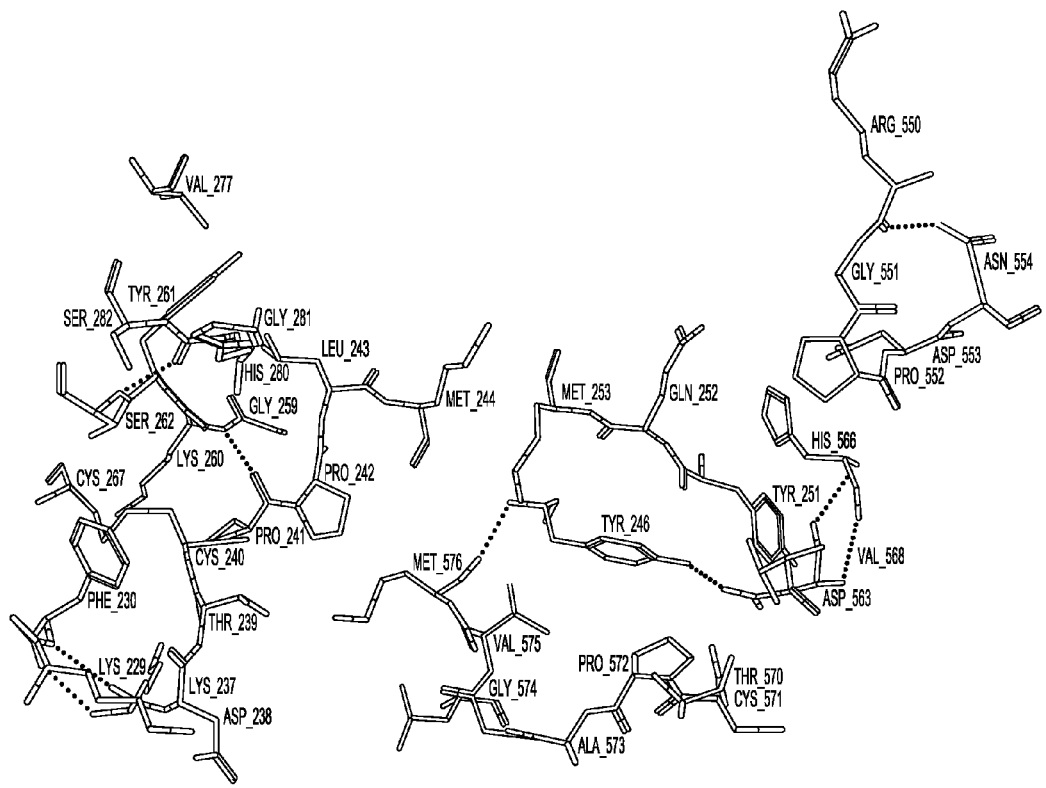
FIG. 1 shows the binding site at the interface of Domain II and Domain IV of the Inactive Form of EGFr (1NQL.pdb) as determined by the site finder in MOE. The Carbon Atoms of the Domain II Residues are Colored Red and those of the Domain IV Residues are Colored Blue.

Described herein are compounds and compositions having an anti-proliferative effect, along with methods of therapeutic treatment with such compounds and methods of discovery of such compounds. Various small molecule compounds described herein can hold proteins of multiple domains together in a tethered, inactive state. Also provided are methods to identify the structural requirements of such inhibitors, screen for effective inhibitors, optimize the structure of identified candidates, and utilize identified small molecule compounds in therapeutic treatment regimes.

One aspect of the invention is directed to small molecule compounds efficacious in treating proliferative diseases or conditions. Various embodiments of compounds described herein can have an anti-proliferative effect. Various embodiments of compounds described herein can hold multiple domain proteins in a tethered, inactive state. Various embodiments of compounds described herein can have an inhibitory effect on EGFR. Compounds described herein have been demonstrated to be empirically effective in treating proliferative diseases and conditions.

One aspect of the invention is directed to therapeutic treatment of proliferative diseases and disorders using compounds and compositions described herein.

One aspect of the invention is directed to compounds, methods, and apparatuses for developing one or more drugs for one or more targeted therapies. More specifically, the approach described herein identifies modulators of the activity of multi-domain proteins comprising a dimerization arm and interdomain tether, where an untethered, extended conformation is the active state and a tethered conformation is the inactive state, resulting in an autoinhibited configuration. The pharmacophoric approach described herein is based upon a mechanistic understanding of conformation-dependent protein receptor activation mechanisms, thus avoiding conventional combinatorial chemistry and high throughput screening techniques.

Biomolecule Target Selection

Desirable target enzymes include those for which there exists crystallography data sufficient to discern a ligand binding, activation, and/or dimerization mechanism. The various methods of the invention can be used to generate pharmacophore models for a variety of multi-domain protein targets (crystallized with and/or without ligand) having an interdomain tether associated with activation state. Thus is provided compounds that can prevent untethering and stabilization of the extended conformation, and methods for identifying such compounds.

It shall be understood that the types of biomolecule target for the lead molecules generated by the methods of the present invention can include one or more of EGFR (i.e., ErbB1), HER2/c-neu (ErbB-2), Her 3 (ErbB-3), and Her 4 (ErbB-4).

EGFR

Described herein is targeting of various portions of the domains of EGFR so as to prevent stabilization of the untethered, extended conformation. In other words, a small molecule inhibitor can be used to hold proteins of domain II and IV together in the tethered, inactive state. This strategy can provide for some retention of the basal levels of EGFR signaling, retention of EGF response, and/or reduce EGF-independent dimerization. Such a therapeutic effect would slow rapid growth of cancer cells (which are more sensitive given increased expression levels of EGFR) but retain at least a portion of basal EGFR activity necessary for healthy tissue function.

Known strategies of EGFR inhibition are directed to antibody binding of domain III to provide steric hindrance of the required configuration change (e.g., Erbitux). Other conventional strategies are directed to antibody binding of domain II, specifically the dimerization arm, so as to prevent dimerization (e.g., pertuzumab). Still other conventional strategies are directed to antibody binding of domain IV residues that participate in the intramolecular tether (e.g., trastuzumab, Herceptin). But, in contrast to the approach described herein, the above conventional strategies do not prevent untethering or stabilization of the extended conformation.

Figure 7:
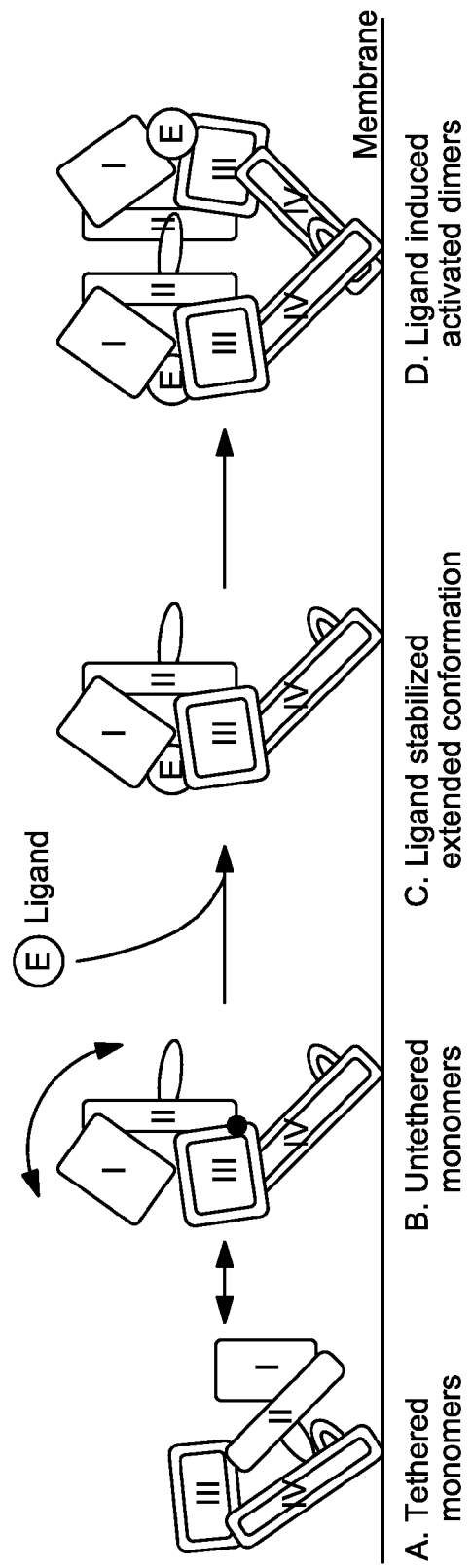
FIG. 7 is a cartoon depicting conformations of EGFR.
Figure 8:
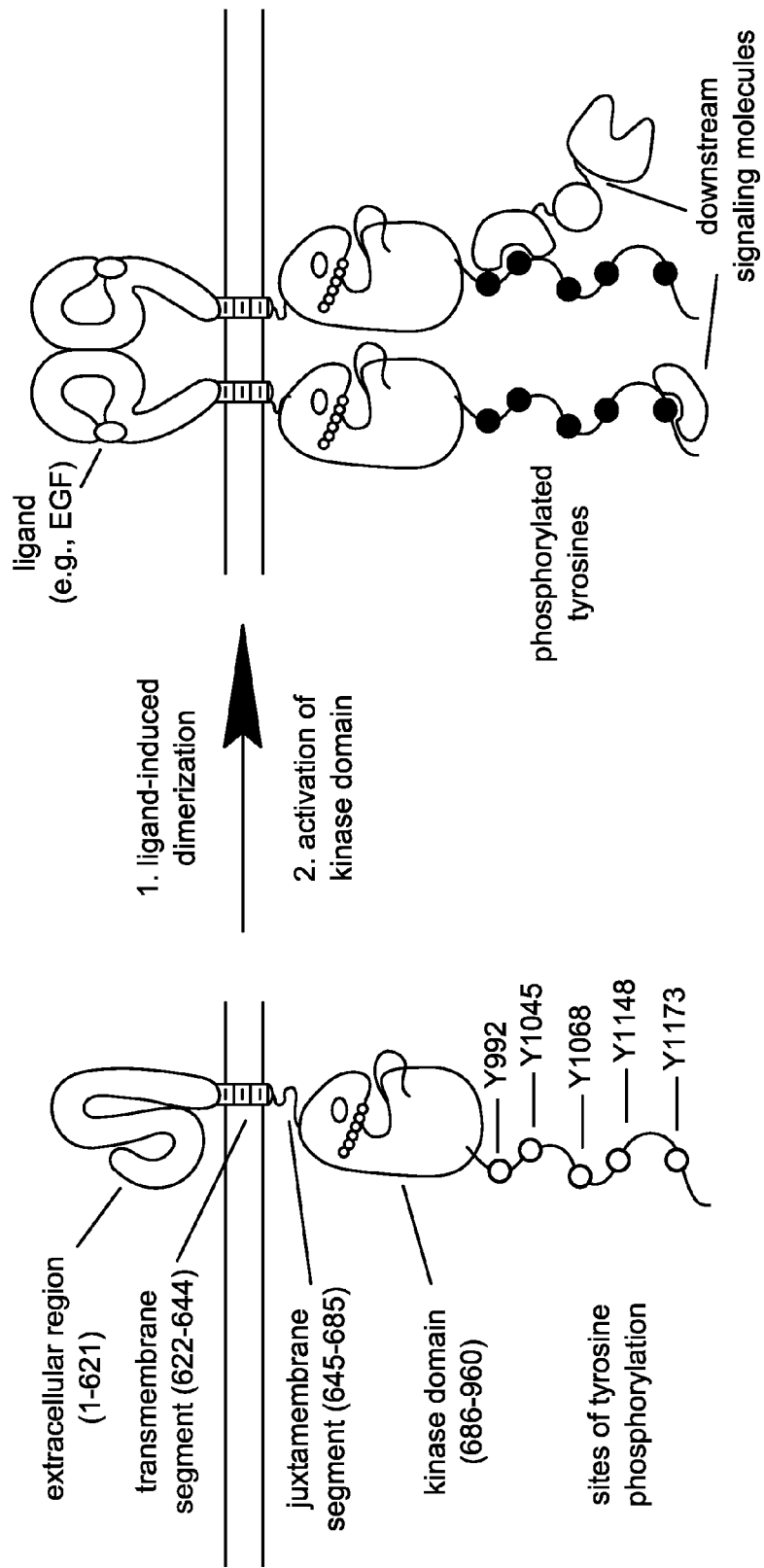
FIG. 8 is a cartoon depicting ligand-induced dimerization and activation of the kinase domain of EGFR.

As described above, EGFR has an autoinhibited configuration in which the dimerization arm of domain II is completely occluded by intramolecular interactions with domain IV (see e.g., FIG. 7). EGF activates its receptor by inducing dimerization of the extracellular region of EGFR (see e.g., FIG. 7D). Almost all receptor/receptor contacts observed in the crystal structures of EGFR are mediated by domain II, specifically, a prominent loop (residues 242-259 of EGFR) that extends from the second C1 module (module 5) of each domain II (i.e., the dimerization arm). The unactivated configuration is characterized by a direct intramolecular interaction between cysteine-rich domains II and IV, which restrains the domain II/III relationship (see e.g., FIG. 7A). This interdomain "tether" is stabilized by essentially identical interactions between the two cysteine rich domains (II and IV) in inactive sEGFR. Switching between the unactivated and activated configurations of sEGFR requires domains I and III to be drawn toward one another through a 130° rotation of the rigid domain I/II pair in one plane and a 20° rotation in another (see e.g., FIG. 7B). Only this extended configuration of sEGFR is capable of both high-affinity ligand binding (see e.g., FIG. 7C) and efficient dimerization (see e.g., FIG. 7D). In the activated and dimerized configuration, the dimerization arm of domain II reaches across the interface to interact primarily with the corresponding domain II arm of its dimerization partner (see e.g., FIG. 7D). EGFR dimerization also requires interaction of contact sites in modules 2 and 6 of domain III. The presence of EGF ligand and subsequent binding to domains I and III of the non-tethered form will drive the equilibrium toward the non-tethered form, trapping receptor molecules in the extended state that can dimerize.

The approach described herein provides for some retention of the basal levels of EGFR signaling. In healthy individuals there exists a baseline signal from EGFR necessary for growth, with enhanced EGF levels promoting accelerated growth in, for example, wound recovery. But cancer cells have been demonstrated to exhibit more EGFR, which increases the probability of the untethered conformation and subsequent EGF binding to the unoccluded domain I/III ligand binding site, thereby activating EGFR. An inhibitor that holds multi-domain proteins of EGFR together in a tethered, inactive state can allow for some basal levels of EGFR signaling.

Figure 14A:
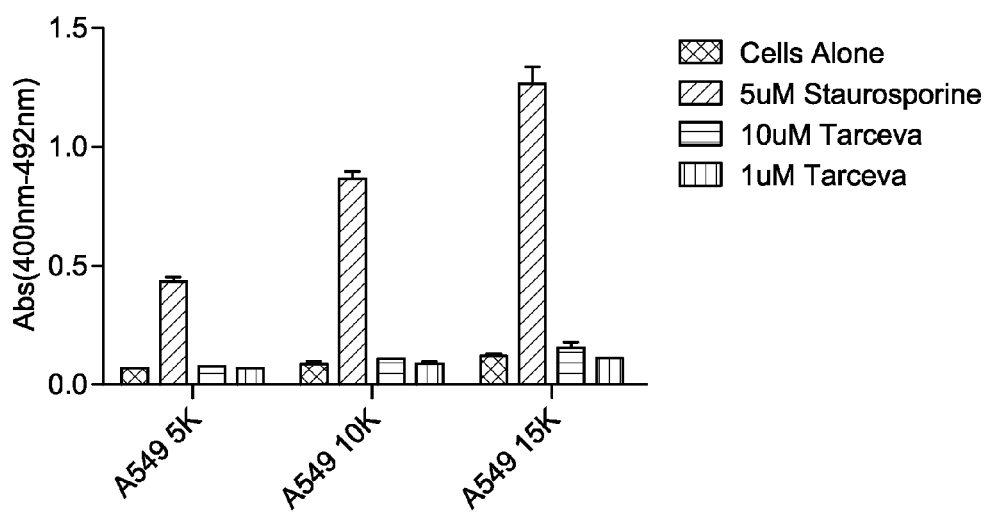
FIG. 14 is a bar graph showing ability of staurosporine (5 µM) or tarceva (10 µM or 1 µM) to induce apoptosis, as measured by an increase in DNA fragmentation, was measured when cells were plated at 5,000, 10,000 and 15,000 cells per well at 6 (FIG. 14A), 24 (FIG. 14B) and 48 (FIG. 14C) hours. Further information regarding methodology is provided in Example 8.
Figure 14B:
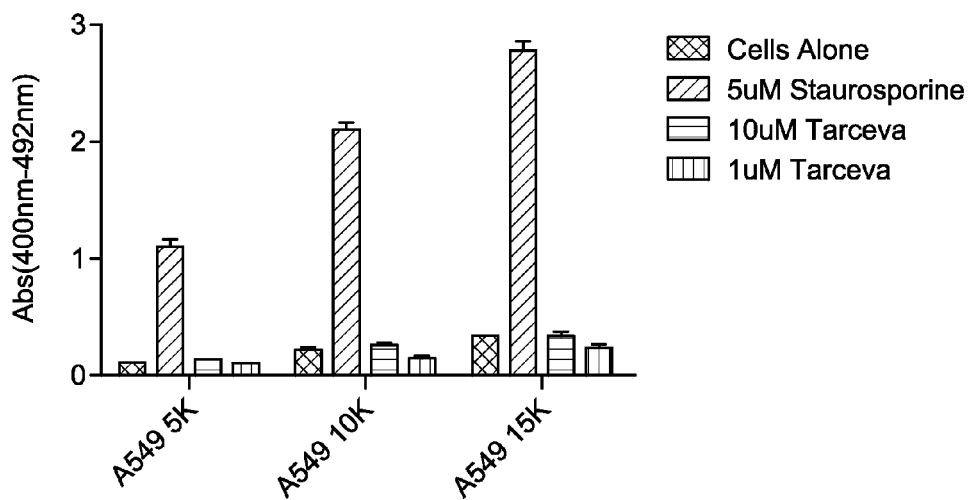
Figure 14C:
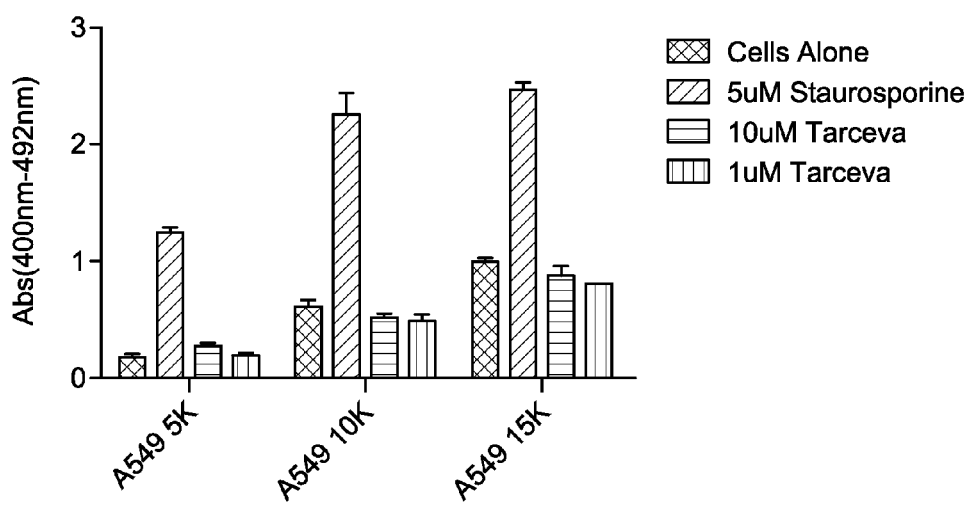

Furthermore, small molecule inhibitors that prevent stabilization of the untethered state (see e.g., FIG. 14B depicting untethered state, and FIG. 14C depicting stabilized untethered state) of EGFR can be used in conjunction with other anti-EGFR therapeutic agents. Use of small molecule inhibitors described herein in conjunction with other anti-EGFR therapeutic modalities can allow decreased dosage and/or increased maximal inhibition. For example, use of such small molecule inhibitors can be used in conjunction with Erbitux (which binds domain III blocking EGF), which would allow a lower dosage of Erbitux and/or increased maximal inhibition.

In various embodiments, domain II of EGFR, as existing in the tethered state, is targeted so as to prevent opening (i.e., the configuration change from tethered to open, see e.g., FIG. 7A-B depicting tethered and untethered conformations). In various embodiments, the cleft between domain II and domain IV is targeted so as to prevent opening (i.e., the configuration change from tethered to open). A single small molecule can be used to span the two domains. Alternatively, a series of small molecules (e.g., at least two small molecules) in several compartments can be used in conjunction so as to span the two domains. In various embodiments, domain II of EGFR, as existing in the untethered state, is targeted so as to prevent stabilization of the untethered state (see e.g., FIG. 7B-C, depicting untethered and stabilized conformations). In various embodiments, domain III of EGFR is targeted (e.g., modules 2 and 6 of domain III, which are interacting contact sites required for EGFR dimerization) so as to prevent stabilization of the untethered state.

Pharmacophoric Approach

One aspect is directed to a pharmacophoric approach for developing a drug targeting a multi-domain protein having an interdomain tether associated with activation state. Based upon the activation and dimerization mechanism of a biomolecule of interest, binding targets are identified and characterized. The mechanism and/or binding target can be characterized, for example, via crystallography data. The target binding domains can be expressed as one or more pharmacophore features and/or compiled in a pharmacophore model comprising one or more pharmacophore features.

Pharmacophore generation can be according to software designed for such a task. Candidate molecules (from, for example, one or more chemical libraries) can be selected from those molecules which align to the pharmacophore models. Preferably, candidate molecules are docked and scored in silico for interaction with the target binding domain. Again, docking and scoring can be according to software designed for such a task. After selection of molecules aligning to one or more pharmacophore models, with optional docking and scoring in silico, the selected molecules can be obtained, for example, by chemical synthesis or from a commercial source. The selected molecules can be measured for binding affinity and/or effect on function for the target biomolecule. Such assessment can be according to a biological assay. The tested molecules can be further selected according to desirable measured parameters. The selected molecules and/or the further selected molecules can optionally be further optimized.

Determining Structure Spatial Position

From the activation and dimerization model of the target biomolecule, target regions can be identified and 3D binding domains can be defined. Definition of the binding domain(s) generally involves the determination of the specific spatial position of the atoms of the portion of the target biomolecule which plays a role in the activation and dimerization mechanism.

Determination of the spatial position of the binding portion can be achieved by means of various in silico techniques. For example, software packages can be used that model the structure of the binding surface and match it to a model of the active surface of the target to assess levels of compatibility. Such software includes CAMAL.

Determination of the spatial position of the binding portion can be achieved by means of X-ray crystallography. X-ray crystallography can be used to determine the structure of atoms within a structure that is known to play a role in the activation and dimerization mechanism, and to then use this structural information to build a synthetic molecule that binds to one or more of these components and interferes with configuration changes and/or stabilization. Techniques for employing X-ray crystallography for structural determination are known in the art (see e.g., Messerschmidt (2007) X-Ray Crystallography of Biomacromolecules: A Practical Guide, John Wiley & Sons, ISBN-10: 3527313966; Woolfson (2003) An Introduction to X-ray Crystallography, 2d Ed., Cambridge University Press, ISBN-10: 0521423597). Creation of X-ray crystal structures are also known in the art (see e.g., U.S. Pat. No. 6,931,325 to Wall and U.S. Pat. No. 6,916,455 to Segelke, each incorporated herein by reference). Except as otherwise noted herein, therefore, the process of the present invention can be carried out in accordance with such processes.

Parameters derived from X-ray crystallography observed diffraction data include, but are not limited to, hydrogen bonders, apolar hydrophobic contacts, salt bridge interactions, polar surface area of the domain, apolar surface area of the domain, shape complementarily score for the antibody-target complex, and explicitly placed water molecules. Also useful is characterization of bonds between atoms. The distance between two atoms that are singly bonded ranges from about 1.45 to about 1.55 Å. Atoms that are double bonded together are typically about 1.2 to about 1.25 Å apart. Bonds that are resonant between single and double bonds typically have an about 1.30 to about 1.35 Å separation.

Construction of Pharmacophores

A pharmacophore model can be constructed from structural information of biomolecule components playing a role in activation and dimerization, including definition of atom position. Small molecules with complementary features to components of the target biomolecule, such as a component playing a role in activation and dimerization, have the potential to interfere with configuration changes and/or stabilization necessary for activation and dimerization and thus have therapeutic utility.

In various embodiments, in silico approaches can be used for de novo structure design with a fragment based approach employing contact statistics, 3D surface models, and docked ligands as templates. From the spatial position information, and/or from other parameters described above, one can derive 3D ligand-receptor models (e.g., interaction pattern, pharmacophore schemes), surface maps (e.g., topography/shape, electrostatic profile, hydrophobicity, protein flexibility), and docking models (e.g., scoring system for ligand binding, minimum energy calculation).

Techniques for pharmacophore model construction are known in the art and described extensively herein (see e.g., Example 4). Except as otherwise noted herein, therefore, the processes of the present invention can be carried out in accordance with such processes.

A pharmacophore model or scheme is generally a set of structural features in a ligand that are related, preferably directly related, to the ligand's recognition at a receptor site and its biological activity. Pharmacophore features can be derived from corresponding donor, acceptor, aromatic, hydrophobic, and/or acidic or basic moieties of the corresponding target biomolecule, especially those features on domains participating in dimerization and activation mechanisms. It shall be understood that additional information about the nature of the atoms in the target biomolecule being used in a pharmacophore scheme, and not simply the spatial location of the atoms, can assist in the modeling process of a new chemical lead. These characteristics include, but are not limited to, the pKa values of the atoms, the rotational rigidity of the bonds holding the atoms in place, the nature of the bonds themselves (single, double, resonant, or otherwise), the projected directionality of hydrogen bond donors and acceptors, etc.

Typical feature components useful in generating a pharmacophore scheme include, but are not limited to, atomic position; atomic radii; hydrogen bond donor features; hydrogen bond acceptor features; aromatic features; donor features; acceptor features; anion features; cation features; acceptor and anion features; donor and cation features; donor and acceptor features; acid and anion features; hydrophobic features, hydrogen bond directionality, and metal ligands (see e.g., Example 4). Such features can be located, for example, at a single atom, centroids of atoms, or at a projected directional position in space.

It is contemplated that numerous pharmacophore queries can be designed for any given target biomolecule. It is further contemplated that these pharmacophore queries will be useful to identify small molecule ligands which interact with the target biomolecule at a site involved with dimerization and activation, especially towards maintaining a tethered, inactive conformation.

Exemplary resources for accomplishing such modeling and queries include, but are not limited to MOE (CGG) (providing pharmacophore query and visualization), Glide (Schrodinger) (providing docking and scoring), Accord for Excel (Accelrys) (providing organization of molecular information including chemical structures and formulas), and the ZINC database (UCSF) (providing a library of commercial compounds). One design tool for the generation of pharmacophores from immune system protein-target biomolecule structural binding characterization is MOE, or Molecular Operating Environment (Chemical Computing Group). Model generation uses geometrical and electronic constraints to determine the 3D positions of features corresponding to the immune system protein. The model of these embodiments consists of spherical features in 3D space. The diameter of the spheres can be adjusted (e.g., about 0.5 to about 3.0 Å). Such models allow matches and/or partial matches of the features.

Pharmacophoric structural features can be represented by labeled points in space. Each ligand can be assigned an annotation, which is a set of structural features that may contribute to the ligand's pharmacophore (see e.g., Example 4). In various embodiments, a database of annotated ligands can be searched with a query that represents a pharmacophore hypothesis (see e.g., Example 5). The result of such a search is a set of matches that align the pharmacophoric features of the query to the pharmacophoric features present in the ligands of the searched database (see e.g., Example 5, Table 8). The number of hits within the database depends, at least in part, upon the size of the database and the restrictiveness of the pharmacophore query (e.g., partial mathces, number of features, etc.). Properties and parameters of the molecules present within the search database are used to focus the outcome of the query. For example, compounds with a defined range of molecular weight (MW) or lipophilicity (log P) can be present in the searched section of the library database of compounds.

Candidate Molecules

The subject methods find use in the screening of a variety of different candidate molecules (e.g., potentially therapeutic candidate molecules). As described above, candidate molecules can be searched using a pharmacophore query. Candidate molecules encompass numerous chemical classes, though typically they are organic molecules, preferably small organic compounds having a molecular weight of more than 50 and less than about 2,500 Daltons. Candidate molecules can comprise functional groups for structural interaction with proteins, particularly hydrogen bonding, and can include at least an amine, carbonyl, hydroxyl or carboxyl group, preferably at least two of the functional chemical groups. The candidate molecules can comprise cyclical carbon or heterocyclic structures and/or aromatic or polyaromatic structures substituted with one or more of the above functional groups.

In preferred embodiments, the candidate molecules are compounds in a library database of compounds. One of skill in the art will be generally familiar with, for example, numerous databases for commercially available compounds for screening (see e.g., ZINC database, UCSF, with 2.7 million compounds over 12 distinct subsets of molecules; Irwin and Shoichet (2005) J Chem Inf Model 45, 177-182). One of skill in the art will also be familiar with a variety of search engines to identify commercial sources or desirable compounds and classes of compounds for further testing (see e.g., ZINC database; eMolecules.com; and electronic libraries of commercial compounds provided by vendors, for example:

ChemBridge, Princeton BiOMolecular, Ambinter SARL, Enamine, ASDI, Life Chemicals etc).

Candidate molecules for screening according to the methods described herein include both lead-like compounds and drug-like compounds. A lead-like compound is generally understood to have a relatively smaller scaffold-like structure (e.g., molecular weight of about 150 to about 350 D) with relatively fewer features (e.g., less than about 3 hydrogen donors and/or less than about 6 hydrogen acceptors; hydrophobicity character x log P of about −2 to about 4) (see e.g., Angewante (1999) Chemie Int. ed. Engl. 24, 3943-3948). In contrast, a drug-like compound is generally understood to have a relatively larger scaffold (e.g., molecular weight of about 150 to about 500 D) with relatively more numerous features (e.g., less than about 10 hydrogen acceptors and/or less than about 8 rotatable bonds; hydrophobicity character x log P of less than about 5) (see e.g., Lipinski (2000) J. Pharm. Tox. Methods 44, 235-249). Preferably, initial screening is performed with lead-like compounds.

When designing a lead from spatial orientation data, it can be useful to understand that certain molecular structures are characterized as being "drug-like". Such characterization can be based on a set of empirically recognized qualities derived by comparing similarities across the breadth of known drugs within the pharmacopoeia. While it is not required for drugs to meet all, or even any, of these characterizations, it is far more likely for a drug candidate to meet with clinical success if it is drug-like.

Several of these "drug-like" characteristics have been summarized into the four rules of Lipinski (generally known as the "rules of fives" because of the prevalence of the number 5 among them). While these rules generally relate to oral absorption and are used to predict bioavailability of compound during lead optimization, they can serve as effective guidelines for constructing a lead molecule during rational drug design efforts such as may be accomplished by using the methods of the present invention.

The four "rules of five" state that a candidate drug-like compound should have at least three of the following characteristics: (i) a weight less than 500 Daltons; (ii) a log of P less than 5; (iii) no more than 5 hydrogen bond donors (expressed as the sum of OH and NH groups); and (iv) no more than 10 hydrogen bond acceptors (the sum of N and O atoms). Also, drug-like molecules typically have a span (breadth) of between about 8 Å to about 15 Å. It will be understood that a candidate molecule, or even a selected molecule, may not meet all, or even any, of these characterizations. Nonetheless, the above guidelines are helpful in drug screening and design.

As explained above, the number of molecules identified as hits to the pharmacophore depend, at least in part, on the size of the database and the restrictiveness of the pharmacophore query. The number of molecules identified as hits from a pharmacophore query can be reduced by further modeling of fit to the binding site of the target biomolecule. Such modeling can be according to docking and scoring methods, as described below.

Docking and Scoring

Candidate molecules identified as being complementary to certain features of a target biomolecule as compared to a pharmacophore model (e.g., through a pharmacophore query as described above) can be further selected according to docking affinity for the target biomolecule (see e.g., Example 5). In addition to pharmacophore model generation for database queries, a second sequential and complementary method for compound identification and design can be employed. Pharmacophore queries can filter out compounds quickly and docking and scoring can evaluate ligand-target biomolecule binding more accurately. In the case of protein or enzyme target biomolecules, amino acid residues of different domains in an inactive conformation can be used to define the docking site.

In various embodiments, selected compounds from the pharmacophore queries are docked to the target binding site using software designed for such analysis (e.g., Glide (Schrodinger, N.Y.). Docking affinity can be calculated as numerical values (e.g., "Glide score") based upon, for example, energy gained upon interaction of the molecule with the protein (e.g., "g_score") and/or energy required to attain the docked conformation relative to the lowest energy conformation (e.g., "e_model") (see e.g., Example 5). For these particular examples, the more negative the score, the better the docking. Preferably, the g_score is less than about −5. Preferably, the e_model score is less than about −30. It is contemplated that the desirable numerical quantification of docking can vary between different target biomolecules.

In various embodiments, a threshold docking score (e.g., g_score and/or e_model score) can be chosen so as to manage the number of molecules for acquisition and further testing. For example, in some docking studies, a g-score of negative 5.0 (or greater magnitude in a negative direction) is considered a desirable docking score and the cut off is adjusted accordingly. As another example, in some docking studies, a g_score of negative 7.5 (or greater magnitude in a negative direction) is considered a desirable docking score and the cut off is adjusted accordingly. Thus, the magnitude of the g_score can be used to adjust a number of hits to a workable number that can be acquired and tested. As an example, if the total number of compounds identified from a pharmacophore query was about 1,000 to about 3,000, the docking scores can be used to rank such compounds so as to select about 100 to about 200 for further testing. It is contemplated the number of compounds to be selected for further testing could be lower or higher than these estimates. Preferably, magnitude of the g_score is used as a selection criteria, but it is contemplated that e_model score could be similarly used, especially where e_model score is of low magnitude. It is further contemplated that the selection criteria can be based upon both g_score and e_model score, preferably weighted toward g_score.

Docking and scoring can result in a group of compounds with multiple conformers. Using suitable modeling software (e.g., MOE), 3D structures can be converted to 2D and duplicates thereby removed. The resulting list of preferred chemical structures can used to search for commercial vendors using, for example, search engines designed for such a task (e.g., eMolecules.com).

Effect on Target Biomolecule

Candidate molecules selected according to pharmacophore query and/or further selected according to docking analysis can be tested for effect on the target biomolecule. Assessment of effect of a molecule on biomolecule function (e.g., inhibition of enzymatic activity) can be assessed by various methods known in the art (see e.g., Examples 1-3). For example, inhibitory effect of a candidate molecule on the catalytic activity of a target enzyme can be assessed by known activity assays specific for the target enzyme (see e.g., Reymond, ed. (2006) Enzyme Assays: High-throughput Screening, Genetic Selection and Fingerprinting, John Wiley & Sons, 386 p., ISBN-10: 3527310959; Eisenthall and Danson, Ed. (2002) Enzyme Assays, 2d edition, Oxford University Press, 384 p., ISBN-10: 0199638209). As described herein, an in-cell Western (ICW) screening protocol can be used to evaluate candidate compounds (see e.g., Example 1; Chen et al. (2005) Analytical Biochemistry 338, 136-142). Also as described herein, a MTT Cell Proliferation Assay can be used to evaluate candidate compounds (see e.g., Example 2). Also as described herein, an EGF inhibitor assay can be used to evaluate candidate compounds (see e.g., Example 3; Mukku (1984) J. Biol. Chem. 259, 6543-6546; Duh et al. (1990) World J. Surgery 14, 410-418; Lokeshwar et al. (1989) J. Biol. Chem. 264(32), 19318-19326).

Further Refinement

Further refinement of candidate molecules can be conducted. For example, data from biological assays can be correlated with the docking model so as to further refine lead-like molecules and/or drug-like molecules. Various software packages (e.g., MOE) can be employed to visualize active compound interaction with a target biomolecule to identify sites on the template suitable for modification by de novo design. Analogs of active compounds can be identified using similarity and sub-structure searches (see e.g., SciFinder; eModel). Available analogs can be analyzed according to docking and scoring procedures described above. Analogs with desirable docking scores can be acquired and further tested for biological effect on the target biomolecule according to methods described herein. One skilled in the art will understand these, and other, methods of refining and further developing candidate molecules identified by the methods presented herein.

Pharmacophores

Provided herein are a series of pharmacophores that can be used to identify small molecules that can substantially maintain a non-extended tether inactive configuration of EGFR or substantially prevent stabilization of an extended tether active configuration of EGFR. Pharmacophores include, but are not limited to, a Scheme I pharmacophore (AD4-1505-like).

Scheme I pharmacophore (AD4-1505-like)

A Scheme I pharmacophore (AD4-1505-like) can include functional groups F(I)1, F(I)2, F(I)3, F(I)4, F(I)5, F(I)6, F(I)7, F(I)8, and F(I)9.

Functional group F(I)1 donates an H-bond or forms a salt bridge to a carboxylate side chain of receptor Asp553 of SEQ ID NO: 1 and has coordinates of $r=56.363$, $\theta$ (theta)=94.368, and $\Phi$ (phi)=−17.752 and a spherical radius of about 1.2 Å.

Functional group F(I)2 donates an H-bond to backbone carbonyl of receptor Thr570 of SEQ ID NO: 1 and has coordinates of $r=53.290$, $\theta$ (theta)=101.494, and $\Phi$ (phi)=−23.244 and a spherical radius of about 1.0 Å.

Functional group F(I)3 forms a hydrophobic contact with a side chain of receptor Val568, an imidazole side chain of receptor His566, and an imidazolidine ring of receptor Pro552 of SEQ ID NO: 1 and has coordinates of $r=53.726$, $\theta$ (theta)=97.830, and $\Phi$ (phi)=−18.378 and a spherical radius of about 1.7 Å.

Functional group F(I)4 donates an H-bond or forms a salt bridge to the side chain carboxylate of receptor Asp563 of SEQ ID NO: 1 and has coordinates of $r=56.103$, $\theta$ (theta)=99.536, and $\Phi$ (phi)=−21.080 and a spherical radius of about 1.2 Å.

Functional group F(I)5 forms a hydrophobic contact with an imidazoline ring of receptor Pro572 and a side chain of Met253 of SEQ ID NO: 1 and has coordinates of $r=53.647$, $\theta$ (theta)=103.844, and $\Phi$ (phi)=−20.990 and a spherical radius of about 1.4 Å.

Functional group F(I)6 donates an H-bond to a backbone carbonyl of receptor Cys571 of SEQ ID NO: 1 and has coordinates of $r=51.088$, $\theta$ (theta)=104.241, and $\Phi$ (phi)=−25.552 and a spherical radius of about 1.2 Å.

Functional group F(I)7 donates an H-bond to a backbone carbonyl of receptor Cys571 of SEQ ID NO: 1 and has coordinates of $r=52.340$, $\theta$ (theta)=103.980, and $\Phi$ (phi)=−27.461 and a spherical radius of about 1.5 Å.

Functional group F(I)8 accepts an H-bond from receptor backbone NH of Ala573 of SEQ ID NO: 1 and has coordinates of $r=51.383$, $\theta$ (theta)=106.455, and $\Phi$ (phi)=−24.319 and a spherical radius of about 1.2 Å.

Functional group F(I)9 accepts an H-bond from receptor backbone NH of Ala573 of SEQ ID NO: 1 and has coordinates of $r=52.861$, $\theta$ (theta)=107.692, and $\Phi$ (phi)=−25.447 and a spherical radius of about 1.5 Å.

A selected candidate compound can substantially align with at least one of functional groups F(I)1, F(I)2, F(I)3, F(I)4, F(I)5, F(I)6, F(I)7, F(I)8, and F(I)9. For example, a selected candidate compound can substantially align with at least two, at least three, at least four, at least five, at least six, at least seven, at least eight, or at least nine of functional groups F(I)1, F(I)2, F(I)3, F(I)4, F(I)5, F(I)6, F(I)7, F(I)8, and F(I)9. Preferably, a selected candidate compound can substantially align with at least six of functional groups F(I)1, F(I)2, F(I)3, F(I)4, F(I)5, F(I)6, F(I)7, F(I)8, and F(I)9.

One aspect provides a method for identifying an epidermal growth factor receptor (EGFR) inhibitor comprising: providing a pharmacophore comprising Scheme I as input to a 3-dimensional database; comparing a three dimensional structure of a candidate compound to the three dimensional structure of the pharmacophore; selecting a candidate compound with a three dimensional structure that substantially aligns with six or more functional groups of Scheme I (ADS-1505-like); wherein, similarity between the three-dimensional structure of the candidate compound and the three-dimensional structure of the pharmacophore is indicative of an ability of the candidate compound to inhibit EGFR by substantially maintaining a tethered inactive configuration of EGFR or substantially preventing stabilization of the untethered active configuration of EGFR.

In some embodiments, the method further comprises determining identity and spatial orientation of at least a portion of atoms of EGFR associated with stabilizing a tethered configuration of domain II and domain IV of EGFR in an inactive conformation; and constructing a pharmacophore, wherein the pharmacophore comprises a plurality of pharmacophoric features that approximates the identity and the spatial orientation of the at least a portion of atoms of EGFR associated with stabilizing a tethered configuration of domain II and domain IV of EGFR in an inactive conformation such that the pharmacophore structural features are complementary to the inactive EGFR configuration.

In some embodiments, determining identity and spatial orientation of at least a portion of atoms of EGFR associated with stabilizing a tethered configuration of domain II and domain IV of EGFR in an inactive conformation comprises analysis of X-ray crystallographic data derived from a crystalline form of EGFR in an inactive, tethered conformation.

In some embodiments, at least one pharmacophoric feature approximates identity and spatial orientations of at least a portion of atoms of domain II of EGFR in a tethered inactive conformation. In some embodiments, at least one pharmacophoric feature approximates identity and spatial orientations of at least a portion of atoms of a cleft region between domain II and domain IV of EGFR in a tethered inactive conformation.

In some embodiments, the method further comprises determining a docking affinity of the candidate molecule for the at least a portion of atoms of EGFR associated with stabilizing a tethered configuration of domain II and domain IV of EGFR in an inactive conformation; wherein docking affinity is quantified by energy gained upon interaction of the candidate molecule with the target biomolecule, energy required to attain the docked conformation relative to the lowest energy conformation, or a combination thereof.

Compounds

Another aspect of the present invention includes small molecule compounds, identified by the methods described herein. Compounds described herein can have an anti-proliferative effect useful in, for example, treating a proliferative disease, disorder, or condition. Compounds described herein can be useful for the treatment of diseases, disorders, or conditions related to a target biomolecule according to which they were identified from. Various embodiments of compounds described herein can hold multiple domain proteins in a tethered, inactive state. For example, it is well known that inhibition of growth factor proteins has a benefit in treatment of certain conditions in oncology. As another example, inhibition of EGFR has a benefit in treatment of certain conditions associated with EGFR, as discussed further below. Compounds described herein can have an EGFR inhibitory effect useful in, for example, treating a proliferative disease or disorder associated with EGFR. Compounds described herein have been demonstrated to be empirically effective in treating proliferative diseases and conditions.

Various compounds, including AD4-1505, were identified as EGFR inhibitors through the pharmacophoric approach described herein (see e.g., Example 4). Such compounds, and derivatives thereof, have utility as therapeutic agents for treatment of proliferative diseases or conditions. For example, compounds described herein can be used as a therapeutic agent for the treatment of an EGFR-associated disease, disorder, or condition. Analogs and derivatives of such compounds are expected to have the same or similar anti-proliferative effects and utility (see e.g., Example 5). Identified compounds and analogs and derivatives thereof are further discussed below.

While under no obligation to provide an underlying mechanism and in no way limiting the present invention by doing so, it is presently thought that at least a portion of activity of compounds described herein arise from inhibition of EGFR. It is further contemplated that the presently described compounds may have additional modes of action in their effectiveness in treating a proliferative disease, disorder, or condition. Regardless of the underlying mechanism, compounds described herein have been demonstrated to be empirically effective in treating proliferative diseases and conditions.

The following definitions are provided to better define the present disclosure. Unless otherwise noted, terms are to be understood according to conventional usage by those of ordinary skill in the relevant art.

The expression "alkyl", unless specifically limited, denotes a $C_{1-12}$ alkyl group, suitably a $C_{1-6}$ alkyl group, e.g. $C_{1-4}$ alkyl group. Alkyl groups may be straight chain or branched. Suitable alkyl groups include, for example, methyl, ethyl, propyl (e.g. n-propyl and isopropyl), butyl (e.g. n-butyl, iso-butyl, sec-butyl and tert-butyl), pentyl (e.g. n-pentyl), hexyl (e.g. n-hexyl), heptyl (e.g. n-heptyl) and octyl (e.g. n-octyl). The expression "alk", for example in the expressions "alkoxy", "haloalkyl" and "thioalkyl" should be interpreted in accordance with the definition of "alkyl". Exemplary alkoxy groups include methoxy, ethoxy, propoxy (e.g. n-propoxy), butoxy (e.g. n-butoxy), pentoxy (e.g. n-pentoxy), hexoxy (e.g. n-hexoxy), heptoxy (e.g. n-heptoxy) and octoxy (e.g. n-octoxy).

The expression "cycloalkyl", unless specifically limited, denotes a $C_{3-10}$ cycloalkyl group (i.e., 3 to 10 ring carbon atoms), more suitably a $C_{3-8}$ cycloalkyl group, for example, a $C_{3-6}$ cycloalkyl group. Exemplary cycloalkyl groups include cyclopropyl, cyclobutyl, cyclopentyl, cyclohexyl, cycloheptyl and cyclooctyl. A preferred number of ring carbon atoms is three to six.

The expression "aryl", unless specifically limited, denotes a $C_{6-12}$ aryl group, suitably a $C_{6-10}$ aryl group, more suitably a $C_{6-8}$ aryl group. Aryl groups will contain at least one aromatic ring (e.g. one, two or three rings). An example of a typical aryl group with one aromatic ring is phenyl. An example of a typical aryl group with two aromatic rings is naphthyl.

The expression "heteroaryl", unless specifically limited, denotes an aryl residue, wherein one or more (e.g., 1, 2, 3, or 4, suitably 1, 2 or 3) ring atoms are replaced by heteroatoms selected from N, S and O, or else a 5-membered aromatic ring containing one or more (e.g., 1, 2, 3, or 4, suitably 1, 2 or 3) ring atoms selected from N, S and O. Exemplary monocyclic heteroaryl groups having one heteroatom include: five membered rings (e.g., pyrrole, furan, thiophene); and six membered rings (e.g., pyridine, such as pyridin-2-yl, pyridin-3-yl and pyridin-4-yl). Exemplary monocyclic heteroaryl groups having two heteroatoms include: five membered rings (e.g., pyrazole, oxazole, isoxazole, thiazole, isothiazole, imidazole, such as imidazol-1-yl, imidazol-2-yl imidazol-4-yl); six membered rings (e.g., pyridazine, pyrimidine, pyrazine). Exemplary monocyclic heteroaryl groups having three heteroatoms include: 1,2,3-triazole and 1,2,4-triazole. Exemplary monocyclic heteroaryl groups having four heteroatoms include tetrazole. Exemplary bicyclic heteroaryl groups include: indole (e.g., indol-6-yl), benzofuran, benzthiophene, quinoline, isoquinoline, indazole, benzimidazole, benzthiazole, quinazoline and purine.

A saturated group is generally understood as having no double or triple bonds. For example, in a saturated linear hydrocarbon, each carbon atom is attached to two hydrogen atoms, except those at the ends of the chain, which bear three hydrogen atoms. For example, an unsaturated hydrocarbon is generally understood as a carbon structure containing one or more double or triple bonds.

The term "halogen" or "halo" includes fluorine (F), chlorine (Cl) bromine (Br) or iodine (I).

The term "amino" refers to the group —NH$_2$.

All possible stereoisomers of the claimed compounds are included in the present disclosure. Where a compound described herein has at least one chiral center, it may accordingly exist as enantiomers. Where a compound possess two or more chiral centers it may additionally exist as diastereomers. It is to be understood that all such isomers and mixtures thereof are encompassed within the scope of the present disclosure.

In view of the close relationship between the free compounds and the compounds in the form of their salts, whenever a compound is referred to in this context, a corresponding salt is also intended, provided such is possible or appropriate under the circumstances. The pharmaceutically acceptable salt can take a form in which a basic side chain is protonated with an inorganic or organic acid. Representative organic or inorganic acids include hydrochloric, hydrobromic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benzenesulfonic, oxalic, pamoic, 2-naphthalenesulfonic, p-toluenesulfonic, cyclohexanesulfamic, salicylic, saccharinic or trifluoroacetic acid. Alternatively it may take the form in which an acidic side chain forms a salt with a metal ion (e.g., sodium, potassium ions and the like) or other positive ion such as ammonium. All pharmaceutically acceptable acid addition salt forms of the compounds described herein are intended to be embraced by the scope of this disclosure.

Some of the crystalline forms of the compounds may exist in more than one polymorphic form and as such all forms are intended to be included in the present disclosure. In addition, some of the compounds may form solvates with water (i.e., hydrates) or common organic solvents, and such solvates are also intended to be encompassed within the scope of this disclosure. The compounds, including their salts, can also be obtained in the form of their hydrates, or include other solvents used for their crystallization.

The present disclosure further includes within its scope prodrugs of the compounds described herein. In general, such prodrugs will be functional derivatives of the compounds which are readily convertible in vivo into the desired therapeutically active compound. Thus, in these cases, the methods of treatment of the present invention, the term "administering" shall encompass the treatment of the various disorders described with prodrug versions of one or more of the claimed compounds, but which converts to the above specified compound in vivo after administration to the subject.

As used herein, the term "composition" is intended to encompass a product comprising a claimed compound(s) in a therapeutically effective amount, as well as any product which results, directly or indirectly, from combinations of the claimed compounds.

AD4-1505 is identified as an inhibitor of epidermal growth factor binding to its receptor (see e.g., Example 4).

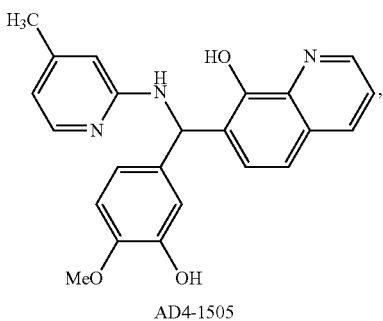

Formula (1)

AD4-1505

As described herein, a pharmacophore model was utilized to identify small molecules that are AD4-1505-like.

Type A AD-4-1505-like

One structure derived from the AD4-1505-like pharmacophore is as follows:

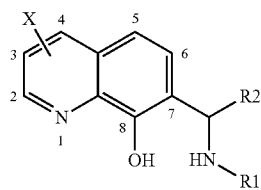

Formula (2)

In the above structure, $X^1$ of Formula (2) can represent one or more functional group from the following Hydrogen atom, 2-Methyl, 5-Chloro, 5-Nitro, or 6-Hydroxyl group.

$R^1$ of Formula (2) can represent:

a 2-Pyridyl ring of Formula (3) wherein $R^{23}$ is selected from the group consisting of hydrogen; fluoro; chloro; trifluoromethyl; methyl; ethyl; and methoxy; $R^3$ is selected from the group consisting of hydrogen; fluoro; chloro; methyl; ethyl; methoxy; a straight chain or branched C-1 to C-4 lower alkyl optionally containing unsaturation; a C-1 to C-6 cycloalkyl optionally containing unsaturation or one oxygen or nitrogen atom; aryl comprising a phenyl or heteroaryl five or six membered ring containing from 1 to 4 N, O, or S atoms; and alkoxy —$OR^{10}$ where $R^{10}$ is a straight chain or branched C-1 to C-4 lower alkyl optionally containing unsaturation or a C-1 to C-6 cycloalkyl optionally containing unsaturation or one oxygen or nitrogen atom; $R^{24}$ is selected from the group consisting of: hydrogen; fluoro; chloro; and trifluoromethyl; and $R^4$ is selected from the group consisting of hydrogen; methyl; a straight chain or branched C-1 to C-4 lower alkyl optionally containing unsaturation; a C-1 to C-6 cycloalkyl optionally containing unsaturation or one oxygen or nitrogen atom; aryl comprising a phenyl or heteroaryl five or six membered ring containing from 1 to 4 N, O, or S atoms; and alkoxy —$OR^{10}$ where $R^{10}$ is a straight chain or branched C-1 to C-4 lower alkyl optionally containing unsaturation or a C-1 to C-6 cycloalkyl optionally containing unsaturation or one oxygen or nitrogen atom;

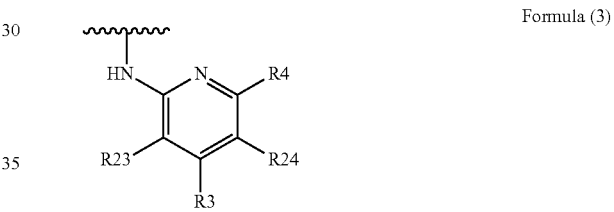

Formula (3)

a 3-Pyridyl ring of Formula (4) wherein $R^5$, $R^6$, and $R^7$ are independently selected from the group consisting of: hydrogen, lower alkyl defined as C-1 to C-4, straight chain, branched, or optionally containing unsaturation, cycloalkyl defined as C-1 to C-6 optionally containing unsaturation, Aryl including phenyl or heteroaryl containing from 1 to 4 N, O, or S atoms, alkoxy (—$OR^{10}$ where $R^{10}$ is defined as a lower alkyl group or cycloalkyl group in the above definition) (e.g., AD4-12908, AD4-13051, AD4-13021, AD4-13021, AD4-13063, AD4-013064, AD4-13065, AD4-13066, AD4-13101);

Formula (4)

a 4-Pyridyl ring of Formula (5) wherein $R^8$ and $R^9$ are independently selected from the group consisting of: lower alkyl defined as C-1 to C-4, straight chain, branched, or optionally containing unsaturation, cycloalkyl defined as C-1 to C-6 optionally containing unsaturation, Aryl including phenyl or heteroaryl containing from 1 to 4 N, O, or S atoms, Alkoxy (—$OR^{10}$ where $R^{10}$ is defined as a lower alkyl group or cycloalkyl group in the above definition);

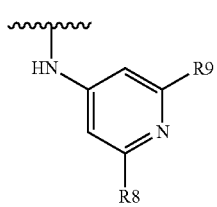

Formula (5)

an unsubstituted phenyl ring or, preferably, a phenyl ring substituted with one or more of the following groups: lower alkyl defined as C-1 to C-4, straight chain, branched, or optionally containing unsaturation, cycloalkyl defined as C-1 to C-6 optionally containing unsaturation, Aryl including phenyl or heteroaryl containing from 1 to 4 N, O, or S atoms, alkoxy (—$OR^{10}$ where $R^{10}$ is defined as a lower alkyl group or cycloalkyl group as in the above definition), trifluoromethyl, trifluoromethoxy, difluoromethoxy, 3,4-methylenedioxy, 2,3-methylenedioxy, Nitro or Halogen (F, Cl, Br, I); or an unsubstituted heteroaryl five or six membered ring containing from 1 to 4 N, O, or S atoms, or a heteroaryl five or six membered ring containing from 1 to 4 N, O, or S atoms which has one or more optional substitution with the substituent defined as one or more of the following groups: lower alkyl defined as C-1 to C-4, straight chain, branched, or optionally containing unsaturation, cycloalkyl defined as C-1 to C-6 optionally containing unsaturation, Aryl including phenyl or heteroaryl five or six membered ring containing from 1 to 4 N, O, or S atoms, Alkoxy (—$OR^{10}$ where $R^{10}$ is defined as a lower alkyl group or cycloalkyl group in the above definition).

It has been found that where $R^1$ is a 2-pyridyl ring of Formula (3) and $R^{24}$ is chloro or $R^{23}$ is methyl, the resulting compound can exhibit increased stability (see Example 10).

It has been found that where $R^1$ is a 2-pyridyl ring of Formula (3) having combinations of substituted halogens and alkyl groups, the resulting compound can exhibit increased antiproliferative activity (see Example 10). For example, where $R^1$ is a 2-pyridyl ring of Formula (3), the following substitutions can provide increased antiproliferative activity: $R^4$ is hydrogen, $R^{24}$ is fluoro, $R^3$ is hydrogen, and $R^{23}$ is fluoro; $R^4$ is methyl, $R^{24}$ is chloro, $R^3$ is hydrogen, and $R^{23}$ is fluoro; $R^4$ is hydrogen, $R^{24}$ is chloro, $R^3$ is ethyl, and $R^{23}$ is fluoro; $R^4$ is hydrogen, $R^{24}$ is fluoro, $R^3$ is methyl, and $R^{23}$ is fluoro; $R^4$ is hydrogen, $R^{24}$ is chloro, $R^3$ is hydrogen, and $R^{23}$ is ethyl; $R^4$ is methyl, $R^{24}$ is chloro, $R^3$ is hydrogen, and $R^{23}$ is chloro; $R^4$ is hydrogen, $R^{24}$ is chloro, $R^3$ is methyl, and $R^{23}$ is fluoro; $R^4$ is hydrogen, $R^{24}$ is trifluoromethyl, $R^3$ is hydrogen, and $R^{23}$ is hydrogen; $R^4$ is hydrogen, $R^{24}$ is chloro, $R^3$ is hydrogen, and $R^{23}$ is methyl; $R^4$ is hydrogen, $R^{24}$ is chloro, $R^3$ is hydrogen, and $R^{23}$ is chloro; $R^4$ is hydrogen, $R^{24}$ is chloro, $R^3$ is methyl, and $R^{23}$ is hydrogen; or $R^4$ is hydrogen, $R^{24}$ is chloro, $R^3$ is chloro, and $R^{23}$ is hydrogen (see Example 10).

It has been found that where $R^1$ is a 2-pyridyl ring of Formula (3) and $R^{24}$ is chloro and there is additionally a chloro or methyl at one or both of $R^3$ or $R^{23}$, the resulting compound can exhibit increased apoptosis (see Example 10). For example, where $R^1$ is a 2-pyridyl ring of Formula (3), the following substitutions can provide increased apoptosis: $R^{24}$ is chloro, $R^3$ is hydrogen, and $R^{23}$ is methyl; $R^{24}$ is chloro, $R^3$ is methyl, and $R^{23}$ is fluoro; $R^{24}$ is chloro, $R^3$ is chloro, and $R^{23}$ is hydrogen; and $R^{24}$ is chloro, $R^3$ is hydrogen, and $R^{23}$ is chloro.

It has been found that, where $R^1$ of Formula (2) is a 2-Pyridyl ring of Formula (3), the group at $R^{24}$ of the aminopyridine can block metabolism in cultured hepatocytes.

As preferred examples, $R^1$ of Formula (2) can represent: an unsubstituted thiazoyl) ring (see Formula (6)) or a 2-(1,3-thiazoyl) ring with groups at the 4- or 5-position of the thiazole ring, for example a 2-(4,5-Dimethyl-1,3-thiazoyl ring (see Formula (7)):

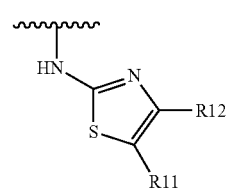

Formula (6)

2-(1,3-THIAZOYL)
RING SUBSTITUTION

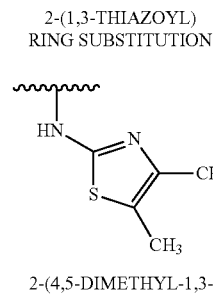

Formula (7)

2-(4,5-DIMETHYL-1,3-
THIAZOYL) GROUP $R^2$ of Formula (2) can represent:

an unsubstituted Phenyl ring or a Phenyl ring substituted at the 2-, 3-, 4-, 5- or 6-position with one or more of the following groups: lower alkyl defined as C-1 to C-4, straight chain, branched, or optionally containing unsaturation, cycloalkyl defined as C-1 to C-6 optionally containing unsaturation, Aryl including phenyl or heteroaryl containing from 1 to 4 N, O, or S atoms, Alkoxy (—$OR^{10}$ where $R^{10}$ is defined as a lower alkyl group or cycloalkyl group as in the above definition), 2,3-Methylenedioxy or 3,4-Methylenedioxy group, Dialkylamino (—$NR_{13}R_{14}$ where $R_{13}$ and $R_{14}$ are independently selected from a Hydrogen atom or lower alkyl group as previously described); Trifluoromethyl, Trifluoromethoxy, Difluoromethoxy, 3,4-methylenedioxy, 2,3-methylenedioxy, Nitro or Halogen (F, Cl, Br, I);

a 2-Thiophene ring of Formula (8) wherein $R^{15}$, $R^{16}$, and $R^{17}$ are independently selected from the group consisting of: hydrogen, lower alkyl, cycloalkyl, Alkoxy, Dialkylamino, Trifluoromethyl, Difluoromethyl, Trifluoromethoxy or halogen as described above;

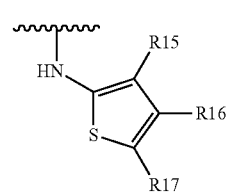

Formula 8

2-THIOPHENE
RING SUBSTITUTION a 3-Thiophene ring of Formula (9) wherein $R^{18}$, $R^{19}$, and $R^{20}$ are independently selected from the group consisting of:

lower alkyl, cycloalkyl, Alkoxy, Dialkylamino, Trifluoromethyl, Difluoromethyl, Trifluoromethoxy or halogen as described above;

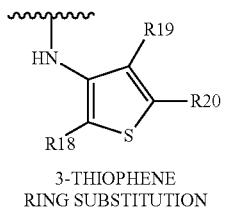

Formula (9)

3-THIOPHENE
RING SUBSTITUTION an unsubstituted 2-Pyridyl ring or a 2-Pyridyl ring substituted at the 4- or 6-position of the pyridine ring with one or more of the following groups: lower alkyl group as defined above, cycloalkyl group as defined above;

an unsubstituted 3-Pyridyl ring or a 3-Pyridyl ring substituted at the 2-, 4- or 6-position of the pyridine ring with one or more of the following groups: lower alkyl group as defined above, cycloalkyl group as defined above; or an unsubstituted 4-Pyridyl ring or a 4-Pyridyl ring substituted at the 2- or 6-position of the pyridine ring with one or more of the following groups: lower alkyl group as defined above, cycloalkyl group as defined above.

It has been found that where $R^2$ is a phenyl ring substituted at the 2- and 4-positions, the resulting compound can exhibit increased stability (see Example 10). For example, where $R^2$ is 4-trifluoromethylphenyl; 2-fluoro,4-trifluoromethylphenyl; or 2,4-dichlorophenyl, the resulting compound can exhibit increased stability (see Example 10).

It has been found that where $R^2$ is a phenyl ring substituted with a combination of halogens and trifluoromethyl groups, the resulting compound can exhibit increased antiproliferative activity (see Example 10). For example, where $R^2$ is 4-chlorophenyl; 2-fluoro,4-trifluoromethylphenyl; 3-fluoro,4-chlorophenyl; 2-fluoro,4-chlorophenyl; 2,3-dichlorophenyl; 2,3,5-trichlorophenyl; 2,4-dichlorophenyl; 3,4-dichlorophenyl; or 3,5-dichlorophenyl, the resulting compound can exhibit increased antiproliferative activity (see Example 10).

It has been found that where $R^2$ is a phenyl ring substituted at the 4 position with chloro and additionally substituted at the 2- or 3-position with chloro or fluoro, the resulting compound exhibits increased apoptosis (see Example 10). For example, where $R^2$ is 2,4-dichlorophenyl or 2-chloro,4-fluorophenyl, the resulting compound can exhibits increased apoptosis (see Example 10).

In some embodiments, the compound(s) are the enantiomeric isomers of Formula (2).

In some embodiments, the compound(s) of Formula (2) are according to R1 and R2 as provided in the following TABLES 1-4:

TABLE 1

| R1 and R2 substitution combinations (Pyr = pyridine; Ani = aniline) | | | | | |
|---|---|---|---|---|---|
| R2 phenyl substitution | R1 = 5ClPyr | R1 = 5FPyr | R1 = 4ClPyr | R1 = 4Me—5ClPyr | R1 = 4Me—5FPyr |
| 2Cl | AD4-13087 | AD4-13104 | | AD4-13141 | AD4-13116 |
| 3Cl | AD4-13151 | | | | |
| 4Cl | AD4-13152 | | | AD4-13157 | |
| 2,3-diCl | AD4-13086 | AD4-13103 | | AD4-13153 | AD4-13126 |
| 3,4-diCl | AD4-13054 | AD4-13113 | AD4-13069 | AD4-13166 | AD4-13127 |
| 2,4-diCl | AD4-13097 | AD4-13110 | | AD4-13123 | AD4-13128 |
| 2,5-diCl | AD4-13095 | AD4-13102 | | AD4-13158 | AD4-13118 |
| 3,5-diCl | AD4-13094 | AD4-13098 | | AD4-13122 | AD4-13114 |
| 2,6-diCl | AD4-13109 | AD4-13120 | | AD4-13148 | AD4-13125 |
| 2,3,5-triCl | AD4-13111 | AD4-13132 | | AD4-13156 | |
| 2Cl—4F | AD4-13088 | AD4-13099 | | AD4-13149 | AD4-13115 |
| 2Cl—6F | AD4-13091 | AD4-13112 | | AD4-13140 | AD4-13117 |
| 3F—4Cl | | | | | |
| 3Cl—4F | | | | | |
| 4CF3 | AD4-13053 | | AD4-13044 | AD4-13121 | |
| 3F—4CF3 | AD4-13055 | AD4-13061 | AD4-13048 | AD4-13106 | |
| 2Cl—5CF3 | AD4-13052 | AD4-13049 | AD4-13060 | | |
| 4Cl—5CF3 | AD4-13067 | AD4-13071 | AD4-13047 | AD4-13108 | |
| 2,4-diCF3 | | | | AD4-13124 | |
| 3CF3 | | | | AD4-13107 | |
| 2F-4CF3 | | | AD4-13046 | AD4-13129 | |
| 2,3,5,6-F4 | | AD4-13070 | | AD4-13136 | |
| 2,4-diF | | AD4-13050 | AD4-13045 | | |
| 3-Me-4-OMe | | | | | |
| 2-F | | | | | |
| 2,3,5,6-F4-4-OCH2CF3 | | | | | |
| 2-Me | | | | | |
| 3-F | | | | | |
| 4-OCF3 | | | | | |
| 3-OH-4-OMe | | | | AD4-13186 | |
| 2-OH-5-Me | | | | | |
| 3,4-diOMe | | | | AD4-13194 | |
| 2,3,4-triOMe | | | | AD4-13196 | |

TABLE 2

R1 and R2 substitution combinations (Pyr = pyridine; Ani = aniline)

| R2 phenyl substitution | R1 = 3Me—5Cl | R1 = 5-CF3Pyr | R1 = Pyr | R1 = 4-MePyr | R1 = 6-MePyr | R1 = 3,5-diFPyr |
|---|---|---|---|---|---|---|
| 2Cl | AD4-13134 | | | AD4-12907 | AD4-12904 | AD4-13183 |
| 3Cl | AD4-13159 | | | | | AD4-13173 |
| 4Cl | AD4-13154 | | | | | AD4-13174 |
| 2,3-diCl | AD4-13147 | | AD4-10051 | AD4-12906 | AD4-12905 | |
| 3,4-diCl | AD4-13119 | AD4-13030 | AD4-13037 | AD4-12917 | AD4-12916 | AD4-13182 |
| 2,4-diCl | AD4-13130 | AD4-13033 | AD4-13039 | AD4-12912 | AD4-12911 | AD4-13175 |
| 2,5-diCl | AD4-13137 | | AD4-12910 | AD4-12954 | AD4-12955 | AD4-13155 |
| 3,5-diCl | AD4-13131 | | AD4-12914 | AD4-12915 | AD4-12913 | AD4-13176 |
| 2,6-diCl | AD4-13142 | | AD4-13019 | | | AD4-13138 |
| 2,4,5-triCl | AD4-13167 | | | AD4-13072 | AD4-13023 | AD4-13181 |
| 2Cl—4F | AD4-13139 | | AD4-13027 | AD4-13026 | AD4-13024 | AD4-13146 |
| 2Cl—6F | AD4-13135 | | | AD4-13020 | AD4-12959 | AD4-13133 |
| 3F—4Cl | AD4-13229 | | | | | |
| 3Cl—4F | | | | | | |
| 4CF3 | AD4-13041 | AD4-13028 | AD4-10460 | AD4-10486 | AD4-10628 | |
| 3F—4CF3 | AD4-13043 | AD4-13034 | AD4-13040 | | | |
| 2Cl—5CF3 | AD4-13058 | AD4-13056 | AD4-13035 | | | |
| 4Cl—5CF3 | | AD4-13032 | AD4-13057 | | | |
| 2,4-diCF3 | | | | | | |
| 3CF3 | | AD4-13164 | | | AD4-12903 | |
| 2F—4CF3 | AD4-13042 | AD4-13031 | AD4-13038 | AD4-13096 | | |
| 2,3,5,6-F4 | AD4-13059 | | | | AD4-12918 | |
| 2,4-diF | AD4-13068 | AD4-13029 | AD4-13036 | | | |
| 3-Me-4-OMe | | | AD4-12965 | | | |
| 2-F | | | | | | |
| 2,3,5,6-F4-4-OCH2CF3 | | | AD4-13093 | AD4-13092 | AD4-13085 | |
| 2-Me | | | | AD4-12935 | | |
| 3-F | | | | AD4-12953 | | |
| 4-OCF3 | | | | | AD4-12902 | |
| 3-OH-4-OMe | AD4-13190 | | | AD4-1505 | AD4-12909 | |
| 2-OH-5-Me | | | | | AD4-12936 | |
| 3,4-diOMe | AD4-13193 | | | | | |
| 2,3,4-triOMe | AD4-13208 | | | | | |
| 2,4-diCl (2MeQ) | AD4-13200 | | | | | |

TABLE 3

R1 and R2 substitution combinations (Pyr = pyridine; Ani = aniline)

| R2 phenyl substitution | R1 = 3F—5ClPyr | R1 = 5-Cl-6-MePyr | R1 = 3-F-5-CF3Pyr | R1 = 3-F-4,5-diClPyr | R1 = 3-F-4-Me-5-ClPyr | R1 = 3,5-diCl-6-MePyr |
|---|---|---|---|---|---|---|
| 2Cl | | | | | | |
| 3Cl | | | | AD4-13188 | | |
| 4Cl | | AD4-13161 | | AD4-13187 | | |
| 2,3-diCl | | | | AD4-13172 | AD4-13192 | AD4-13211 |
| 3,4-diCl | AD4-13150 | | | AD4-13177 | | AD4-13202 |
| 2,4-diCl | AD4-13143 | | AD4-13165 | AD4-13178 | AD4-13199 | AD4-13206 |
| 2,5-diCl | | | | AD4-13179 | | AD4-13220 |
| 3,5-diCl | | | | AD4-13189 | | AD4-13223 |
| 2,6-diCl | | | | | | |
| 2,3,5-triCl | | AD4-13209 | | AD4-13180 | | AD4-13213 |
| 2Cl—4F | | | | AD4-13185 | | |
| 2Cl—6F | | | | | | |
| 3F—4Cl | | | | AD4-13224 | | AD4-13230 |
| 3Cl—4F | | | | | | |
| 4CF3 | AD4-13162 | | | | | |
| 3F—4CF3 | AD4-13144 | | | | | |
| 2Cl—5CF3 | | | | | | |
| 3CF3-4-Cl | | | | AD4-13184 | | |
| 2,4-diCF3 | | | | | | |
| 3CF3 | AD4-13145 | | | | | |
| 2F—4CF3 | | | | | | |
| 2,3,5,6-F4 | AD4-13163 | | | | | |
| 2,4-diF | | | | | | |
| 3-Me-4-OMe | | | | | | |
| 2-F | | | | | | |
| 2,3,5,6-F4-4-OCH2CF3 | | | | | | |
| 2-Me | | | | | | |
| 3-F | | | | | | |
| 4-OCF3 | | | | | | |

TABLE 3-continued

R1 and R2 substitution combinations (Pyr = pyridine; Ani = aniline)

| R2 phenyl substitution | R1 = 3F—5ClPyr | R1 = 5-Cl-6-MePyr | R1 = 3-F-5-CF3Pyr | R1 = 4,5-diClPyr | R1 = 3-F-4-Me-5-ClPyr | R1 = 3,5-diCl-6-MePyr |
|---|---|---|---|---|---|---|
| 3-OH-4-OMe | | | | AD4-13191 | AD4-13203 | |
| 2-OH-5-Me | | | | | | |
| 3,4-diOMe | | | | AD4-13195 | | |
| 2,3,4-triOMe | | | | AD4-13197 | | AD4-13210 |

TABLE 4

R1 and R2 substitution combinations (Pyr = pyridine; Ani = aniline)

| R2 phenyl substitution | R1 = 2-Me-4-Cl-Ani | R1 = 3-Me-4-Cl-Ani | R1 = 3-MeO-ClPyr | R1 = 3-Et-5-ClPyr | R1 = 3-F-4-Et-5-ClPyr | R1 = 3,5-diClPyr |
|---|---|---|---|---|---|---|
| 2Cl | | | | | | |
| 3Cl | | | | | | |
| 4Cl | | | | AD4-13225 | | |
| 2,3-diCl | | | | AD4-13215 | AD4-13222 | |
| 3,4-diCl | AD4-13204 | AD4-13207 | | | | |
| 2,4-diCl | AD4-13201 | | | AD4-13217 | AD4-13218 | AD4-13231 |
| 2,5-diCl | | | AD4-13221 | AD4-13227 | | |
| 3,5-diCl | | | AD4-13216 | AD4-13226 | | |
| 2,6-diCl | | | | | | |
| 2,3,5-triCl | | | AD4-13228 | | | |
| 2Cl—4F | AD4-13198 | AD4-13205 | | | | |
| 2Cl—6F | | | | | | |
| 3F—4Cl | | | | | | |
| 3Cl—4F | | | | | | |
| 4CF3 | | | | | | |
| 3F—4CF3 | | | | | | |
| 2Cl—5CF3 | | | | | | |
| 3CF3-4-Cl | | | | | | |
| 2,4-diCF3 | | | | | | |
| 3CF3 | | | | | | |
| 2F—4CF3 | | | | | | |
| 2,3,5,6-F4 | | | | | | |
| 2,4-diF | | | | | | |
| 3-Me-4-OMe | | | | | | |
| 2-F | | | | | | |
| 2,3,5,6-F4-4-OCH2CF3 | | | | | | |
| 2-Me | | | | | | |
| 3-F | | | | | | |
| 4-OCF3 | | | | | | |
| 3-OH-4-OMe | | | | | | |
| 2-OH-5-Me | | | | | | |
| 3,4-diOMe | | | | | | |
| 2,3,4-triOMe | | | AD4-13214 | AD4-13219 | | |

In some embodiments, the compound of Formula (2) is AD4-1505.

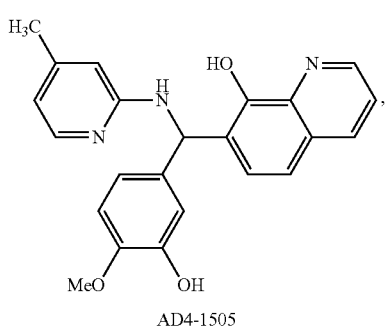

AD4-1505

Formula (1)

In some embodiments, the compound of Formula (2) is selected from a compound of TABLE 5.

TABLE 5

Compounds of Formula (2)

AD4-12902

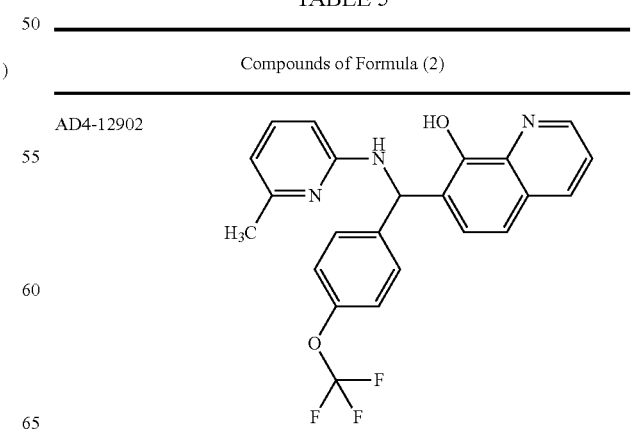

TABLE 5-continued

Compounds of Formula (2)

| ID | Structure |
|---|---|
| AD4-12903 | 6-methylpyridin-2-yl-NH-CH(3-(trifluoromethyl)phenyl)-(8-hydroxyquinolin-7-yl) |
| AD4-12904 | 6-methylpyridin-2-yl-NH-CH(2-chlorophenyl)-(8-hydroxyquinolin-7-yl) |
| AD4-12905 | 6-methylpyridin-2-yl-NH-CH(2,3-dichlorophenyl)-(8-hydroxyquinolin-7-yl) |
| AD4-12906 | 4-methylpyridin-2-yl-NH-CH(2,3-dichlorophenyl)-(8-hydroxyquinolin-7-yl) |
| AD4-12907 | 4-methylpyridin-2-yl-NH-CH(2-chlorophenyl)-(8-hydroxyquinolin-7-yl) |
| AD4-12908 | pyridin-3-yl-NH-CH(2,3-dichlorophenyl)-(8-hydroxyquinolin-7-yl) |
| AD4-12909 | 6-methylpyridin-2-yl-NH-CH(3-hydroxy-4-methoxyphenyl)-(8-hydroxyquinolin-7-yl) |
| AD4-12910 | pyridin-2-yl-NH-CH(2,5-dichlorophenyl)-(8-hydroxyquinolin-7-yl) |
| AD4-12911 | 6-methylpyridin-2-yl-NH-CH(2,4-dichlorophenyl)-(8-hydroxyquinolin-7-yl) |
| AD4-12912 | 4-methylpyridin-2-yl-NH-CH(2,4-dichlorophenyl)-(8-hydroxyquinolin-7-yl) |
| AD4-12913 | 6-methylpyridin-2-yl-NH-CH(3,5-dichlorophenyl)-(8-hydroxyquinolin-7-yl) |
| AD4-12914 | pyridin-2-yl-NH-CH(3,5-dichlorophenyl)-(8-hydroxyquinolin-7-yl) |

TABLE 5-continued

Compounds of Formula (2)

AD4-12915, AD4-12916, AD4-12917, AD4-12918, AD4-12935, AD4-12936, AD4-12937, AD4-12953, AD4-12954, AD4-12955, AD4-12958, AD4-12959

TABLE 5-continued
Compounds of Formula (2)
AD4-12965 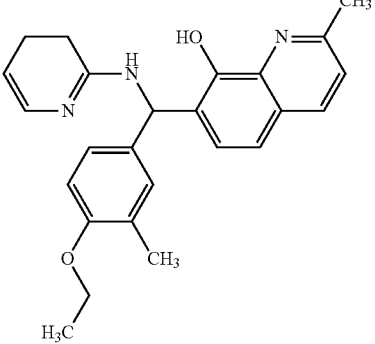
AD4-12966 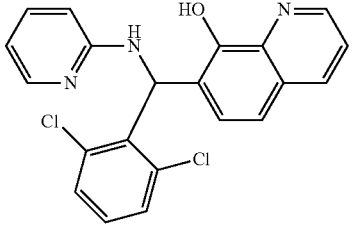 [SMILES: Oc1c(C(Nc2ccccn2)c2c(Cl)cccc2Cl)ccc2cccnc12]
AD4-12990 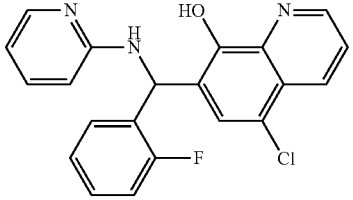 [SMILES: Oc1c(C(Nc2ccccn2)c2ccccc2F)cc(Cl)c2cccnc12]
AD4-12991 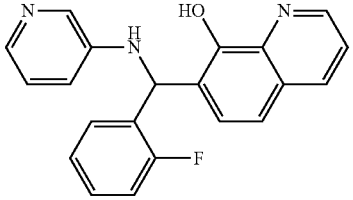 [SMILES: Oc1c(C(Nc2cccnc2)c2ccccc2F)ccc2cccnc12]
AD4-13018 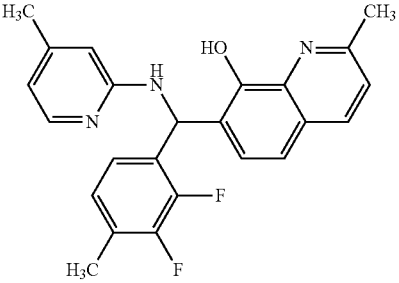 [SMILES: Cc1ccnc(NC(c2ccc(C)c(F)c2F)c2ccc3ccc(C)nc3c2O)c1]
AD4-13019 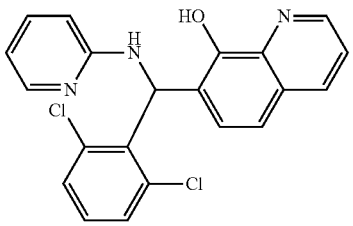 [SMILES: Oc1c(C(Nc2ccccn2)c2c(Cl)cccc2Cl)ccc2cccnc12]
AD4-13020 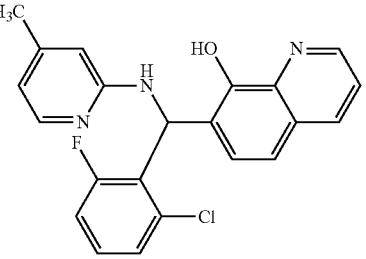
AD4-13021A 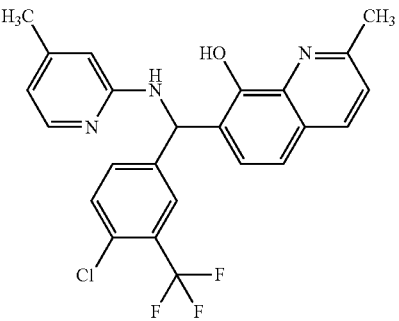 [SMILES: Cc1ccnc(NC(c2ccc(Cl)c(C(F)(F)F)c2)c2ccc3ccc(C)nc3c2O)c1]
AD4-13021B 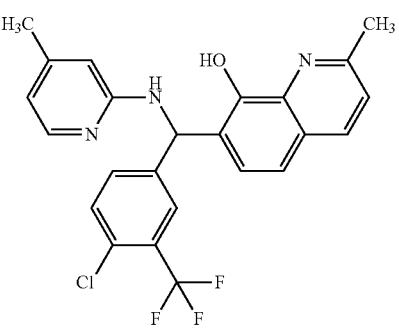 [SMILES: Cc1ccnc(NC(c2ccc(Cl)c(C(F)(F)F)c2)c2ccc3ccc(C)nc3c2O)c1]
AD4-13022 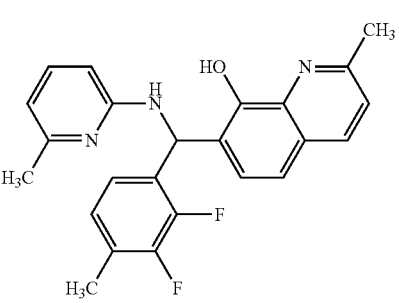 [SMILES: Cc1cccc(NC(c2ccc(C)c(F)c2F)c2ccc3ccc(C)nc3c2O)n1]
AD4-13023 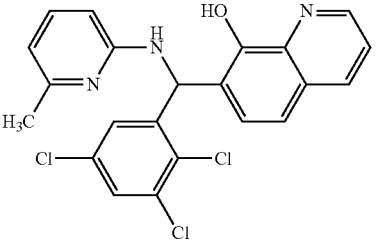 [SMILES: Cc1cccc(NC(c2cc(Cl)cc(Cl)c2Cl)c2ccc3cccnc3c2O)n1]

TABLE 5-continued

Compounds of Formula (2)

| AD4-13024 | (structure) |
| AD4-13025 | (structure) |
| AD4-13026 | (structure) |
| AD4-13027 | (structure) |
| AD4-13028 | (structure) |
| AD4-13029 | (structure) |
| AD4-13030 | (structure) |
| AD4-13031 | (structure) |
| AD4-13032 | (structure) |
| AD4-13033-1 | (structure) |
| AD4-13033-2 | (structure) |
| AD4-13034 | (structure) |

TABLE 5-continued

Compounds of Formula (2)

| AD4-13035 | (structure) |
| AD4-13036 | (structure) |
| AD4-13037 | (structure) |
| AD4-13038 | (structure) |
| AD4-13039 | (structure) |
| AD4-13040 | (structure) |
| AD4-13041 | (structure) |
| AD4-13042 | (structure) |
| AD4-13043 | (structure) |
| AD4-13044 | (structure) |
| AD4-13045 | (structure) |

TABLE 5-continued

Compounds of Formula (2)

AD4-13046

AD4-13047

AD4-13048

AD4-13049

AD4-13050

AD4-13051

AD4-13052

AD4-13053

AD4-13054

AD4-13055

AD4-13056

TABLE 5-continued
Compounds of Formula (2)
AD4-13057 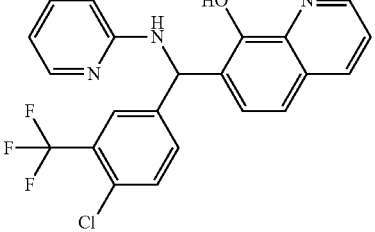
AD4-13058 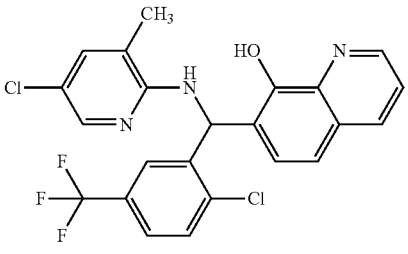 [SMILES: Cc1cc(Cl)cnc1NC(c1cc(C(F)(F)F)ccc1Cl)c1ccc2cccnc2c1O]
AD4-13059 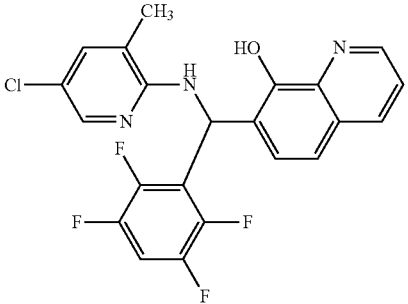 [SMILES: Cc1cc(Cl)cnc1NC(c1ccc2cccnc2c1O)c1c(F)c(F)cc(F)c1F]
AD4-13060 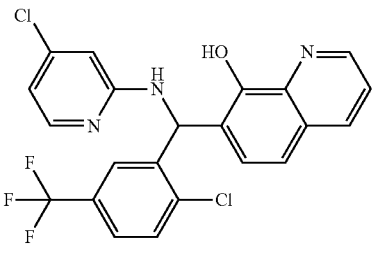 [SMILES: Oc1c(C(Nc2cc(Cl)ccn2)c2cc(C(F)(F)F)ccc2Cl)ccc2cccnc12]
AD4-13061 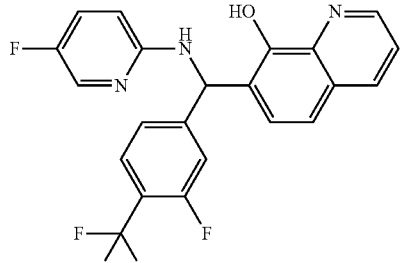
AD4-13062 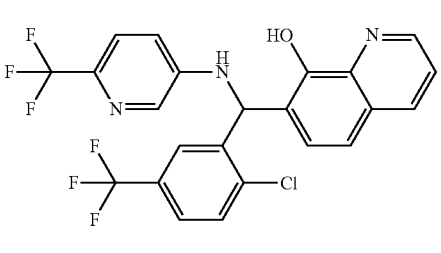
TABLE 5-continued
Compounds of Formula (2)
AD4-13063 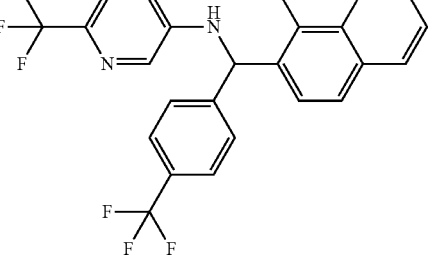
AD4-13064 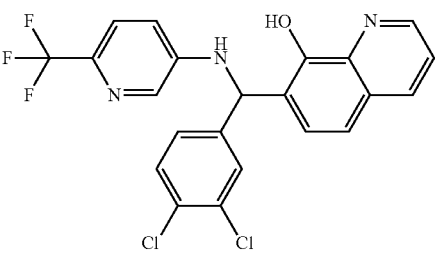 [SMILES: Oc1c(C(Nc2ccc(C(F)(F)F)nc2)c2ccc(Cl)c(Cl)c2)ccc2cccnc12]
AD4-13065 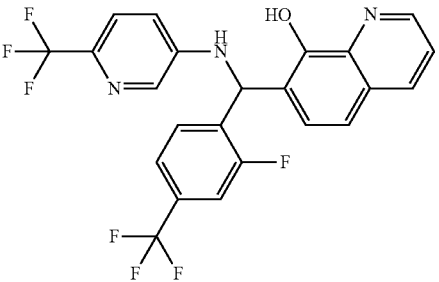 [SMILES: Oc1c(C(Nc2ccc(C(F)(F)F)nc2)c2ccc(C(F)(F)F)cc2F)ccc2cccnc12]
AD4-13066 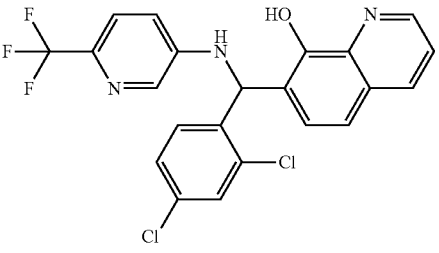 [SMILES: Oc1c(C(Nc2ccc(C(F)(F)F)nc2)c2ccc(Cl)cc2Cl)ccc2cccnc12]
AD4-13067 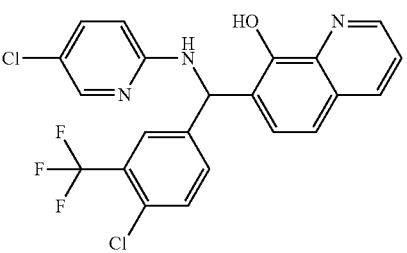 [SMILES: Oc1c(C(Nc2ccc(Cl)cn2)c2ccc(Cl)c(C(F)(F)F)c2)ccc2cccnc12]

TABLE 5-continued
Compounds of Formula (2)
AD4-13068 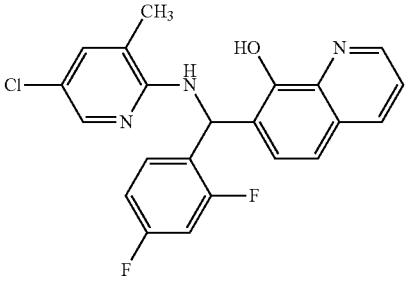 [SMILES: Cc1cc(Cl)cnc1NC(c1ccc(F)cc1F)c1ccc2cccnc2c1O]
AD4-13069 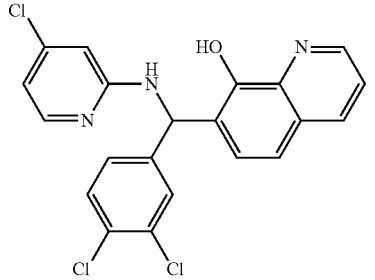 [SMILES: Oc1c(C(Nc2cc(Cl)ccn2)c2ccc(Cl)c(Cl)c2)ccc2cccnc12]
AD4-13070 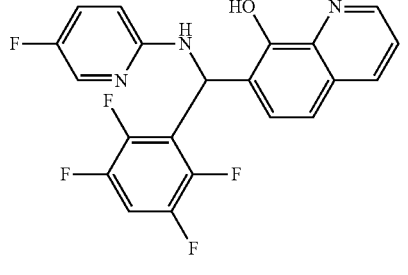 [SMILES: Oc1c(C(Nc2ccc(F)cn2)c2c(F)c(F)cc(F)c2F)ccc2cccnc12]
AD4-13071 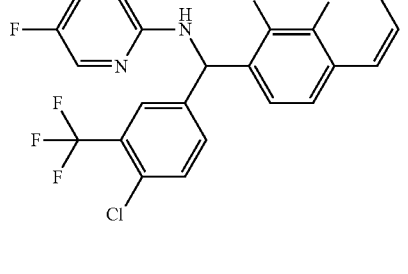
AD4-13072 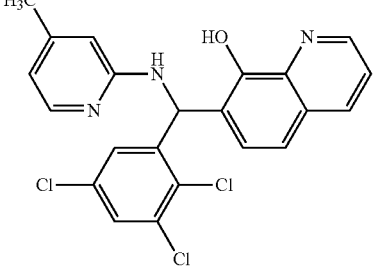
AD4-13073 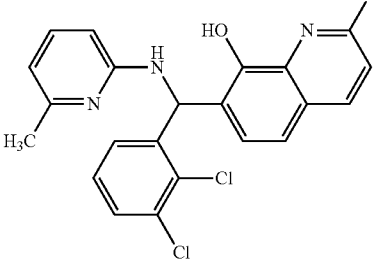
AD4-13074 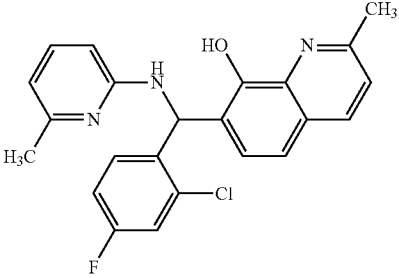 [SMILES: Cc1cccc(NC(c2ccc(F)cc2Cl)c2ccc3ccc(C)nc3c2O)n1]
AD4-13074-2 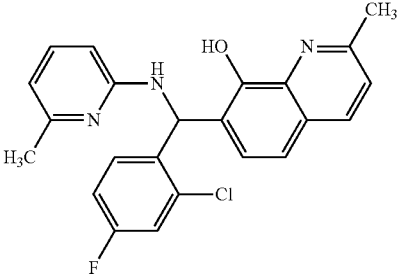
AD4-13075 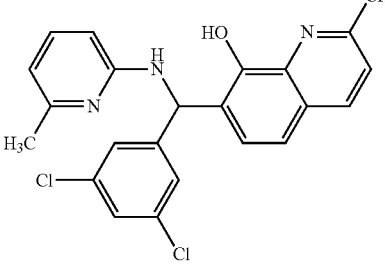
AD4-13076 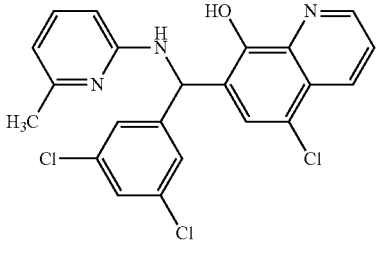 [SMILES: Cc1cccc(NC(c2cc(Cl)cc(Cl)c2)c2cc(Cl)c3cccnc3c2O)n1]

TABLE 5-continued

Compounds of Formula (2)

AD4-13077

AD4-13078

AD4-13079

AD4-13080

AD4-13081

AD4-13080

AD4-13081

AD4-13082

AD4-13083

AD4-13084

TABLE 5-continued

Compounds of Formula (2)

AD4-13085

AD4-13086

AD4-13087

AD4-13088

AD4-13089

AD4-13090

AD4-13091

AD4-13092

AD4-13093

AD4-13094

AD4-13095

TABLE 5-continued

Compounds of Formula (2)

AD4-13096

AD4-13097

AD4-13098

AD4-13099

AD4-13100

AD4-13101

AD4-13102

AD4-13103

AD4-13104

AD4-13105

TABLE 5-continued

Compounds of Formula (2)

| ID | Structure |
|---|---|
| AD4-13106 | (chemical structure) |
| AD4-13107 | (chemical structure) |
| AD4-13108 | (chemical structure) |
| AD4-13109 | (chemical structure) |
| AD4-13110 | (chemical structure) |
| AD4-13111 | (chemical structure) |
| AD4-13112 | (chemical structure) |
| AD4-13113 | (chemical structure) |
| AD4-13114 | (chemical structure) |
| AD4-13115 | (chemical structure) |
| AD4-13116 | (chemical structure) |

TABLE 5-continued
Compounds of Formula (2)
AD4-13117 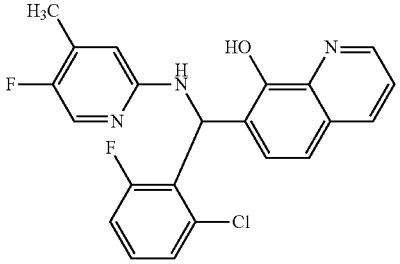 [SMILES: Cc1cc(NC(c2ccc3cccnc3c2O)c2c(F)cccc2Cl)ncc1F]
AD4-13118 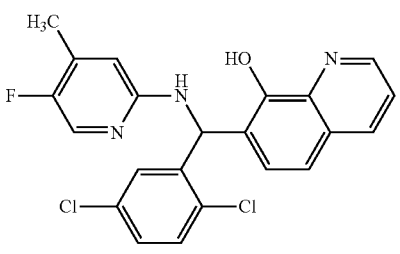 [SMILES: Cc1cc(NC(c2cc(Cl)ccc2Cl)c2ccc3cccnc3c2O)ncc1F]
AD4-13119 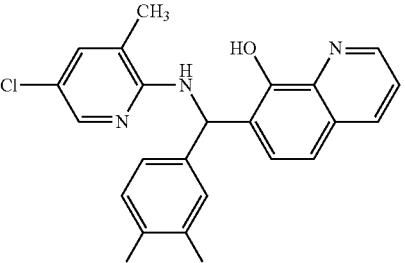
AD4-13120 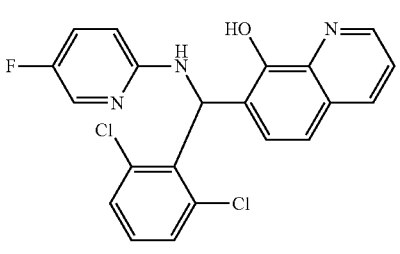 [SMILES: Oc1c(C(Nc2ccc(F)cn2)c2c(Cl)cccc2Cl)ccc2cccnc12]
AD4-13121 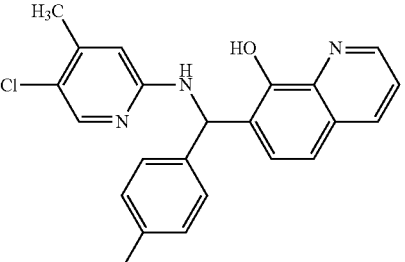
AD4-13122 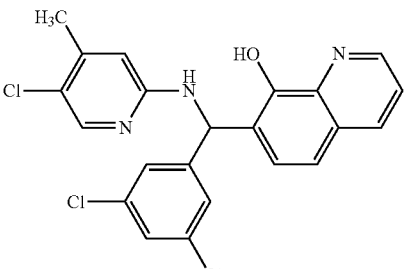
AD4-13123 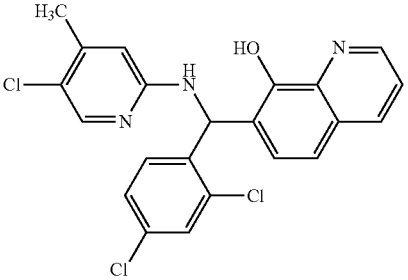
AD4-13124 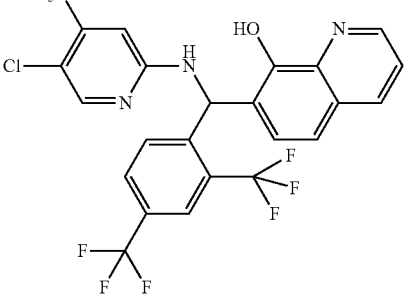
AD4-13125 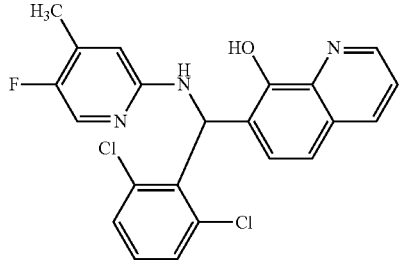 [SMILES: Cc1cc(NC(c2ccc3cccnc3c2O)c2c(Cl)cccc2Cl)ncc1F]
AD4-13126 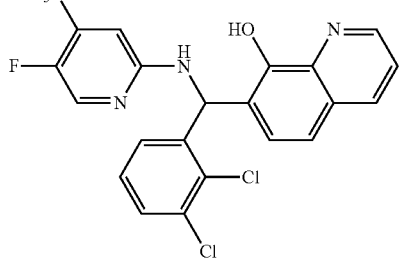

TABLE 5-continued
Compounds of Formula (2)
AD4-13127 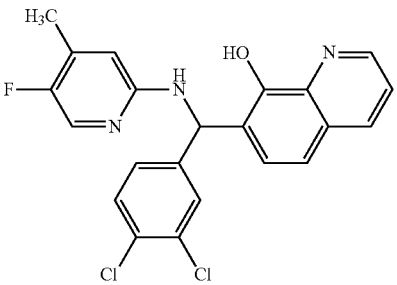 [SMILES: Cc1cc(NC(c2ccc(Cl)c(Cl)c2)c2ccc3cccnc3c2O)ncc1F]
AD4-13128 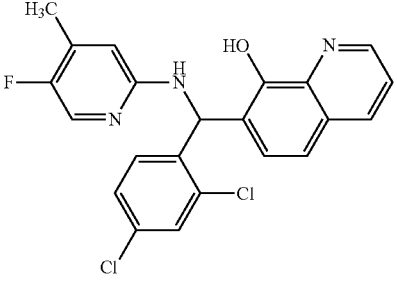
AD4-13129 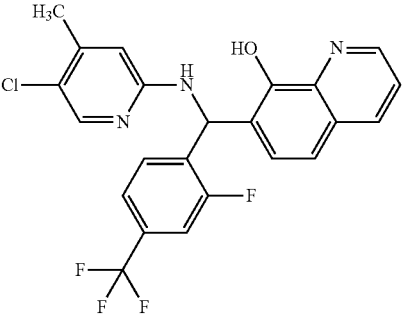 [SMILES: Cc1cc(NC(c2ccc(C(F)(F)F)cc2F)c2ccc3cccnc3c2O)ncc1Cl]
AD-13130 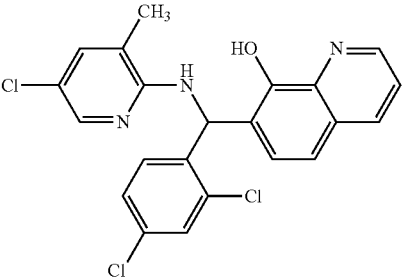
AD4-13131 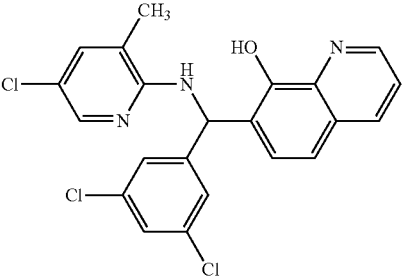
AD4-13132 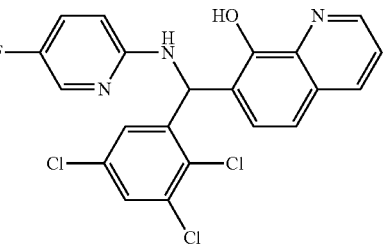
AD4-13133 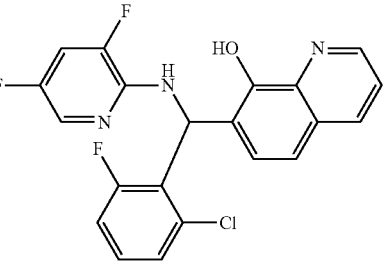
AD4-13133 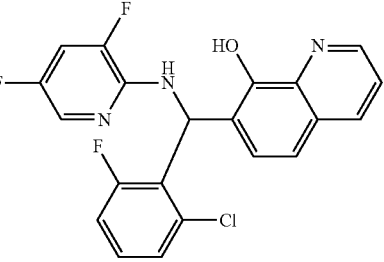
AD4-13134 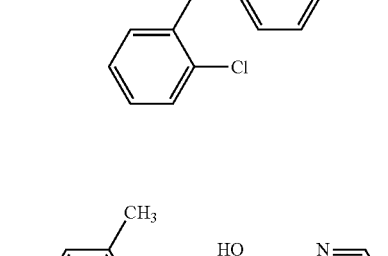
AD4-13135

TABLE 5-continued
Compounds of Formula (2)
AD4-13136 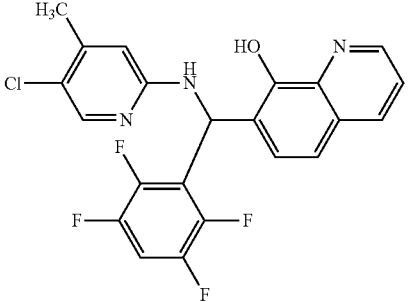 [SMILES: Cc1cc(NC(c2ccc3cccnc3c2O)c2c(F)c(F)cc(F)c2F)ncc1Cl]
AD4-13137 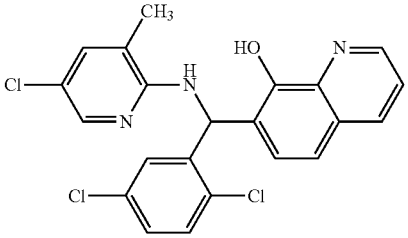 [SMILES: Cc1cc(Cl)cnc1NC(c1cc(Cl)ccc1Cl)c1ccc2cccnc2c1O]
AD4-13138 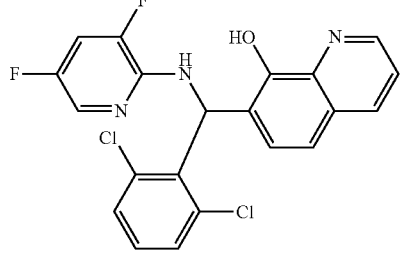
AD4-13139 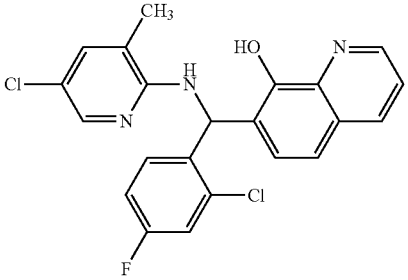 [SMILES: Cc1cc(Cl)cnc1NC(c1ccc(F)cc1Cl)c1ccc2cccnc2c1O]
AD4-13140 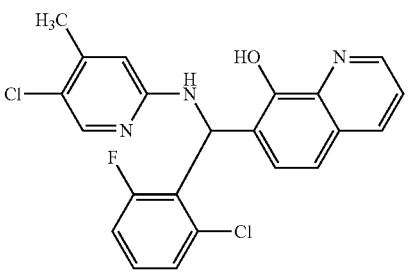 [SMILES: Cc1cc(NC(c2ccc3cccnc3c2O)c2c(F)cccc2Cl)ncc1Cl]
AD4-13141 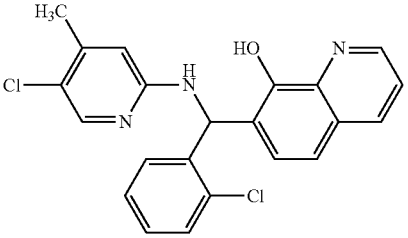 [SMILES: Cc1cc(NC(c2ccccc2Cl)c2ccc3cccnc3c2O)ncc1Cl]
AD4-13142 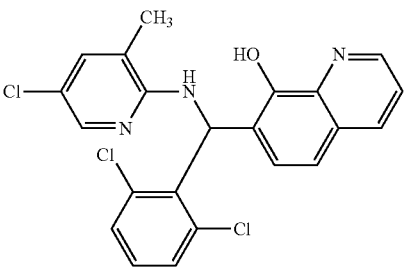 [SMILES: Cc1cc(Cl)cnc1NC(c1ccc2cccnc2c1O)c1c(Cl)cccc1Cl]
AD4-13143 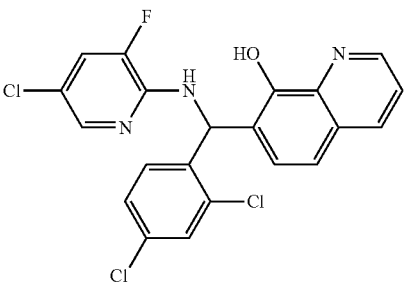
AD4-13144 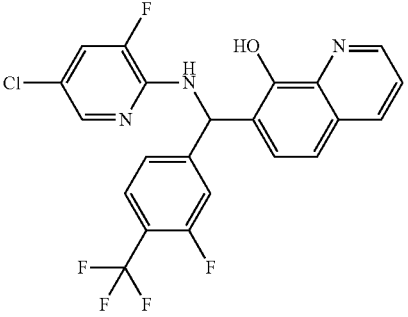 [SMILES: Oc1c(C(Nc2ncc(Cl)cc2F)c2ccc(C(F)(F)F)c(F)c2)ccc2cccnc12]
AD4-13145 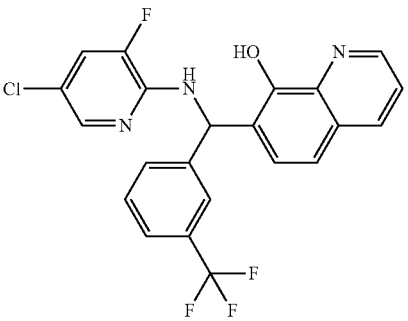 [SMILES: Oc1c(C(Nc2ncc(Cl)cc2F)c2cccc(C(F)(F)F)c2)ccc2cccnc12]

TABLE 5-continued

Compounds of Formula (2)

AD4-13146

AD4-13147

AD4-13148

AD4-13149

AD4-13150

AD4-13151

AD4-13152

AD4-13153

AD4-13154

AD4-13155

AD4-13156

TABLE 5-continued
Compounds of Formula (2)
AD4-13157 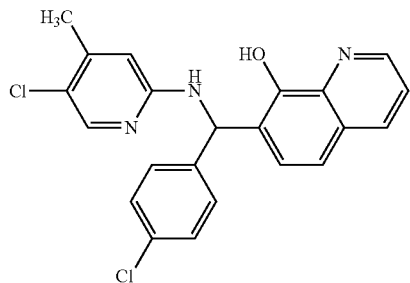 [SMILES: Cc1cc(NC(c2ccc(Cl)cc2)c2ccc3cccnc3c2O)ncc1Cl]
AD4-13158 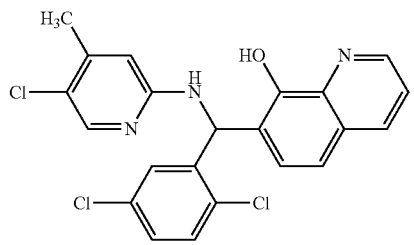 [SMILES: Cc1cc(NC(c2cc(Cl)ccc2Cl)c2ccc3cccnc3c2O)ncc1Cl]
AD4-13159 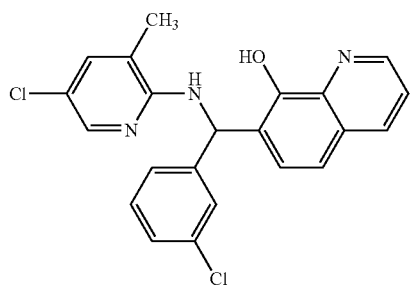 [SMILES: Cc1cc(Cl)cnc1NC(c1cccc(Cl)c1)c1ccc2cccnc2c1O]
AD4-13160 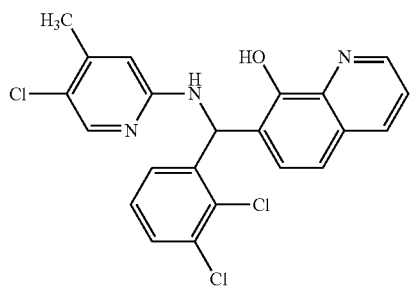
AD4-13161 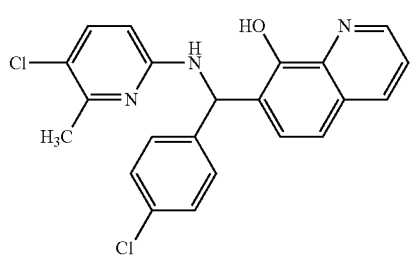 [SMILES: Cc1nc(NC(c2ccc(Cl)cc2)c2ccc3cccnc3c2O)ccc1Cl]
TABLE 5-continued
Compounds of Formula (2)
AD4-13162 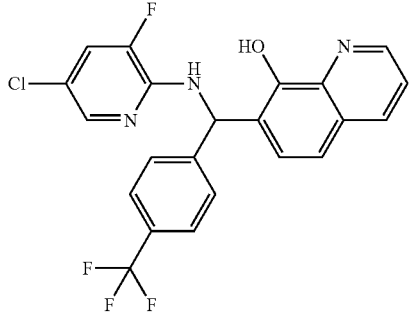 [SMILES: Oc1c(C(Nc2ncc(Cl)cc2F)c2ccc(C(F)(F)F)cc2)ccc2cccnc12]
AD4-13163 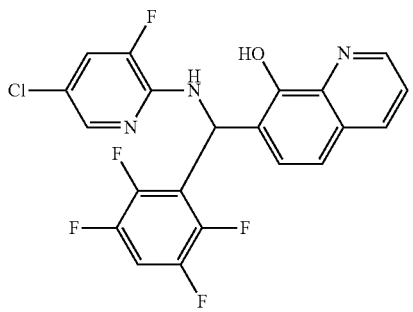 [SMILES: Oc1c(C(Nc2ncc(Cl)cc2F)c2c(F)c(F)cc(F)c2F)ccc2cccnc12]
AD4-13164 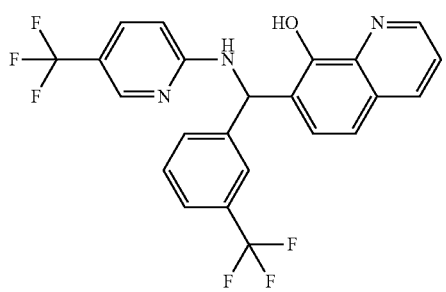 [SMILES: Oc1c(C(Nc2ccc(C(F)(F)F)cn2)c2cccc(C(F)(F)F)c2)ccc2cccnc12]
AD4-13165 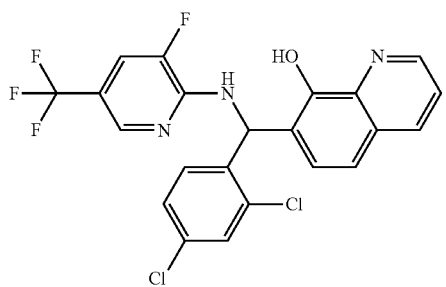 [SMILES: Oc1c(C(Nc2ncc(C(F)(F)F)cc2F)c2ccc(Cl)cc2Cl)ccc2cccnc12]
AD4-13166 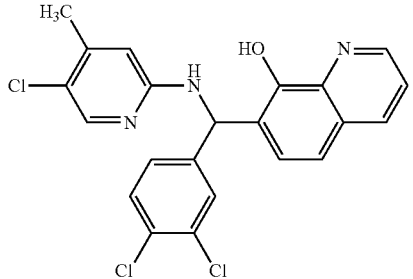

TABLE 5-continued

Compounds of Formula (2)

AD4-13167

AD4-13172

AD4-13173

AD4-13174

AD4-13175

AD4-13176

AD4-13177

AD4-13178

AD4-13179

AD4-13180

TABLE 5-continued

Compounds of Formula (2)

AD4-13181

AD4-13182

AD4-13183

AD4-13184

AD4-13185

AD4-13186

AD4-13187

AD4-13188

AD4-13189

AD4-13190

TABLE 5-continued
Compounds of Formula (2)
AD4-13191 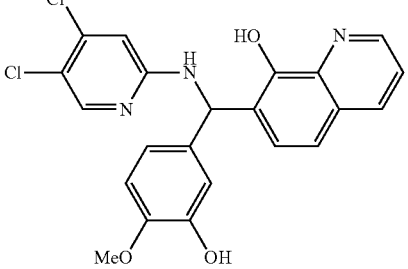
AD4-13192 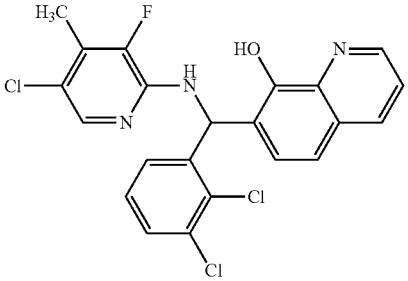 [SMILES: Cc1c(Cl)cnc(NC(c2cccc(Cl)c2Cl)c2ccc3cccnc3c2O)c1F]
AD4-13193 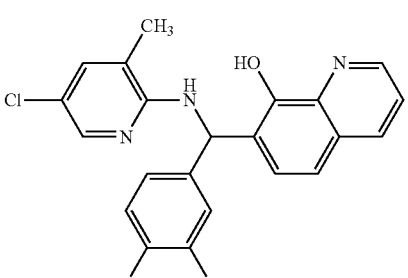
AD4-13194 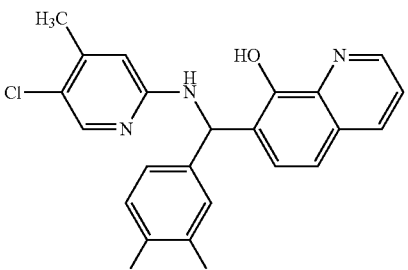
AD4-13195 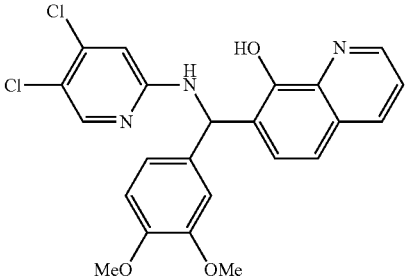 [SMILES: COc1ccc(C(Nc2cc(Cl)c(Cl)cn2)c2ccc3cccnc3c2O)cc1OC]
AD4-13196 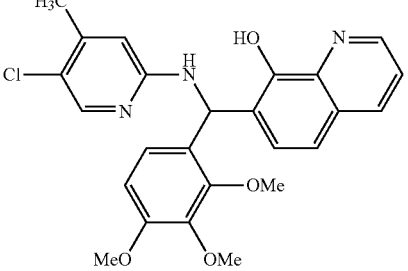
AD7-13197 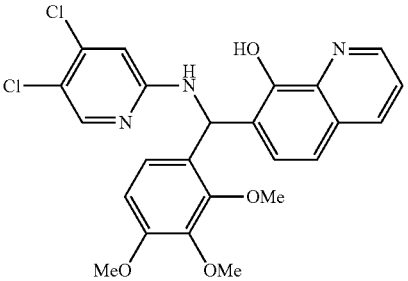 [SMILES: COc1ccc(C(Nc2cc(Cl)c(Cl)cn2)c2ccc3cccnc3c2O)c(OC)c1OC]
AD4-13198 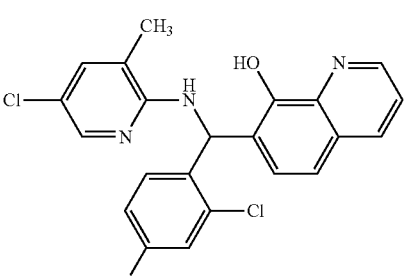
AD4-13199 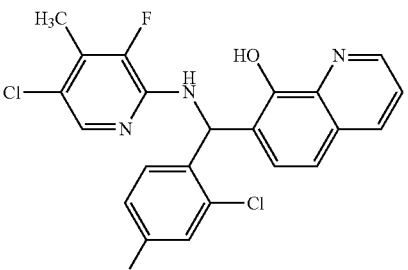
AD4-13200 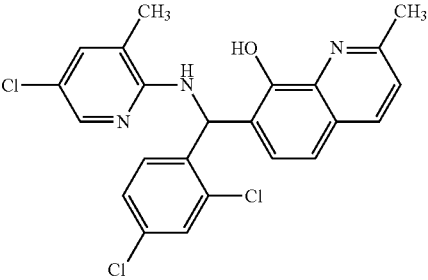 [SMILES: Cc1ccc2ccc(C(Nc3ncc(Cl)cc3C)c3ccc(Cl)cc3Cl)c(O)c2n1]

TABLE 5-continued

Compounds of Formula (2)

AD4-13201
AD4-13202
AD4-13203
AD4-13204
AD4-13205
AD4-13206
AD4-13207
AD4-13208
AD4-13208
AD4-13209

TABLE 5-continued
Compounds of Formula (2)
AD4-13210 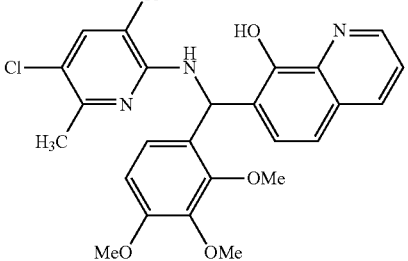
AD4-13211 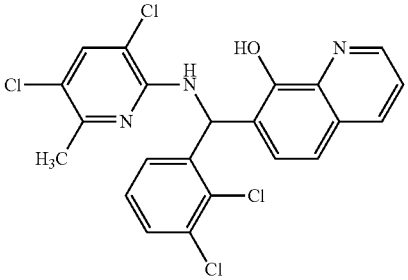 [SMILES: Cc1nc(NC(c2cccc(Cl)c2Cl)c2ccc3cccnc3c2O)c(Cl)cc1Cl]
AD4-13212 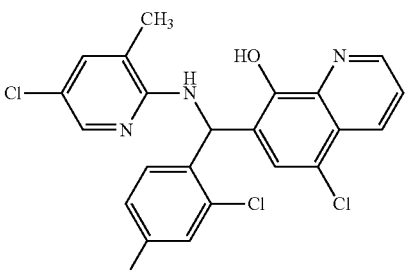
AD4-13213 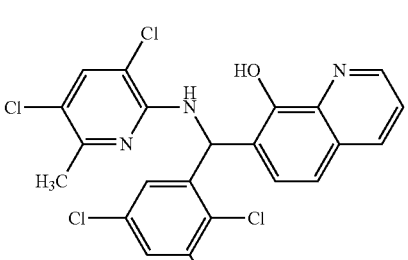
AD4-13214 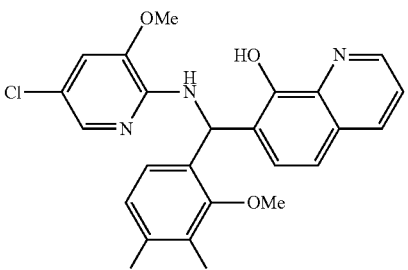
AD4-13215 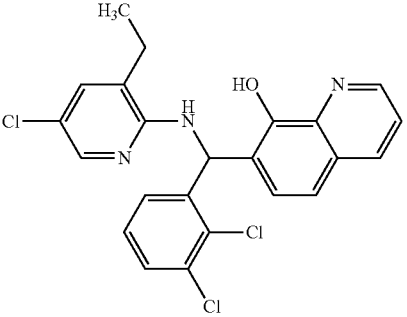 [SMILES: CCc1cc(Cl)cnc1NC(c1cccc(Cl)c1Cl)c1ccc2cccnc2c1O]
AD4-13216 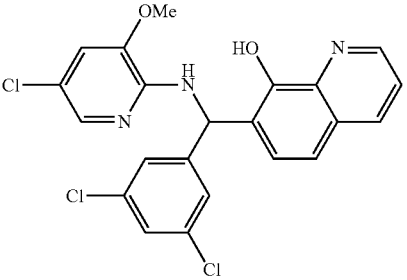 [SMILES: COc1cc(Cl)cnc1NC(c1cc(Cl)cc(Cl)c1)c1ccc2cccnc2c1O]
AD4-13217 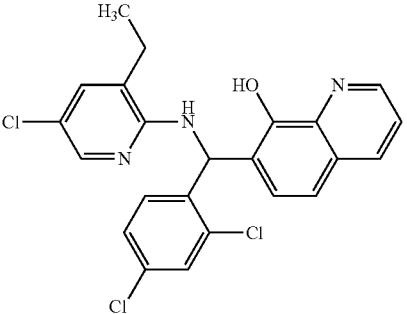 [SMILES: CCc1cc(Cl)cnc1NC(c1ccc(Cl)cc1Cl)c1ccc2cccnc2c1O]
AD4-13218 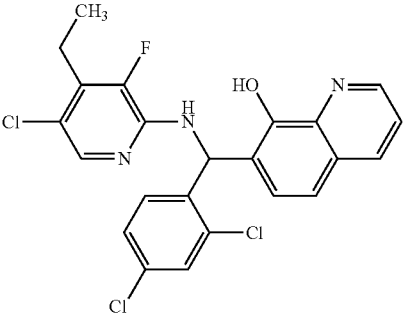 [SMILES: CCc1c(Cl)cnc(NC(c2ccc(Cl)cc2Cl)c2ccc3cccnc3c2O)c1F]
AD4-13219 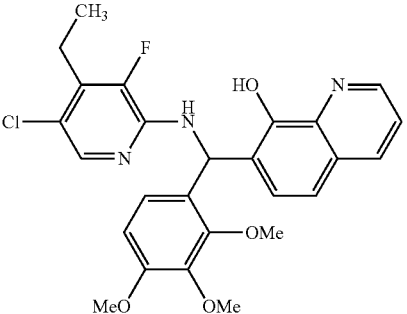 [SMILES: CCc1c(Cl)cnc(NC(c2ccc(OC)c(OC)c2OC)c2ccc3cccnc3c2O)c1F]

TABLE 5-continued

Compounds of Formula (2)

AD4-13220

AD4-13221

AD4-13222

AD4-13223

AD4-13224

TABLE 5-continued

Compounds of Formula (2)

AD4-13225

AD4-13226

AD4-13227

AD4-13228

AD4-10484

TABLE 5-continued

Compounds of Formula (2)

| Compound | Structure |
|---|---|
| AD4-10315 | (pyridin-3-yl)NH-CH(thiophen-2-yl)-(8-hydroxyquinolin-7-yl) |
| AD4-13229 | (5-chloro-3-methylpyridin-2-yl)NH-CH(3,4-dichloro-5-fluorophenyl)-(8-hydroxyquinolin-7-yl) |
| AD4-13230 | (3,5-dichloro-6-methylpyridin-2-yl)NH-CH(3,4-dichloro-5-fluorophenyl)-(8-hydroxyquinolin-7-yl) |
| AD4-13231 | (3,5-dichloropyridin-2-yl)NH-CH(2,4-dichlorophenyl)-(8-hydroxyquinolin-7-yl) |
| AD4-10628 | (6-methylpyridin-2-yl)NH-CH(4-trifluoromethylphenyl)-(8-hydroxyquinolin-7-yl) |
| AD4-10963 | (4-methylpyridin-2-yl)NH-CH(3-methylthiophen-2-yl)-(8-hydroxyquinolin-7-yl) |

In some embodiments, the compound(s) of Formula (2) excludes compound AD4-1505, Formula (1).

In some embodiments, the compound(s) of Formula (2) excludes one or more of the following compounds:

[Structures shown: phenyl-(4-nitrophenyl)NH-(8-hydroxyquinolin-7-yl)methane; phenyl-(quinolin-8-yl)NH-(8-hydroxyquinolin-7-yl)methane; phenyl-(pyridin-2-yl)NH-(8-hydroxyquinolin-7-yl)methane; (4-trifluoromethylphenyl)-(pyridin-3-yl)NH-(8-hydroxyquinolin-7-yl)methane; (2-fluorophenyl)-(pyridin-3-yl)NH-(8-hydroxyquinolin-7-yl)methane, and (4-ethoxyphenyl)-(pyridin-3-yl)NH-(5-chloro-8-hydroxyquinolin-7-yl)methane.]

In some embodiments, for example methods of therapeutic treatment, the compound(s) of Formula (2) can include one or more of the above compounds.

Type B AD4-1505-Like

Another structure derived from the AD4-1505-like pharmacophore is as follows:

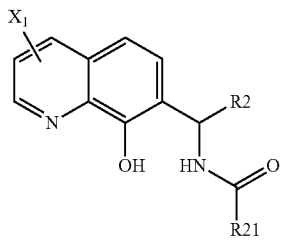

Formula (10)

In the above structure, $X^1$ and $R^2$ of Formula (10) are defined as above for structural sub-class Type A, Formula (2).

$R^{21}$ of Formula (10) can represent:

a lower alkyl group with one to 6 carbons (C-1 to C-6), straight chain, branched, or optionally containing unsaturation, cycloalkyl defined as five or six aliphatic ring (C-1 to C-6) optionally containing unsaturation;

an unsubstituted Phenyl ring or a Phenyl ring substituted at the 2-, 3-, 4-, 5- or 6-position with one or more of the following groups: lower alkyl defined as C-1 to C-4, straight chain, branched, or optionally containing unsaturation, cycloalkyl defined as C-1 to C-6 optionally containing unsaturation, Aryl including phenyl or heteroaryl containing from 1 to 4 N, O, or S atoms, Alkoxy (—$OR^{10}$ where $R^{10}$ is defined as a lower alkyl group or cycloalkyl group as in the above definition), 2,3-Methylenedioxy or 3,4-Methylenedioxy group, Dialkylamino (—$NR_{13}R_{14}$, where $R_{13}$ and $R_{14}$ are independently selected from a Hydrogen atom or lower alkyl group as previously described); Trifluoromethyl, Trifluoromethoxy, Difluoromethoxy, 3,4-methylenedioxy, 2,3-methylenedioxy, Nitro or Halogen (F, Cl, Br, I);

an unsubstituted 2-Pyridyl ring or a 2-Pyridyl ring substituted at the 4- or 6-position of the pyridine ring with one or more of the following groups: lower alkyl group as defined above, cycloalkyl group as defined above;

an unsubstituted 3-Pyridyl ring or a 3-Pyridyl ring substituted at the 2-, 4- or 6-position of the pyridine ring with one or more of the following groups: lower alkyl group as defined above, cycloalkyl group as defined above;

an unsubstituted 4-Pyridyl ring or a 4-Pyridyl ring substituted at the 2- or 6-position of the pyridine ring with one or more of the following groups: lower alkyl group as defined above, cycloalkyl group as defined above; or a heteroaryl five or six membered ring containing from 1 to 4 N, O, or S atoms.

In some embodiments, the compound(s) are the enantiomeric isomers of Formula (10).

In some embodiments, the compound of Formula (10) is AD4-10950.

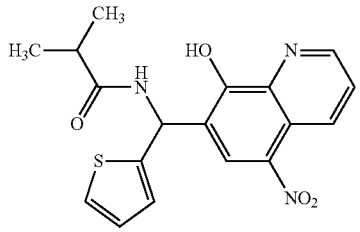

AD4-10950

In some embodiments, the compound of Formula (10) is AD4-10960.

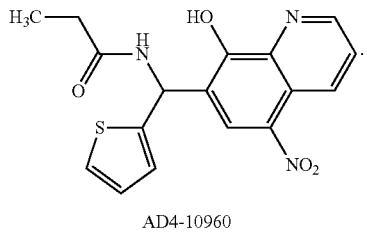 [SMILES: CCC(=O)NC(c1cccs1)c1cc([N+](=O)[O-])c2cccnc2c1O]

AD4-10960

In some embodiments, the compound(s) of Formula (10) excludes compound AD4-1505, Formula (1).

Type C AD-4-1505-like

Another structure derived from the AD4-1505-like pharmacophore is as follows:

Formula (11)

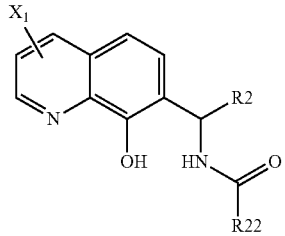

In the above structure, $X^1$ and $R^2$ of Formula (11) are defined as above for structural sub-class Type A, Formula (2).

$R^{22}$ of Formula (11) can represent a lower alkyl group with one to 6 carbons (C-1 to C-6), straight chain, branched, optionally containing unsaturation, or substitution at the C-1 or C-2 carbons with one or more of the following substituents: an unsubstituted Phenyl ring or a Phenyl ring substituted at the 2-, 3-, 4-, 5- or 6-position with one or more of the following groups: lower alkyl defined as C-1 to C-4, straight chain, branched, or optionally containing unsaturation, cycloalkyl defined as C-1 to C-6 optionally containing unsaturation or one oxygen or nitrogen atom, Heteroaryl containing from 1 to 4 N, O, or S atoms, hydroxyl (—OH), Alkoxy (—$OR^{10}$ where $R^{10}$ is defined as a lower alkyl group or cycloalkyl group as in the above definition), Dialkylamino (—$NR_{13}R_{14}$, where $R_{13}$ and $R_{14}$ are independently selected from a Hydrogen atom or lower alkyl group as previously described); Trifluoromethyl, Trifluoromethoxy, Difluoromethoxy, or Halogen (F, Cl, Br, I).

A cycloalkyl is defined as five or six aliphatic ring (C-1 to C-6) optionally containing unsaturation or one oxygen or nitrogen atom.

In some embodiments, the compound(s) are the enantiomeric isomers of Formula (11).

In some embodiments, the compound of Formula (11) is AD4-10535.

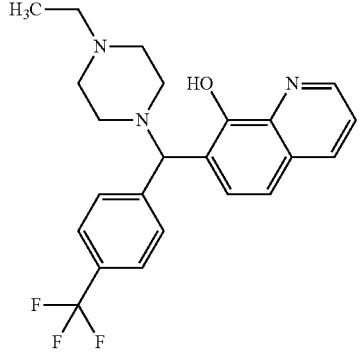

AD4-10535

In some embodiments, the compound(s) of Formula (11) excludes compound AD4-1505, Formula (1).

Structure and Function

Compositions describe herein can have structural features associated with one or more desired functions, such as stability, antiproliferative activity, and apoptotic activity.

It has been found that groups at the 5-position of the aminopyridine of compounds described herein provide analogs having increased stability (e.g., more stable toward liver microsome incubation) (see Example 10). In some embodiments, a compound substituted at the 5-position of the aminopyridine can exhibit increased stability. As shown herein, AD4-13053 and AD4-13041 (both having a chlorine atom at the 5-position of the aminopyridine) show increased stability over AD4-10628 (see Example 10). In some embodiments, a compound substituted with a chlorine atom at the 5-position of the aminopyridine can exhibit increased stability increases stability.

It has been found that combinations of halogens and alkyl groups on the aminopyridine ring of compounds described herein provide compounds with increased antiproliferative activity (see Example 10). In some embodiments, a compound with the following aminopyridine ring substitutions provide increased antiproliferative activity: 3,5-diF; 3-F,5-CL,6-Me; 3-F,5-Cl,6-Me; 3-F,5-Cl,4-Et; and 3,5-diF,4-Me. In some embodiments, a compound with the following aminopyridine ring substitutions provide further increased antiproliferative activity: 3-Et,5-Cl; 3,5-diCl,6-Me; 3-F,5-Cl,4-Me; and 5-CF3. In some embodiments, a compound with the following aminopyridine ring substitutions provide even further increased antiproliferative activity: 3-Me,5-Cl; 3,5-diCl; 4-Me,5-Cl; and 4,5-diCl.

It has been found that a chloro group at the 5-position of the aminopyridine ring and additional chloro or methyl groups at the 3- or 4-positions on the aminopyridine ring of compounds described herein provide compounds with increased apoptotic activity (see Example 10). In some embodiments, a compound with the following aminopyridine ring substitutions provide increased apoptotic activity: 3-Me,5-Cl; 3-F,5-Cl,4-Me; 4,5-diCl; and 3,5-diCl.

It has been found that groups at the 2- and 4-position of the benzene ring of compounds described herein provide analogs having increased stability (e.g., more stable toward liver microsome incubation) (see Example 10). In some embodiments, a compound substituted at the 2- and 4-position of the benzene ring of compounds can exhibit increased stability. As shown herein, AD4-13041, AD4-13042, AD4-13165, and AD4-13206 show increased stability (see Example 10). In some embodiments, a compound substituted with a halogen atom at the 2- or 4-position of the benzene ring of the aminopyridine can exhibit increased stability increases stability. For example, a compound substituted with a chlorine atom at the 2- and 4-position of the benzene ring of the aminopyridine can exhibit increased stability increases stability. As another example, a compound substituted with a flourine atom at the 2- and 4-position of the benzene ring of the aminopyridine can exhibit increased stability increases stability. As another example, a compound substituted with a trifluoromethyl at the 4-position or a flourine atom at the 2-position and a trifluoromethyl at the 4-position of the benzene ring of the aminopyridine can exhibit increased stability increases stability.

It has been found that combinations of halogens and trifluoromethyl groups on the benzene ring of compounds described herein provide compounds with increased antiproliferative activity (see Example 10). In some embodiments, a compound with the following benzene ring substitutions provide increased antiproliferative activity: 4-Cl; 2-F,4-CF$_3$; and 3-F,4-Cl. In some embodiments, a compound with the following benzene ring substitutions provide further increased antiproliferative activity: 2-F,4-Cl; 2,3-diCl; and 2,3,5-triCl. In some embodiments, a compound with the following benzene ring substitutions provide even further increased antiproliferative activity: 2,4-diCl; 3,4-diCl; and 3,5-diCl.

It has been found that a chloro group at the 4-position of the benzene ring and additional chloro or fluoro groups at the 2- or 3-positions on the benzene ring of compounds described herein provide compounds with increased apoptotic activity (see Example 10). In some embodiments, a compound with the following benzene ring substitutions provide increased apoptotic activity: 2,4-diCl (see e.g., AD4-13130, AD4-13178); and 2-Cl,4-F (see e.g., AD4-13185).

Synthesis

One aspect provides methods for the synthesis of compounds described herein.

AD4-1505-Like Compounds

As shown herein, an AD4-1505-like compound can be synthesized by reacting an amino pyridine intermediate compound, an aldehyde intermediate, compound and a hydroxyquinoline (see Example 12). Methods for synthesis of intermediate compounds are also described herein (see Example 11).

In some embodiments, the reaction can include combining the amino pyridine intermediate compound, the aldehyde intermediate compound and the hydroxyquinoline in ethanol (e.g., absolute ethanol).

The amino pyridine intermediate compound can have functional groups corresponding to the aminopyridine ring of an AD4-1505-like compound described herein. For example, the amino pyridine intermediate compound of 2-Amino-6-picoline can be used in the synthesis of AD4-12902, where R1 of Formula (2) is a 2-Pyridyl ring of Formula (3), R4 is methyl, and R24, R3, and R23 are hydrogen (see Example 12). Provided with the guidance of Example 11 and Example 12, one of ordinary skill can determine the structure of an amino pyridine intermediate compound for an AD4-1505-like compound of Formula (2). Synthesis of an amino pyridine intermediate compound can be according to Example 11.

The aldehyde intermediate compound can have functional groups corresponding to the benzaldehyde derived ring of an AD4-1505-like compound described herein. For example, the aldehyde intermediate compound 4-trifluoromethoxybenzaldehyde can be used in the synthesis of AD4-12902, where R2 of Formula (2) is a phenyl ring substituted at position 1 with —CHO (i.e., benzaldehyde) and position 4 with trifluoromethoxy (see Example 12). Provided with the guidance of Example 11 and Example 12, one of ordinary skill can determine the structure of an aldehyde intermediate compound for an AD4-1505-like compound of Formula (2). Synthesis of an aldehyde intermediate compound can be according to Example 11.

The hydroxyquinoline intermediate compound can have functional groups corresponding to the hydroxyquinoline portion of an AD4-1505-like compound described herein. For example, the hydroxyquinoline intermediate compound 8-hydroxyquinoline can be used in the synthesis of AD4-12902, where X of Formula (2) is hydrogen (see Example 12). For example, the hydroxyquinoline intermediate compound 5-chloro-8-hydroxyquinoline can be used in the synthesis of AD4-12910, where X of Formula (2) is 5-chloro (see Example 12). Provided with the guidance of Example 11 and Example 12, one of ordinary skill can determine the structure of a hydroxyquinoline intermediate compound for an AD4-1505-like compound of Formula (2). A hydroxyquinoline intermediate compound can be obtained commercially or synthesized according to methods known in the art.

The reaction can occur in a solvent, such as an alcohol solvent. For example, the reaction can occur in ethanol, isopropanol, or butanol (e.g., n-butanol, tert-butanol, sec-butanol, isobutanol). A solvent can be absolute or at some purity such as at least about 90%, at least about 95%, or at least about 99%. The reaction can occur in the absence or substantial absence of a solvent. One or more intermediates can be a liquid at room temperature or some temperature above room temperature. When the reaction occurs at our above a temperature at which one or more intermediates are a liquid, the reaction can take place without an additional solvent. For example, the amino pyridine intermediate compound, the aldehyde intermediate compound and the hydroxyquinoline (at least one of which being a liquid at the temperature of the reaction) can be mixed in the absence or substantial absence of a solvent and the reaction can proceed accordingly. As another example, where at least one intermediate is a liquid at 50° C. or greater, the reaction can occur at a temperature of at least 50° C. in the absence or substantial absence of a solvent.

The reaction can occur at about room temperature. The reaction can include mixing (e.g., stirring) of components for a period of time (e.g., about 1, about 2, about 3, about 4, about 5, about 6, about 7, about 8, about 9, about 10, about 11, about 12, about 13, about 14, about 15, about 16, about 17, about 18, about 19, or about 20 days, or more).

Isolation and purification of the reaction product(s) can be according to any suitable method known in the art. For example, isolation and purification of the reaction product can be according to crystallization from the reaction mixture, crystallization from a solvent fraction (e.g., hexane/ethyl acetate; hexane/acetone), evaporative concentration, fractional distillation, filtration, column chromatography (e.g., silica gel stationary phase), High Performance Liquid Chromatography, or combinations thereof. Isolation and purification of the reaction product can be according to protocols described in Example 12.

The above reactions can include any condition or combination of conditions disclosed in Examples 12-13.

Aminopyridine Intermediate Compound

Another aspect is aminopyridine intermediate compounds and methods of their manufacture. An aminopyridine intermediate compound can have functional groups corresponding to the aminopyridine ring of an AD4-1505-like compound described herein.

An aminopyridine compound can be formed by combining a substituted or unsubstituted 2-aminopyridine and N-chlorosuccinimide in a solvent comprising, for example, ethylacetate or dimethylformamide under conditions sufficient to form a 2-amino-5-chloropyridine derivative (see e.g., Example 11). The substituted or unsubstituted 2-aminopyridine can correspond to the aminopyridine portion of a portion of an AD4-1505-like compound described herein. For example, the substituted or unsubstituted 2-aminopyridine can correspond to the aminopyridine portion of compound according to Formula (2), where $R^1$ comprises Formula (3). The 2-aminopyridine of the above reaction can have a structure of Formula (12), wherein $R^{23}$, $R^3$, and $R^4$ can be as defined as above (see Formula (3)), and $R^{24}$ can be hydrogen. The 2-amino-5-chloropyridine derivative of the above reaction can have a structure of Formula (12), wherein $R^{23}$, $R^3$, and $R^4$ can be the same as for the 2-aminopyridine of the reaction and $R^{24}$ can be chloro. The above reaction can include any condition or combination of conditions disclosed in Examples 12-13.

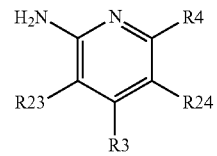

Formula (12)

An aminopyridine compound can be formed by conducting an alkylation of the 4-position of a halogenated 2-aminopyridine acetamide derivative and subsequent removal of the acetamide (see e.g., Example 11). A 2-aminopyridine with fluoro, chloro, or bromo groups at the 3-position and 5-position can be converted to the corresponding acetamide derivative by treatment with, for example, acetic anhydride in glacial acetic acid. The acetamide derivative can be alkylated at the position between the halogens by deprotonation with, for example, diisopropyl amine and butyllithium in tetrahydrofuran at a suitable temperature, such as about −70° C., and subsequent treatment with a lower alkyl halide, such as iodomethane or iodoethane. The acetamide group can be removed by treating with concentrated acid, such as concentrated hydrochloric acid, in a suitable solvent, such as methanol, at a suitable temperature, such as about 50° C., to provide a 2-amino-3,5-dihalo-4-alkylaminopridine. The substituted 2-aminopyridine of the above reaction can have a structure of Formula (12), wherein $R^{23}$ can be fluoro, chloro, or bromo; $R^3$ can be hydrogen; $R^4$ can be as defined in claim 1; and $R^{24}$ can be fluoro, chloro, or bromo. The substituted 2-aminopyridine of the above reaction can have a structure of Formula (12), wherein $R^{23}$ can be fluoro, chloro, or bromo; $R^3$ can be hydrogen; $R^4$ can be as defined as above (see Formula (3)); and $R^{24}$ can be fluoro, chloro, or bromo. The above reaction can include any condition or combination of conditions disclosed in Examples 12-13.

Also provided are aminopyridine intermediate compounds useful for their biological activity as well as a starting material for formation of other compounds disclosed herein. The aminopyridine intermediate compound can be 2-Amino-3-methoxy-5-chloropyridine; 2-Amino-4,5-dichloropyridine; 2-Amino-5-chloro-6-methylpyridine; 2-Amino-5-chloro-3-methylpyridine; 2-Amino-3,5-dichloro-4-methylpyridine; 2-Amino-3,5-dichloro-4,6-dimethylpyridine; 2-Amino-3-fluoro-4-methyl-5-chloropyridine; 2-Amino-3-ethyl-5-chloropyridine; 2-Amino-3-fluoro-4-ethyl-5-chloropyridine; and 2-Amino-4-methyl-3,5-difluoropyridine, or an aminopyridine compound formed according to the above described reactions. For example, the amino pyridine compound can be 2-Amino-3-fluoro-4-methyl-5-chloropyridine; 2-Amino-3-ethyl-5-chloropyridine; 2-Amino-3-fluoro-4-ethyl-5-chloropyridine; or 2-Amino-4-methyl-3,5-difluoropyridine.

Pharmaceutical Formulations

Embodiments of the compositions of the invention include pharmaceutical formulations of the various compounds described herein. A compound described herein can be employed in pure form or, where such forms exist, in pharmaceutically acceptable salt form and with or without a pharmaceutically acceptable excipient. The compounds described herein can be formulated by any conventional manner using one or more pharmaceutically acceptable carriers and/or excipients as described in, for example, Remington's Pharmaceutical Sciences (A. R. Gennaro, Ed.), 21st edition, ISBN: 0781746736 (2005). Such formulations will contain a therapeutically effective amount of the agent, preferably in purified form, together with a suitable amount of carrier so as to provide the form for proper administration to the subject.

The formulation should suit the mode of administration. The agents of use with the current invention can be formulated by known methods for administration to a subject using several routes which include, but are not limited to, parenteral, pulmonary, oral, topical, intradermal, intramuscular, intraperitoneal, intravenous, subcutaneous, intranasal, epidural, ophthalmic, buccal, and rectal. The individual agents may also be administered in combination with one or more additional agents of the present invention and/or together with other biologically active or biologically inert agents. Such biologically active or inert agents may be in fluid or mechanical communication with the agent(s) or attached to the agent(s) by ionic, covalent, Van der Waals, hydrophobic, hydrophillic or other physical forces.

Controlled-release (or sustained-release) preparations may be formulated to extend the activity of the agent and reduce dosage frequency. Controlled-release preparations can also be used to effect the time of onset of action or other characteristics, such as blood levels of the agent, and consequently affect the occurrence of side effects.

Combination with Kinase Inhibitors

Compounds described herein can be used with, or formulated with, known therapeutic compounds. Combination therapy is understood as a therapeutic regimen comprising, e.g., an anti-proliferative compound described herein and a second agent. An anti-proliferative compound and a second agent can be formulated for separate administration or may be formulated for administration together.

Compounds described herein can be combined with another anti-prolifative compound, such as the EGFR kinase inhibitors, Tykerb, Iressa, and Tarceva, or Erbitux, a humanized monoclonal antibody to the EGF receptor, to produce a greater therapeutic effect than either agent alone. As shown herein, when AD4 compounds were evaluated in a cell proliferation assay with Tykerb, Iressa, Tarceva or Erbitux, the effect of the combination of agents to inhibit cell proliferation was greater than the effect of any of the agents alone (see e.g., Example 6). Specifically, compounds described herein were evaluated with Tykerb, Iressa, Tarceva or Erbitux at a fixed concentration ratio, which was ascertained from the results of dose-response curves of each agent alone.

An compound described herein, such as an EGFR inhibitor, can be used with, or formulated and used with a second agent that inhibits vascularization of a tumor. Vascularization of a solid tumor generally refers to formation of blood vessels in a solid tumor. An agent that inhibits the vascularization of a tumor can inhibit vessel initiation, development, or maintenance leading to, for example, the reduction in the number or density of vessels in a tumor.

A compound described herein can be used with, or formulated and used with a second agent that modifies, for example increasing, permeability of a solid tumor. Permeability of a solid tumor generally refers to the permeability of a solid tumor to a therapeutic. A solid tumor may be said to be permeable to a therapeutic if the therapeutic is able to reach cells at the center of the tumor.

A compound described herein can be used with, or formulated and used with, a chemotherapeutic second agent. A chemotherapeutic agent refers to a molecule or composition used to treat a malignancy. Such agents can be used in combination with a compound described herein or with a combination therapy described herein. Chemotherapeutic agents include agents that can be conjugated to a compound described herein or can be used in combination with the combination therapy in unconjugated form.

A compound described herein can be used with, or formulated and used with a second agent that is a biological agent. A biological agent, also called a biologic, are generally understood as a product of a biological system, e.g., an organism, cell, or recombinant system. Examples of such biologic agents include, but are not limited to, nucleic acid molecules (e.g., antisense nucleic acid molecules), interferons, interleukins, colony-stimulating factors, antibodies (e.g., monoclonal antibodies), and cytokines.

A compound described herein can be used or formulated with an EGFR inhibitor approved for treatment of an EGFR-related condition or disorder. For example, compounds described herein can be used with or formulated with one or more of Tykerb, Iressa, Tarceva, or Erbitux. Tykerb, Iressa, and Tarceva are kinase inhibitors that block EGFR tyrosine kinase activity. Erbitux is a humanized monoclonal antibody that binds to an extracellular epitope on EGFR. Erbitux blocks activation of the receptor by preventing both ligand binding and receptor dimerization. In various embodiments, a compound described herein can lock EGFR into a dimerization incompetent conformation. Thus, compounds described herein and known EGFR inhibitors, such as those described above, can act in a complementary or synergistic fashion.

A compound described herein, such as AD4-1505-like compounds, can be used or formulated with Tykerb. Compounds described herein, such as AD4-1505-like compounds, can be used or formulated with Iressa. A compound described herein, such as AD4-1505-like compounds, can be used or formulated with or Tarceva.

Therapeutic Use

Another aspect is a process of treating a proliferative disease, disorder, or condition with a compound described herein. In various embodiments, a proliferative disease, disorder, or condition is associated with a target biomolecule having an interdomain tether associated with activation state, such as EGFR. The therapeutic method can include administration of a therapeutically effective amount of a compound of the invention to a subject in need thereof. In some embodiments, the compound is a compound described herein having anti-proliferative effects. In some embodiments, the compound is a compound described herein EGFR inhibitory activity. In some embodiments, the compound is an EGFR inhibitor that acts to bind one or more domains of EGFR so as to prevent tether extension and maintain an inactive conformation.

In various embodiments, the therapeutic method includes administration of one or more compounds described herein.

For example, the therapeutic method can include administration of one or more compounds of TABLE 5, or a stereoisomer or pharmaceutically acceptable salt thereof. As another example, the therapeutic method can include administration of one or more compounds of Formula (2), Formula (10), or Formula (11), or a stereoisomer or pharmaceutically acceptable salt thereof.

As another example, the therapeutic method can include administration of one or more compounds selected from the following: AD4-1505 (Formula (1)), or a stereoisomer or pharmaceutically acceptable salt thereof.

As another example, the therapeutic method can include administration of one or more compounds selected from the following:

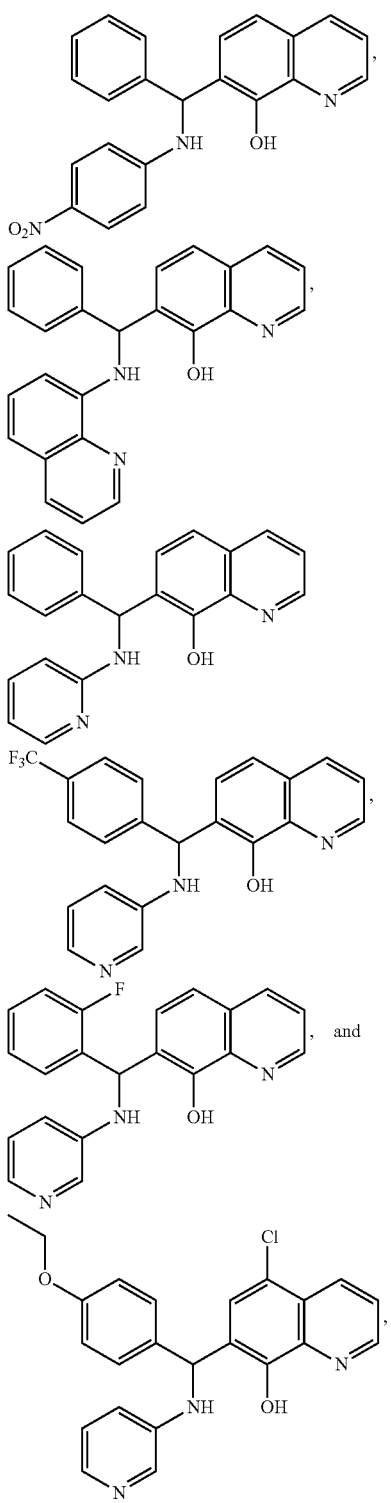

or a stereoisomer or pharmaceutically acceptable salt thereof.

Methods described herein are generally performed on a subject in need thereof. For example, a subject in need of the therapeutic methods described herein can be diagnosed with a proliferative disease, disorder, or condition, or at risk thereof. As another example, a subject in need of the therapeutic methods described herein can be diagnosed with a disease, disorder, or condition associated with EGFR, or at risk thereof. A determination of the need for treatment can be assessed by a history and physical exam consistent with the disease, disorder, or condition at issue. Diagnosis of the various conditions treatable by the methods described herein is within the skill of the art. The subject can be an animal subject, preferably a mammal, more preferably horses, cows, dogs, cats, sheep, pigs, mice, rats, monkeys, guinea pigs, and chickens, and most preferably a human.

Examples of proliferative diseases or conditions treatable with compositions described herein include, but are not limited to, cancer; blood vessel proliferative disorders; fibrotic disorders; mesangial cell proliferative disorders; psoriasis; actinic keratoses; seborrheic keratoses; warts; keloid scars; eczema; and hyperproliferative diseases caused by virus infections, such as papilloma virus infection.

While under no obligation to provide an underlying mechanism and in no way limiting the present invention by doing so, it is presently thought that at least a portion of activity of compounds described herein arise from inhibition of EGFR. It is further contemplated that the presently described compounds may have additional modes of action in their effectiveness in treating a proliferative disease, disorder, or condition. Regardless of the underlying mechanism, compounds described herein have been demonstrated to be empirically effective in treating proliferative diseases and conditions.

Various compounds described herein can be effective for inhibiting EGFR, and thus, effective against diseases or conditions associated with EGFR, such as include, but are not limited to, proliferative diseases. In some embodiments, the proliferative disease treated by a compound described herein is a condition caused by excessive growth of cancer or non-cancer cells that express a member of the EGFR family of receptors. The excess cells generated by a proliferative disease can express EGFR at normal levels or can overexpress EGFR. Particularly suitable diseases or conditions associated with EGFR can be those stimulated by a ligand of EGFR or mutations of such ligands. Examples of such ligands that stimulate EGFR include, but are not limited to, EGF, TGF-alpha, heparin-binding growth factor (HBGF), β-cellulin, and Cripto-1. Examples of proliferative disease associated with EGFR include, but are not limited to, cancer; blood vessel proliferative disorders; fibrotic disorders; mesangial cell proliferative disorders; psoriasis; actinic keratoses; seborrheic keratoses; warts; keloid scars; eczema; and hyperproliferative diseases caused by virus infections, such as papilloma virus infection.

Cancer, or neoplasia, refers generally to any malignant neoplasm or spontaneous growth or proliferation of cells. A subject having "cancer", for example, may have a leukemia, lymphoma, or other malignancy of blood cells. In certain embodiments, the subject methods are used to treat a solid tumor. Exemplary solid tumors include but are not limited to non small cell lung cancer (NSCLC), testicular cancer, lung cancer, ovarian cancer, uterine cancer, cervical cancer, pancreatic cancer, colorectal cancer (CRC), breast cancer, as well as prostate, gastric, skin, stomach, esophageal, and bladder cancer.

Treatment of cancer or treating a subject having cancer can include inhibition of replication of cancer cells, inhibition of spread of cancer, reduction in tumor size, lessening or reducing the number of cancerous cells in the body of a subject, or amelioration or alleviation of symptoms of cancer. A treatment can be considered therapeutic if there is a decrease in mortality or morbidity, and can be performed prophylactically, or therapeutically.

Methods described herein can be used to treat (e.g., reduce tumor size, decrease the vascularization, and/or increase the permeability of) an established tumor. An established tumor is generally understood as a solid tumor of sufficient size such that nutrients, e.g., oxygen, can no longer permeate to the center of the tumor from the subject's vasculature by osmosis and therefore the tumor requires its own vascular supply to receive nutrients. Methods described herein can be used to treat a solid tumor that is not quiescent and is actively undergoing exponential growth.

A therapeutic protocol can be modified according to permeability of a solid tumor. Permeability of a solid tumor generally refers to the permeability of a solid tumor to a therapeutic. A solid tumor may be said to be permeable to a therapeutic if the therapeutic is able to reach cells at the center of the tumor. An agent that increases the permeability of a tumor may for example, normalize, e.g., maintain, the vasculature of a solid tumor. Tumor vascularization or tumor permeability can be determined by a variety of methods known in the art, such as, e.g. by immunohistochemical analysis of biopsy specimens, or by imaging techniques, such as sonography of the tumor, computed tomography (CT) or magnetic resonance imaging (MRI) scans.

Different types of psoriasis display characteristics such as pus-like blisters (pustular psoriasis), severe sloughing of the skin (erythrodermic psoriasis), drop-like dots (guttae psoriasis) and smooth inflamed lesions (inverse psoriasis). The treatment of all types of psoriasis (e.g., psoriasis vulgaris, psoriasis pustulosa, psoriasis erythrodermica, psoriasis arthropathica, parapsoriasis, palmoplantar pustulosis) is contemplated by the invention.

Blood vessel proliferative disorders refer to angiogenic and vasculogenic disorders generally resulting in abnormal proliferation of blood vessels. The formation and spreading of blood vessels, or vasculogenesis and angiogenesis, respectively, play important roles in a variety of physiological processes such as embryonic development, corpus luteum formation, wound healing, and organ regeneration. They also play a pivotal role in cancer development. Other examples of blood vessel proliferation disorders include, but are not limited to, arthritis, where new capillary blood vessels invade the joint and destroy cartilage, and ocular diseases, like diabetic retinopathy, where new capillaries in the retina invade the vitreous, bleed and cause blindness. Disorders related to the shrinkage, contraction or closing of blood vessels, such as restenosis, are also implicated.

Fibrotic disorders refer to the abnormal formation of extracellular matrix. Examples of fibrotic disorders include, but are not limited to, hepatic cirrhosis and mesangial cell proliferative disorders. Hepatic cirrhosis is characterized by the increase in extracellular matrix constituents resulting in the formation of a hepatic scar. Hepatic cirrhosis can cause diseases such as cirrhosis of the liver. An increased extracellular matrix resulting in a hepatic scar can also be caused by viral infection such as hepatitis. Lipocytes appear to play a major role in hepatic cirrhosis. Other fibrotic disorders implicated include atherosclerosis.

Mesangial cell proliferative disorders refer to disorders brought about by abnormal proliferation of mesangial cells. Mesangial proliferative disorders include, but are not limited to, various human renal diseases, such as glomerulonephritis, diabetic nephropathy, malignant nephrosclerosis, thrombotic microangiopathy syndromes, transplant rejection, and glomerulopathies.

EGFR (Tuzi et al., 1991, Br. J. Cancer 63:227-233; Torp et al., 1992, APMIS 100:713-719) HER2/neu (Slamon et al., 1989, Science 244:707-712) and the PDGF-R (Kumabe et al., 1992, Oncogene 7:627-633) are known to be overexpressed in many tumors and/or persistently activated by autocrine loops. Overexpression of the receptor and autocrine loops have been demonstrated in most common and severe cancers (see e.g., Akbasak and Suner-Akbasak et al., 1992, J. Neurol. Sci. 111:119-133; Dickson et al., 1992, Cancer Treatment Res. 61:249-273; Korc et al., 1992, J. Clin. Invest. 90:1352-1360; Lee and Donoghue, 1992, J. Cell. Biol. 118:1057-1070). Overexpression of EGFR is known to be associated with cancers of the bladder, brain, head and neck, pancreas, lung, breast, ovary, colon, prostate, and kidney. (see e.g., Atalay et al., 2003, Ann. Oncology 14:1346-1363; Herbst and Shin, 2002, Cancer 94:1593-1611; Modjtahedi et al., 1996, Br. J. Cancer 73:228-235). Overexpression of EGFR can be correlated or associated with poor prognosis of the patients (see e.g., Herbst and Shin, 2002, Cancer 94:1593-1611; Modjtahedi et al., 1996, Br. J. Cancer 73:228-235). HER2 has been associated with breast, ovarian, gastric, lung, pancreas and bladder cancer.

An inhibitor compound described herein can be used therapeutically either as exogenous materials or as endogenous materials. Exogenous agents are those produced or manufactured outside of the body and administered to the body. Endogenous agents are those produced or manufactured inside the body by some type of device (biologic or other) for delivery to within or to other organs in the body.

According to the methods described herein, administration can be parenteral, pulmonary, oral, topical, intradermal, intramuscular, intraperitoneal, intravenous, subcutaneous, intranasal, epidural, ophthalmic, buccal, or rectal administration.

An effective amount of a compound described herein is generally that which can exhibit an anti-proliferative effect to an extent such as to ameliorate the treated condition. For example, an effective amount of a compound described herein may inhibit EGFR to an extent such as to ameliorate the treated condition. In some embodiments, an effective amount is that amount of therapy (or combination therapy) that is sufficient to affect a desired result on a cancerous cell or tumor, including, but not limited to, for example, reducing tumor size, reducing tumor volume, decreasing vascularization of a solid tumor, or increasing the permeability of a solid tumor to an agent, either in vitro or in vivo. In certain embodiments, an effective amount of therapy (or combination therapy) is the amount that results in a percent tumor inhibition of more than about 55%, about 60%, about 65%, about 70%, about 75%, about 80%, about 85%, about 90%, about 95%, about 99%, or about 100%. In certain embodiments, an effective amount of therapy (or combination therapy) is sufficient to achieve a desired clinical result, including but not limited to, for example, ameliorating disease, stabilizing a subject, preventing or delaying the development of, or progression of cancer in a subject. An effective amount of therapy (or combination therapy) can be determined based on one administration or repeated administration. Methods of detection and measurement of the indicators above are known to those of skill in the art. Such methods include, but are not limited to measuring reduction in tumor burden, reduction of tumor size, reduction of tumor volume, reduction in proliferation of secondary tumors, decreased solid tumor vascularization, expression of genes in tumor tissue, presence of biomarkers, lymph node involvement, histologic grade, and nuclear grade.

In some embodiments, tumor burden can be determined. Tumor burden, also referred to as tumor load, generally refers to a total amount of tumor material distributed throughout the body of a subject. Tumor burden can refer to a total number of cancer cells or a total size of tumor(s), throughout the body, including lymph nodes and bone barrow. Tumor burden can be determined by a variety of methods known in the art, such as, for example, by measuring the dimensions of tumor(s) upon removal from the subject, e.g., using calipers, or while in the body using imaging techniques, e.g., ultrasound, computed tomography (CT) or magnetic resonance imaging (MRI) scans. Tumor size can be determined, for example, by determining tumor weight or tumor volume.

When used in the methods of the invention, a therapeutically effective amount of a compound described herein can be employed in pure form or, where such forms exist, in pharmaceutically acceptable salt form and with or without a pharmaceutically acceptable excipient. For example, the agents of the invention can be administered, at a reasonable benefit/risk ratio applicable in a sufficient amount sufficient to inhibit the target biomolecule for which the compound is specific for the treatment or prophylaxis of a disease, disorder, or condition associated with the target biomolecule.

Toxicity and therapeutic efficacy of such compounds, and pharmaceutical formulations thereof, can be determined by standard pharmaceutical procedures in cell cultures and/or experimental animals for determining the $LD_{50}$ (the dose lethal to 50% of the population) and the $ED_{50}$, (the dose therapeutically effective in 50% of the population). The dose ratio between toxic and therapeutic effects is the therapeutic index that can be expressed as the ratio $LD_{50}/ED_{50}$, where large therapeutic indices are preferred.

The amount of a compound described herein may be combined with a pharmaceutically acceptable carrier to produce a single dosage form will vary depending upon the host treated and the particular mode of administration. It will be appreciated by those skilled in the art that the unit content of agent contained in an individual dose of each dosage form need not in itself constitute a therapeutically effective amount, as the necessary therapeutically effective amount could be reached by administration of a number of individual doses.

Administration of a compound described herein can occur as a single event, a periodic event, or over a time course of treatment. For example, modulators can be administered daily, weekly, bi-weekly, or monthly. As another example, a compound can be adminstered in multiple treatment sessions, such as 2 weeks on, 2 weeks off, and then repeated twice; or every 3rd day for 3 weeks. One of ordinary skill will understand these regimes to be exemplary and could design other suitable periodic regimes. For treatment of acute conditions, the time course of treatment will usually be at least several days. Certain conditions could extend treatment from several days to several weeks. For example, treatment could extend over one week, two weeks, or three weeks. For more chronic conditions, treatment could extend from several weeks to several months or even a year or more.

The specific therapeutically effective dose level for any particular subject will depend upon a variety of factors including the disorder being treated and the severity of the disorder; activity of the specific compound employed; the specific composition employed; the age, body weight, general health, sex and diet of the patient; the time of administration; the route of administration; the rate of excretion of the composition employed; the duration of the treatment; drugs used in combination or coincidental with the specific compound employed; and like factors well known in the medical arts (see e.g., Koda-Kimble et al. (2004) Applied Therapeutics: The Clinical Use of Drugs, Lippincott Williams & Wilkins, ISBN 0781748453; Winter (2003) Basic Clinical Pharmacokinetics, 4$^{th}$ ed., Lippincott Williams & Wilkins, ISBN 0781741475; Sharqel (2004) Applied Biopharmaceutics & Pharmacokinetics, McGraw-Hill/Appleton & Lange, ISBN 0071375503). For example, it is well within the skill of the art to start doses of the composition at levels lower than those required to achieve the desired therapeutic effect and to gradually increase the dosage until the desired effect is achieved. If desired, the effective daily dose may be divided into multiple doses for purposes of administration. Consequently, single dose compositions may contain such amounts or submultiples thereof to make up the daily dose. It will be understood, however, that the total daily usage of the compounds and compositions of the present invention will be decided by an attending physician within the scope of sound medical judgment.

Compounds of the invention that inhibit a target biomolecule can also be used in combination with other therapeutic modalities. Thus, in addition to the therapies described herein, one may also provide to the subject other therapies known to be efficacious for particular conditions linked to the target biomolecule. Treatment in accord with the methods described herein can be performed prior to, concurrent with, or after conventional treatment modalities for a disease, disorder, or condition associated with a target biomolecule for which the compound is specific.

Kits

Also provided are kits. Such kits can include the compositions of the present invention and, in certain embodiments, instructions for administration. Such kits can facilitate performance of the methods described herein, for example, treatment methodologies or screening methodologies. When supplied as a kit, the different components of the composition can be packaged in separate containers and admixed immediately before use. Components include, but are not limited to one or more compounds described herein, vectors, diagnostic reagents, assay reagents, and/or combinations thereof. Such packaging of the components separately can, if desired, be presented in a pack or dispenser device which may contain one or more unit dosage forms containing the composition. The pack may, for example, comprise metal or plastic foil such as a blister pack. Such packaging of the components separately can also, in certain instances, permit long-term storage without losing activity of the components.

Kits may also include reagents in separate containers such as, for example, sterile water or saline to be added to a lyophilized active component packaged separately. For example, sealed glass ampules may contain a lyophilized component and in a separate ampule, sterile water, or sterile saline, each of which has been packaged under a neutral non-reacting gas, such as nitrogen. Ampules may consist of any suitable material, such as glass, organic polymers, such as polycarbonate, polystyrene, ceramic, metal or any other material typically employed to hold reagents. Other examples of suitable containers include bottles that may be fabricated from similar substances as ampules, and envelopes that may consist of foil-lined interiors, such as aluminum or an alloy. Other containers include test tubes, vials, flasks, bottles, syringes, and the like. Containers may have a sterile access port, such as a bottle having a stopper that can be pierced by a hypodermic injection needle. Other containers may have two compartments that are separated by a readily removable membrane that upon removal permits the components to mix. Removable membranes may be glass, plastic, rubber, and the like.

In certain embodiments, kits can be supplied with instructional materials. Instructions may be printed on paper or other substrate, and/or may be supplied as an electronic-readable medium, such as a floppy disc, mini-CD-ROM, CD-ROM, DVD-ROM, Zip disc, videotape, audio tape, and the like. Detailed instructions may not be physically associated with the kit; instead, a user may be directed to an Internet web site specified by the manufacturer or distributor of the kit.

Compositions and methods described herein utilizing molecular biology protocols can be according to a variety of standard techniques known to the art (see, e.g., Sambrook and Russel (2006) Condensed Protocols from Molecular Cloning: A Laboratory Manual, Cold Spring Harbor Laboratory Press, ISBN-10: 0879697717; Ausubel et al. (2002) Short Protocols in Molecular Biology, 5th ed., Current Protocols, ISBN-10: 0471250929; Sambrook and Russel (2001) Molecular Cloning: A Laboratory Manual, 3d ed., Cold Spring Harbor Laboratory Press, ISBN-10: 0879695773; Elhai, J. and Wolk, C. P. 1988. Methods in Enzymology 167, 747-754; Studier (2005) Protein Expr Purif. 41(1), 207-234; Gellissen, ed. (2005) Production of Recombinant Proteins: Novel Microbial and Eukaryotic Expression Systems, Wiley-VCH, ISBN-10: 3527310363; Baneyx (2004) Protein Expression Technologies, Taylor & Francis, ISBN-10: 0954523253).

Definitions and methods described herein are provided to better define the present disclosure and to guide those of ordinary skill in the art in the practice of the present disclosure. Unless otherwise noted, terms are to be understood according to conventional usage by those of ordinary skill in the relevant art.

In some embodiments, numbers expressing quantities of ingredients, properties such as molecular weight, reaction conditions, and so forth, used to describe and claim certain embodiments of the present disclosure are to be understood as being modified in some instances by the term "about." In some embodiments, the term "about" is used to indicate that a value includes the standard deviation of the mean for the device or method being employed to determine the value. In some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable. The numerical values presented in some embodiments of the present disclosure may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein.

In some embodiments, the terms "a" and "an" and "the" and similar references used in the context of describing a particular embodiment (especially in the context of certain of the following claims) can be construed to cover both the singular and the plural, unless specifically noted otherwise. In some embodiments, the term "or" as used herein, including the claims, is used to mean "and/or" unless explicitly indicated to refer to alternatives only or the alternatives are mutually exclusive.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and can also cover other unlisted steps. Similarly, any composition or device that "comprises," "has" or "includes" one or more features is not limited to possessing only those one or more features and can cover other unlisted features.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the present disclosure and does not pose a limitation on the scope of the present disclosure otherwise claimed. No language in the specification should be construed as indicating any non-claimed element essential to the practice of the present disclosure.

Groupings of alternative elements or embodiments of the present disclosure disclosed herein are not to be construed as limitations. Each group member can be referred to and claimed individually or in any combination with other members of the group or other elements found herein. One or more members of a group can be included in, or deleted from, a group for reasons of convenience or patentability. When any such inclusion or deletion occurs, the specification is herein deemed to contain the group as modified thus fulfilling the written description of all Markush groups used in the appended claims.

Citation of a reference herein shall not be construed as an admission that such is prior art to the present disclosure.

Having described the present disclosure in detail, it will be apparent that modifications, variations, and equivalent embodiments are possible without departing the scope of the present disclosure defined in the appended claims. Furthermore, it should be appreciated that all examples in the present disclosure are provided as non-limiting examples.

EXAMPLES

The following non-limiting examples are provided to further illustrate the present invention. It should be appreciated by those of skill in the art that the techniques disclosed in the examples that follow represent approaches the inventors have found function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention.

Example 1

EGFR Inhibition Assay

The following example describes general EGFR in-cell Western (ICW) screening protocol. Methods are according to Chen et al. (2005) Analytical Biochemistry 338, 136-142 (incorporated herein by reference), except as otherwise noted.

Cell Plates: A431 cells (ATCC # CRL-1555) were grown in Dulbecco's Modified Eagle Medium (DMEM; ATCC #30-2002) supplemented with 10% fetal bovine serum, 105 units/ml pen/strep (Invitrogen #15140155) and 2.1 mM L-glutamine (ATCC #30-2214). Cells were seeded into 96 well tissue culture plates (BD Falcon #353948) at a density of 30,000 cells per well and incubated at 37° C. with 5% $CO_2$ overnight. Two cell plates were prepared for each compound plate.

Serum Starvation: The cells were serum starved prior to compound addition. The media was removed by aspiration and the cells washed with PBS (200 µl/well; Invitrogen #20012-027). The PBS was removed by aspiration and replaced with 200 µl of DMEM (ATCC #30-2002) supplemented with 105 units/ml pen/strep (Invitrogen #15140155) and 2.1 mM l-glutamine (ATCC #30-2214). The cell plates were incubated at 37° C./5% $CO_2$ for 2 hours.

Compound Plate Preparation: The test compounds were solvated in 100% DMSO (Sigma #472301-2L) at a concentration of 25 mM. Compounds found not to be completely soluble in 100% DMSO at 25 mM were diluted to 10 mM with 100% DMSO and TFA (Fluka #91699) added to a final concentration of 0.2%. 40 µl of test compound was added to the appropriate well of a 96 well plate (Falcon #351190). As controls, 6 µM EGFR kinase inhibitor PD168393 (EMD/Calbiochem #513033) in 100% DMSO and DMSO alone were added to various wells. Prepared compound plates were stored at RT prior to use and at 4° C. long term.

Compound Dilution Plate Preparation: 250 µl of DMEM supplemented with 1 mg/ml BSA (Sigma A3059-10G) was added to the appropriate wells of a 96 well plate to prepare the compound dilution plates. Using a multichannel pipettor, 1.25 µl of compound from the compound plate was transferred into the compound dilution plate. This dilution rate will give a compound concentration in the assay of 125 µM.

Compound Addition: The starve media was removed from the cell plates by aspiration. Using a multichannel pipettor, the compound dilution plates were mixed by pipetting up and down three times. 50 µl of mixed, diluted compound was added to each of two rows/columns on each of two cell plates. The cell plates with compound were incubated at 37° C./5% $CO_2$ for 4 hours.

EGF Addition: 20 ng/ml EGF (Upstate #01-107) was prepared in DMEM supplemented with 1 mg/ml BSA. 50 µl of 20 or 0 ng/ml EGF was added to the appropriate wells without the removal of compound. The compound and EGF were mixed by pipetting up and down three times. The plates were incubated at 37° C./5% $CO_2$ for 10 min. In some screening assays the final concentration of EGF used for simulation was 6.6, or 12.5 ng/ml rather than 10 ng/ml.

Fixation and Triton Washing: The EGF+compound was removed by aspiration and 150 µl of freshly prepared Fixation Solution (1×PBS, Sigma P3813-10PK, and 4% Formaldehyde, Pierce #28908) was immediately added. The plates were incubated at RT for 20 min without shaking. The Fixation Solution was removed by aspiration and the plates washed four times with 200 µl each of Triton Wash Solution (1×PBS, Sigma P3813-10PK, and 0.1% Triton X-100, T8787-50ML) for 5 min with gentle shaking.

Blocking and Probing: Following the last Triton Wash, the plates were blocked for 1.5 h at RT with shaking using 150 µl of Odyssey Blocking Buffer (LI-COR #927-40000). The block was removed by aspiration and 50 µl of diluted primary Ab mix was added. The plates were incubated at 4° C. overnight with gentle shaking. The plates were washed five times with 200 µl of PBST (1×PBS, Sigma P3813-10PK, and 0.1% Tween-20, Sigma P9416-50ML) for 5 min each with shaking. 50 µl of diluted secondary Ab mix was added and the plates incubated at RT for 1 h with shaking. The plates were washed 5× with 200 µl of PBST for 5 min each with shaking. One final wash with 200 µl of PBS (Sigma P3813-10PK) for 5 min with shaking was performed prior to scanning.

Primary Ab Mix contained: 0.1% Tween-20 (Sigma P9416-50ML); 1/500 dilution anti-total EGFR (Invitrogen #AHR5062); 1/800 dilution anti-phospho EGFR (Tyr 1173; Cell Signalling #4407); and Odyssey Blocking Buffer (LI-COR #927-40000). Some screening assays used a 1/100 dilution of anti-phospho EGFR (Tyr1045; Cell Signalling #2237) rather than the anti-phospho EGFR Ab indicated above.

Secondary Ab Mix contained: 0.2% 10% Tween-20 (Sigma P9416-50ML); 1/1200 dilution anti-mouse IR680 conjugate (LI-COR 926-32220); 1/1200 dilution anti-rabbit IR800CW conjugate (LI-COR 926-32211); and Odyssey Blocking Buffer (LI-COR #927-40000). In some screening assays, the dilution of the secondary Ab conjugates was 1/800 rather than 1/1200.

Plate Scanning: The plates were scanned on an Odyssey Infrared Imaging System from LI-COR Biosciences. The focus offset was set at 3.5 mm and the scanning intensity set at 3 for the 700 channel and 7 for the 800 channel.

Data Analysis: The % of Maximum and % Inhibition values were calculated as follows. 700 Channel=signal for total EGFR (used to control for variation in cell number). 800 Channel=signal for phosphorylated EGFR. $800_{-EGF}$=basal level EGFR phosphorylation+non-specific signal (no compound). $800_{+EGF}$=$800_{-EGF}$+EGF dependent EGFR receptor phosphorylation (no compound). $700/800_{com}$=700 or 800 channel signals with compound. % Maximum=$\{[(800_{com}/700_{com})-(800_{-EGF}/700_{-EGF})]/[(800_{+EGF}/700_{+EGF})-(800_{-EGF}/700_{-EGF})]\} \times 100\%$. % Inhibition=100%−(% Maximum).

Example 2

MTT Assay

The following example describes the MTT Cell Proliferation Assay. The MTT Cell Proliferation Assay served as a secondary screen to evaluate active compounds from the primary cell based ICW screening protocol, described above. The MTT assay was used to evaluate toxicity through viability and proliferation effects, and compares the growth of an epithelial carcinoma A431 cell line (American Type Culture Collections (ATCC) cat #CRL-155) and an MDBK line (ATCC cat #CCL-22) derived from a healthy bovine kidney after a three day compound treatment and incubation.

The MTT Cell Proliferation Assay is a colorimetric assay system that measures the reduction of the tetrazolium salt MTT (3-(4,5-dimethylthiazol-2-yl)-2,5-diphenyltetrazolium bromide) into insoluble formazan crystals, produced by the mitochondria of viable cells. After incubation of the cells with the MTT, the formazan crystals formed are solubilized by the addition of a detergent or DMSO (ACS Reagent grade, Sigma cat#472301). The color can then be quantified by spectrophotometric means. Among the applications for the method are drug sensitivity, cytotoxicity, response to growth factors, and cell activation. The reduction of tetrazolium salts is now recognized as a safe, accurate alternative to radiometric testing.

Methods are according to manufacturer instructions for MTT Cell Proliferation Assay, ATCC, Cat. No. 30-1010K, except as otherwise noted.

Each MTT assay tested 11 compounds and 1 standard in a dose response curve with 5 concentrations, and 2.5 fold dilutions. Two replicates on each cell plate and 2 duplicate plates gave 4 individual replicates of each concentration, in each cell line. Concentrations were diluted in 100% DMSO from 25 mM stocks. Initial concentrations used and final concentrations tested were as follows: 20 mM to 100 µM; 8 mM to 40 µM; 3.2 mM to 16 µM; 1.3 mM to 6.4 µM; and 0.51 mM to 2.6 µM.

Twelve 96 well plates of each cell line were plated. Plating was done by dislodging cells as in passage protocol, counting on a hemocytometer, re-suspending in standard growth media, and plating using a multichannel pippetor.

Standards: AD4-10289 was used as the dose response standard, run at one concentration lower than the test compounds; 40, 16, 6.4, 2.6, and 1.0 µM final concentrations. 10289 was run in place of 1 test compound, with the same number of replicates. 16 µl of 25 mM stock+34 µl DMSO=8 mM starting concentrations, and serial diluted as with test compounds in same plate. These concentrations were used on each plate to give 100%, and less than 100% activity in A431, while also giving less than 50% and 0 activity in DMBK cells. Two replicates of each concentrations was run on each cell plate. All compound addition and cell treatments were done using aseptic technique under a laminar flow aseptic hood.

Control: 0.5% DMSO in treatment media was used as the control. The assay was demonstrated to tolerate up to 1.0% DMSO with no significant growth differences.

MTT dye (Thiazolyl Blue Tetrazolium Bromide, Sigma cat #M5655) stock was prepared in bulk and stored at 4° C. for use: 5 mgs/ml sterile PDS, shielded from light. 4 ul of this stock per 100 uls treatment media per well was used. 130 ml of MTT/treatment was prepared fresh to dye 12 plates; 124.8 ml treatment media+522 mls of MTT stock.

Cells (harvested from 95% confluent flasks) were plated at densities of 7500 cells per well. Plates were incubated overnight prior to treatment, with treatment day=Day 0. Compound treatments were prepared prior to washing cells to minimize time cells were dry at room temperature after final aspiration. Compounds were diluted in 100% DMSO in 96 well polypropylene plates: 40 µl 25 mM stock+10 µl DMSO=20 mM; 20 µl of 20 mM+30 µl DMSO=8 mM; 20 µl of 8 mM+30 µl DMSO=3.2 mM; 20 µl of 3.2 mM+30 µl DMSO=1.3 mM; 20 µl of 1.3 mM+30 µl DMSO=0.51 mM.

5.0 µl/ml were added to treatment media, in sterile, 2.2 ml deep well plates=0.5% dmso final. Ten µl of each dmso concentration was added to 2.0 ml of treatment media and then mixed using a 1200 µl multichannel pipettor. Cell plates were treated from the deep well plates. Treatment media was standard growth media containing 0.5% FBS and standard additions. This reduced FBS concentration allowed for a slower growth rate in cells. In plate 1 of each cell line, standard AD4-10289 was run in lane 3 (see above for rates).

Media was aspirated from cell plates, and washed with 200 µl/well sterile PBS. Aspirated PBS wash, and cell plates were treated with 200 µl of compound/treatment media per well, and incubated at 37° C., 5% $CO_2$ for 3 days.

Prior to harvesting, visual observations were made under an inverted microscope. Plates were harvested by: aspirating the growth media; adding back MTT dye/100 µl treatment media; and incubating plates at 37° C. for 1 hour. MTT dye was aspirated. 100 µl/well dmso was added, and then shaken on a Bellco plate shaker for 5 minutes, at 4.5 setting.

Plates were read in a Tecan Sunrize UV plate reader, at 560 nm. Settings: Read mode, Outside Normal 2 sec; Shake settle time 3 sec. Data is reported as % inhibition, calculated for individual plates using control values from that plate.

Example 3

Testing of Identified Compounds from Pharmacophores for EGFR Inhibition

Identified compounds, representing various pharmacaphore models, were tested for ability to inhibit EGFR at 25 µM.

AD4-compounds were identified using pharmacophore models (see Example 3) and then were docked with the binding site of EGFR (SEQ ID NO: 1) that is recognized by defined CDRs of cetuximab. The inhibition of epidermal growth factor binding by AD4-compounds was then determined (NovaScreen BioSciences, Hanover, Md.). Inhibition of EGF binding was determined at 25 µM concentration.

For the inhibitor assays, $K_D$ (binding affinity) was 1.04 nM, while $B_{max}$ (receptor number) was 43.0 fmol/mg tissue (wet weight). Receptor source was rat liver membranes. The radioligand was $[^{125}I]EGF$ (150-200 Ci/µg) at a final ligand concentration of 0.36 nM. A non-specific determinant was used as EGF-[100 nM]. The reference compound and positive control was EGF. Reactions were carried out in 10 mM HEPES (pH 7.4) containing 0.1% BSA at 25° C. for 60 minutes. The reaction was terminated by rapid vacuum filtration onto glass fiber filters. Radioactivity trapped onto the filters was determined and compared to control values to ascertain any interactions of test compounds with the EGF binding site. The EGF inhibitor assays were modified from, for example, Mukku (1984) J. Biol. Chem. 259, 6543-6546; Duh et al. (1990) World J. Surgery 14, 410-418; Lokeshwar et al. (1989) J. Biol. Chem. 264(32), 19318-19326.

Example 4

Generation of Pharmacophores for Target Inhibition from Inactive EGFR Crystal Structure The following example describes analysis of the target protein crystal structure and generation of pharmacophores for EGFR inhibition. The ligands found by this methodology will interact with residues from Dom II and Dom IV of EGFR and thereby yielding an inactive form of the receptor.

The protein crystal structure of the inactive conformation of EGFR has been reported by Ferguson et al. (Ferguson, K. M., Berger, M. B., Mendrola, J. M., Cho, H., Leahy, D. J., Lemmon, M. A. (2003) EGF activates its receptor by removing interactions that auto-inhibit ectodomain dimerization Mol. Cell 11: 507-517). The binding site was determined using the site finder module in the MOE software. It consists of the interface of residues from Domain II (23 residues, Lys227, Phe228, Lys 235, Asp236, Thr237, Cys238, Pro239, Pro240, Leu241, Met242, Tyr244, Tyr249, Gln250, Met251, Gly257, Lys258, Tyr259, Ser260, Cys265, Val275, His278, Gly279 and Ser280) and Domain IV (16 residues, Arg548, Gly549, Pro550, Asp551, Asn552, Asp561, His564, Val566, Thr568, Cys569, Pro570, Ala571, Gly572, Val573, Met574 and Leu580) (see e.g., FIG. 1).

The pharmacophore feature generation and pharmacophore virtual screening module of the Molecular Operating Environment (MOE) software from Chemical Computing Group (CCG) (Montreal, Quebec, Canada) was used in the pharmacophore definitions described below. MOE's pharmacophore applications use a general notion of a pharmacophore being a set of structural features in a ligand that are directly related to the ligand's recognition at a receptor site and its biological activity.

In MOE, pharmacophoric structural features are represented by labeled points in space. Each ligand is assigned an annotation, which is a set of structural features that may contribute to the ligand's pharmacophore. A database of annotated ligands can be searched with a query that represents a pharmacophore hypothesis. The result of such a search is a set of matches that align the pharmacophoric features of the query to the pharmacophoric features present in the ligands of the searched database. The MOE software suite provides for interactive modifications (positions, radii, as well as other characteristics of the pharmacophoric query can be interactively adjusted); systematic matching (all possible matches of the ligand and the query are systematically examined); partial matching (the search algorithm is capable of finding ligands that match only a portion of the query); and volume filtering (the query can be focused by adding restrictions on the shape of the matched ligands in the form of a set of volumes).

The pharmacophore features of this example were generated using the Pharmacophore Query Editor in MOE. All hydrogen bond donor features are spheres of 1.2 Angstroms in radius and are colored purple. All hydrogen bond acceptor features are spheres of 1.2 Angstroms in radius and are colored cyan. All aromatic features are spheres of 1.2 Angstroms in radius and are colored green. All combined acceptor-anion pharmacophore features are spheres of 1.2 Angstroms in radius and are colored grey. All combined donor-acceptor features are spheres of 1.2 Angstroms in radius and are colored pink. All combined donor-cation features are spheres of 1.2 Angstroms and are colored red. All donor, acceptor, aromatic, combined acid-anion, and combined donor-acceptor directionality features are spheres of 1.5 Angstroms in radius and colored dark grey for donors, dark cyan for acceptors, dark green for aromatics, dark cyan for combined acid-anions, and dark grey for combined donor-acceptors. A feature that is marked essential in the pharmacophore query must be contained in the ligand in order for that ligand to be a hit.

The Contact statistics calculated, using the 3D atomic coordinates of a receptor, preferred locations for hydrophobic and hydrophilic ligand atoms using statistical methods. Using this method hydrophobic-aromatic and H-bonding features were placed, as noted in the individual pharmacophore definitions. Structural information which was derived from contact statistics and MFSS in the program MOE was used to construct pharmacophore models used to identify small molecules having similar atoms in similar positions.

The MultiFragment Search (MFSS) essentially places a relatively large number of copies of a fragment (e.g., 200 copies of ethane) into a receptor's active site. The fragments are placed randomly around the active site atoms and are assumed not to interact with each other; no regard is paid to fragment overlap. Next, a special energy minimization protocol is used to refine the initial placement: the receptor atoms feel the average forces of the fragments, while each fragment feels the full force of the receptor but not of the other fragments. Using this technique it was possible to place hydrophobic, H-bond donors, acceptors and anions and cations in favorable positions within the receptors for use as MOE pharmacophore features.

Methods provided in the MOE software are used to place pharmacophore features which correspond to the hit AD4-1505. These are contact statistics and MFSS, as described above. Both the contact statistics and MFSS algorithms were applied to the Domain II-Domain IV interface binding site of the inactive form of EGFr (1NQL.pdb, see figure above).

Excluded volumes were generated in MOE by selecting the receptor residues of the binding site at the Domain Hand Domain IV interface described above and selecting "union" from the pharmacophore query editor in MOE. Excluded volumes are positions in space where ligand atoms must be excluded in order to avoid bumping into the receptor.

In the Individual Pharmacophore Definitions described below, abbreviations were as follows: F=pharmacophore feature; Donor=Don, Acceptor=Acc, Anion=Ani, Cation=Cat, Acceptor and Anion=Acc&Ani, Donor and Cation=Don&Cat, Donor and Acceptor=Don&Acc, Aromatic=Aro, Hydrophobe=Hyd.

Figure 2:
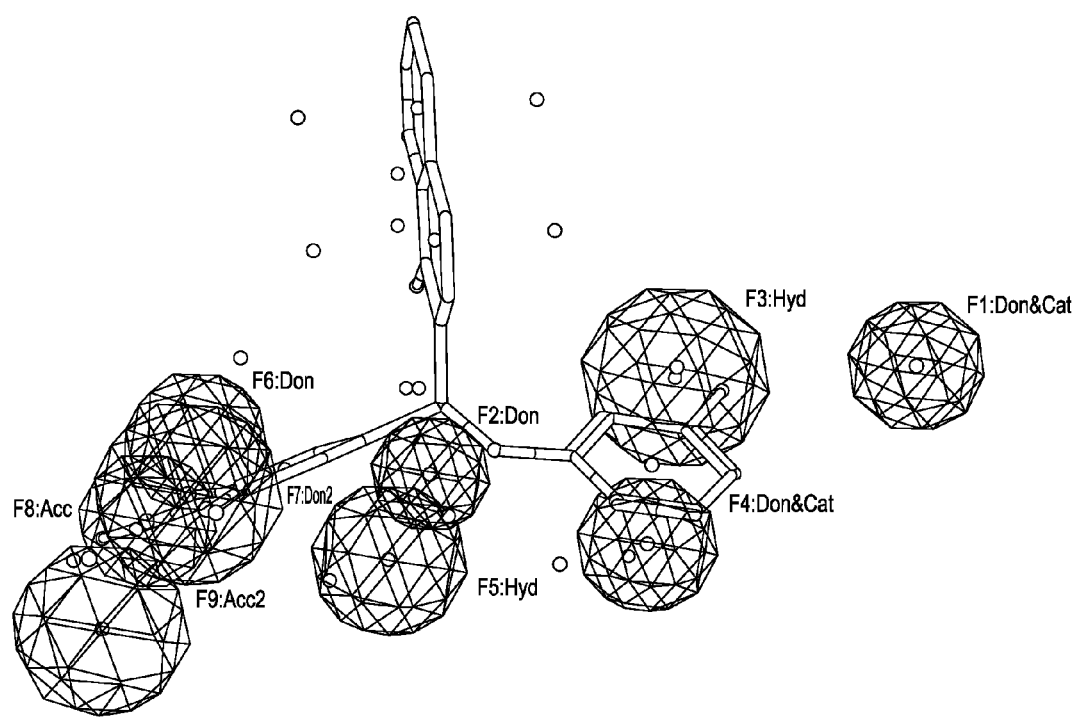
FIG. 2 shows Pharm-1nql-glue-5 aligned to the hit AD4-1505.

Pharmacophore model Pharm-1nql-glue-5 (see TABLE 6 and TABLE 7; FIG. 2) afforded the hit AD4-1505. This is a partial match model. The ligand must match at least 6 pharmacophore features.

In the Individual Pharmacophore Definitions described below, abbreviations were as follows: F=pharmacophore feature; Donor=Don, Acceptor=Acc, Anion=Ani, Cation=Cat, Acceptor and Anion=Acc&Ani, Donor and Cation=Don&Cat, Donor and Acceptor=Don&Acc, Aromatic=Aro, Hydrophobe=Hyd.

TABLE 6

| | | |
|---|---|---|
| Pharm-1nql-glue-5 Partial match, ligand must match at least 6 pharmacophore features. FIG. 2 | F(I)1 Don&Cat | Derived from MFSS (see above). Ligand donates an H-bond or forms a salt bridge to the carboxylate side chain of receptor Asp553 |
| | F(I)2 Don | Derived from MFSS. Ligand donates an H-bond to backbone carbonyl of receptor Thr570 |
| | F(I)3 Hyd | Derived from hydrophobic contact statistics. Ligand forms hydrophobic contacts with side chain of receptor Val568, imidazole side chain of receptor His566 and with the imidazolidine ring of receptor Pro552. This feature is marked essential |
| | F(I)4 Don&Cat | Derived from MFSS. Ligand donates an H-bond or forms a salt bridge to the side chain carboxylate of receptor Asp563. This feature is marked essential |
| | F(I)5 Hyd | Derived from hydrophobic contact statistics. Ligand forms hydrophobic contacts with the imidazoline ring of receptor Pro572 and the side chain of Met253 |
| | F(I)6 Don | Derived from MFSS. Ligand donates an H-bond to backbone carbonyl of receptor Cys571. This feature is marked essential |
| | F(I)7 Don2 | Directionality of F6 with respect to backbone carbonyl of receptor Cys571 |
| | F(I)8 Acc | Derived from MFSS. Ligand accepts an H-bond from receptor backbone NH of Ala573. This feature is marked essential |
| | F(I)9 Acc2 | Directionality of F8 with respect to backbone NH of Ala573 |
| | V1 | Excluded volume |

TABLE 7

Cartesian and spherical coordinates of features for pharmacophore Pharm-1nql-Glue-5.

| Feature | X | Y | Z | r | θ (theta) | φ (phi) | sphere radius (A) | sphere volume (A$^3$) | Preferred features |
|---|---|---|---|---|---|---|---|---|---|
| F(I)1 Don&Cat | 53.523 | −17.135 | −4.293 | 56.363 | 94.368 | −17.752 | 1.2 | 7.2 | |
| F(I)2 Don | 47.983 | −20.609 | −10.619 | 53.290 | 101.494 | −23.244 | 1 | 4.2 | |
| F(I)3 Hyd | 50.511 | −16.781 | −7.319 | 53.726 | 97.830 | −18.378 | 1.7 | 20.6 | preferred |
| F(I)4 Don&Cat | 51.625 | −19.900 | −9.294 | 56.103 | 99.536 | −21.080 | 1.2 | 7.2 | preferred |
| F(I)5 Hyd | 48.632 | −18.658 | −12.837 | 53.647 | 103.844 | −20.990 | 1.4 | 11.5 | |
| F(I)6 Don | 44.675 | −21.359 | −12.568 | 51.088 | 104.241 | −25.552 | 1.2 | 7.2 | preferred |
| F(I)7 Don2 | 45.067 | −23.421 | −12.644 | 52.340 | 103.980 | −27.461 | 1.5 | 14.1 | |
| F(I)8 Acc | 44.906 | −20.294 | −14.555 | 51.383 | 106.455 | −24.319 | 1.2 | 7.2 | preferred |
| F(I)9 Acc2 | 45.475 | −21.639 | −16.064 | 52.861 | 107.692 | −25.447 | 1.5 | 14.1 | |

Example 5

Ligand Docking and Scoring to Inactive EGFR Protein

The compounds selected for docking to the target protein, the inactive folded conformation of EGFr (PDB accession number 1NQL) were those which were found to align to the pharmacophore models generated in the MOE modeling software. These compounds were obtained in MOE database format. The 3-dimensional atomic coordinates of these compounds were written to a structure data format (*.sdf) file using the export command in the MOE database window without adding hydrogens.

The LigPrep software module of Maestro modeling software (Schrodinger LLC, NY, N.Y.) was next employed to prepare the compounds for docking. The *.sdf file was converted into Maestro format using LigPrep. Hydrogens were then added and any charged groups neutralized. Ionization states were generated for the ligands at 7.0+/−1.0 pH units. After this, tautomers were generated when necessary, alternate chiralities were generated and low energy ring conformers were produced. This was followed by removing any problematic structures and energy minimizing the resulting ligands using MacroModel software module. Finally a Maestro file (*.mae) was written of the ligands which were now ready for docking. All of these steps were automated via a python script supplied by Schrodinger, LLC.

The following describes protein preparation. The protein crystal structure of EGFr in its inactive state (1NQL.PBD) was imported into Maestro in PDB format. Hydrogens were added and any errors such as incomplete residues were repaired. The protein structure was checked for metal ions and cofactors. Charges and atom types were set for metal ions and cofactors as needed. Ligand bond orders and formal charges were adjusted if necessary. The binding site was determined by picking a ligand, ZINC3304802 which was one of the pharmacophore hits found by MOE, in Maestro (Glide). The program determines the centroid of the picked ligand and draws a 20 Angstrom box which is the default setting with the centroid of the ligand at the center of the box. The box was the binding site for the ligands to be docked. The protein preparation facility, which is automated in Glide, consists of two components, preparation and refinement. The preparation component added hydrogens and neutralized side chains that are not close to the binding site and do not participate in salt bridges. The refinement component performed a restrained minimization of the co-crystallized complex which reoriented side-chain hydroxyl groups and alleviated potential steric clashes.

The following describes receptor grid generation. Glide searches for favorable interactions between one or more ligand molecules and a receptor molecule, usually a protein. The shape and properties of the receptor are represented on a grid by several different sets of fields including hydrogen bonding, coulombic (i.e., charge-charge) interactions hydrophobic interactions, and steric clashes of the ligand with the protein. In the first step the receptor must be defined. This was done by picking the ligand. The unpicked part of the structure was the receptor. The ligand was not included in the grid calculation but was used to define the binding site as described above. Scaling of the nonpolar atoms of the receptor was not included in the present docking runs. The grids themselves were calculated within the space of the enclosing box. This is the box described above and all of the ligand atoms must be contained in this box. No pharmacophore constraints were used because the Glide extra precision scoring function performs better without these constraints.

To use Glide, each ligand must be a single molecule, while the receptor may include more than one molecule, e.g., a protein and a cofactor. Glide can be run in rigid or flexible docking modes; the latter automatically generates conformations for each input ligand. The combination of position and orientation of a ligand relative to the receptor, along with its conformation in flexible docking, is referred to as a ligand pose. All docking runs are done using the flexible docking mode. The ligand poses that Glide generates pass through a series of hierarchical filters that evaluate the ligand's interaction with the receptor. The initial filters test the spatial fit of the ligand to the defined active site, and examine the complementarity of ligand-receptor interactions using a grid-based method. Poses that pass these initial screens enter the final stage of the algorithm, which involves evaluation and minimization of a grid approximation to the OPLS-AA nonbonded ligand-receptor interaction energy. Final scoring is then carried out on the energy-minimized poses. By default, Schrödinger's proprietary GlideScore multi-ligand scoring function is used to score the poses. If GlideScore was selected as the scoring function, a composite Emodel score is then used to rank the poses of each ligand and to select the poses to be reported to the user. Emodel combines GlideScore, the nonbonded interaction energy, and, for flexible docking, the excess internal energy of the generated ligand conformation. Conformational flexibility is handled in Glide by an extensive conformational search, augmented by a heuristic screen that rapidly eliminates unsuitable conformations, such as conformations that have long-range internal hydrogen bonds.

The settings used in the docking runs of this example were as follows. Grid file was read in. Extra precision (XP) scoring function was used. Docked using conformational flexibility. 5000 poses per ligand for the initial Glide screen were kept (default). Scoring window for keeping initial poses was 100.0 (default). Best 800 poses per ligand for the energy minimization was kept (default). For the energy minimization, a distance dependent dielectric constant of 2.0 was used and maximum number of conjugate gradient steps was 100 (defaults). The ligand file was then loaded. Molecules with >120 atoms and/or >20 rotatable bonds were not docked (default). Van der Waals radii of ligand atoms with partial charges <0.15 were scaled by 0.80. This was done to mimic receptor flexibility. Constraints and similarity were not used. Poses with Coulomb plus Van der Waals energies >0.0 were rejected. To ensure that poses for each molecule were conformationally distinct, poses with RMS deviation <0.5 and/or maximum atomic displacement of 1.3 Angstroms were discarded.

The following describes Glide Scoring. The choice of best-docked structure for each ligand was made using a model energy score (Emodel) that combines the energy grid score, the binding affinity predicted by GlideScore, and (for flexible docking) the internal strain energy for the model potential used to direct the conformational-search algorithm. Glide also computed a specially constructed Coulomb-van der Waals interaction-energy score (CvdW) that was formulated to avoid overly rewarding charge-charge interactions at the expense of charge-dipole and dipole-dipole interactions. This score was intended to be more suitable for comparing the binding affinities of different ligands than is the "raw" Coulomb-van der Waals interaction energy. In the final data work-up, one can combine the computed GlideScore and "modified" Coulomb-van der Waals score values to give a composite score that can help improve enrichment factors in database screening applications. The mathematical form of the Glide score is:

$$GScore=0.065*EvdW+0.130*Coul+Lipo+Hbond+Metal+BuryP+RotB+Site$$

where EvdW is van der Waals energy (calculated with reduced net ionic charges on groups with formal charges, such as metals, carboxylates, and guanidiniums); Coul is the Coulomb energy (calculated with reduced net ionic charges on groups with formal charges, such as metals, carboxylates, and guanidiniums); Lipo is the lipophilic contact term (rewards favorable hydrophobic interactions); HBond is the hydrogen-bonding term (separated into differently weighted components that depend on whether the donor and acceptor are neutral, one is neutral and the other is charged, or both are charged); metal is the metal-binding term (only the interactions with anionic acceptor atoms are included; if the net metal charge in the apo protein is positive, the preference for anionic ligands is included; if the net charge is zero, the preference is suppressed); BuryP is the penalty for buried polar groups; RotB is the penalty for freezing rotatable bonds; and Site is polar interactions in the active site (polar but non-hydrogen-bonding atoms in a hydrophobic region are rewarded).

The following describes generation of the virtual compound library that was screened. The lead-like compounds from a free, virtual database of commercially available compounds was downloaded in structure data format (sdf, Molecular Design Limited) from the ZINC database (Irwin and Shoichet (2005) J. Chem. Inf. Model. 45(1), 177-182). The lead-like database is comprised of approximately 890,000 compounds divided into 33 segments. This was used to generate the database of conformers for screening by MOE. Hydrogens were then added. For a pharmacophore search, a database of low energy conformers must be generated. The Conformation Import command was applied to the sdf file above. After the conformers were generated, preprocessing of the conformer database was applied. This step, called feature annotation, determined the types of pharmacophore features in each molecule/conformation and their geometrical relationships. This was then compared with the query and those molecules/conformations that matched the query within the given tolerance were saved as hits.

Analysis of compounds from the ZINC database against the pharmacophores identified from the 1NQL.PDB crystal structure of protein EGFR according to the methods described above identified compound AD4-1505.

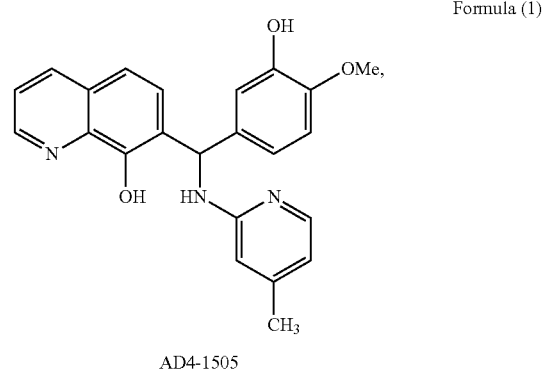 [SMILES: COc1ccc(C(Nc2cc(C)ccn2)c2ccc3cccnc3c2O)cc1O]

Formula (1)

AD4-1505

The AD4-1505-like compounds in the following tables were identified via structure similarity searches and were docked to the 1NQL.PDB binding site to obtain their Glide and Emodel scores.

The compounds in TABLE 8 were identified via AD4-1505 structure similarity searches and were docked to the 1NQL.PDB binding site to obtain their Glide and Emodel scores. Also depicted in TABLE 8 is ICW assay and MTT assay results (See Example 1, Example 2, Example 5).

TABLE 8

Glide Score, E-Model score, ICW assay, and MTT Assay Results for AD4-1505-like Compounds.

| Compound | AD4-Number | G-Score | E-Model Score | ICW Screen | Re-Test | MTT-72 h A431/MDBK (ratio) | MTT (10 Point follow-up) | Pharmacophore Model |
|---|---|---|---|---|---|---|---|---|
| (structure) | 10963 | −6.63 | −46.58 | 100.4 | 99.05 | 13.87/27.45 (1.98) 40% Max | | 1NQL-AD4-1505 LIKE |
| (structure) | 10961 | −6.19 | −46.38 | 94.69 | 71.58 | 32.41/43.48 (1.34) 50% Max | | 1NQL-AD4-1505 LIKE |
| (structure) | 10945 | −7.68 | −57.26 | 82.22 | 81.41 | 2.79/1.87 (0.67) | 2.45/1.87 (0.76) | 1NQL-AD4-1505 LIKE |
| (structure) | 10315 | −6.07 | −37.37 | 80.77 | 92.46 | 4.52/5.69 (1.26) | 0.697/0.783 (1.12) | AD4-1505 LIKE Dockpharm |
| (structure) | 10965 | −6.34 | −50.24 | 74.54 | 92.26 | 3.83/3.83 (1.00) | | 1NQL-AD4-1505 LIKE |
| (structure) | 10944 | −5.11 | −44.6 | 68.22 | 67.75 | 2.03/2.96 (1.46) | 1.86/2.73 (1.47) | 1NQL-AD4-1505 LIKE |

TABLE 8-continued

Glide Score, E-Model score, ICW assay, and MTT Assay Results for AD4-1505-like Compounds.

| Compound | AD4-Number | G-Score | E-Model Score | ICW Screen | Re-Test | MTT-72 h A431/MDBK (ratio) | MTT (10 Point follow-up) | Pharmacophore Model |
|---|---|---|---|---|---|---|---|---|
| (structure) | 11015 | −6.99 | −50.79 | 64.21 | 57.97 | 5.07/3.87 (0.76) | | 1NQL-AD4-10664 LIKE - WANG |
| (structure) | 10664 | −6.31 | −42.67 | 64.09 | 69.21 | 1.92/2.14 (1.12) | | 1NQL-Glue-AD4-1505 LIKE - WANG |
| (structure) | 1978 | −6.36 | −59.67 | 63.53 | 41.95 | 7.30/10.7 (1.47) | | 1NQL-Glue - AD4-1505 LIKE |
| (structure) | 10087 | −7.14 | −52.29 | 62.13 | 41.13 | 5.23/5.79 (1.11) | 4.70/5.55 (1.18) | 1NQL-Glue-AD4-1505 LIKE |
| (structure) | 10013 | −6.27 | −49.84 | 61.2 | 62.77 | 3.56/6.42 (1.80) | 3.53/6.32 (1.79) | 1NQL-Glue-AD4-1505 LIKE |
| (structure) | 10958 | −5.69 | −43.69 | 60.73 | 70.92 | 14.8/9.67 (0.65) | | 1NQL-AD4-1505 LIKE |

TABLE 8-continued

Glide Score, E-Model score, ICW assay, and MTT Assay Results for AD4-1505-like Compounds.

| Compound | AD4-Number | G-Score | E-Model Score | ICW Screen | Re-Test | MTT-72 h A431/MDBK (ratio) | MTT (10 Point follow-up) | Pharmacophore Model |
|---|---|---|---|---|---|---|---|---|
| (structure) | 11152 | −7.22 | −52.49 | 60.41 | 48.96 | 9.0/8.24 (0.92) | | 1NQL-AD4-10664 LIKE - WANG |
| (structure) | 10602 | −6.13 | −37.04 | 57.72 | 43.06 | 3.56/2.31 (0.65) | 3.30/2.35 (0.71) | AD4-1505 LIKE Dockpharm |
| (structure) | 10942 | −8.04 | −54.57 | 56.15 | 95.43 | 33.33/36.24 (1.09) | | 1NQL-AD4-1505 LIKE |
| (structure) | 1505 | −7.06 | −51.44 | 55.71 | 47.05 | 8.36/9.33 (1.12) | | 1NQL-Glue |
| (structure) | 1973 | −7.29 | −47.24 | 54.76 | 53.31 | 14.23/7.50 (0.53) | | 1NQL-Glue-AD4-1505 LIKE |
| (structure) | 1073 | −7.49 | −54.79 | 54.34 | 38.77 | 4.83/7.41 (1.53) | | 1NQL-AD4-10664 LIKE - WANG |

TABLE 8-continued

Glide Score, E-Model score, ICW assay, and MTT Assay Results for AD4-1505-like Compounds.

| Compound | AD4-Number | G-Score | E-Model Score | ICW Screen | Re-Test | MTT-72 h A431/MDBK (ratio) | MTT (10 Point follow-up) | Pharmacophore Model |
|---|---|---|---|---|---|---|---|---|
| (structure) | 10086 | −7.19 | −48.51 | 53.89 | 25.94 | 5.96/4.61 (0.77) | | 1NQL-Glue-AD4-1505 LIKE |
| (structure) | 11042 | −6.7 | −46.5 | 53.72 | 71.32 | 3.93/3.72 (1.06) | | 1NQL-AD4-10664 LIKE - WANG |
| (structure) | 10975 | −6.02 | −44.09 | 53.5 | 34.86 | 52.17/35.58 (0.68) | | 1NQL-AD4-1505 LIKE |
| (structure) | 11103 | −6.76 | −54.18 | 50.55 | 45.86 | 20.78/36.37 (1.75) | | 1NQL-AD4-10664 LIKE - WANG |
| (structure) | 10974 | −8.46 | −54.71 | 50.44 | 44.13 | 4.19/4.77 (1.14) | | 1NQL-AD4-1505 LIKE |
| (structure) | 10957 | −5.45 | −45.84 | 49.8 | 39.03 | 17.52/14.09 (0.80) | | 1NQL-AD4-1505 LIKE |

TABLE 8-continued

Glide Score, E-Model score, ICW assay, and MTT Assay Results for AD4-1505-like Compounds.

| Compound | AD4-Number | G-Score | E-Model Score | ICW Screen | Re-Test | MTT-72 h A431/MDBK (ratio) | MTT (10 Point follow-up) | Pharmacophore Model |
|---|---|---|---|---|---|---|---|---|
| *(structure)* | 10952 | −7.26 | −48.81 | 49.39 | 43.94 | 10.50/7.77 (0.74) | | 1NQL-AD4-1505 LIKE |
| *(structure)* | 10033 | −5.85 | −40.98 | 49.36 | 5.98 | 1.85/4.62 (2.49) | 1.81/4.43 (2.44) | 1NQL-Glue-AD4-1505 LIKE |
| *(structure)* | 11105 | −6.8 | −46.19 | 48.25 | 17.88 | 5.46/7.03 (1.29) | 4.72/6.50 (1.38) | 1NQL-AD4-10664 LIKE - WANG |
| *(structure)* | 10042 | −5.1 | −46.89 | 47.99 | −8.06 | 1.49/1.49 (1.00) | 9.62/6.63 (0.69) | 1NQL-Glue-AD4-1505 LIKE |
| *(structure)* | 11014 | −5.9 | −42.04 | 47.81 | 32.53 | 4.68/4.32 (0.92) | | 1NQL-AD4-10664 LIKE - WANG |
| *(structure)* | 1991 | −5.54 | −57.53 | 47.06 | 30.75 | 9.08/7.14 (0.79) | | 1NQL-Glue-AD4-1505 LIKE |

TABLE 8-continued

Glide Score, E-Model score, ICW assay, and MTT Assay Results for AD4-1505-like Compounds.

| Compound | AD4-Number | G-Score | E-Model Score | ICW Screen | Re-Test | MTT-72 h A431/MDBK (ratio) | MTT (10 Point follow-up) | Pharmacophore Model |
|---|---|---|---|---|---|---|---|---|
| (structure) | 1968 | −6.87 | −45.76 | 46.48 | 20.95 | 7.14/6.15 (0.86) | | 1NQL-Glue-AD4-1505 LIKE |
| (structure) | 10143 | −7.04 | −53.91 | 45.61 | 27.18 | 4.74/4.33 (0.92) | | 1NQL-Glue-AD4-1505 LIKE |
| (structure) | 10041 | −5.93 | −50.66 | 45.08 | 3.45 | 2.95/2.94 (1.00) | 1.59/2.34 (1.47) | 1NQL-Glue-AD4-1505 LIKE |
| (structure) | 10048 | −4.85 | −45.12 | 44.94 | 15.3 | 81% @ 2.6 μM | 5.46/5.23 (0.96) | 1NQL-Glue-AD4-1505 LIKE |
| (structure) | 11057 | −6.87 | −46.98 | 44.4 | 73.29 | 7.99/7.86 (0.98) | | 1NQL-AD4-10664 LIKE - WANG |

TABLE 8-continued

Glide Score, E-Model score, ICW assay, and MTT Assay Results for AD4-1505-like Compounds.

| Compound | AD4-Number | G-Score | E-Model Score | ICW Screen | Re-Test | MTT-72 h A431/MDBK (ratio) | MTT (10 Point follow-up) | Pharmacophore Model |
|---|---|---|---|---|---|---|---|---|
| (structure) | 11102 | −8.69 | −51.71 | 44.31 | 39.06 | 7.39/7.66 (1.04) | | 1NQL-AD4-10664 LIKE - WANG |
| (structure) | 10943 | −7.66 | −53.85 | 44.28 | 68.79 | 1.31/2.10 (1.60) | 1.25/1.88 (1.50) | 1NQL-AD4-1505 LIKE |
| (structure) | 10017 | −6.59 | −54.84 | 44.27 | 30.11 | 3.72/3.51 (0.94) | 3.52/2.98 (0.85) | 1NQL-Glue-AD4 1505 LIKE |
| (structure) | 10948 | −5.76 | −39.8 | 44.24 | 30.99 | 8.87/11.89 (1.34) | | 1NQL-AD4-1505 LIKE |
| (structure) | 11072 | −6.64 | −45.28 | 44.06 | 36.82 | 43.17/21.05 (0.49) 12% Max | | 1NQL-AD4-10664 LIKE-WANG |

TABLE 8-continued
Glide Score, E-Model score, ICW assay, and MTT Assay Results for AD4-1505-like Compounds.
| Compound | AD4-Number | G-Score | E-Model Score | ICW Screen | Re-Test | MTT-72 h A431/MDBK (ratio) | MTT (10 Point follow-up) | Pharmacophore Model |
|---|---|---|---|---|---|---|---|---|
| 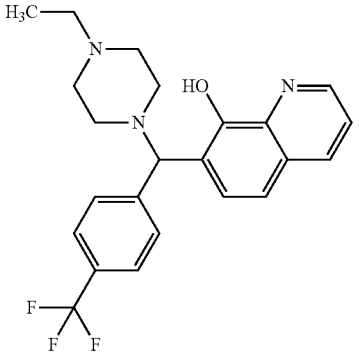 [SMILES: CCN1CCN(C(c2ccc(C(F)(F)F)cc2)c2ccc3cccnc3c2O)CC1] | 10535 | −6.17 | −40.69 | 44.02 | 52.63 | 2.72/3.95 (1.45) | 2.04/2.91 (1.43) | AD4-1505 LIKE Dockpharm |
| 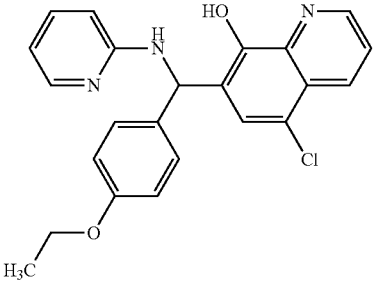 [SMILES: CCOc1ccc(C(Nc2ccccn2)c2cc(Cl)c3cccnc3c2O)cc1] | 10101 | −7.83 | −56.24 | 44.01 | 7.53 | 5.77/9.52 (1.66) | 2.88/2.59 (0.90) | 1NQL-Glue-AD4-1505 LIKE |
| 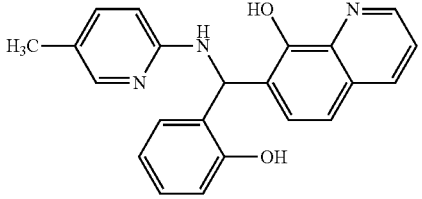 [SMILES: Cc1ccc(NC(c2ccccc2O)c2ccc3cccnc3c2O)nc1] | 10430 | −5.99 | −48.35 | 43.81 | 48.57 | 6.47/5.58 (0.86) | | 1NQL-Glue-AD4-1505 LIKE |
| 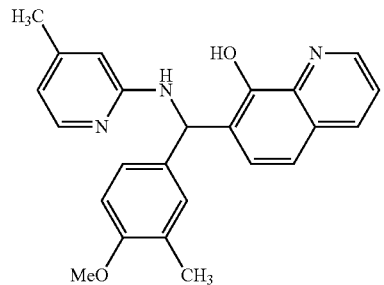 [SMILES: COc1ccc(C(Nc2cc(C)ccn2)c2ccc3cccnc3c2O)cc1C] | 10005 | −7.36 | −45.54 | 43.76 | 33.76 | 3.44/3.69 (1.07) | 3.45/4.14 (1.20) | 1NQL-Glue-AD4-1505 LIKE |
| 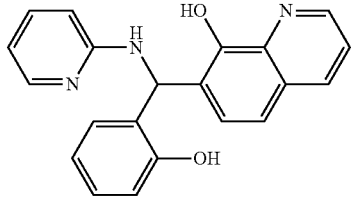 [SMILES: Oc1ccccc1C(Nc1ccccn1)c1ccc2cccnc2c1O] | 10427 | −5.79 | −48.95 | 43.39 | 43.82 | 5.56/4.82 (0.87) | | 1NQL-Glue-AD4-1505 LIKE |

TABLE 8-continued

Glide Score, E-Model score, ICW assay, and MTT Assay Results for AD4-1505-like Compounds.

| Compound | AD4-Number | G-Score | E-Model Score | ICW Screen | Re-Test | MTT-72 h A431/MDBK (ratio) | MTT (10 Point follow-up) | Pharmacophore Model |
|---|---|---|---|---|---|---|---|---|
| [structure] | 10052 | −7.8 | −59.71 | 43.1 | 20.95 | 2.35/?? | 13.80/9.25 (0.67) | 1NQL-Glue-AD4-1505 LIKE |
| [structure] | 10947 | −5.87 | −58.29 | 42.78 | 42.98 | 5.15/2.66 (0.52) | | 1NQL-AD4-1505 LIKE |
| [structure] | 10959 | −6.14 | −51.78 | 42.18 | 87.34 | 0.98/2.43 (2.47) | 0.960/2.07 (2.16) | 1NQL-AD4-1505 LIKE |
| [structure] | 10016 | −6.67 | −44.5 | 41.45 | 29.99 | 25.80/25.78 (1.00) | | 1NQL-Glue-AD4-1505 LIKE |

TABLE 8-continued

Glide Score, E-Model score, ICW assay, and MTT Assay Results for AD4-1505-like Compounds.

| Compound | AD4-Number | G-Score | E-Model Score | ICW Screen | Re-Test | MTT-72 h A431/MDBK (ratio) | MTT (10 Point follow-up) | Pharmacophore Model |
|---|---|---|---|---|---|---|---|---|
| (structure) | 10071 | −7.67 | −52.06 | 40.85 | 43.19 | 7.89/10.78 (1.37) | | 1NQL-Glue-AD4-1505 LIKE |
| (structure) | 10938 | −6.55 | −48.23 | 40.36 | 24.99 | 25.26/22.11 (0.88) | | 1NQL-AD4-1505 LIKE |
| (structure) | 11191 | −6.54 | −51.11 | 40.32 | 22.02 | 5.59/5.53 (0.99) | | 1NQL-Glue-AD4-1505 LIKE |
| (structure) | 10029 | −5.67 | −54.36 | 40.02 | 35.03 | 6.46/5.42 (0.84) | | 1NQL-Glue-AD4-1505 LIKE |
| (structure) | 10518 | −6.07 | −48.79 | 39.93 | 51.72 | 6.52/5.43 (0.83) | | 1NQL-Glue-AD4-1505 LIKE |

TABLE 8-continued

Glide Score, E-Model score, ICW assay, and MTT Assay Results for AD4-1505-like Compounds.

| Compound | AD4-Number | G-Score | E-Model Score | ICW Screen | Re-Test | MTT-72 h A431/MDBK (ratio) | MTT (10 Point follow-up) | Pharmacophore Model |
|---|---|---|---|---|---|---|---|---|
| (structure) | 10144 | −7.75 | −54.81 | 39.73 | 21.02 | 5.67/5.29 (0.93) | | 1NQL-Glue-AD4-1505 LIKE |
| (structure) | 10524 | −5.87 | −49.63 | 38.96 | 30.44 | 5.33/5.09 (0.95) | | 1NQL-Glue-AD4-1505 LIKE |
| (structure) | 10951 | −6.02 | −44.92 | 38.95 | 31.33 | 5.58/5.44 (0.97) | | 1NQL-AD4-1505 LIKE |
| (structure) | 10940 | −7.1 | −52.86 | 38.28 | 72.45 | 13.64/16.57 (1.21) 57% Max | 0.336/0.594 (1.77) | 1NQL-AD4-1505 LIKE |
| (structure) | 10936 | −6.55 | −52.41 | 37.96 | 57 | 5.43/5.68 (1.05) | | 1NQL-AD4-1505 LIKE |

TABLE 8-continued
Glide Score, E-Model score, ICW assay, and MTT Assay Results for AD4-1505-like Compounds.
| Compound | AD4-Number | G-Score | E-Model Score | ICW Screen | Re-Test | MTT-72 h A431/MDBK (ratio) | MTT (10 Point follow-up) | Pharmacophore Model |
|---|---|---|---|---|---|---|---|---|
| 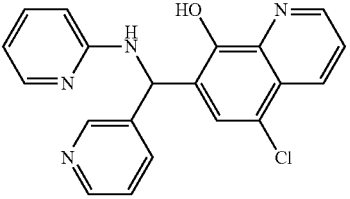 [SMILES: Oc1c(C(Nc2ccccn2)c2cccnc2)cc(Cl)c2cccnc12] | 10955 | −6.87 | −49.16 | 37.33 | 53.58 | 5.50/5.36 (0.97) | | 1NQL-AD4-1505 LIKE |
| 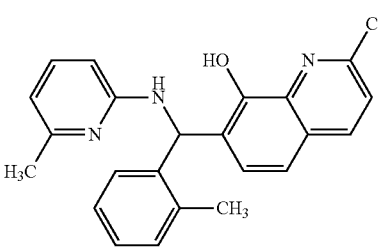 | 10026 | −5.65 | −43.58 | 37.03 | 41.06 | 5.22/5.19 (0.97) | | 1NQL-Glue-AD4-1505 LIKE |
| 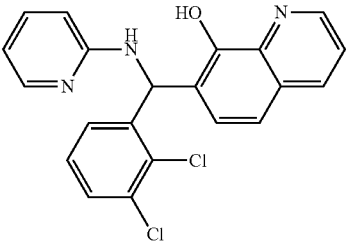 [SMILES: Oc1c(C(Nc2ccccn2)c2cccc(Cl)c2Cl)ccc2cccnc12] | 10051 | −5.92 | −44.03 | 36.47 | NA | 0.79/1.42 (1.80) | 0.545/0.974 (1.79) | 1NQL-Glue-AD4-1505 LIKE |
| 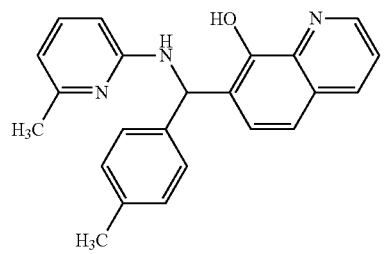 [SMILES: Cc1ccc(C(Nc2cccc(C)n2)c2ccc3cccnc3c2O)cc1] | 10054 | −6.23 | −47.03 | 35.84 | NA | 5.47/5.46 (1.00) | | 1NQL-Glue-AD4-1505 LIKE |
| 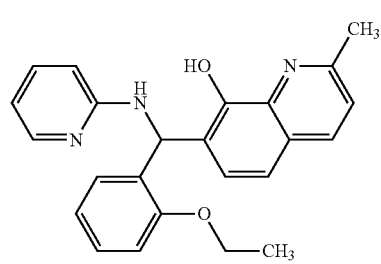 [SMILES: CCOc1ccccc1C(Nc1ccccn1)c1ccc2ccc(C)nc2c1O] | 10049 | −5.45 | −46.29 | 35.57 | NA | 12.18/11.50 (0.94) | | 1NQL-Glue-AD4-1505 LIKE |
| 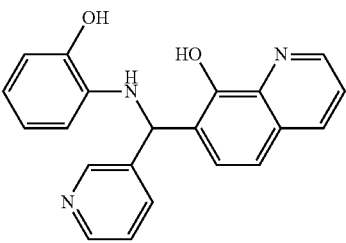 [SMILES: Oc1ccccc1NC(c1cccnc1)c1ccc2cccnc2c1O] | 11151 | −6.76 | −42.93 | 35.56 | 45.66 | 8.25/6.23 (0.76) | | 1NQL-AD4-10664 LIKE - WANG |

TABLE 8-continued

Glide Score, E-Model score, ICW assay, and MTT Assay Results for AD4-1505-like Compounds.

| Compound | AD4-Number | G-Score | E-Model Score | ICW Screen | Re-Test | MTT-72 h A431/MDBK (ratio) | MTT (10 Point follow-up) | Pharmacophore Model |
|---|---|---|---|---|---|---|---|---|
| (structure) | 10006 | −7.36 | −53.23 | 35.13 | 45.57 | 11.01/15.12 (1.37) | | 1NQL-Glue-AD4-1505 LIKE |
| (structure) | 10043 | −6.25 | −45.79 | 34.63 | NA | 77% @ 2.6 µM | 5.46/5.29 (0.97) | 1NQL-Glue-AD4-1505 LIKE |
| (structure) | 10031 | −7.19 | −50.93 | 34.62 | NA | 9.39/6.09 (0.65) | | 1NQL-Glue-AD4-1505 LIKE |
| (structure) | 10056 | −5.88 | −49 | 34.16 | 44.46 | 5.38/5.18 (0.96) | | 1NQL-Glue-AD4-1505 LIKE |
| (structure) | 10950 | −5.09 | −38.43 | 33.87 | 99.56 | 0.56/0.95 (1.70) | 0.540/0.878 (1.63) | 1NQL-AD4-1505 LIKE |

TABLE 8-continued
Glide Score, E-Model score, ICW assay, and MTT Assay Results for AD4-1505-like Compounds.
| Compound | AD4-Number | G-Score | E-Model Score | ICW Screen | Re-Test | MTT-72 h A431/MDBK (ratio) | MTT (10 Point follow-up) | Pharma-cophore Model |
|---|---|---|---|---|---|---|---|---|
| 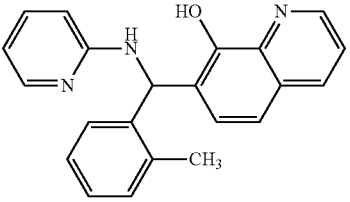 [SMILES: Cc1ccccc1C(Nc1ccccn1)c1ccc2cccnc2c1O] | 10019 | −6.92 | −42.42 | 33.75 | NA | 5.35/5.25 (0.98) | 4.49/3.21 (0.71) | 1NQL-Glue-AD4-1505 LIKE |
| 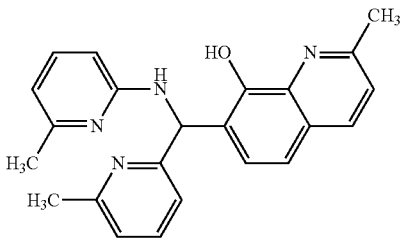 [SMILES: Cc1cccc(NC(c2cccc(C)n2)c2ccc3ccc(C)nc3c2O)n1] | 10976 | −6.08 | −41.04 | 33.22 | 21.78 | 25.11/19.65 (0.78) | | 1NQL-AD4-1505 LIKE |
| 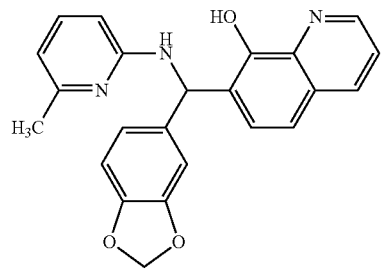 [SMILES: Cc1cccc(NC(c2ccc3c(c2)OCO3)c2ccc3cccnc3c2O)n1] | 10487 | −7.84 | −60.37 | 33.14 | NA | 5.51/5.28 (0.96) | 1.33/0.963 (0.72) | 1NQL-Glue-AD4-1505 LIKE |
| 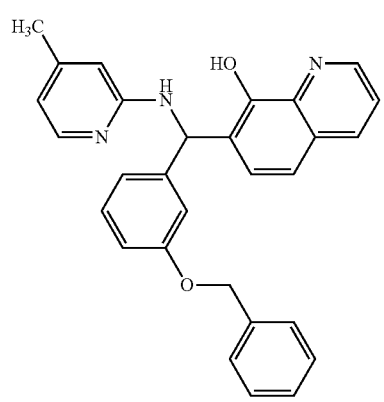 [SMILES: Cc1ccnc(NC(c2cccc(OCc3ccccc3)c2)c2ccc3cccnc3c2O)c1] | 10053 | −6.44 | −56.83 | 32.85 | NA | 77% @ 2.6 μM | 3.98/0.440 (0.11) | 1NQL-Glue-AD4-1505 LIKE |
| 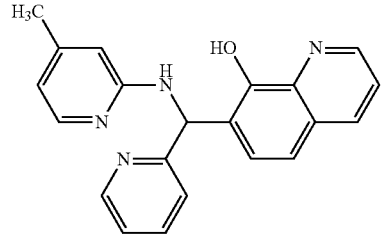 [SMILES: Cc1ccnc(NC(c2ccccn2)c2ccc3cccnc3c2O)c1] | 10939 | −6.15 | −37.13 | 32.68 | 33.81 | 5.67/6.78 (1.20) | | 1NQL-AD4-1505 LIKE |

TABLE 8-continued

Glide Score, E-Model score, ICW assay, and MTT Assay Results for AD4-1505-like Compounds.

| Compound | AD4-Number | G-Score | E-Model Score | ICW Screen | Re-Test | MTT-72 h A431/MDBK (ratio) | MTT (10 Point follow-up) | Pharmacophore Model |
|---|---|---|---|---|---|---|---|---|
| (structure) | 10960 | −4.84 | −36.55 | 32.5 | 91.3 | 0.67/1.02 (1.52) | 0.648/0.967 (1.49) | 1NQL-AD4-1505 LIKE |
| (structure) | 11056 | −5.45 | −46.32 | 32.48 | 18.32 | 6.35/5.94 (0.94) | | 1NQL-AD4-10664 LIKE - WANG |
| (structure) | 10037 | −5.27 | −53.05 | 32.12 | NA | 42.99/18.18 (0.42) | | 1NQL-Glue-AD4-1505 LIKE |
| (structure) | 10050 | −6.63 | −51.02 | 32.11 | NA | 5.39/5.35 (0.97) | | 1NQL-Glue-AD4-1505 LIKE |
| (structure) | 10550 | −6.49 | −42.05 | 31.84 | NA | 9.59/7.60 (0.79) | | AD4-1505 LIKE Dockpharm |

TABLE 8-continued

Glide Score, E-Model score, ICW assay, and MTT Assay Results for AD4-1505-like Compounds.

| Compound | AD4-Number | G-Score | E-Model Score | ICW Screen | Re-Test | MTT-72 h A431/MDBK (ratio) | MTT (10 Point follow-up) | Pharma-cophore Model |
|---|---|---|---|---|---|---|---|---|
| | 10509 | −5.48 | −43.38 | 31.55 | NA | 1.28/2.05 (1.60) | 1.25/1.95 (1.56) | 1NQL-Glue-AD4-1505 LIKE |
| | 10954 | −7.12 | −41.92 | 31.09 | NA | 1.72/2.29 (1.33) | 1.62/2.17 (1.26) | 1NQL-AD4-1505 LIKE |
| | 10548 | −6.74 | −34.66 | 31.03 | NA | 9.05/8.07 (0.89) | | AD4-1505 LIKE Dockpharm |
| | 10953 | −7.81 | −56.88 | 30.86 | 41.04 | 5.42/5.56 (1.03) | | 1NQL-AD4-1505 LIKE |
| | 10969 | −5.36 | −54.59 | 30.17 | 73.15 | 77% @ 2.6 μM | 0.510/0.520 (1.02) | 1NQL-AD4-1505 LIKE |

TABLE 8-continued

Glide Score, E-Model score, ICW assay, and MTT Assay Results for AD4-1505-like Compounds.

| Compound | AD4-Number | G-Score | E-Model Score | ICW Screen | Re-Test | MTT-72 h A431/MDBK (ratio) | MTT (10 Point follow-up) | Pharmacophore Model |
|---|---|---|---|---|---|---|---|---|
| (structure) | 10028 | −7.6 | −55.04 | 30.12 | NA | 5.69/5.38 (0.95) | | 1NQL-Glue-AD4-1505 LIKE |
| (structure) | 10628 | −5.3 | −50.97 | 30.02 | NA | 0.32/0.76 (2.38) | 0.311/0.689 (2.22) | 1NQL-Glue-AD4-1505 LIKE |
| (structure) | 10068 | −6.52 | −53.71 | 29.92 | NA | 5.72/5.19 (0.91) | | 1NQL-Glue-AD4-1505 LIKE |
| (structure) | 1969 | −6.89 | −46.44 | 29.61 | 39.58 | 15.04/13.58 (0.90) | | 1NQL-Glue-AD4-1505 LIKE |
| (structure) | 10551 | −7.17 | −40.53 | 29.14 | NA | 20.06/11.37 (0.57) | | A04-1505 LIKE Dockpharm |

TABLE 8-continued

Glide Score, E-Model score, ICW assay, and MTT Assay Results for AD4-1505-like Compounds.

| Compound | AD4-Number | G-Score | E-Model Score | ICW Screen | Re-Test | MTT-72 h A431/MDBK (ratio) | MTT (10 Point follow-up) | Pharma-cophore Model |
|---|---|---|---|---|---|---|---|---|
| (structure) | 1997 | −6.28 | −41.92 | 29 | NA | 46.75/24.32 (0.52) | | 1NQL-Glue-AD4-1505 LIKE |
| (structure) | 10058 | −5.22 | −46.37 | 28.52 | NA | 5.14/5.83 (1.13) | 1.08/1.68 (1.56) | 1NQL-Glue-AD4-1505 LIKE |
| (structure) | 10038 | −7.89 | −56.99 | 28.31 | NA | 5.75/5.42 (0.94) | | 1NQL-Glue-AD4-1505 LIKE |
| (structure) | 10534 | −5.52 | −39.11 | 28.31 | NA | 10.83/9.18 (0.85) | | AD4-1505 LIKE Dockpharm |
| (structure) | 11153 | −6.23 | −42.43 | 28.24 | 20.64 | 13.09/5.58 (0.43) | | 1NQL-AD4-10664 LIKE - WANG |

TABLE 8-continued
Glide Score, E-Model score, ICW assay, and MTT Assay Results for AD4-1505-like Compounds.
| Compound | AD4-Number | G-Score | E-Model Score | ICW Screen | Re-Test | MTT-72 h A431/MDBK (ratio) | MTT (10 Point follow-up) | Pharmacophore Model |
|---|---|---|---|---|---|---|---|---|
| 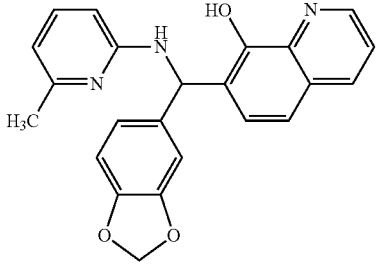 [SMILES: Cc1cccc(NC(c2ccc3c(c2)OCO3)c2ccc3cccnc3c2O)n1] | 10055 | −5.62 | −50.09 | 28.09 | NA | 12.05/8.17 (0.68) | | 1NQL-Glue-AD4-1505 LIKE |
| 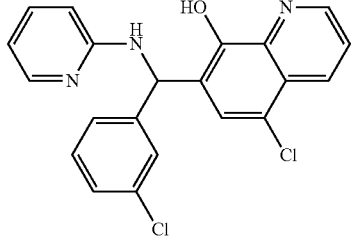 | 10097 | −5.42 | −44.92 | 28.02 | NA | 6.23/6.09 (0.98) | 1.25/2.07 (1.66) | 1NQL-Glue-AD4-1505 LIKE |
| 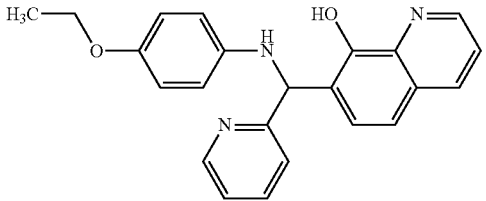 [SMILES: CCOc1ccc(NC(c2ccccn2)c2ccc3cccnc3c2O)cc1] | 11000 | −7.1 | −58.19 | 27.62 | NA | 11.39/11.24 (0.99) | | 1NQL-AD4-10664 LIKE - WANG |
| 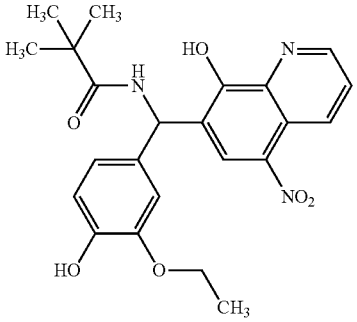 [SMILES: CCOc1cc(C(NC(=O)C(C)(C)C)c2cc([N+](=O)[O-])c3cccnc3c2O)ccc1O] | 10941 | −3.24 | −45.2 | 27.61 | 67.81 | 5.92/6.05 (1.02) | 1.12/1.75 (1.56) | 1NQL-AD4-1505 LIKE |
| 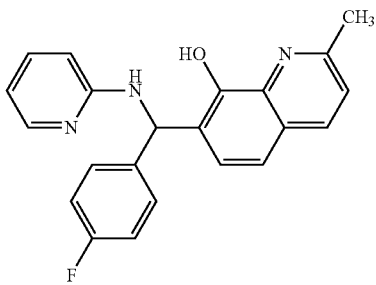 [SMILES: Cc1ccc2ccc(C(Nc3ccccn3)c3ccc(F)cc3)c(O)c2n1] | 10045 | −5.39 | −38.19 | 27.22 | NA | 13.49/9.85 (0.73) | | 1NQL-Glue-AD4-1505 LIKE |

TABLE 8-continued

Glide Score, E-Model score, ICW assay, and MTT Assay Results for AD4-1505-like Compounds.

| Compound | AD4-Number | G-Score | E-Model Score | ICW Screen | Re-Test | MTT-72 h A431/MDBK (ratio) | MTT (10 Point follow-up) | Pharma-cophore Model |
|---|---|---|---|---|---|---|---|---|
| (structure) | 10034 | −7.29 | −44.28 | 27.1 | NA | 12.00/7.16 (0.60) | | 1NQL-Glue-AD4-1505 LIKE |
| (structure) | 1979 | −5.27 | −41.84 | 27.02 | NA | 5.69/5.38 (0.95) | | 1NQL-Glue-AD4-1505 LIKE |
| (structure) | 10968 | −6.1 | −39.69 | 27 | NA | 11.10/7.84 (0.71) | | 1NQL-AD4-1505 LIKE |
| (structure) | 10949 | −6.6 | −51.81 | 26.99 | NA | 5.63/5.79 (1.03) | | 1NQL-AD4-1505 LIKE |
| (structure) | 1976 | −6.61 | −43.66 | 26.91 | NA | 26.15/13.00 (0.50) | | 1NQL-Glue-AD4-1505 LIKE |

TABLE 8-continued
Glide Score, E-Model score, ICW assay, and MTT Assay Results for AD4-1505-like Compounds.
| Compound | AD4-Number | G-Score | E-Model Score | ICW Screen | Re-Test | MTT-72 h A431/MDBK (ratio) | MTT (10 Point follow-up) | Pharmacophore Model |
|---|---|---|---|---|---|---|---|---|
| 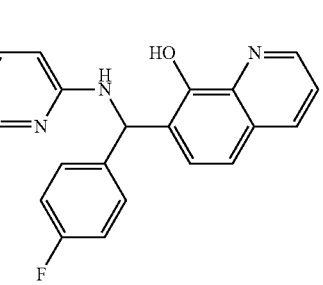 | 10522 | −6.3 | −47.33 | 26.6 | NA | 70% @ 2.6 μM | 1.65/1.89 (1.14) | 1NQL-Glue-AD4-1505 LIKE |
| 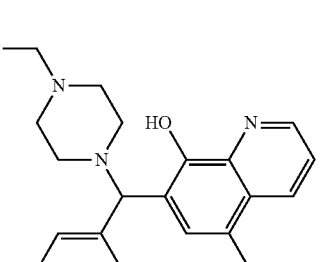 | 10547 | −5.84 | −49.69 | 26.4 | NA | 11.45/5.96 (0.52) | | AD4-1505 LIKE Dockpharm |
| 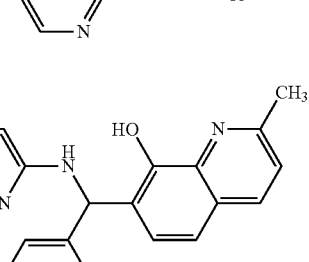 | 1970 | −6.53 | −46.83 | 26.33 | NA | 39.71/32.35 (0.81) | | 1NQL-Glue-AD4-1505 LIKE |
| 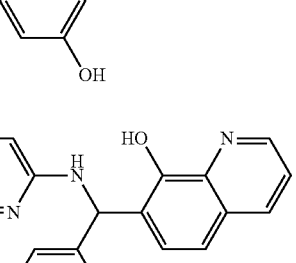 | 10484 | −6.33 | −44.93 | 26.3 | NA | 0.32/0.85 (2.70) | 0.305/0.679 (2.12) | 1NQL-Glue-AD4-1505 LIKE |
| 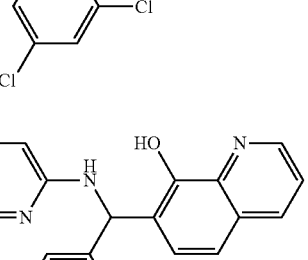 | 10015 | −5.49 | −41.91 | 25.99 | NA | 66% @ 2.6 μM | 3.31/3.28 (0.99) | 1NQL-Glue-AD4-1505 LIKE |

TABLE 8-continued

Glide Score, E-Model score, ICW assay, and MTT Assay Results for AD4-1505-like Compounds.

| Compound | AD4-Number | G-Score | E-Model Score | ICW Screen | Re-Test | MTT-72 h A431/MDBK (ratio) | MTT (10 Point follow-up) | Pharmacophore Model |
|---|---|---|---|---|---|---|---|---|
| (structure) | 10967 | −6.84 | −44.14 | 25.98 | 15.92 | 46.03/31.00 (0.67) | | 1NQL-AD4-1505 LIKE |
| (structure) | 10481 | −5.95 | −50.26 | 25.82 | NA | 86% @ 2.6 μM | 0.798/1.23 (1.54) | 1NQL-Glue-AD4-1505 LIKE |
| (structure) | 11018 | −6.22 | −41.05 | 25.31 | 21.62 | 9.11/8.10 (0.89) | | 1NQL-AD4-10664 LIKE - WANG |
| (structure) | 10546 | −5.84 | −37.65 | 25.23 | NA | 7.03/5.92 (0.84) | | AD4-1505 LIKE Dockpharm |
| (structure) | 10093 | −7.27 | −48.84 | 25.13 | NA | 31.37/21.48 (0.68) | | 1NQL-Glue-AD4-1505 LIKE |

TABLE 8-continued

Glide Score, E-Model score, ICW assay, and MTT Assay Results for AD4-1505-like Compounds.

| Compound | AD4-Number | G-Score | E-Model Score | ICW Screen | Re-Test | MTT-72 h A431/MDBK (ratio) | MTT (10 Point follow-up) | Pharmacophore Model |
|---|---|---|---|---|---|---|---|---|
| (structure) | 1017 | −4.62 | −51.88 | 25.07 | NA | 11.62/9.66 (0.83) | | 1NQL-AD4-10664 LIKE - WANG |
| (structure) | 10486 | −5.20 | −46.24 | 25.02 | NA | 0.29/0.80 (2.76) | 0.275/0.844 (3.07) | 1NQL-Glue-AD4-1505 LIKE |
| (structure) | 10460 | −5.35 | −42.22 | 23.17 | NA | 0.29/0.53 (1.84) | 0.279/0.375 (1.34) | 1NQL-Glue-AD4-1505 LIKE |
| (structure) | 10090 | −5.77 | −40.23 | 21.53 | NA | 5.28/5.62 (1.06) | 1.76/2.60 (1.48) | 1NQL-Glue-AD4-1505 LIKE |
| (structure) | 10100 | −6.90 | −50.40 | 18.12 | NA | 97% @ 2.6 μM | 1.06/1.72 (1.62) | 1NQL-Glue-AD4-1505 LIKE |

TABLE 8-continued

Glide Score, E-Model score, ICW assay, and MTT Assay Results for AD4-1505-like Compounds.

| Compound | AD4-Number | G-Score | E-Model Score | ICW Screen | Re-Test | MTT-72 h A431/MDBK (ratio) | MTT (10 Point follow-up) | Pharmacophore Model |
|---|---|---|---|---|---|---|---|---|
| (structure) | 10483 | −4.93 | −49.21 | 17.58 | NA | 0.26/0.49 (1.91) | 0.253/0.481 (1.90) | 1NQL-Glue-AD4-1505 LIKE |
| (structure) | 10466 | −5.19 | −46.73 | 17.15 | NA | 0.73/0.95 (1.31) | 0.717/0.775 (1.08) | 1NQL-Glue-AD4-1505 LIKE |
| (structure) | 10482 | −6.04 | −45.24 | 16.45 | NA | 81% @ 2.6 μM | 0.356/0.455 (1.28) | 1NQL-Glue-AD4-1505 LIKE |
| (structure) | 10488 | −6.05 | −49.59 | 15.95 | NA | 69% @ 2.6 μM | 1.85/2.22 (1.20) | 1NQL-Glue-AD4-1505 LIKE |
| (structure) | 10108 | −7.89 | −56.07 | 15.91 | NA | 93% @ 2.6 μM | 1.13/1.73 (1.53) | 1NQL-Glue-AD4-1505 LIKE |
| (structure) | 10512 | −6.70 | −45.25 | 12.86 | NA | 75% @ 2.6 μM | 0.517/0.991 (1.92) | 1NQL-Glue-AD4-1505 LIKE |

TABLE 8-continued

Glide Score, E-Model score, ICW assay, and MTT Assay Results for AD4-1505-like Compounds.

| Compound | AD4-Number | G-Score | E-Model Score | ICW Screen | Re-Test | MTT-72 h A431/MDBK (ratio) | MTT (10 Point follow-up) | Pharmacophore Model |
|---|---|---|---|---|---|---|---|---|
| (structure) | 10046 | −5.93 | −41.65 | 12.78 | NA | 93% @ 2.6 μM | 1.66/3.10 (1.87) | 1NQL-Glue-AD4-1505 LIKE |
| (structure) | 10109 | −6.37 | −47.41 | 12.75 | NA | 91% @ 2.6 μM | 0.534/1.38 (2.58) | 1NQL-Glue-AD4-1505 LIKE |
| (structure) | 10067 | −6.31 | −53.97 | 12.5 | NA | 2.15/3.45 (1.60) | 1.38/2.95 (2.14) | 1NQL-Glue-AD4-1505 LIKE |
| (structure) | 10064 | −6.15 | −43.64 | 9.336 | NA | 86% @ 2.6 μM | 1.56/2.01 (1.29) | 1NQL-Glue-AD4-1505 LIKE |
| (structure) | 10074 | −4.82 | −43.45 | 6.951 | NA | 89% @ 2.6 μM | 1.38/1.60 (1.16) | 1NQL-Glue-AD4-1505 LIKE |
| (structure) | 10105 | −5.87 | −35.09 | 3.88 | NA | 1.29/1.45 (1.12) | 0.605/0.850 (1.40) 77% Max | 1NQL-Glue-D4-1505 LIKE |

Figure 3A:
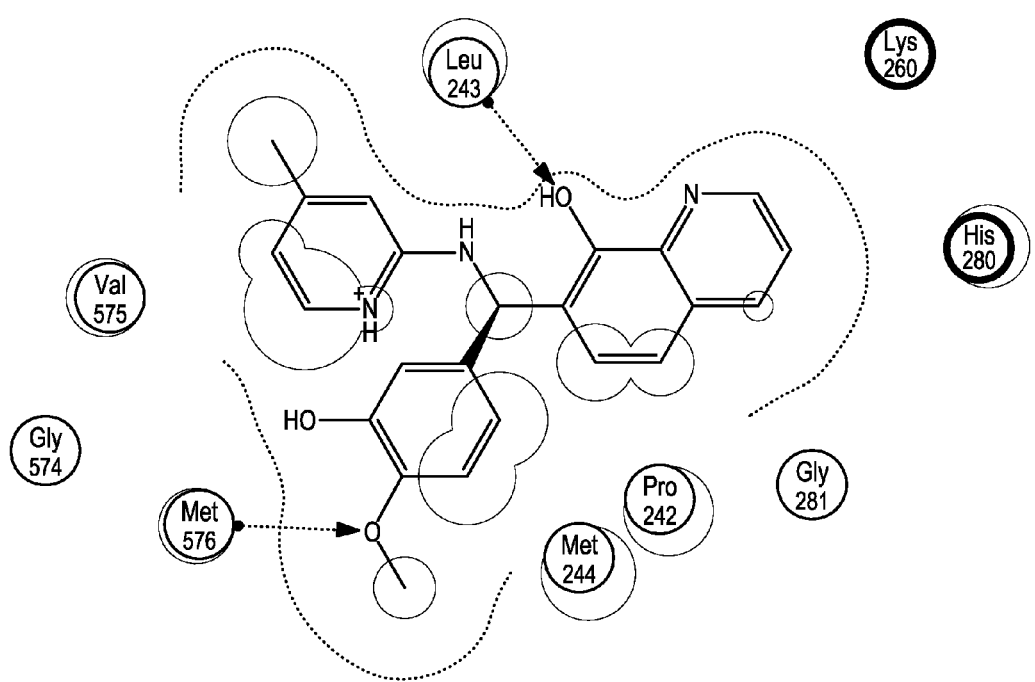
FIG. 3 is a series of two-dimensional representations of AD4-1505 and AD4-1505-like compounds docked with inactive EGFR. Docking of compound AD4-1505 to EGFR is depicted, for example, in FIG. 3A. Docking of compound AD4-10963 (an AD4-1505-like compound) to EGFR is depicted, for example, in FIG. 3B. Docking of compound AD4-10961 (an AD4-1505-like compound) to EGFR is depicted, for example, in FIG. 3C. Docking of compound AD4-10945 (an AD4-1505-like compound) to EGFR is depicted, for example, in FIG. 3D. Docking of compound AD4-10315 (an AD4-1505-like compound) to EGFR is depicted, for example, in FIG. 3E. Docking of compound AD4-10965 (an AD4-1505-like compound) to EGFR is depicted, for example, in FIG. 3F.
Figure 3B:
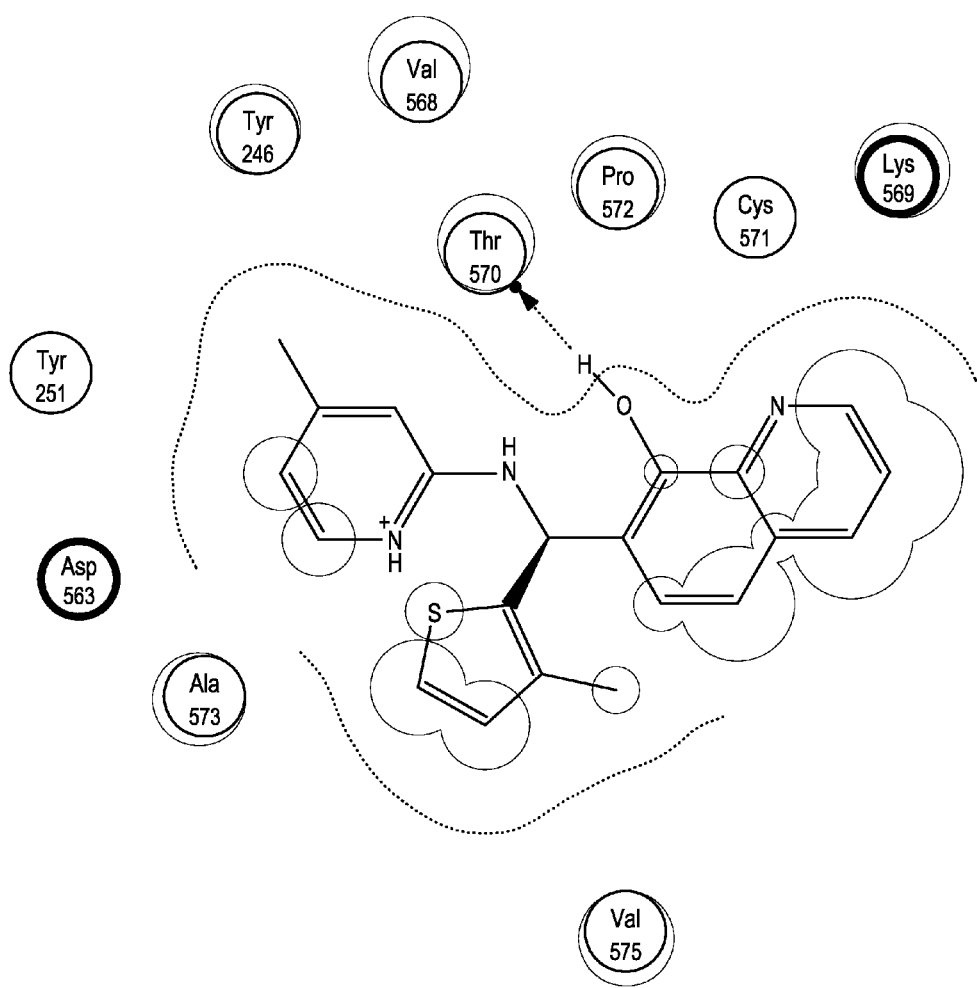
Figure 3C:
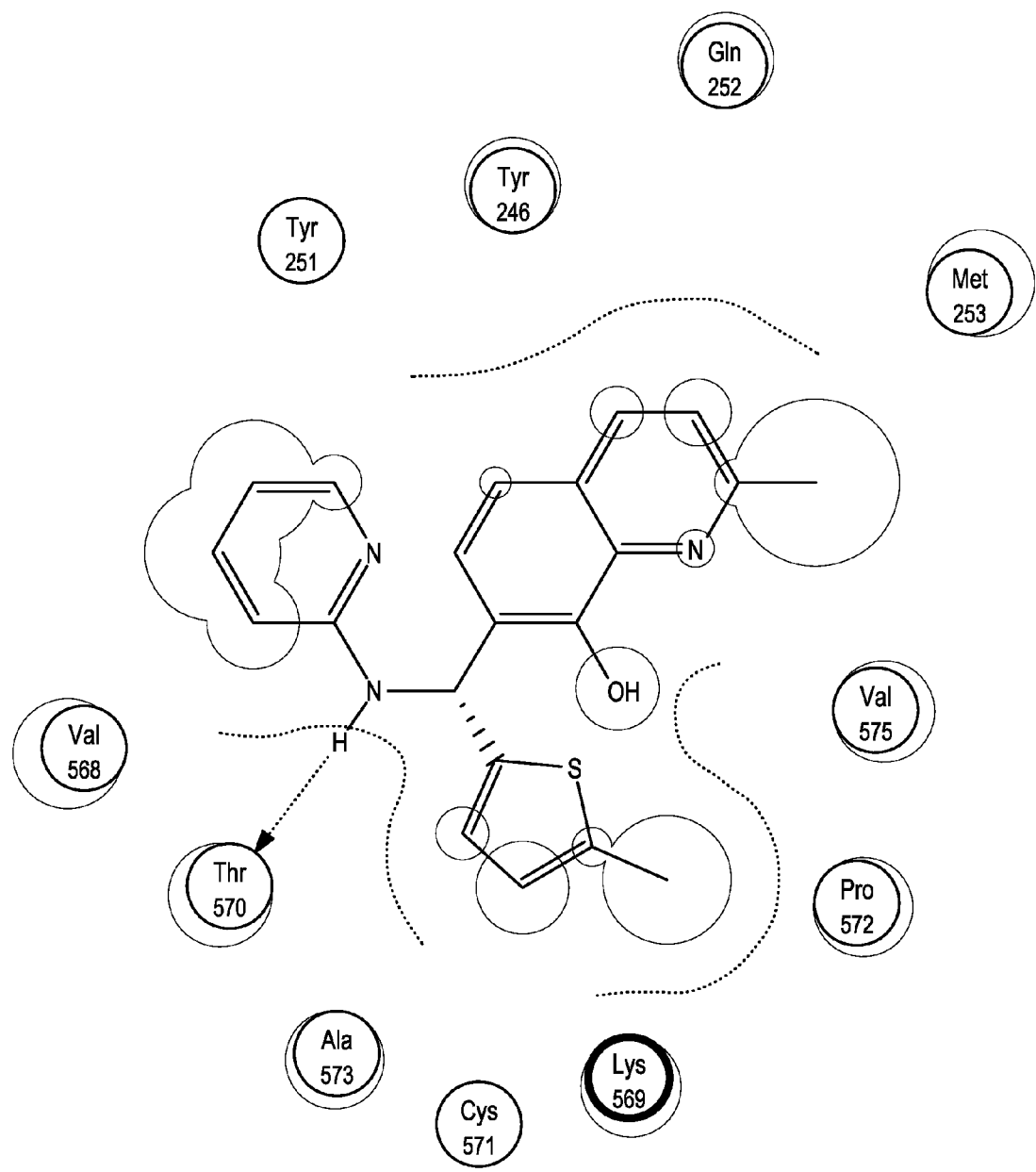
Figure 3D:
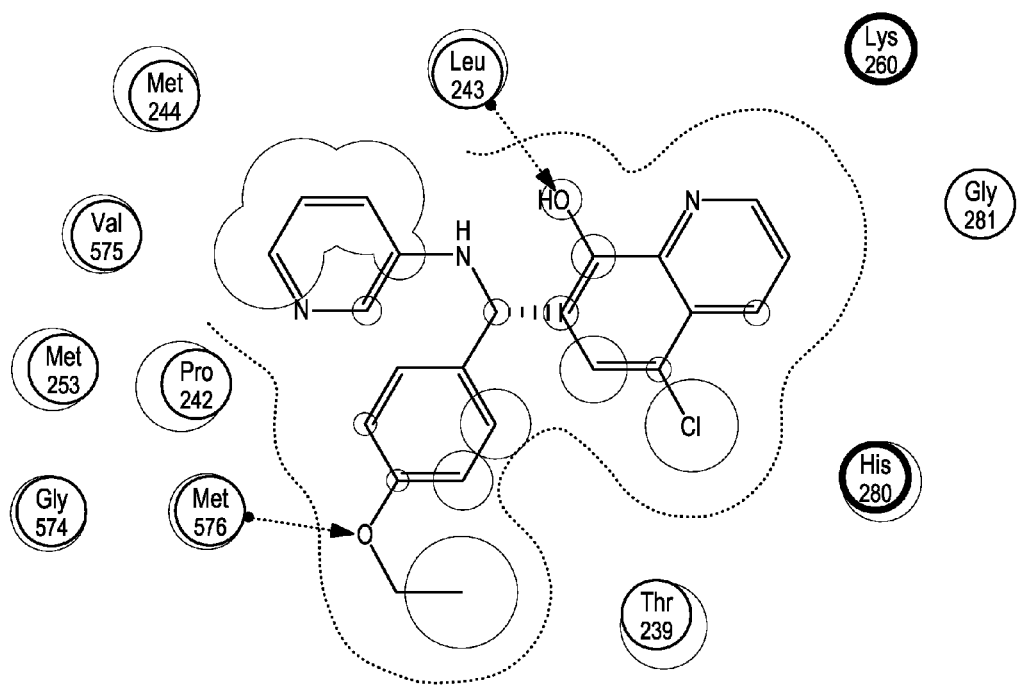
Figure 3E:
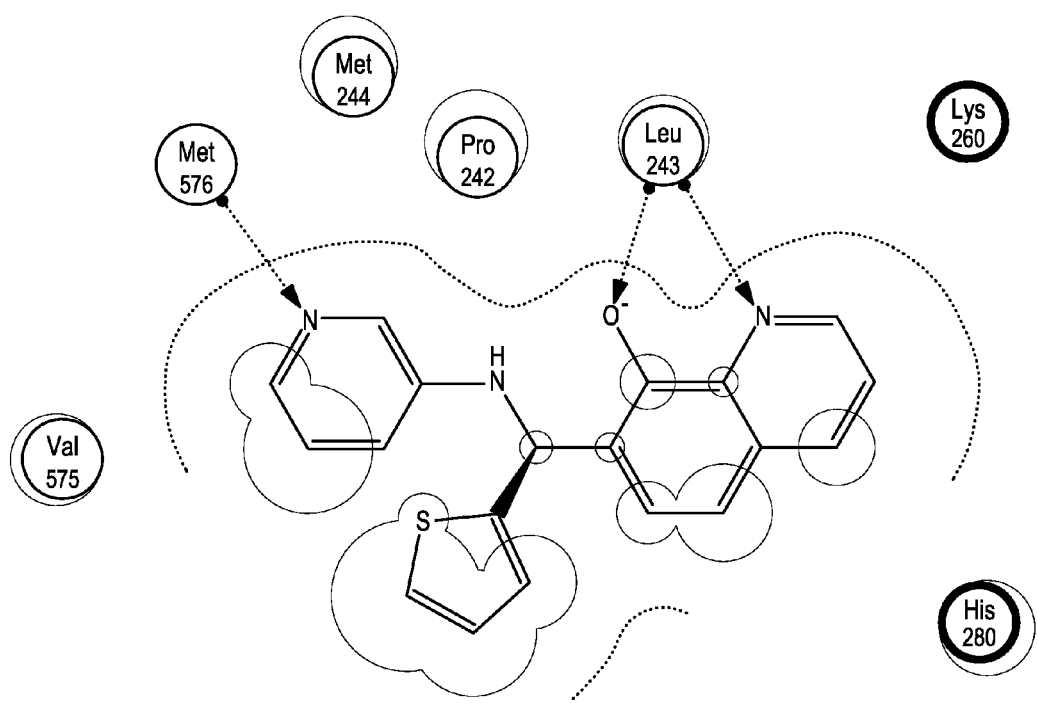
Figure 3F:
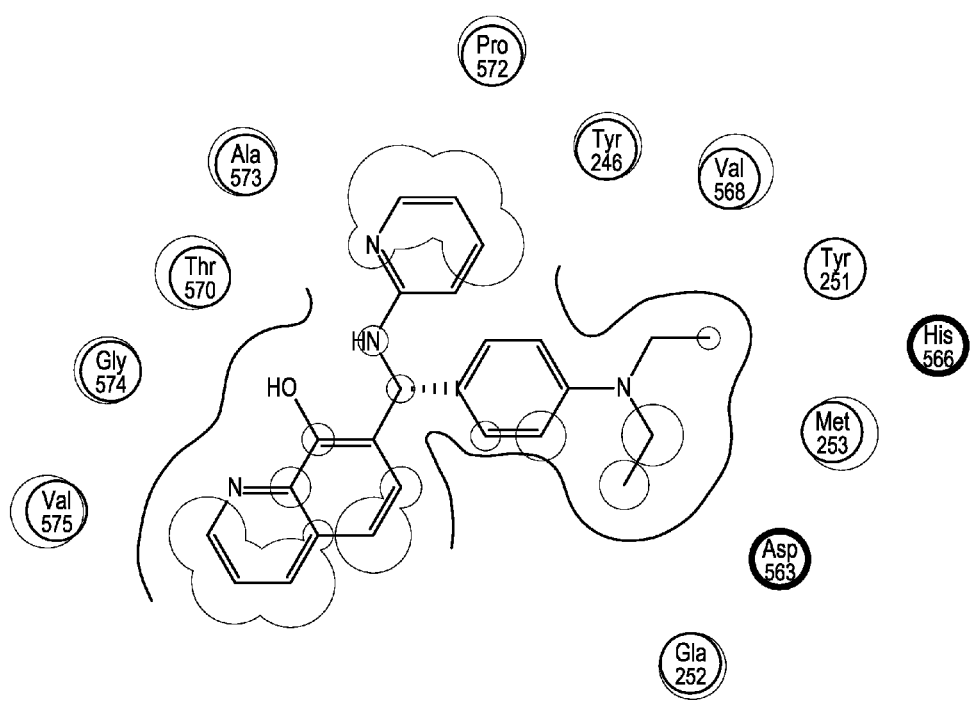

Two-dimensional representations of the docked pose of AD4-1505 compounds, along with AD4-1505-like compounds, were produced. Docking of compound AD4-1505 to EGFR is depicted, for example, in FIG. 3A. Docking of compound AD4-10963 (an AD4-1505-like compound) to EGFR is depicted, for example, in FIG. 3B. Docking of compound AD4-10961 (an AD4-1505-like compound) to EGFR is depicted, for example, in FIG. 3C. Docking of compound AD4-10945 (an AD4-1505-like compound) to EGFR is depicted, for example, in FIG. 3D. Docking of compound AD4-10315 (an AD4-1505-like compound) to EGFR is depicted, for example, in FIG. 3E. Docking of compound AD4-10965 (an AD4-1505-like compound) to EGFR is depicted, for example, in FIG. 3F.

Example 6

Combinatorial Studies

Studies were initiated to evaluate the ability of various compounds disclosed herein to synergize with several compounds known to inhibit the function of the EGF receptor in a cell proliferation assay (MTT assay). These compounds include Tarceva, Tykerb (non-selective inhibitor of EGFR and HER2 tyrosine kinases), Iressa (selective inhibitor of EGFR kinase), and a mouse antibody homolog of Erbitux (clone 225; inhibits binding of EGF to the EGF receptor). The rationale for this hypothesis is based on the idea that the AD4 compounds interact with a different site than the EGFR antibody, Erbitux, and have a different mechanism of action than the EGFR kinase inhibitors, Tykerb, Iressa or Tarceva.

Methods are according to Examples above except as indicated otherwise.

Known EGFR inhibitors Tykerb (AD4-0003), Iressa (AD4-0004), Tarceva (AD4-0005) and Clone 225 (from which Erbitux was derived) were titrated in the absence or presence of a fixed concentration of AD4 compound. The EGFR kinase inhibitors and AD4 compound were pre-diluted in 100% DMSO (DMSO+0.2% TFA for AD4 10381) as necessary such that a 1/200 dilution into DMEM+BSA resulted in 2× the final concentration desired. Clone 225 was diluted similarly with the exception that the pre-dilution was made in DMEM+BSA rather than DMSO. The EGFR inhibitor and AD4 compound dilutions were then mixed 1:1 in a 96 well plate. 50 µl of the mix was then added to the cell plate.

For the Clone 225 Combination Experiment, Clone 225 (Lab Vision/Thermo Scientific; #MS-269) was tested at concentration of 1, 0.5, 0.25, 0.125, 0.0625 and 0 µg/ml. The EGF concentration used for stimulation was 10 ng/ml. For the Tarceva Combination Experiment, Tarceva was tested at concentrations of 156, 63, 25, 10, 4 and 0 nM. The EGF concentration used for stimulation was 5 ng/ml. For the Tykerb Combination Experiment, Tykerb was tested at concentrations of 78, 31.25, 12.5, 5, 2 and 0 nM. The EGF concentration used for stimulation was 5 ng/ml. For the Iressa Combination Experiment, Iressa was tested at concentrations of 156, 63, 25, 10, 4 and 0 nM. The EGF concentration used for stimulation was 5 ng/ml.

The concentration of AD4 compound used in each experiment are provided in the graphs and data tables. A shifting of the inhibitor curve to the left indicates an increase in the effectiveness of the AD4-compound.

In these studies, the ability of an AD4 compound and the known compound (e.g. Tykerb), either alone or combined in a fixed constant ratio, were evaluated for their ability to inhibit cell proliferation in the MTT assay. From these studies, the following values were calculated: $IC_{50}$ values for the AD4 compound alone, for Tykerb (or other test compound) alone, and for each compound when combined; the Combination Index (CI), which reflects the degree of antagonism or synergism (see TABLE 9 below); and the Dose Reduction Index (DRI), which is a measure of how many fold the dose of each drug in a synergistic combination may be reduced at a given effect level when compared with the doses of each drug alone.

TABLE 9

Combination Index
KEY:

| Range of C | Description | Graded Symbols |
|---|---|---|
| <0.1 | Very strong synergism | + + + + + |
| 0.1-0.3 | Strong synergism | + + + + |
| 0.3-0.7 | Synergism | + + + |
| 0.7-0.85 | Moderate synergism | + + |
| 0.85-0.9 | Slight synergism | + |
| 0.9-1.10 | Nearly additive | +/− |
| 1.10-1.20 | Slight antagonism | − |
| 1.20-1.45 | Moderate antagonism | − − |
| 1.45-3.3 | Antagonism | − − − |
| 3.3-10 | Strong antagonism | − − − − |
| >10 | Very strong antagonism | − − − − − |

Results showed the following. A series of AD4-Pharma compounds produce a synergistic effect with Tykerb, Iressa and Erbitux to enhance their effect in a cell proliferation assay. These synergistic effects were demonstrated by significant changes in the Dose Reduction Index, the Combination Index and shifts in the dose-response curves.

The effects of a number of compounds appear to involve positive cooperativity because the effect increases as the concentration of the compound increases. Compounds that demonstrated the greatest degree of positive co-operativity usually demonstrated high DRI values. Some of the compounds that demonstrate the greatest degree of positive co-operativity also show synergistic behavior as evidenced by a low CI value. Iressa and Tarceva, another selective inhibitor of EGFR kinase, did not produce synergistic effects with Tykerb. Compounds acting at the same target (i.e., EGFR kinase) should not be synergistic.

Figure 4A:
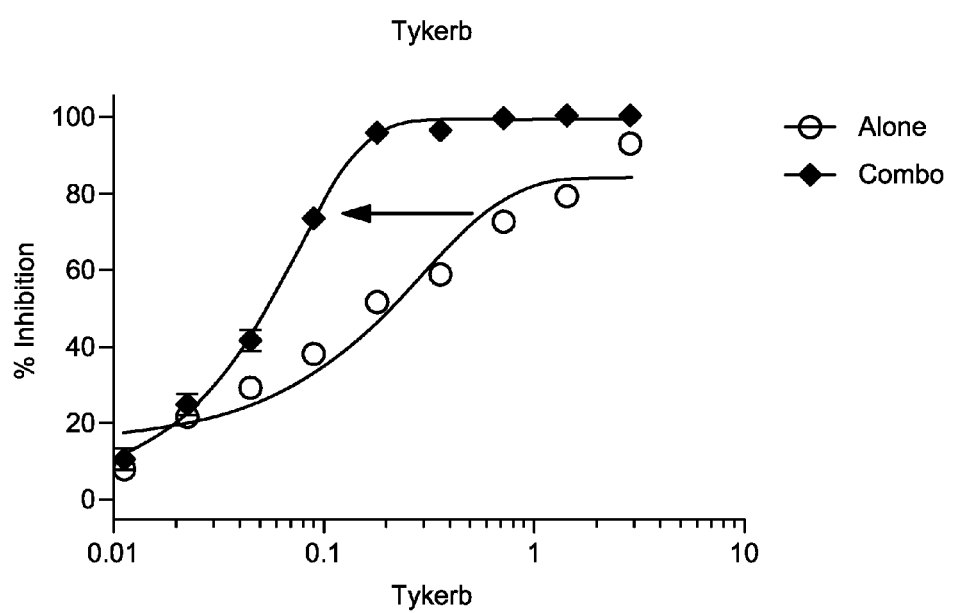
FIG. 4 is a series of line and scatter plots showing % inhibition of EGFR as a function of concentration of Tykerb (FIG. 4A) or Iressa (FIG. 1B) either alone or in combination with AD4-10628. A shift in the dose-response curve to the left indicates a more potent response.
Figure 4B:
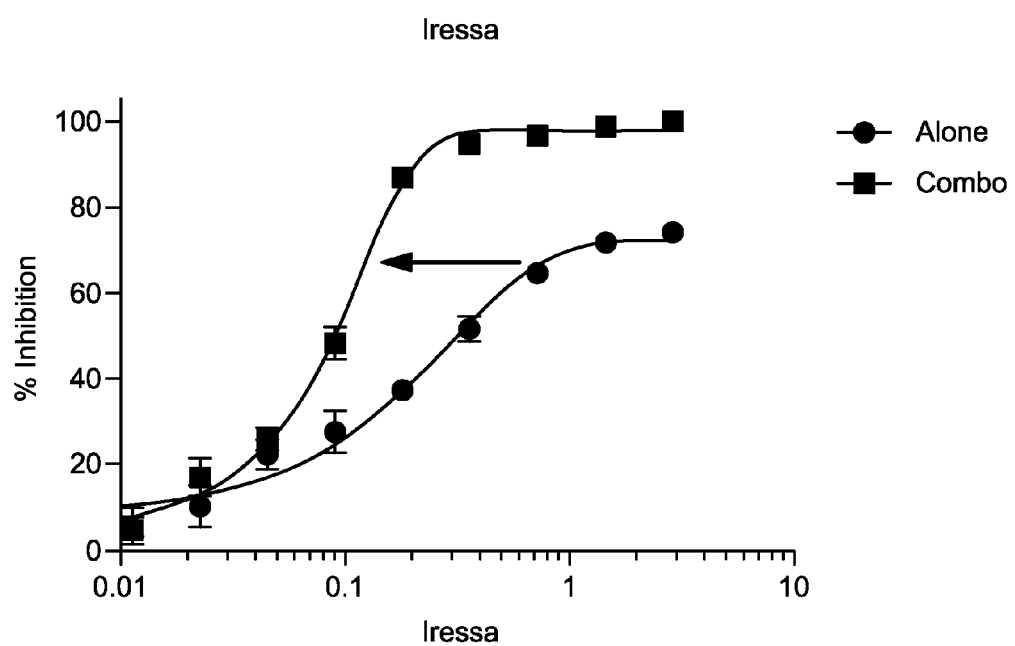

An example of a shift in the dose-response curve is shown in FIG. 4, where AD4-10628 produced a leftward shift (higher potency) in the dose-response curves for both Tykerb and Iressa. The effect is more evident at higher concentrations of the compound, indicating a positive co-operativity effect may be involved in the compound's action.

Results for several of the more potent compounds are summarized in TABLE 10. AD4-10628, AD4-1505 and AD4-11511 produce a leftward shift (i.e., greater potency) in Tykerb's dose-response curve, and demonstrate very high DRI values. Although significant shifts in the dose-response curves for the EGFR kinase inhibitors are produced, these effects are not translated into significant shifts in the $IC_{50}$ values (50% inhibition), since the effects of the AD4 compounds are observed to a greater degree at higher concentrations.

TABLE 10

Summary of Median Effect Analysis Studies

| Compound | $IC_{50}$ Tykerb (nM) | $IC_{50}$ Tykerb + Compound (nM) | DRI @ ED97 | CI @ ED90 |
|---|---|---|---|---|
| AD4-10628 | 178 | 59 | 126 | 0.55 |
| AD4-1505 | 492 | 116 | 203 | 0.10 |
| AD4-11511 | 189 | 118 | 84 | 0.87 |

TABLE 10-continued

Summary of Median Effect Analysis Studies

| Iressa | 307 | 160 | 2 | 1.15 |
|---|---|---|---|---|

| | $IC_{50}$ Iressa (nM) | $IC_{50}$ Iressa + Compound (nM) | DRI @ ED97 | CI @ ED90 |
|---|---|---|---|---|
| AD4-10628 | 207 | 93 | 105 | 0.91 |
| AD4-1505 | 78 | 133 | 78 | 0.59 |
| AD4-11511 | 326 | 245 | 96 | 0.93 |

Figure 5:
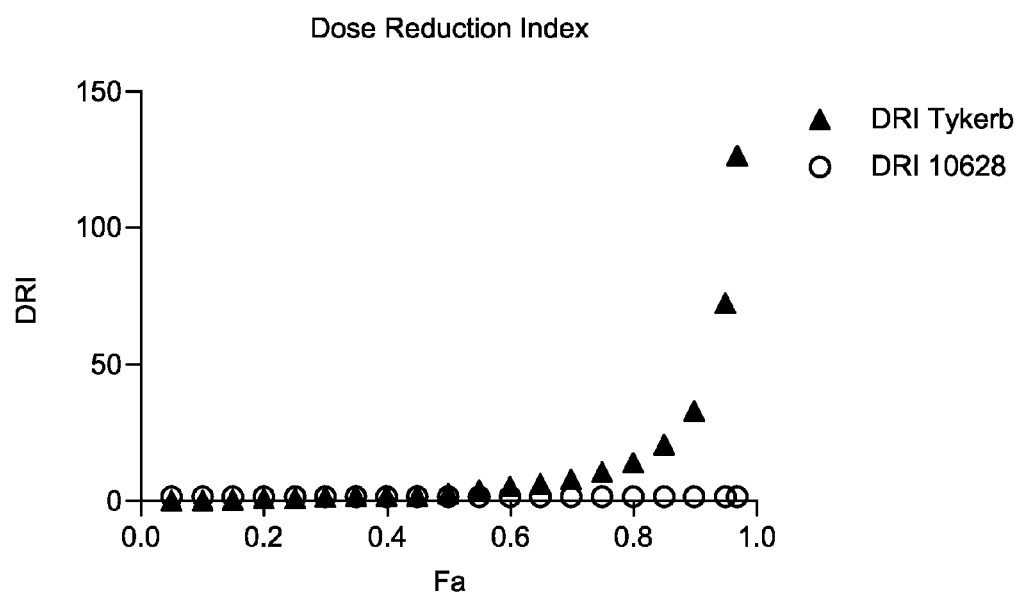
FIG. 5 is a scatter plot showing Dose Reduction Index (DRI) as a function of Fa for DRI Tykerb and DRI AD4-10628.

DRI values were calculated for the effect of the test compound on Tykerb, as well as for Tykerb's effect on the test compound. In general, most compounds enhanced the effect of Tykerb, as demonstrated by a high DRI, whereas Tykerb usually had a minimal effect on the test compound. As a result, the reported DRI is for the effect of the test compound on Tykerb. This can best be observed/by plotting DRI as a function of Fa, or percent effect, ranging from 5% to 97% (see e.g., FIG. 5). AD4-10628 had a significant effect on the activity of Tykerb, which becomes greater at higher activity levels (or doses), whereas Tykerb has little effect on AD4-10628 (see e.g., FIG. 5). As shown in TABLE 10, AD4-10628, AD4-1505 and AD4-11511 all produced a fairly high DRI for both Tykerb and Iressa.

Figure 6:
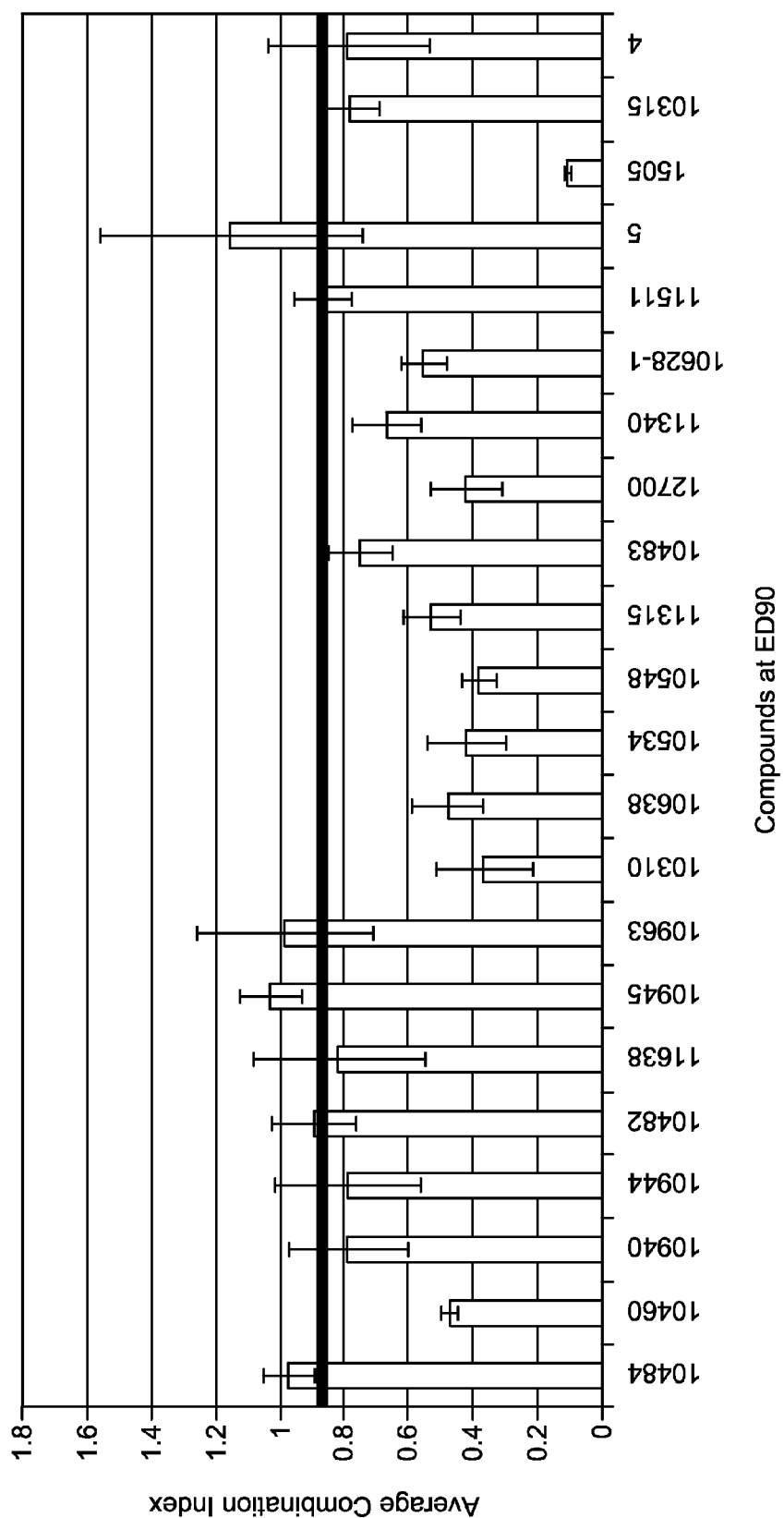
FIG. 6 is a histogram showing a summary of Combination Index (CI) values at 90% inhibition (ED90) for a series of AD4 compounds in combination with Tykerb. Compound 4 is Iressa. Compound 5 is Tarceva. The balance of compounds are AD4 compounds described herein. Response below the dark middle line (i.e., CI<0.9) indicates synergism.

CI values were calculated where the combined effect of the compounds produces 50%, 90%, 95% and 97% (i.e., $ED_{50}$, $ED_{90}$, $ED_{95}$ and $ED_{97}$) inhibition of cell proliferation. A graph showing the CI values at 90% inhibition is displayed in FIG. 6. Response below the red line (i.e CI<0.9) indicates synergism. As indicated in FIG. 6, a number of compounds demonstrated synergism. For example, the CI values for AD4-10628 and AD4-1505 shows synergy with Iressa based on the CI value. Since Iressa and Tykerb have similar mechanisms of action, minimal interaction would be expected between these two compounds. As shown in TABLE 10, little interaction is observed based on the DRI and CI values for Iressa.

These results show that the AD4 compounds produce a significant effect on EGF receptor-mediated cell proliferation through a site that is distinct from either EGF receptor kinase or the EGF receptor. Furthermore, based on their synergistic effect, the compounds may provide a unique method to achieve the same or enhanced therapeutic effect while using a lower therapeutic dose of the marketed compounds, Tykerb, Iressa or Erbitux.

Example 7

Cell Proliferation Assays

The following example demonstrates the cell proliferation assays based on A549, H1975, and HT-29 cells. Each of the A549, H1975, and HT-29 cell proliferation assays employ the MTT assay for determination of the number of viable cells. Cell proliferation assays can be utilized to determine whether or not compounds have an effect on cancer cell growth. The MTT assay is first described, followed by each of A549, H1975, and HT-29 cell proliferation assays. Preliminary results of each cell proliferation assay are reported in this example with further testing of compounds subsequently presented.

MTT Assay.

Cell proliferation is determined using the MTT assay. The MTT cell proliferation assay is a colorimetric assay system which measures the reduction of a tetrazolium component (MTT) into an insoluble formazan product by the mitochondria of viable cells. After incubation of the cells with the MTT reagent, DMSO is added to solubilize the colored crystals and the samples read at a wavelength of 560 nm. The amount of color produced is directly proportional to the number of viable cells.

3-(4,5-Dimethylthiazol-2-yl)-2,5-diphenyltetrazolium Bromide (MTT) dye (Aesar, cat no. L11939) was prepared at 5 mg/ml in PBS. To each well, 20 µl of MTT solution was added to existing media and mixed thoroughly with 5 mins of gentle shaking at room temperature. Plates were incubated at 37° C., 5% $CO_2$ for approximately 2 hrs. After 2-3 hrs incubation, media was aspirated out and plates were patted dry. 200 µl/well 100% DMSO (Sigma, cat no. 472301) was added. Plates were incubated at 37° C., 5% $CO_2$ for 10 min and mix thoroughly with 5 mins of gentle shaking at room temperature. Plates were read on the PolarStar plate reader at 560 nm. Percent (%) inhibition was calculated as 100%−(OD560 nm experimental−blank)×100%/OD560 nm control-blank. Blank=wells+serum free media+0.5% DMSO. Experimental=wells+cells+treatment+0.5% DMSO. Control=wells+cells+0.5% DMSO. $IC_{50}$ values were calculated in GraphPad Prism using non-linear regression curve fitting. All statistical analyses was done either in GraphPad Prism or Microsoft Excel.

A549 Cell Proliferation Assay.

The A549 Cell Proliferation Assay measures the ability of compounds to inhibit cell proliferation in the A549 non-small cell lung cancer (NSCLC) cell line (see e.g., Tang et al. 2008 Br J Cancer 99, 911-922; de La Motte Rouge 2007 Cancer Res 67, 6253-6262; Magesh et al. 2009 Phytother Res 23, 1385-1391). Briefly, compounds are added to cells plated in 96-well plates. The cells are allowed to grow for 72 hours before MTT treatment. The effect of the compounds on cell proliferation is analyzed using GraphPad Prism.

A549 cells are a non-small cell lung cancer cell line that have wild type EGFR and p53 but have point mutations in KRAS gene which transform it into an oncogene. Compounds that inhibit the growth of A549 cells may serve as potential therapeutic treatments for lung cancer patients. These new compounds could be used either alone or in combination with the existing molecules to produce synergistic combinations.

For the A549 Cell Proliferation Assay, on day 1, A549 cells (ATCC, Cat no. CRL-185, lot no. 7502546) were seeded at 8,000 cells/well in 200 µl media containing 0% fetal bovine serum (FBS) (Hyclone, cat no. SH30071.03, lot no. ATB31500), 1% Pen Strep (Gibco, cat no. 15140), and 1% L-Glutamine (Gibco, cat no. 25030) in 96 well, tissue culture-treated plates (BD, cat no. 353916). Plates were incubated overnight at 37° C., 5% $CO_2$, 85% humidity in a tissue culture incubator. On day 2, working solutions of compounds at 200× were prepared. To 200 µl media was added 1 µl 200× compound diluted in 100% DMSO for final DMSO concentration of 0.5%. Plates were incubated for 72 hours before analyzing them with MTT (as described above). The $IC_{50}$ value generated from each treatment indicates the concentration of the drug needed to reduce the viability of the cells by half (i.e., 50% of maximum viability).

Figure 9A:
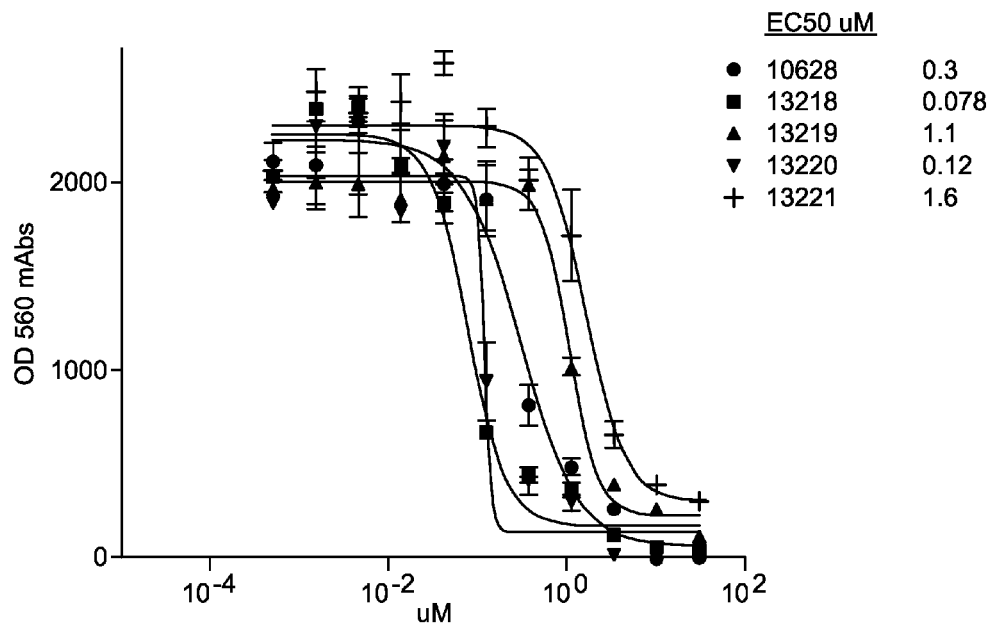
FIG. 9A shows OD 560 mAbs as a function of compound (AD4-10628, AD4-13218, AD4-13219, AD4-13220, AD4-13221) concentrations.
Figure 9B:
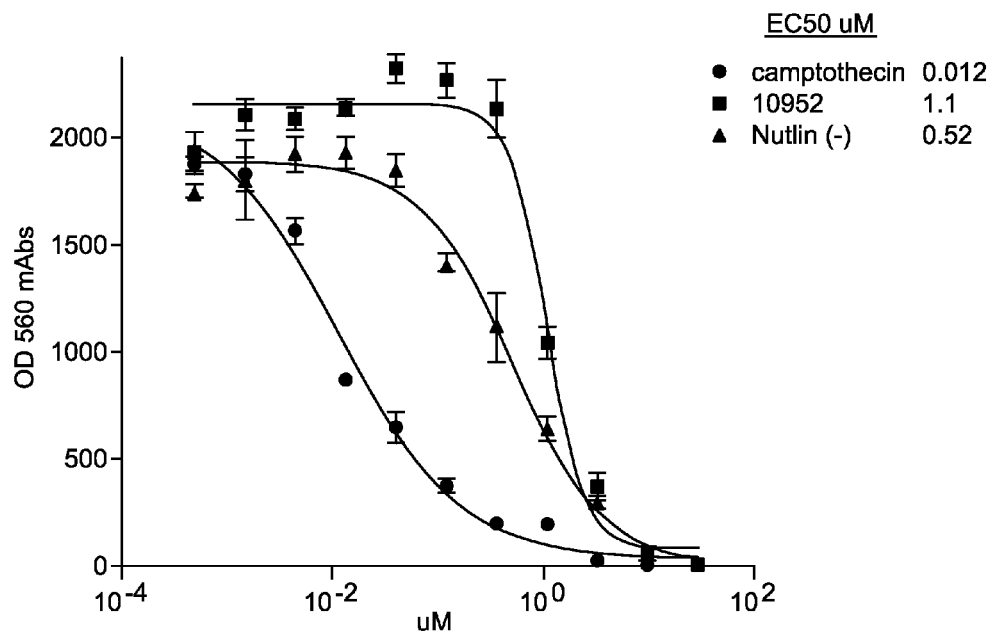
FIG. 9B shows OD 560 mAbs as a function of compound (camptothecin, AD4-10952, Nutlin (−)) concentrations. Further information regarding methodology is provided in Example 7.

Preliminary results in the A549 cell proliferation assay showed compounds inhibited cell proliferation in the A549 NSCLC cell line using the MTT assay (see e.g., FIG. 9). The A549 Cell Proliferation Assay readily discriminates the ability of compounds to inhibit cell proliferation. In this experiment, the difference between the most and least potent compounds was greater than 100-fold.

H1975 Cell Proliferation Assay.

The A549 Cell Proliferation Assay measures the ability of compounds to inhibit cell proliferation in H1975 cells (see e.g., Naumov et al. 2009 Clin Cancer Res 15, 3484-3494). Briefly, compounds are added to cells plated in 96-well plates. The cells are allowed to grow for 72 hours before MTT treatment. The effect of the compounds on cell proliferation is analyzed using GraphPad Prism.

H1975 cells are a non-small cell lung cancer (NSCLC) cell line that have developed mutations rendering them resistant to EGF receptor inhibitors, such as Tarceva. Compounds that inhibit the growth of H1975 cells may serve as potential therapeutic treatments for lung cancer patients that have developed resistance to Tarceva, or other EGF receptor inhibitors.

For the H1975 cell proliferation assay, on day 1, H1975 cells are seeded at 2,000 cells/well in 200 µl media containing 5% fetal bovine serum (FBS) (Hyclone, cat no. SH30071.03, lot no. ATB31500), 1% Pen Strep (Gibco, cat no. 15140), and 1% L-Glutamine (Gibco, cat no. 25030) in 96 well, tissue culture-treated plates (BD, cat no. 353916). Plates were incubated overnight at 37° C., 5% $CO_2$. On day 2, working solutions of compounds at 200× were prepared. To 200 µl media was added 1 µl 200× compound diluted in 100% DMSO for final DMSO concentration of 0.5%. Plates were incubated for 72 hours at 37° C., 5% $CO_2$ before analyzing them with MTT on day 5 (as described above). The $IC_{50}$ value generated from each treatment indicates the concentration of the drug needed to reduce the viability of the cells by half (i.e., 50% of maximum viability).

Figure 10:
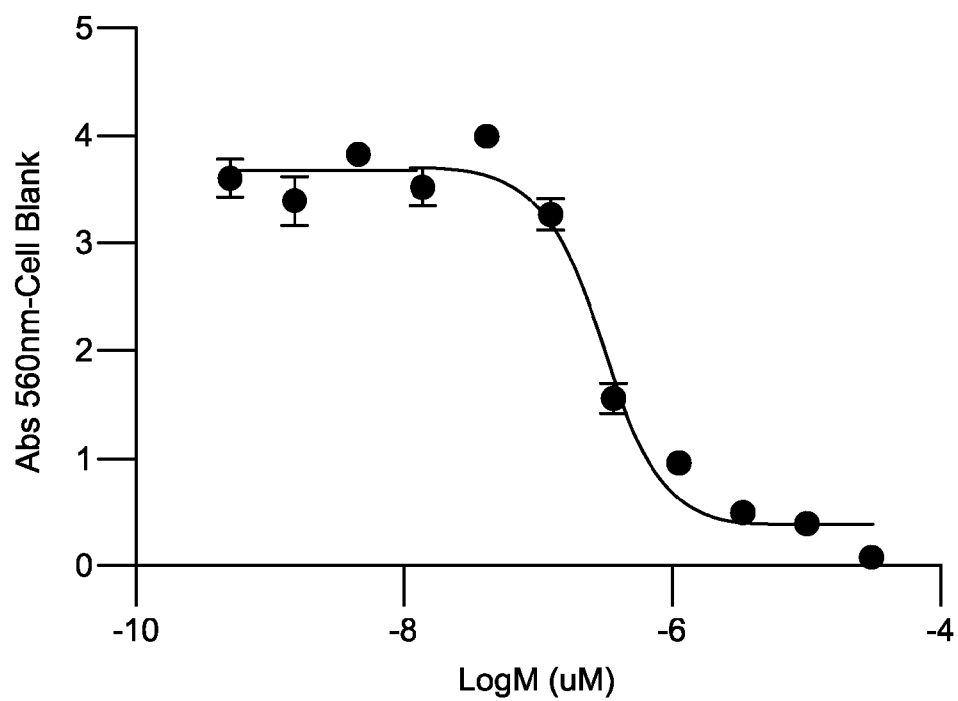
FIG. 10 is a scatter and line plots showing MTT cell proliferation assay for H1975 cells.

Preliminary results in the H1975 cell proliferation assay showed the effect of compound AD4-10460 on the viability of cells cultured for 72 hours post compound treatment (see e.g., FIG. 10). According to the H1975 cell proliferation assay, the $IC_{50}$ value for AD4-10460 was 0.3 µM (best fit values from FIG. 10: bottom 0.3898, top 3.692, LogIC50 −6.517, HillSlope −1.931, IC50 3.039e-007, Span 3.302).

HT-29 Cell Proliferation Assay.

The HT-29 Cell Proliferation Assay measures the ability of compounds to inhibit cell proliferation in HT-29 cells (see e.g., Zhang et al. 2006 Worl J Gastroenterol 12, 3581-3584; Tang et al. 2007 Postgrad Med J 83, 338-343). Briefly, compounds are added to cells plated in 96-well plates. The cells are allowed to grow for 72 hours before MTT treatment. The effect of the compounds on cell proliferation is analyzed using GraphPad Prism.

HT-29 cells are a colon cancer cell line that is utilized to assess the ability of compounds to inhibit the proliferation of cells in tumors of the colon.

For the HT-29 cell proliferation assay, on day 1, HT-29 cells are seeded at 3,000 cells/well in 100 µl media containing 10% FBS, 1× Pen-Strep, and 1×L-Glutamine in 96 well, tissue culture-treated plates. Plates are incubated overnight at 37° C., 5% $CO_2$ in 85% humidity in tissue culture incubator. On day 2, complete media was replaced with media containing 2.5% FBS (180 µl/well). Working solutions of compounds were prepared (at 400× in 100% DMSO). To 200 µl media, 20 µl of a 5× compound (diluted in plain media) was added for a final DMSO concentration of 0.5%. Plates were incubated for 72 hrs at 37° C., 5% $CO_2$ in 85% humidity. On day 5, plates were analyzed for cell growth using the MTT assay. The $IC_{50}$ value generated from each treatment indicates the concentration of the drug needed to reduce the viability of the cells by half (i.e., 50% of maximum viability).

Preliminary results in the HT-29 cell proliferation assay showed the effect of cell density and percent fetal bovine serum in the HT-29 cell line (see e.g., TABLE 11, TABLE 12). Results showed that 5,000 cells/well using an FBS concentration of 5% consistently generates better results for the three EGF receptor kinase inhibitors—Tykerb, Iressa, and Tarceva (see e.g, TABLE 11).

TABLE 11

HT-29 Cell Proliferation Assay Results

| | 5% Serum | | 10% Serum | |
|---|---|---|---|---|
| | 2,500 cells/well | 5,000 cells/well | 2,500 cells/well | 5,000 cells/well |
| Tykerb | 5.0 µM | 5.1 µM | 8.5 µM | 9.2 µM |
| Tarceva | 37 µM | 12 µM | No Effect | No Effect |
| Iressa | 17 µM | 18 µM | 20 µM | 21 µM |

Furthermore, there was no difference in the $IC_{50}$ values for Tykerb or Tarceva when HT-29 cells are incubated for either 48 or 72 hours, as shown in TABLE 12.

TABLE 12

Comparison of Incubation Times in HT-29 Cell Proliferation Assay

| | 48 hours | | 72 hours | |
|---|---|---|---|---|
| | 2.5% serum | 5.0% serum | 2.5% serum | 5.0% serum |
| Tykerb | 2.7 µM | 4.4 µM | 2.3 µM | 4.2 µM |
| Tarceva | 12.0 µM | 28 µM | 15 µM | 24 µM |

Figure 11:
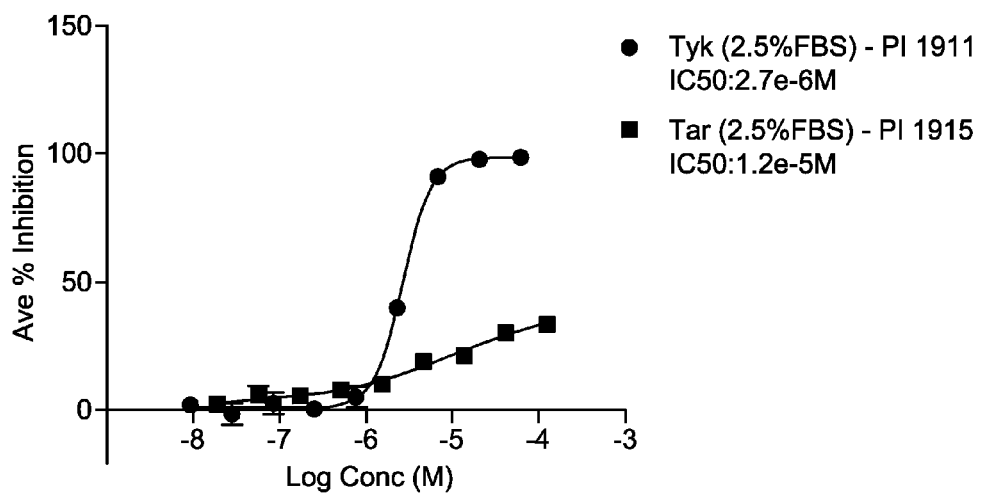
FIG. 11 is a scatter and line plot showing MTT cell proliferation for HT-29 cells.

The dose-response curves using the HT-29 Cell Proliferation Assay for the EGF receptor kinase inhibitors, Tykerb and Tarceva, are shown in FIG. 11. The $IC_{50}$ values for Tykerb and Tarceva were calculated as 2.7 µM and 12 µM, respectively.

Compounds in the AD4-1505-like series inhibit the growth of cancer cells from several different organs, including lung and colon cancer cells. Studies reveal that compounds in this chemical series inhibit cell proliferation in A549 non-small cell lung cancer (NSCLC) cells, H1975 NSCLC cells which are resistant to the EGF receptor kinase inhibitor, Tarceva, and in HT-29 colon cancer cells. TABLE 13 provides a summary of those compounds with an IC50 value <200 nM in the A549 cell proliferation assay.

TABLE 13

Cell Proliferation Data

| | $IC_{50}$ Value (µM) | | |
|---|---|---|---|
| Compound | A549 Cells | H1975 Cells | HT-29 Cells |
| AD4-12955 | 0.17 | 0.5 | |
| AD4-13023 | 0.17 | 0.61 | |
| AD4-13028 | 0.14 | 0.26 | |
| AD4-13030 | 0.17 | 0.22 | |
| AD4-13031 | 0.12 | 0.24 | |
| AD4-13032 | 0.17 | 0.21 | |
| AD4-13033 | 0.13 | 0.23 | |
| AD4-13024 | 0.18 | 0.63 | |
| AD4-13041 | 0.11 | 0.17 | 1.1 |
| AD4-13042 | 0.11 | 0.13 | 1.3 |
| AD4-13046 | 0.16 | 0.12 | |
| AD4-13048 | 0.18 | 0.17 | |
| AD4-13052 | 0.13 | 0.24 | |
| AD4-13053 | 0.18 | 0.18 | |
| AD4-13060 | 0.19 | 0.58 | |
| AD4-13072 | 0.15 | 0.29 | |
| AD4-13081 | 0.17 | 0.33 | 6.2 |
| AD4-13085 | 0.14 | 0.15 | 11 |
| AD4-13086 | 0.16 | 0.15 | 1.2 |

TABLE 13-continued

Cell Proliferation Data

| Compound | IC$_{50}$ Value (μM) | | |
|---|---|---|---|
|  | A549 Cells | H1975 Cells | HT-29 Cells |
| AD4-13090 | 0.16 | 1.3 | 3.7 |
| AD4-13092 | 0.16 | 0.21 | 3.9 |
| AD4-13095 | 0.11 | 0.44 | 5.4 |
| AD4-13108 | 0.14 | 0.3 | 3.3 |
| AD4-13111 | 0.14 | 0.37 | 8.9 |
| AD4-13119 | 0.18 | 0.12 | 1.5 |
| AD4-13121 | 0.18 | 0.33 | 1.8 |
| AD4-13123 | 0.12 | 0.36 | 1.3 |
| AD4-13124 | 0.10 | 0.97 | 1.5 |
| AD4-13130 | 0.12 | 0.088 | 0.64 |
| AD4-13131 | 0.10 | 0.10 | 0.92 |
| AD4-13132 | 0.17 | 0.31 | 1.6 |
| AD4-13134 | 0.19 | 0.12 | 1.2 |
| AD4-13135 | 0.18 | 0.21 | 0.79 |
| AD4-13137 | 0.16 | 0.12 | 0.78 |
| AD4-13138 | 0.17 | 0.30 | 1.1 |
| AD4-13141 | 0.19 | 0.26 | 2.6 |
| AD4-13142 | 0.14 | 0.95 | 3.1 |
| AD4-13143 | 0.13 | 0.13 | 1.1 |
| AD4-13145 | 0.16 | 1.7 | 2.1 |
| AD4-13146 | 0.14 | 0.24 | 2.0 |
| AD4-13147 | 0.11 | 0.29 | 0.77 |
| AD4-13148 | 0.13 | 0.31 | 1.1 |
| AD4-13150 | 0.14 | 0.45 | 1.9 |
| AD4-13153 | 0.19 | 0.19 | 0.79 |
| AD4-13154 | 0.17 | 0.15 | 0.76 |
| AD4-13159 | 0.11 | 0.13 | 1.2 |
| AD4-13165 | 0.16 | 0.14 | 5.0 |
| AD4-13167 | 0.10 | 0.31 | 1.5 |
| AD4-13172 | 0.14 | 0.15 | 1.3 |
| AD4-13175 | 0.17 | 3.8 | 2.0 |
| AD4-13177 | 0.14 | 0.27 | 1.5 |
| AD4-13178 | 0.084 | 0.19 | 0.79 |
| AD4-13179 | 0.14 | 0.14 | 4.1 |
| AD4-13180 | 0.10 | 0.86 | 1.7 |
| AD4-13181 | 0.12 | 0.58 | 2.2 |
| AD4-13182 | 0.19 | 1.8 | 8.3 |
| AD4-13184 | 0.11 | 0.24 | 2.2 |
| AD4-13185 | 0.18 | 0.23 | 1.2 |
| AD4-13187 | 0.15 | 0.26 | 1.3 |
| AD4-13188 | 0.14 | 0.28 | 0.86 |
| AD4-13192 | 0.15 | 0.19 | 2.2 |
| AD4-13199 | 0.12 | 0.16 | 0.75 |
| AD4-13202 | 0.090 | 0.72 | 2.3 |
| AD4-13204 | 0.19 | 1.4 | 4.5 |
| AD4-13206 | 0.074 | 0.36 | 2.1 |
| AD4-13209 | 0.17 | 0.14 | 2.3 |
| AD4-13211 | 0.082 | 0.16 | 2.0 |
| AD4-13212 | 0.13 | 0.16 | 3.5 |
| AD4-13213 | 0.16 |  | 5.4 |
| AD4-13215 | 0.16 |  | 0.97 |
| AD4-13216 | 0.12 |  | 1.6 |
| AD4-13217 | 0.12 |  | 0.96 |
| AD4-13218 | 0.086 |  | 0.92 |
| AD4-13220 | 0.12 |  | 3.3 |
| AD4-13223 | 0.11 |  | 2.5 |

As seen in TABLE 13, the most potent compounds from this series inhibit cell proliferation in A549 or H1975 cells with an IC$_{50}$≤100 nM. These compounds include AD4-13124, AD4-13130, AD4-13131, AD4-13178, AD4-13202, AD4-13206, AD4-13211 and AD4-13218.

Based on the results in the cell proliferation assays in the A549 and H1975 cells, compounds in this chemical series are expected to have therapeutic benefit for the treatment of non-small cell lung cancers. Because these compounds are also effective in inhibiting cell proliferation in H1975 cells, which are resistant to EGF receptor kinase inhibitors, such as Tarceva, these compounds are expected to have therapeutic benefit in the treatment of NSCLC that are no longer responsive to Tarceva. Furthermore, compounds from this series can have therapeutic benefit in colon cancer, based on their ability to inhibit cell proliferation in HT-29 cells.

Example 8

Apoptosis Assays

The following example demonstrates the cell apoptosis assays, including the Capsase 3,7 assay, DNA fragmentation assay, and Annexin V assay. In addition to inhibiting the proliferation or growth of cancer cells, another desirable activity is the ability of compounds to induce apoptosis, or cell death. The ability of compounds in the AD4-1505-like series to induce apoptosis was identified in three different assays: induction of caspase 3,7 activity in A431 cells; induction of DNA fragmentation in A549 cells; and induction of Annexin V expression in A549 cells. Preliminary results of each cell apoptosis assay are reported in this example with further testing of compounds subsequently presented.

Capsase 3,7 Assay.

The capsase 3,7 assay measures the ability of compounds to induce caspase 3,7 activity, which is an early indicator of cell apoptosis (see e.g., Garcio-Calvo et al. 1999 Cell Death Differ. 6, 362-369; Nicholson and Thornberry 1997 Trends Biochem. Sci. 22, 299-306; Thornberry et al. 1997 J. Biol. Chem. 272, 17907-17911; Thornberry and Lazebnik 1998 Science 281, 1312-1316; Bayascas et al. 2002 Cell Death Differ. 9, 1078-1089; Le et al. 2002 Proc. Natl. Acad. Sci USA 99, 15188-15193; Mooney et al. 2002 Br. J. Cancer 87, 909-917; Karvinen et al. 2002 J. Biomol. Screening 7, 223-231; Gopalakrishnan et al. 2002, J. Biomol. Screening 7, 317-323; Préaudat et al. 2002 J. Biomol. Screening 7, 267-274; Zhang et al. 1999 J. Biomol. Screening 4, 67-73; Farfan et al. 2004 Cell Notes 10 15-17; Larson and Worzella 2005 Cell Notes 12, 13-16; Weis et al. 1995 Exp. Cell Res. 219, 699-708; Schlegel et al. 1996 J. Biol. Chem. 271, 1841-1844). As described below, the capsase 3,7 assay uses the Promega Caspase-Glo 3/7 assay kit (cat no. G8092).

The Caspase-Glo® 3/7 Assay is a luminescent assay that measures caspase-3 and -7 activities in purified enzyme preparations or cultures of adherent or suspension cells. The assay provides a proluminescent caspase-3/7 substrate, which contains the tetrapeptide sequence, DEVD. This substrate is cleaved to release aminoluciferin, a substrate of luciferase used in the production of light. The Caspase-Glo® 3/7 Reagent has been optimized for caspase activity, luciferase activity and cell lysis. The addition of the single Caspase-Glo® 3/7 Reagent in an "add-mix-measure" format results in cell lysis, followed by caspase cleavage of the substrate and generation of a "glow-type" luminescent signal. The Caspase-Glo® 3/7 Assay is designed for use with multiwell plate formats, making it ideal for automated high-throughput screening of caspase activity or apoptosis.

In brief, the capsase 3,7 apoptosis assay was validated by conducting a cell titration study (cells seeded at 1,000, 3,000, 5,000 and 10,000 cells/well in 384-well Costar plates), varying compound exposure times (2, 4, 6 and 24 hour), and varying the reading time of the plate after detection reagent addition (30, 60, 90, 120 and 180 min). Staurosporine was used as a positive control. The results from these experiments indicated that optimal results are obtained when cells, seeded at a density of 2,000 cells/well, are incubated in the presence of compound for 2 hrs, and the plates read after 60 min incubation in detection reagent.

For the tissue culture portion of the capsase 3,7 assay, on day 1, A431 cells (ATCC, cat no. CRL-1555, lot no. 4323817) were seeded at 2,000 cells/well at 25 µl/well in DMEM (Cellgro, cat no. 10-017-CV) with 1% sodium pyruvate (Sigma, cat no. S8636), 1% Pen-Strep (Gibco, cat no. 15140), 1% L-Glutamine (Gibco, cat no. 25030) and 10% FBS (Hyclone, cat no. SH30071.03, lot no. ATB31500) in Costar 384-well, tissue culture-treated plates. Plates were incubated overnight at 37° C., 5% $CO_2$. On day 2, media was removed from plates and 25 µl DMEM minus FBS was added. Plates were incubated overnight at 37° C., 5% $CO_2$. On day 3, media was removed and replaced with 25 µl of compound diluted in DEM, with no FBS and 1 mg/ml BSA (Sigma, cat no. A3059). The final DMSO (Sigma, cat no. D2650) concentration for all wells was 0.5%. Cell culture was followed by the capsase 3,7 assay.

For the capsase 3,7 assay, cells were incubated for 5.5 hrs at 37° C., 5% $CO_2$. The plate was removed from the incubator and equilibrated to room temperature. After 30 min, 25 µl Caspase 3/7 detection reagent (Promega Caspase-Glo 3/7 assay kit, cat no. G8092) was added to each well. The plate was covered with tin foil and shaken on a plate shaker at speed 4 for 3 min. The plate was then incubated for an additional 60 min at room temperature. Luminescence was detected using the PolarStar plate reader.

Percent (%) Apoptosis Stimulation Relative to 10 µM Tarceva was calculated as 100×((Experimental RLU Value–Cells Only RLU Value)/(10 µM Tarceva RLU Value–Cells Only RLU Value)). Percent (%) Apoptosis Stimulation Relative to 10 µM Staurosporine where 10 µM Staurosporine represents 100% Apoptosis was calculated as 100×((Experimental RLU Value–Cells Only RLU Value)/(10 µM Staurosporine RLU Value–Cells Only RLU Value)). All statistical analyses were done using GraphPad Prism.

Figure 12:
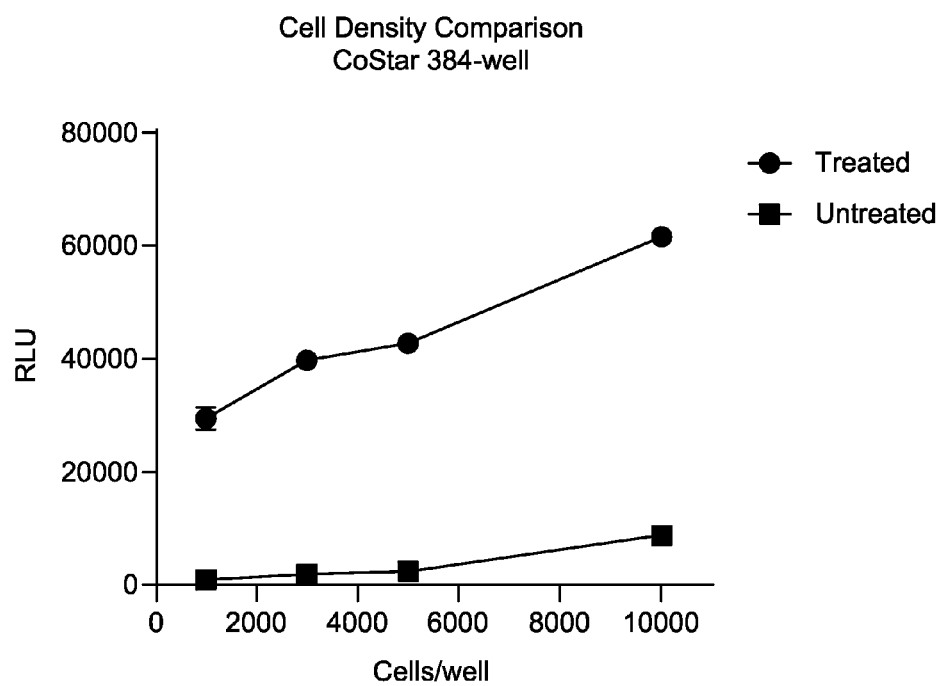
FIG. 12 is a scatter and line plot showing cell density comparison for the capsase 3,7, assay. RLU is shown as a function of cells/well. Further information regarding methodology is provided in Example 8.

As described above, caspase 3,7 activity was evaluated in untreated A431 cells and with those treated for 6 hrs with 3 µM staurosporin at varying cell densities. Based on these results (see e.g., FIG. 12), a cell density of 2,000 cells/well was selected. A time course experiment revealed that the signal for caspase 3,7 induction by staurosporin at 6 hrs was greater than at 4 or 2 hrs (data not shown).

Additive Effect with Tarceva Using Capsase 3,7 Assay.

Figure 13:
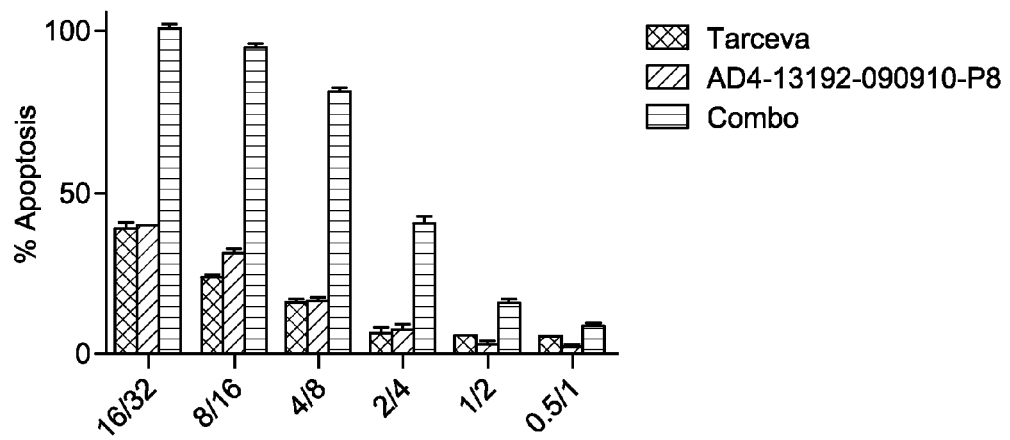
FIG. 13 is a bar graph showing additive effect of AD4-13192 with Tarceva in the caspase 3,7 assay. Treatments included Tarceva (0.5, 1, 2, 4, 8, or 16 µM), AD4-13192 (1, 2, 4, 8, 16, or 32 µM), or Tarceva plus AD4-13192 (Tarceva/AD4-13192). Percent apoptosis is shown as a function of concentration of Tarceva or AD4-13192. Further information regarding methodology is provided in Example 8.

The ability of compounds to produce an additive effect with Tarceva in the caspase 3,7 assay was investigated. A431 cells, plated at 2000 cells/well, were incubated in the presence of Tarceva alone (0.5, 1, 2, 4, 8, or 16 µM), AD4-13192 compound alone (1, 2, 4, 8, 16, or 32 µM) or Tarceva plus AD4 compound (Tarceva/AD4-13192). The assay was stopped after 6 hrs and the presence of caspase was measured using the Promega Caspase-Glo® 3/7 Assay. Results showed that AD4-13192 produced a synergistic (greater-than-additive) effect on Tarceva to increase caspase 3,7 activity (see e.g., FIG. 13).

Thus, the caspase 3,7 assay shows the effect of a given drug on caspase 3/7 activity, an early marker of cellular apoptotic activity. In addition, the ability of compounds to produce synergy (e.g., Tarceva and AD4-13192) can be readily detected in the caspase 3,7 assay.

Some compounds in the AD4-1505-like series were shown to induce caspase 3,7 activity in A431 cells, which overexpress the EGF receptor. The effect of the compounds is summarized in TABLE 14.

TABLE 14

Effect of Compounds to Induce Caspase 3,7 Activity in A431 Cells

| Compound | % Total Apoptosis | | Ability to Synergize with Tarceva |
|---|---|---|---|
| | 16 µM | 8 µM | |
| Tarceva | 43% | 26% | |
| AD4-13072 | 49% | 38% | +++ |
| AD4-13181 | 47% | 43% | ++ |
| AD4-13192 | 32% | 29% | +++ |
| AD4-13215 | 27% | 20% | ++ |
| AD4-13220 | 40% | 32% | + |

At both 16 and 8 µM concentrations, the percent increase in caspase 3,7 activity is shown as a percentage of the maximal response, which is produced by 0.5 µM staurosporin, the reference compound used in the assay (see TABLE 14). Furthermore, each of the compounds enhanced the ability of Tarceva, an EGF receptor kinase inhibitor, by a greater-than-additive effect, to induce apoptosis as measured by an increase in caspase 3,7 activity (see TABLE 14). These results indicate that compounds in the AD4-1505-like series can be used to enhance the ability of Tarceva to induce apoptosis in certain types of cancer.

DNA Fragmentation Assay.

The DNA Fragmentation Assay measures the ability of compounds to induce DNA fragmentation, an indicator of cell apoptosis. Two distinct forms of eukaryotic cell death can be classified by morphological and biochemical criteria: necrosis and apoptosis (Wyllie et al. 1980 Int. Rev. of Cytol. 68, 251-306; Duvall and Wyllie 1986 Immunol. Today 7, 115-119). Necrosis is accompanied by increased ion permeability of the plasma membrane; the cells swell and the plasma membrane ruptures within minutes (osmotic lysis). Apoptosis is characterized by membrane blebbing (zeiosis), condensation of cytoplasm, and the activation of an endogenous endonuclease. This $Ca^{2+}$ and $Mg^{2+}$ dependent nuclease cleaves double stranded DNA at the most accessible internucleosomal linker region, generating mono- and oligo-nucleosomes. In contrast, the DNA of the nucleosomes is tightly complexed with the core histones H2A, H2B, H3 and H4 and is therefore protected from cleavage by the endonuclease (Burgoyne et al. 1974 Biochem. J. 14, 67-72; Stach et al. 1979 J Neurochem 33, 257-261). The DNA fragments yielded are discrete multiples of an 180 bp subunit which is detected as a "DNA ladder" on agarose gels after extraction and separation of the fragmented DNA. The enrichment of mono- and oligonucleosomes in the cytoplasm of the apoptotic cell is due to the fact that DNA degradation occurs several hours before plasma membrane breakdown (Duke and Cohen 1986 Lymphokine Res. 5, 289-299). Apoptosis is the most common form of eukaryotic cell death. It occurs (e.g., during embryogenesis) in parallel with the deletion of autoreactive cells during thymic maturation, in senescence of neutrophil polymorphs, and following removal of specific growth factors, like IL-2, or the addition of physiological stimuli like tumor necrosis factor and glucocorticoids (Scanlon et al. 1989 Proc. Natl. Acad. Sci. USA 86, 182-186; Arends et al. 1990 µm. J. Pathol. 136, 593-608). Apoptosis is also induced by cytotoxic T lymphocytes and natural killer (NK) cells (Sanderson 1981 Biol. Rev. 56, 53-196; Wyllie 1987 Int. Rev. Cytol. 17(Suppl.), 755) and by ionizing radiation (Yamada and Ohyama 1988 Int. J. Radiat. Biol. 53, 65) and monoclonal antibodies like anti-Fas (Yonehara et al. 1989 J. Exp. Med. 169, 1747-1756) and anti-APO-1 (Trauth et al. 1989 Science 245, 301-305; Oehm et al. 1992 J. Biol. Chem. 267, 10709-10715).

The DNA Fragmentation Assay described below uses the Roche Cell Death Detection ELISA kit (cat no. 11920 685 001). The DNA Fragmentation Assay is based on the quantitative sandwich-enzyme-immunoassay-principle using mouse monoclonal antibodies directed against DNA and histones, respectively. The DNA Fragmentation Assay includes the following steps: Fixation of anti-histone antibody by adsorption on the wall of the microplate module; Saturation of non-specific binding sites on the wall by treatment with Incubation buffer (=Blocking solution); Binding of nucleosomes contained in the sample via their histone components to the immobilized anti-histone antibody; Addition of anti-DNA-peroxidase (POD) which reacts with the DNA-part of the nucleosome; Removal of unbound peroxidase conjugate by a washing step; Determination of the amount of peroxidase retained in the immunocomplex with ABTS (2,2'-azino-di-[3-ethylbenzthiazoline sulfonate (6)])*, as a substrate.

For the tissue culture portion of the DNA Fragmentation Assay, on day 1, A549 cells (ATCC, cat no. CCL-185, lot no. 7502546) were seeded at 10,000 cells/well at 200 μl/well in RPMI-1640 (Gibco, cat no. 11875, lot no. ATB31500) with 1% sodium pyruvate, 1% Pen-Strep (Gibco, cat no. 25030, lot no. 568177), 1% L-Glutamine (Gibco, cat no. 11920685001) and 10% FBS (Hyclone, cat no. SH30071.03, lot no. ATB31500) in 96-well, tissue culture-treated plates. Plates were incubated overnight at 37° C., 5% $CO_2$. On day 2, media was removed from plates and 160 μl media containing 5% FBS is added. 40 μl of media containing test compound in 100% DMSO prepared at 5× the dosing concentration was then added to the existing media for a final DMSO concentration of 0.5%. Cells were then incubated in the presence of compound for 24 hrs @ 37° C., 5% $CO_2$.

For the DNA Fragmentation Assay, after 24 hrs, plates were centrifuged at 200×g for 10 min. The media was removed by gently inverting and catching drops with a paper towel. The plates were gently tapped to remove excess media. 200 μl lysis buffer was added to each well, and shaken at 300 rpm, followed by incubation at room temperature for 30 min. Plates were centrifuged at 200×g for 10 min and 20 μl of lysis supernatant was gently removed for ELISA analysis. 20 μl cell lysis supernatant was placed into streptavidin-coated plates along with 20 μl positive control and 20 μl incubation buffer negative control. 80 μl immunoreagent DNA fragment detection (Roche, cat no. 11920 685 001) was added to each well. Wells were covered with foil adhesive and shake at 300 rpm for 2 h at room temperature. Solution was removed and each well washed 3 times with 300 μl incubation buffer. 100 μl ABTS detection substrate (Roche, cat no. 11920 685 001) was added to each well. Plates were incubated on plate shaker at 250 rpm for approximately 10-20 min. 100 μl ABTS stop buffer was added. Plates were read at 400 and 492 nm on PolarStar plate reader. Percent (%) Apoptosis Stimulation Relative to Cell Baseline was calculated as 100×((Experimental Abs 400-492 nm Value−Cells Only Abs 400-492 nm Value)/(Cells Only 400-492 nm Value)). Percent (%) Apoptosis Stimulation Relative to 1 μM Staurosporine where 1 μM Staurosporine represents 100% Apoptosis was calculated as 100×((Experimental Abs 400-492 nm Value−Cells Only Abs 400-492 nm Value)/(1 μM Staurosporine Abs 400-492 nm Value-Cells Only Abs 400-492 nm Value)). All statistical analyses are done either in GraphPad Prism.

Using the DNA Fragmentation Assay, the ability of compounds to induce apoptosis was measured when cells were plated at 5,000, 10,000 and 15,000 cells per well. In addition, the effect of the compounds was assessed at 6, 24 and 48 hours. Based on the results produced by the reference compound, staurosporin (see e.g., FIG. 14A-C), a cell density of 10,000 cells per well and a treatment time of 24 hrs (see FIG. 14B) was selected.

Figure 15:
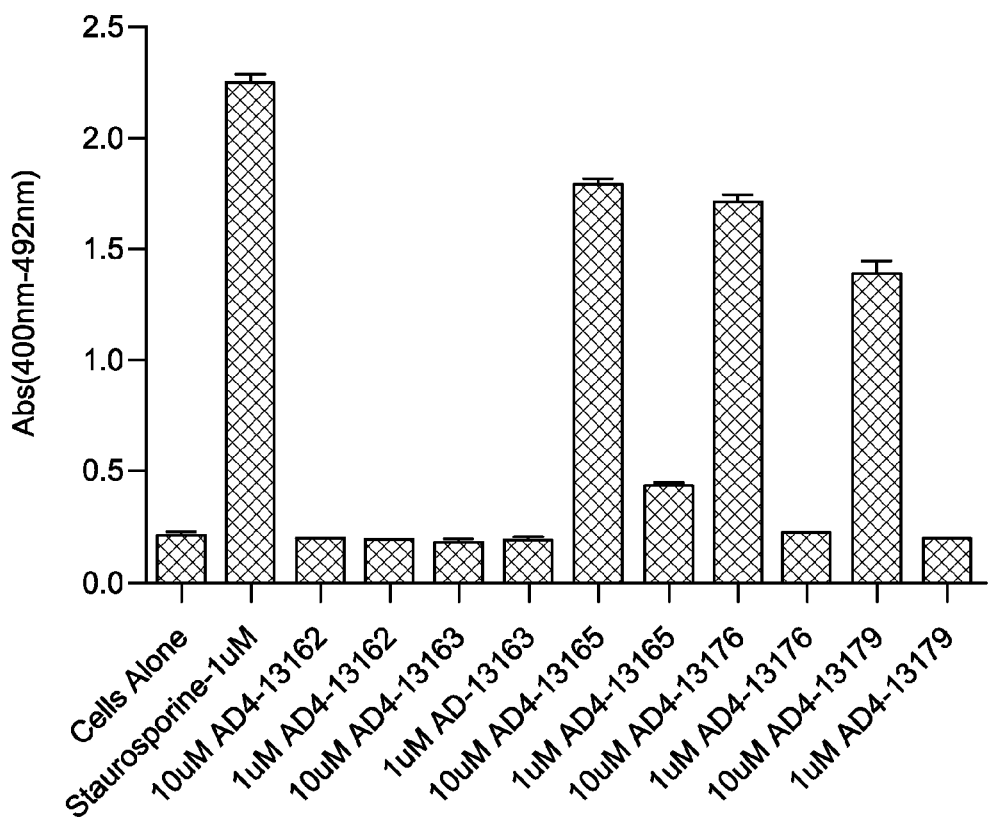
FIG. 15 is a bar graph showing ability of compounds to induce apoptosis in A549 cells according to the DNA Fragmentation Assay. Absorbance at 400 nm-492 nm is shown for each compound and concentration. Further information regarding methodology is provided in Example 8.

The ability of the DNA fragmentation assay to detect activity from a series of test compounds was evaluated. Several compounds, including AD4-13165, AD4-13176 and AD4-13179 at a concentration of 10 μM were shown to induce apoptosis in A549 cells (see e.g., FIG. 15).

Some compounds in the AD4-1505-like series were shown to induce DNA fragmentation in A549 cells, a non-small cell lung cancer cell line. The data for the compounds is summarized in TABLE 15.

TABLE 15

Effect of Compounds to Induce DNA Fragmentation in A549 Cells

| Compound | Conc. | % Increase over Background | % Increase Relative to Staurosporin |
|---|---|---|---|
| AD4-13123 | 10 μM | 476% | 51% |
|  | 1 μM | 366% | 40% |
| AD4-13130 | 10 μM | 684% | 69% |
|  | 1 μM | 630% | 62% |
| AD4-13134 | 10 μM | 469% | 46% |
|  | 1 μM | 573% | 56% |
| AD4-13137 | 10 μM | 628% | 55% |
|  | 1 μM | 182% | 18% |
| AD4-13147 | 10 μM | 462% | 52% |
|  | 1 μM | 406% | 49% |
| AD4-13161 | 10 μM | 678% | 68% |
|  | 1 μM | 254% | 25% |
| AD4-13164 | 10 μM | 788% | 58% |
|  | 1 μM | 525% | 39% |
| AD4-13165 | 10 μM | 582% | 74% |
|  | 1 μM | 172% | 24% |
| AD4-13172 | 10 μM | 782% | 70% |
|  | 1 μM | 355% | 32% |
| AD4-13178 | 10 μM | 581% | 68% |
|  | 1 μM | 395% | 48% |
| AD4-13185 | 10 μM | 576% | 62% |
|  | 1 μM | 285% | 32% |
| AD4-13187 | 10 μM | 543% | 62% |
|  | 1 μM | 388% | 47% |
| AD4-13192 | 10 μM | 561% | 55% |
|  | 1 μM | 131% | 11% |
| AD4-13199 | 10 μM | 492% | 55% |
|  | 1 μM | 130% | 15% |
| AD4-13224 | 10 μM | 662% | 59% |
|  | 1 μM | 296% | 25% |
| AD4-13225 | 10 μM | 697% | 52% |
|  | 1 μM | 702% | 52% |

The results show the effect of the compounds to increase DNA fragmentation compared to background, and compared to the maximal response, which is produced by 0.5 staurosporin, the reference compound used in the assay (see TABLE 15). Compounds were considered active if they increased DNA fragmentation at a concentration of 10 or 1 μM by 50% or 20% relative to staurosporin, respectively (see TABLE 15). Based on these results, compounds in this chemical series are expected to have therapeutic benefit for the treatment of non-small cell lung cancers.

Annexin V Assay

The Annexin V Assay shows ability of compounds to increase annexin V activity, which is a measure of cell apoptosis (see e.g., Hotz et al. 1994 Cytometry 15, 237-244; Telford et al. 1992 Cytometry 13, 137-143; Vermes et al. 1995 J. Immun. Meth. 184, 39-51). Assays that measure apoptosis are utilized to determine whether or not compounds can induce programmed cell death in cancer cells. Annexin V is a protein that is used to detect apoptosis by binding to phosphatidylserine expressed on membranes of dead or dying cells. Fluorescently tagged with FITC, it can be used in conjunction with 7-aminoactinomycin D to determine the percentage of cells undergoing apoptosis via flow cytometry. Cells in early apoptosis will emit an FITC signal which will eventually be replaced by the far red 7-AAD signal that is associated with cell membrane permeability due to necrosis.

In brief, for the Annexin V Assay, compounds were added to cells plated in 6-well plates. Treated cells were incubated for up to 30 hours before addition of fluorescent cell marker probes that detect the presence of annexin V. The percentage of cells undergoing apoptosis and necrosis were determined by flow cytometry. The compounds tested induced apoptosis equivalent to, or slightly better than, the positive controls, camptothecin or staurosporin.

For the tissue culture portion of the Annexin V Assay, On day 1, A549 cells (ATCC, cat no. CRL-185, lot no. 7502546) were seeded at 100,000 cells/well in 2.0 ml media containing 5% FBS (Hyclone, cat no. SH30071.03, lot no. ATB31500), 1% Pen-Strep (Gibco, cat no. 15140, lot no. 841383), and 1% L-Glutamine (Gibco, cat no. 25030, lot no. 568177) in 6-well, tissue culture treated plates. Plates were incubated overnight at 37° C., 5% $CO_2$ and 85% relative humidity. On day 2, working solutions of compounds (at 1000×) were prepared. To 2.0 ml media/well was added 2 µl 1000× compound diluted in 100% DMSO for final DMSO concentration of 0.1%. On day 3, plates were incubated for 30 hrs. After 30 hrs, cells were washed with PBS, then cells were trypsinized (CellGro, cat no. 25-0530Cl, lot no. 25053253) for 8 min at 37° C. Cells were collected by centrifugation at 300×g for 5 min.

For the Annexin V Assay, cell pellets were resuspended with 500 µl of PBS/2.5 mM calcium chloride supplemented with 0.15 µg/well of Annexin V FITC (BioVision, cat no. 1001-200, lot no. 50601) and 0.25 µg of 7-AAD (eBioscience, cat no. 00-6993-50, lot no. 50601). Cells were incubated for 20 min at room temperature in the dark then washed once with PBS/$CaCl_2$, and resuspended in 500 µA of PBS/$CaCl_2$, 2% v/v formaldehyde (ThermoScientific, cat no. 28908, lot no. JG1141272), 0.1% v/v pluronic F-68 (MP, cat no. 2750049, lot no. 821-4K), and 10 µg/ml actinomycin D (Acros, cat no. 294940050, lot no. A0257010). Resuspended cells were stored at 4° C. in the dark, until flow cytometry analysis.

For flow cytometry analysis of the Annexin V Assay, sample acquisition was on the BD LSR II manufactured by BD Biosciences, San Jose, Calif. Annexin was excited by a 50 mW Coherent Sapphire solid-state CW blue laser (Coherent Inc., Santa Clara, Calif.) at a wavelength of 488 nm and collected using a 530/30 bandpass filter. 7-AAD was excited by a 50 mW Coherent Sapphire solid state CW yellow laser at 561 nm and the emission signal was collected with a 630/30 bandpass filter. 10,000 events were collected based on a stopping gate of forward scatter vs side scatter light. Acquisition was done through BD FACS DiVa software version 6.1.1 on high flow rate (60 µL/min). Calculations were as follows: Quadrant 3=lower left=live cells; Quadrant 4=lower right=early apoptosis; Quadrant 2=upper right=late apoptosis; Quadrant 1=upper left=dead cells. Percent (%) Total apoptosis was calculated as early (quadrant 4)+late (quadrant 2). Percent (%) ratio apoptosis was calculated as (experimental–No treatment/positive control)*100. All statistical analyses are done using GraphPad Prism or Microsoft Excel.

Figure 16A:
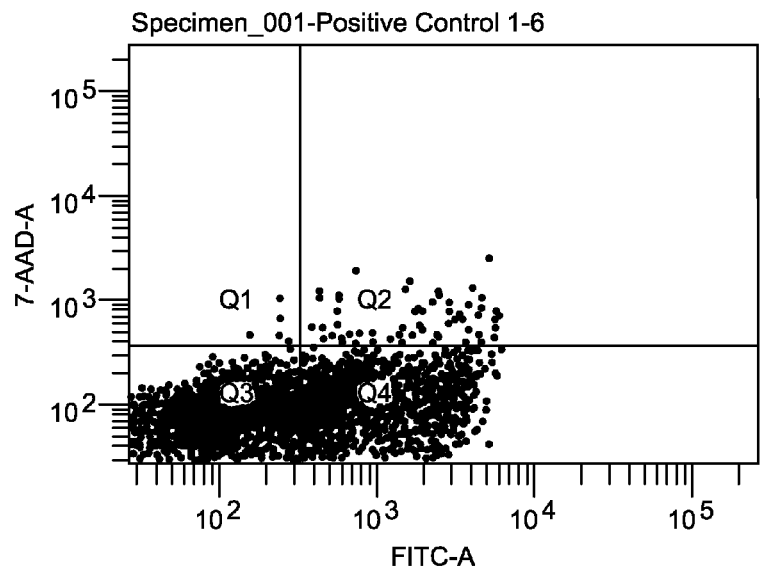
FIG. 16A is a flow cytometry dot plot for 7-AAD-A as a function of FITC-A, where Quadrant 3=lower left=live cells; Quadrant 4=lower right=early apoptosis; Quadrant 2=upper right=late apoptosis; Quadrant 1=upper left=dead cells.
Figure 16B:
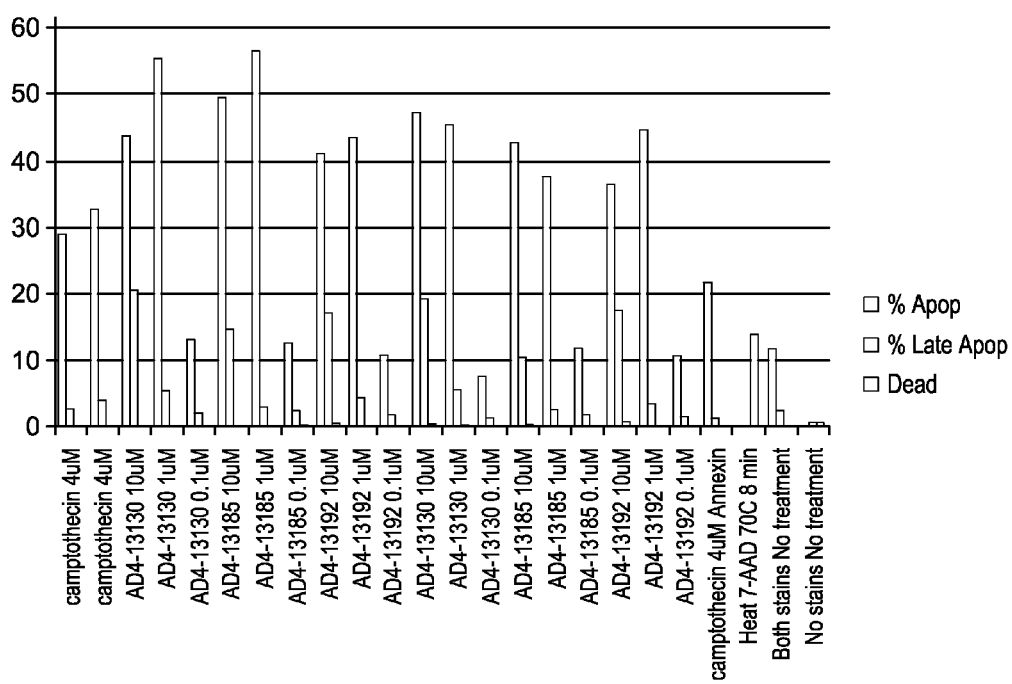
FIG. 16B is a bar graph showing percent (%) total apoptosis (early (quadrant 4)+late (quadrant 2) of FIG. 16A) and percent (%) ratio apoptosis (experimental−No treatment/positive control)*100. Further information regarding methodology is provided in Example 8.

Results of the Annexin V Assay show the utility of the Annexin V, flow cytometry approach for determining the apoptotic potential of our compound leads. AD4 compounds were shown to induce apoptosis in A549 cells to the same extent or to a greater degree than the reference compound, camptothecin, after 29 hours of treatment (see e.g., FIG. 16B). At a concentration of 1 µM, both AD4-13130 and AD4-13185 induce apoptosis in greater than 50% of the cell population (see e.g., FIG. 16B). At a concentration of 10 µM, these compounds also stimulate late apoptosis in up to 20% of the cell population (see e.g., FIG. 16B). AD4-13192 elicits similar but slightly reduced responses (see e.g., FIG. 16B).

Some compounds in the AD4-1505-like series were shown to induce the expression of annexin V in A549 cells, a non-small cell lung cancer cell line. The data for the compounds is summarized in TABLE 16.

TABLE 16

Effect of Compounds to Induce Caspase 3,7 Activity in A431 Cells

| Compound | Conc. | % Total Apoptosis | % Relative to Reference Cpd. |
| --- | --- | --- | --- |
| AD4-13130 | 10 µM | 38% | 166% |
|  | 1 µM | 32% | 178% |
| AD4-13147 | 10 µM | 28% | 92% |
|  | 1 µM | 29% | 95% |
| AD4-13185 | 10 µM | 30% | 202% |
|  | 1 µM | 42% | 161% |
| AD4-13192 | 10 µM | 30% | 146% |
|  | 1 µM | 29% | 152% |

The results show the percentage of cells in early- and late-stage apoptosis (i.e. total apoptosis), which is indicated by the expression of annexin V, and the effect of the compounds as a percentage compared to the maximal response, which is produced by either 4.0 µM camptothecin or 1.0 µM staurosporin, the reference compounds used in the assay (see TABLE 16). Compounds were considered active if they induced total apoptosis by >20% (see TABLE 16). Based on these results, compounds in this chemical series are expected to have therapeutic benefit for the treatment of non-small cell lung cancers.

Example 9

Pharmacokinetics

In this example, the oral bioavailability of AD4-13130 and AD4-13192 was investigated after a 1 and 5 mg/kg intravenous and oral dose in male CD-1 mice, respectively. Plasma levels of the test compounds were determined by LC-MS/MS. Data was analyzed by non compartmental pharmacokinetic model by using WinNonlin. The results are summarized in TABLE 17.

TABLE 17

Pharmacokinetic Parameters for AD4-13130 and AD4-13192

| Parameter | AD4-13130 | | AD4-13192 | |
| --- | --- | --- | --- | --- |
|  | i.v. | p.o. | i.v. | p.o. |
| Cmax (ng/mL) | 669 | 131 | 3550 | 59 |
| AUC (hr · ng/mL) | 609 | 278 | 1387 | 115 |
| Tmax (hr) | 0.083 | 1.0 | 0.083 | 0.5 |
| Clearance (L/hr/kg) | 1.64 | | 0.72 | |
| Vd (L/kg) | 3.24 | | 0.56 | |
| Half-life ($t_{1/2}$; h) | 1.86 | | 1.47 | |
| BA (%) | | 10.1 | | 1.7 |

After intravenous dosing at 1 mg/kg, AD4-13130 and AD4-13192 reached an average Cmax of 669±45 and 3550±571 ng/mL, respectively (see TABLE 17). The average clearance and volume of distribution were 1.64 L/hr/kg and 3.24 L/Kg, respectively for AD4-13130 and 0.72 L/hr/kg and 0.56 L/Kg, respectively for AD4-13192 (see TABLE 17). The average half-life appears to be similar ranging from 1.47 to 1.86 hours for AD4-13192 and AD4-13130, respectively (see TABLE 17). After oral dosing at 5 mg/kg, AD4-13130 and AD4-13192 reached an average Cmax of 131±51 and 59±21 ng/mL at 1 and 0.5 hours, respectively (see TABLE 17). Both test compounds exhibited oral bioavailability (%): AD4-13130 (10.1), and AD4-13192 (1.7) (see TABLE 17).

Example 10

Structure and Function of 1505-Like Compounds

The following example shows structure of 1505-like compounds associated with stability, antiproliferative activity, and apoptosis for an aminopyridine ring and a benzaldehyde derived ring.

Stability of Aminopyridine Ring.

Stability of hydroxyquinoline analogs were determined (see e.g., TABLE 18). MLM represents the percentage left after incubation with mouse liver microsomes for 30 minutes. HLM represents the percentage left after incubation with human liver microsomes for 30 minutes.

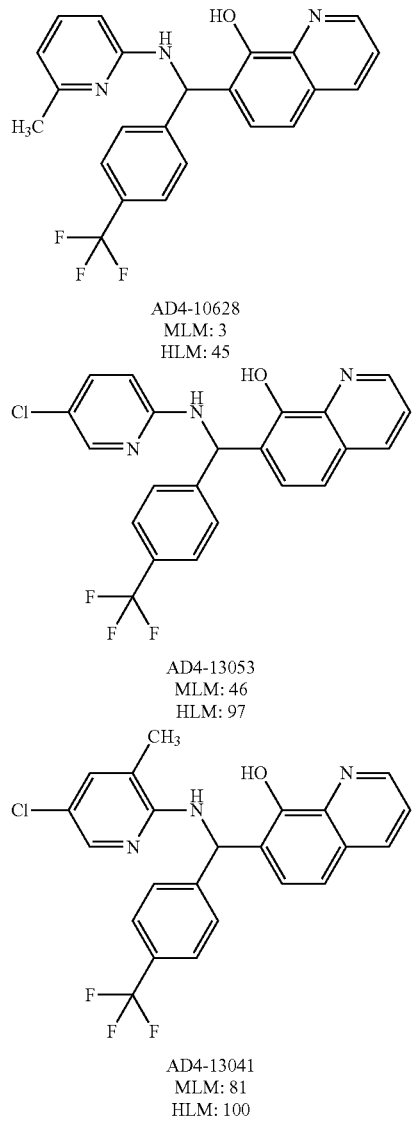

Results showed that substitution at the 5-position of an aminopyridine with a chlorine atom increased stability. Additional substitution at the 3-position of the aminopyridine with a methyl group was shown to further increase stability.

Antiproliferative Activity of Aminopyridine Ring.

Antiproliferative activity (i.e., suppression of proliferation of cancer cells in vitro) for compounds having various combinations of halogens and alkyl groups on the aminopyridine ring were determined.

Results showed that the following substitution patterns had good antiproliferative activity:

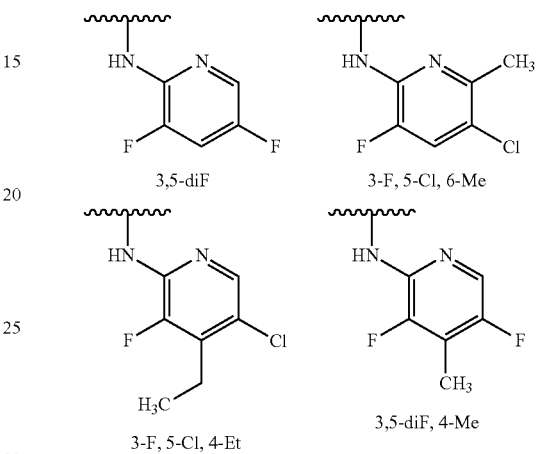

Results showed that the following substitution patterns had very good antiproliferative activity:

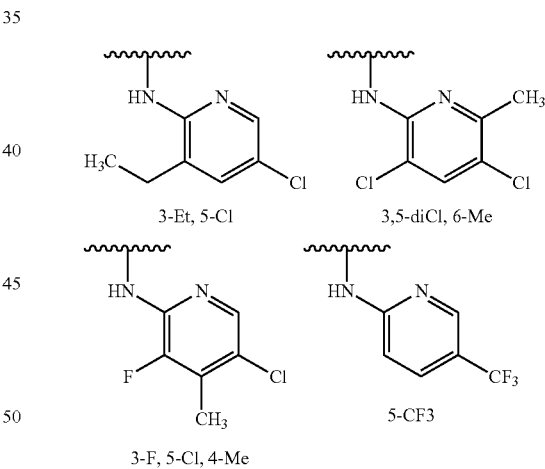

The following substitution patterns showed the best antiproliferative activity of compounds tested:

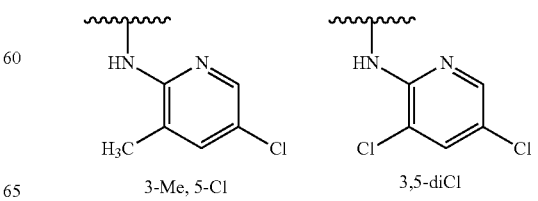

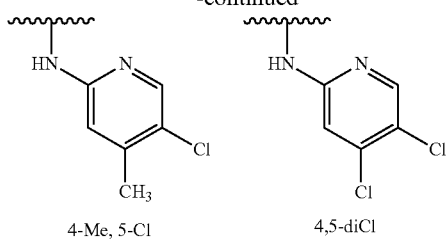

4-Me, 5-Cl     4,5-diCl

Apoptotic Activity of Aminopyridine Ring.

Apoptotic activity (i.e., Caspase, DNA Fragmentation, Annexin-V) for compounds having substitutions on the aminopyridine ring were determined.

Results showed that analogs with a chloro group at the 5-position of the aminopyridine ring and additional chloro or methyl groups at the 3- or 4-positions exhibited increased apoptosis. Examples of analogs with a chloro group at the 5-position of the aminopyridine ring and additional chloro or methyl groups at the 3- or 4-positions include:

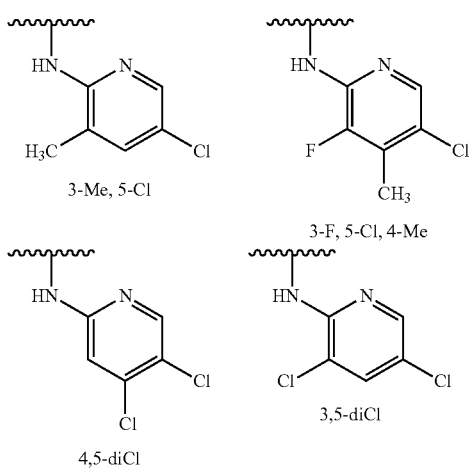

3-Me, 5-Cl     3-F, 5-Cl, 4-Me 4,5-diCl     3,5-diCl

Stability of Benzaldehyde Derived Ring.

Stability of analogs having a benzaldehyde derived ring were determined (see e.g., TABLE 18). MLM represents the percentage left after incubation with mouse liver microsomes for 30 minutes. HLM represents the percentage left after incubation with human liver microsomes for 30 minutes.

Results showed that groups at the 2- and 4-position of the benzene ring provide analogs that are stable toward liver microsome incubation.

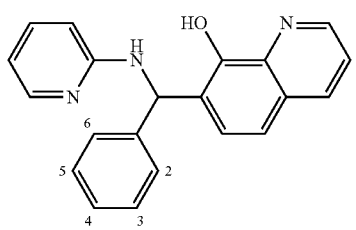 [SMILES: Oc1c(C(Nc2ccccn2)c2ccccc2)ccc2cccnc12]

Exemplary results are as follows:

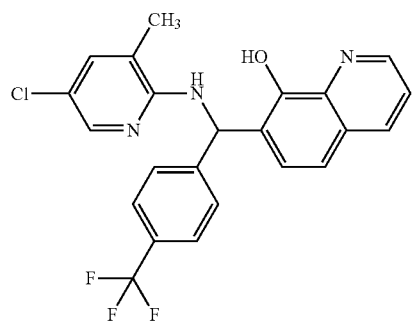

AD4-13041
MLM 81
HLM 100

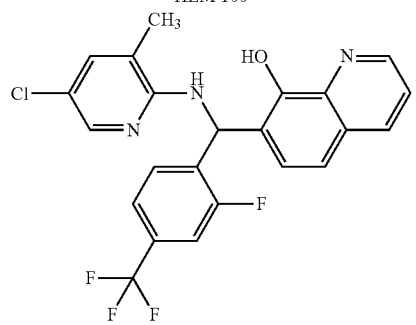

AD4-13042
MLM 99
HLM 100

Results also showed that the 2,4-dichloro substitution pattern also provides good stability as exemplified by the following examples of AD4-13165 and AD4-13206:

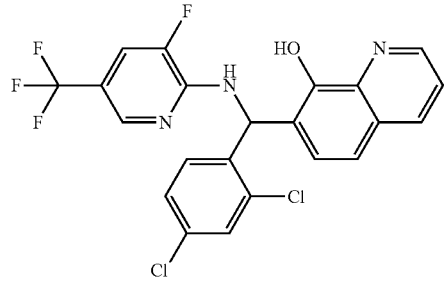

AD4-13165
MLM 100
HLM 100

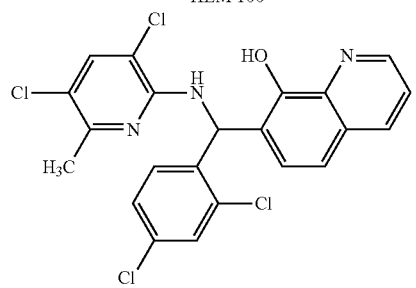

AD4-13206
MLM 93
HLM 99

Antiproliferative Activity of Benzaldehyde Derived Ring.

Antiproliferative activity (i.e., suppression of proliferation of cancer cells in vitro) for compounds having various combinations of halogens and trifluoromethyl groups on the benzene ring were determined. Examples of desirable substitution patterns on the benzene ring are provided below.

Results showed that the following substitution patterns had good antiproliferative activity:

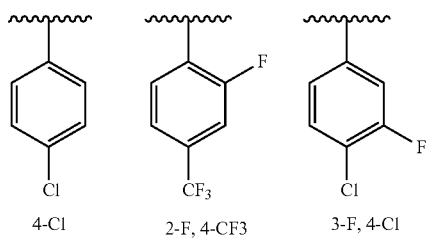

Results showed that the following substitution patterns had very good antiproliferative activity:

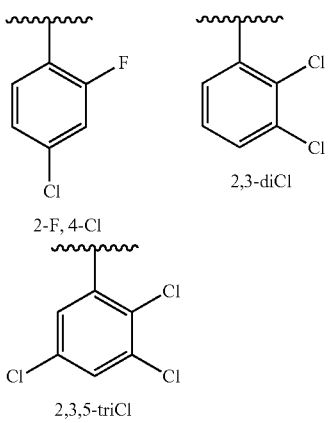

The following substitution patterns showed the best antiproliferative activity of compounds tested:

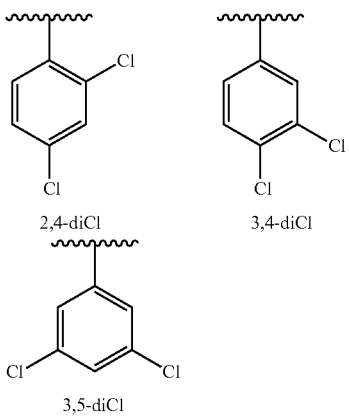

Apoptotic Activity of Benzaldehyde Derived Ring.

Apoptotic activity (i.e., Caspase, DNA Fragmentation, Annexin-V) for compounds having substitutions on the benzaldehyde ring were determined.

Results showed that analogs with a chloro group at the 4-position of the benzene ring and additional chloro or fluoro groups at the 2- or 3-positions exhibited increased apoptosis. Examples of analogs having increased apoptotic activity include AD4-1313-, AD4-13185, and AD4-13178:

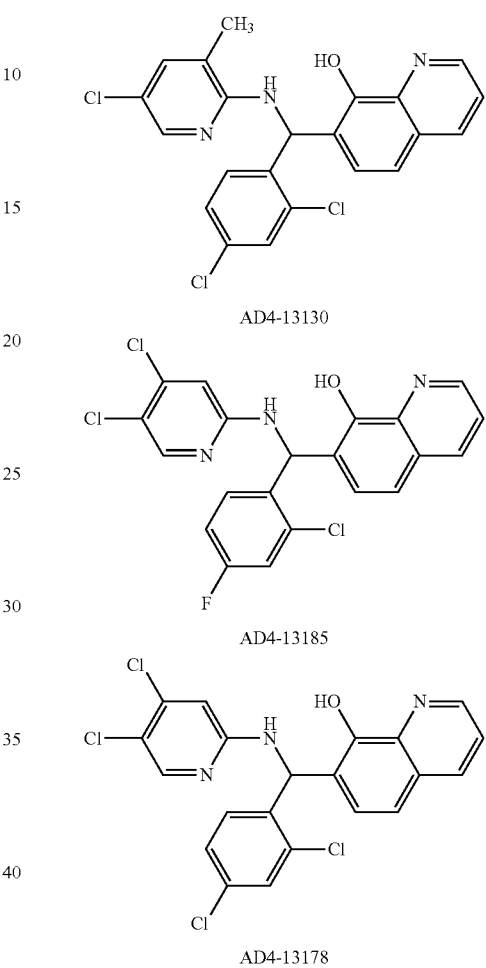

TABLE 18

Compound Stability

| Compound | MLM % Remaining@ 30 Min | HLM % Remaining@ 30 Min |
| --- | --- | --- |
| AD4-10628 | 3 | 45 |
| AD4-11511 | 6 | 6 |
| AD4-11601 | 31 | 9 |
| AD4-12902 | 17 | 72 |
| AD4-12905 | 23 | 63 |
| AD4-12907 | 5 | 14 |
| AD4-12908 | 6 | 48 |
| AD4-12911 | 17 | 57 |
| AD4-12912 | 10 | 38 |
| AD4-12915 | 25 | 71 |
| AD4-12917 | 11 | 53 |
| AD4-12918 | 15 | 51 |
| AD4-12921 | 5 | 9 |
| AD4-12923 | 10 | 14 |
| AD4-12924 | 66 | 79 |
| AD4-12926 | 4 | 4 |
| AD4-12925 | 5 | 12 |

TABLE 18-continued

| | Compound Stability | |
|---|---|---|
| Compound | MLM % Remaining@ 30 Min | HLM % Remaining@ 30 Min |
| AD4-12903 | 18 | 46 |
| AD4-12909 | 13 | 50 |
| AD4-12913 | 41 | 61 |
| AD4-12916 | 26 | 80 |
| AD4-12922 | 17 | 9 |
| AD4-13042 | 99 | 101 |
| AD4-12955 | 41 | 61 |
| AD4-12959 | 15 | 42 |
| AD4-13022 | 5 | 36 |
| AD4-13024 | 20 | 47 |
| AD4-13023 | 60 | 95 |
| AD4-13041 | 81 | 100 |
| AD4-13045 | 26 | 77 |
| AD4-13058 | 60 | 75 |
| AD4-13043 | 77 | 98 |
| AD4-13059 | 64 | 92 |
| AD4-13068 | 46 | 96 |
| AD4-13053 | 46 | 97 |
| AD4-13054 | 46 | 80 |
| AD4-13033 | 84 | 100 |
| AD4-13031 | 87 | 93 |
| AD4-13056 | 85 | 88 |
| AD4-13067 | 46 | 89 |
| AD4-13076 | 28 | 70 |
| AD4-13075 | 13 | 64 |
| AD4-13065 | 47 | 83 |
| AD4-13063 | 42 | 80 |
| AD4-13055 | 57 | 100 |
| AD4-13061 | 58 | 93 |
| AD4-13106 | 42 | 86 |
| AD4-13111 | 87 | 92 |
| AD4-13132 | 66 | 98 |
| AD4-13131 | 83 | 100 |
| AD4-13029 | 77 | 76 |
| AD4-13108 | 25 | 93 |
| AD4-13130 | 69 | 89 |
| AD4-13086 | 37 | 72 |
| AD4-13107 | 28 | 83 |
| AD4-13095 | 60 | 88 |
| AD4-13123 | 30 | 84 |
| AD4-13051 | 40 | 72 |
| AD4-13122 | 60 | 94 |
| AD4-13114 | 40 | 99 |
| AD4-13094 | 52 | 85 |
| AD4-13143 | 76 | 96 |
| AD4-13147 | 44 | 98 |
| AD4-13150 | 85 | 100 |
| AD4-13153 | 62 | 96 |
| AD4-13165 | 100 | 100 |
| AD4-13166 | 71 | 100 |
| AD4-13172 | 80 | 100 |
| AD4-13177 | 86 | 86 |
| AD4-13178 | 83 | 100 |
| AD4-13185 | 57 | 98 |
| AD4-13192 | 63 | 100 |
| AD4-13199 | 63 | 100 |
| AD4-13200 | 67 | 94 |
| AD4-13202 | 97 | 100 |
| AD4-13206 | 93 | 99 |

Example 11

Synthesis of Intermediate Compounds

The following example describes synthesis of intermediate compounds used in the synthesis of AD4-1505-like compounds described herein.

Preparation of 2-Amino-3-fluoro-4-methyl-5-chloropyridine

Not Identified in CAS

Step 1:

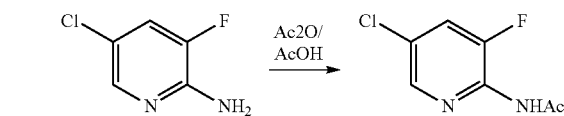 [SMILES: Nc1ncc(Cl)cc1F ; CC(=O)Nc1ncc(Cl)cc1F]

2-Amino-3-fluoro-5-chloropyridine (Wonda Science, cat. #01060, CAS[246847-98-3]; 14.6 g, 0.1 mol) is treated with Ac2O (15 g) in AcOH (10 g) with a small amount of FeCl3 (50 mg). The mixture is stirred at room temperature for 3 h during which time a white solid forms. Water (300 ml) is added and the mixture is stirred for 1 hr at room temperature. The mixture is filtered and the solid is washed with water (3×500 ml). The solid is air dried and recrystallized from EtOAc/hexanes to give N-(3-fluoro-5-chloro)-2-acetamidopyridine, as white solid (MP 165-166° C.).

Step 2:

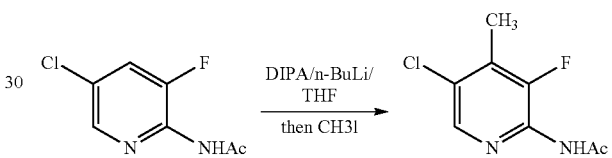

N-(3-fluoro-5-chloro)-2-acetamidopyridine (14.6 g, 0.10 mol) and diisopropylamine (25.3 g, 0.25 mol) are dissolved in anhydrous THF (200 ml), stirred and cooled to −70 C in a dry ice-acetone bath. n-BuLi (2.5 M in hexane, 100 ml, 0.25 mol) is added drop-wise, keeping the internal temperature below −60 C, while stirring is continued for 2 hr. Iodomethane (28.4 g, 0.20 mol) is then added drop-wise. The reaction mixture is stirred in between −60 to −70 C for an additional 2 hrs. Saturated aqueous NH4Cl solution is added slowly at −70 C to the reaction. The mixture is stirred and warmed to room temperature. The mixture is extracted with EtOAc (3×100 ml) and the combined organic extracts, washed with water and brine, then dried over MgSO4 and filtered. The solvent is evaporated using a rotovap and the residue is purified by flash chromatography. The appropriate fractions are evaporated on a rotovap and the residue is triturated with hexanes to form a white solid. The solid is filtered to give N-(3-fluoro-4-methyl-5-chloro)-2-acetamidopyridine as a white solid (MP 124-125° C.).

Step 3:

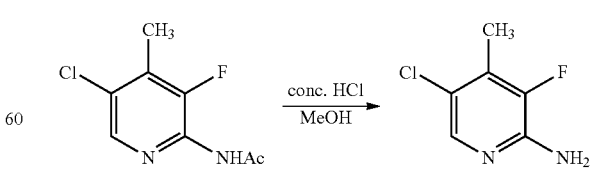

N-(3-fluoro-4-methyl-5-chloro)-2-acetamidopyridine (13.6 g, 0.085 mmol) is dissolved in MeOH (30 ml) and treated with conc. HCl (20 ml). The mixture is stirred and warmed to reflux temperature for 4 hrs. The mixture is cooled to room temperature and the solvent is removed using a rotovap. To the residue is added ice and 3N NaOH to adjust the pH to 9-10. The mixture is extracted with Et₂O and dried over MgSO₄. The solution is filtered and the solvent removed on a rotovap. The residue is purified using a flash silica-gel column eluting with 10% EtOAc in hexane to give 2-amino-3-fluoro-4-methyl-5-chloropyridine as a white solid (MP 136-138° C.).

BBM-001-072

Preparation of 2-Amino-3-ethyl-5-chloropyridine

Not Identified in CAS

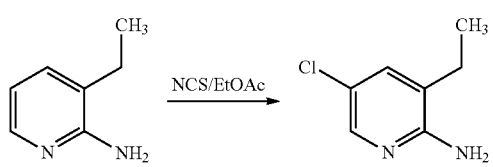

2-Amino-3-ethylpyridine (Wonda Science, CAS[42753-67-3]; 12.2 g, 0.1 mol) is dissolved by stirring in 500 ml of ethyl acetate with 10 ml DMF. A thermometer is placed in the solution to monitor temperature. N-Chlorosuccinimide (13.3 g, 0.1 mol) is added in several portions to keep the solution at room temperature. The solution becomes dark in color and is stirred at room temperature overnight. The supernatant is decanted from the dark solids that formed and transferred to a separatory funnel. The organic solution is washed with 500 ml saturated aqueous sodium bisulfite and then 500 ml brine. The organic layer is dried with MgSO₄ and concentrated on a rotovap. The dark brown crude product is chromatographed on 500 g of flash silica-gel eluting with 35% EtOAc/Hexanes. Concentration of the appropriate fractions on a rotovap gives a light-tan oil. The oil is dissolved in hexanes and decolorized with activated carbon. The solvent is cooled to −20° C. and the solid which forms is isolated by filtration to give the product as a flaky off-white solid. (MP 67-68° C.).

BBM-001-011

Preparation of 2-Amino-3-methoxy-5-chloropyridine

CAS 1242336-53-3

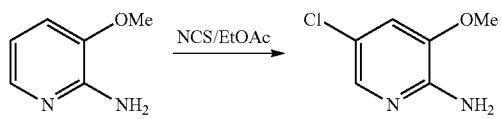 [SMILES: COc1cccnc1N ; COc1cc(Cl)cnc1N]

3-Methoxy-2-aminopyridine (Wonda Science, cat #01683; 12.4 g, 0.01 mol) is dissolved by stirring in 500 ml of ethyl acetate. A thermometer is placed in the solution to monitor temperature. N-Chlorosuccinimide (13.3 g, 0.01 mol) is added in several portions to keep the solution at room temperature. The solution becomes dark in color and is stirred at room temperature overnight. The supernatant is decanted from the dark solids that formed and transferred to a separatory funnel. The organic solution is washed with 500 ml saturated aqueous sodium bisulfite and then 500 ml brine. The organic layer is dried with MgSO4 and concentrated on a rotovap. The dark brown crude product is chromatographed on 500 g of flash silica-gel eluting with 30% EtOAc/Hexanes. Concentration of the appropriate fractions on a rotovap gives a yellow solid. The solid is suspended in hexanes, stirred and filtered to give the product as a bright yellow solid. (MP 93-94° C.).

BBM-001-049

Preparation of 2-Amino-4,5-dichloropyridine

CAS 188577-68-6

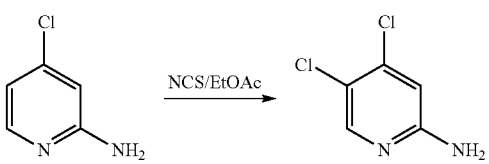 [SMILES: Nc1cc(Cl)ccn1 ; Nc1cc(Cl)c(Cl)cn1]

4-Chloro-2-aminopyridine (Matrix Scientific, cat. #23809; 1.29 g, 0.01 mol) is dissolved by stirring in 500 ml of ethyl acetate. A thermometer is placed in the solution to monitor temperature. N-Chlorosuccinimide (13.3 g, 0.01 mol) is added in several portions to keep the solution at room temperature. The solution becomes dark in color and is stirred at room temperature overnight. The supernatant is decanted from the dark solids that formed and transferred to a separatory funnel. The organic solution is washed with 500 ml saturated aqueous sodium bisulfite and then 500 ml brine. The organic layer is dried with MgSO4 and concentrated on a rotovap. The dark brown crude product is chromatographed on 500 g of flash silica-gel eluting with CH2Cl2. Concentration of the appropriate fractions on a rotovap gives a light tan solid. The solid is dissolved in EtOAc and decolorized with activated carbon. EtoAc is removed using a rotovap and the resulting solid is suspended in ice-cold CH₂Cl₂ and filtered to give the product as a white solid. (MP 142-143° C.).

BBM-001-074

Preparation of 2-Amino-3-fluoro-4-ethyl-5-chloropyridine

Not Identified in CAS

Step 1:
As described above in Example BBM-001-065.

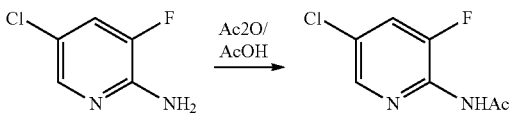

Step 2:

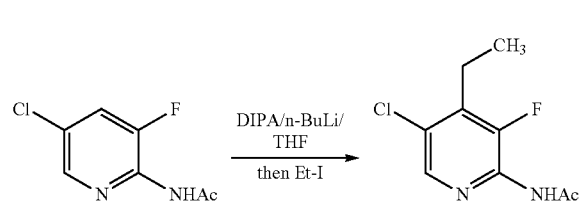

In the manner described above in Example BBM-001-065, N-(3-fluoro-5-chloro)-2-acetamidopyridine (14.6 g, 0.10 mol) and diisopropylamine (25.3 g, 0.25 mol) are combined and treated with n-BuLi (2.5 M in hexane, 100 ml, 0.25 mol)

and then iodoethane (31.2 g, 0.2 mol) to give N-(3-fluoro-4-ethyl-5-chloro)-2-acetamidopyridine as a white solid (MP 112-113° C.).

Step 3:

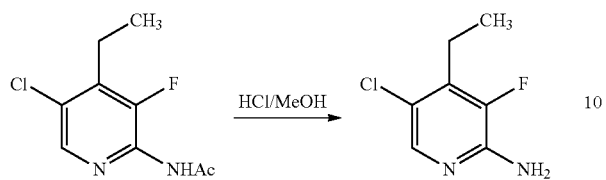

In the manner described above in Example BBM-001-065, N-(3-fluoro-4-ethyl-5-chloro)-2-acetamidopyridine (16.0 g, 0.092 mmol) is treated with MeOH (30 ml) and conc. HCl (20 ml) to give 2-amino-3-fluoro-4-ethyl-5-chloropyridine as a white solid (MP 71-72° C.).

BBM-001-064

Preparation of
2-Amino-4-methyl-3,5-difluoropyridine (Not Identified in CAS)

Step 1:
As described above in Example BBM-001-065.

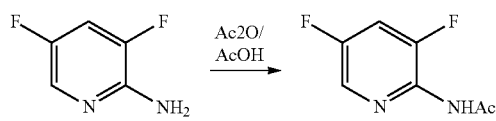 [SMILES: Nc1ncc(F)cc1F ; CC(=O)Nc1ncc(F)cc1F]

N-(3,5-difluoro)-2-acetamidopyridine is crystallized from EtOAc/hexanes and isolated as a white solid (MP 142-144° C.).

Step 2:

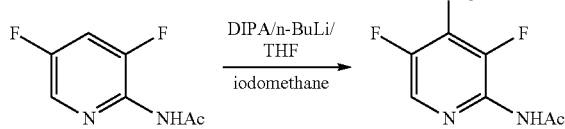

In the manner described above in Example BBM-001-065, N-(3,5-difluoro)-2-acetamidopyridine (13.0 g, 0.10 mol) and diisopropylamine (25.3 g, 0.25 mol) are combined and treated with n-BuLi (2.5 M in hexane, 100 ml, 0.25 mol) and then iodomethane (28.4 g, 0.20 mol) to give N-(3,5-difluoro-4-methyl)-2-acetamidopyridine as a white solid (MP 92-93° C.).

Step 3:

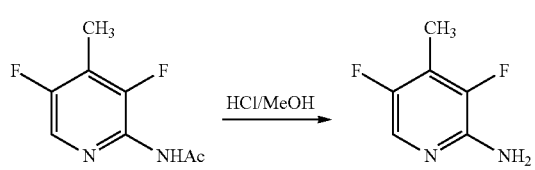

In the manner described above in Example BBM-001-065, N-(3,5-difluoro-4-methyl)-2-acetamidopyridine (13.0 g, 0.09 mol) is treated with MeOH (30 ml) and conc. HCl (20 ml) to give 2-amino-4-methyl-3,5-difluoropyridine as a white solid (MP 92-93° C.).

IJT-001-090

Preparation of 2-Amino-5-chloro-6-methylpyridine

CAS 36936-23-9

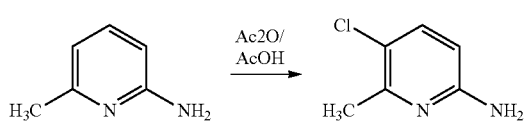

In the manner described above in Example BBM-001-065, 2-amino-6-picoline, Acros Organics (1.08 g, 0.01 mol) is treated with N-chlorosuccinimide to give 2-amino-5-chloro-6-methylpyridine as a light-yellow solid (MP 73-74° C.).

BBM-001-071

Preparation of 2-Amino-5-chloro-3-methylpyridine

CAS 1173019-45-8

In the manner described above in Example BBM-001-065, 2-amino-3-chloropyridine, Matrix Scientific (1.08 g, 0.01 mol) is treated with N-chlorosuccinimide to give 2-amino-5-chloro-3-methylpyridine as a white solid (MP 63-64° C.).

BBM-001-009

Preparation of 2,3,5,6-Tetrafluoro-4-(2'2'2'-trifluoro-ethoxy)benzaldehyde

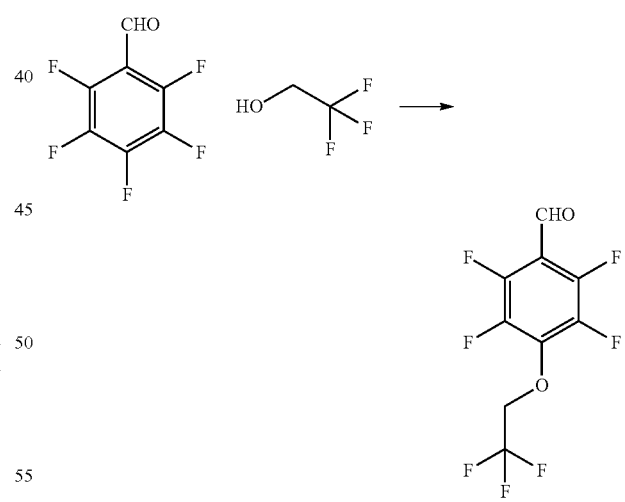

Pentafluorobenzaldehyde (Oakwood Products, cat. #002835, 19.6 g, 0.1 mol) and tetrabutylammonium hydrogensulfate, Bu4NHSO4 (50 mg, 0.0015 mol) are dissolved in 500 ml CH2Cl2. 2,2,2-Trifluoroethanol (10.0 g, 0.01 mol) is added and the mixture is stirred and cooled in an ice-bath. Sodium hydroxide pellets (4.0 g, 0.01 mol) are dissolved in 100 ml of water and slowly added to the mixture with a dropping funnel. The temperature of the mixture is monitored. The rate of addition controlled to keep the temperature below 5° C. After addition is complete the mixture is stirred for an additional 2 h at 5° C. and then transferred to a separatory funnel. The organic layer is separated and dried with Na2SO4. The solvent is evaporated using a rotovap and the residual oil is fractionally distilled with a short path apparatus. The fraction with a boiling range of 105-108° C. contains the desired compound.

IJT-002-059

Preparation of 2-Amino-3,5-dichloro-4-methylpyridine (CAS 31430-47-4

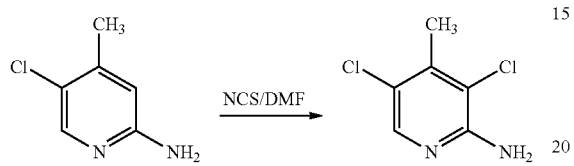

2-Amino-4-picoline (Wonda Science, Cat. #1124, 7.13 g, 0.05 mol) is dissolved by stirring in 25 ml DMF. A thermometer is placed in the solution to monitor the temperature. N-Chlorosuccinimide (6.68 g, 0.05 mol) is added all at once. The mixture is heated to 50 deg. C. for 3 hours. The dark solution is poured into ice water and a solid separated and was collected by filtration and washed with 500 ml water. The solid was allowed to air dry overnight. The solid product was dissolved in ether/hexane (2:1) and treated with activated carbon. The solution was filtered and the solvent was removed on a rotovap. The resulting light tan solid was stirred in 50 ml of hexane, filtered and dried under vacuum. (MP 126-127 deg C.).

Preparation of 2-Amino-3,5-dichloro-4,6-dimethylpyridine

CAS 31430-47-4

Preparation of 2-Amino-3,5-dichloro-4,6-dimethylpyridine can be as described for 2-Amino-3,5-dichloro-4,6-methylpyridine but with 2-amino-4,6-dimethylpyridine as a starting material.

Example 12

Synthesis of AD4-1505-Like Compounds

The following example describes synthesis of AD4-1505-like compounds described herein. Intermediate compounds are according to Example 11, unless otherwise described.

Preparation of AD4-13021:

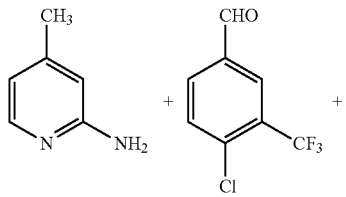

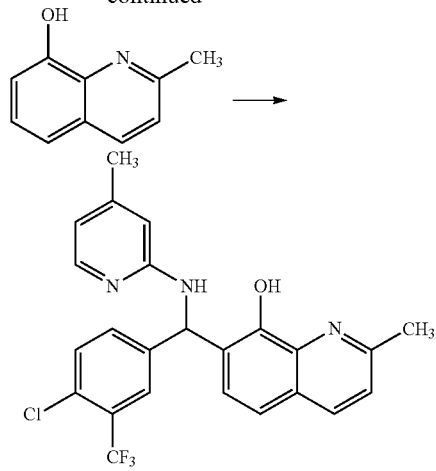

2-Amino-4-picoline (1.08 g, 0.01 mol) and 4-chloro-3-(trifluoromethyl)benzaldehyde (2.08 g, 0.01 mol) are weighed into a 100 ml roundbottom flask and stirred with 50 ml of absolute EtOH to dissolve. 8-Hydroxyquinaldine (1.59 g, 0.01 mol) is added and the mixture stirred, at room temperature, for a few minutes until a clear yellowish solution is obtained. The reaction mixture is then capped with a plastic stopper and stirred, at room temperature, for 14 days. Tlc (silica-gel, 2:1 Hexanes/acetone) indicates some starting material remaining in addition to a major new spot slightly below the 8-hydroxyquinaldine spot. The crude material is chromatographed on 500 ml flash silica-gel eluting with 2-25% acetone/hexanes. The elution solvent is as follows: 1 litre of 2% Acetone/hexanes; 1 litre of 3% acetone/hexanes; 1 litre of 5% acetone/hexanes; 1 liter of 7.5% acetone/hexanes; 1 litre of 10% acetone/hexanes; 1 litre of 15% acetone hexanes; 1 litre of 20% acetone/hexanes and 1 litre of 25% acetone/hexanes. 150 ml fractions are collected. Fractions 1-3 contain unreacted 8-hydroxyquinaldine. Fractions 11-13, containing the product, are concentrated on a rotovap to give a light-green oil. The oil is dissolved in 200 ml hexanes with a few ml of acetone. The resulting solution is allowed to stand at room temperature overnight. 2.9 g of the product forms as an off white crystalline solid and is isolated by filtration.

TLC:
2,3-Difluoro-4-methylbenzaldehyde Rf=0.8
8-Hydroxyquinaldine Rf=0.7
Product Rf=0.55
2-Amino-4-picoline Rf=0.2
8-Hydroxyquinaldine and the product both glow bright yellow under long wavelength (366 nM) UV light and the product also glows bright yellow under the short wavelength (254 nM) UV light. After standing for several hours in the air tlc spots from both 8-hydroxyquinaldine and the product turn yellow and then brown without any staining.

Preparation of AD4-13022:

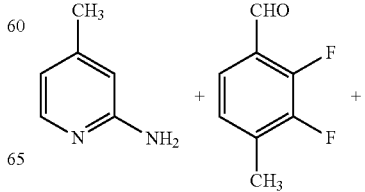

-continued

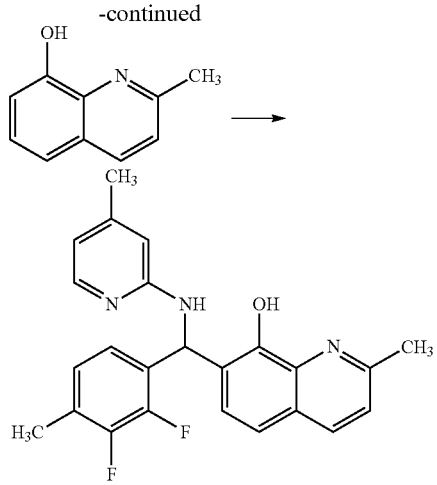

2-Amino-4-picoline (1.08 g, 0.01 mol) and 2,3-Difluoro-4-methylbenzaldehyde (1.56 g, 0.01 mol) were weighed into a 100 ml roundbottom flask and then stirred with 50 ml of absolute EtOH to dissolve. 8-Hydroxyquinaldine (1.59 g, 0.01 mol) was added and the mixture stirred, at room temperature, for a few minutes until a clear yellowish solution was obtained. The reaction mixture was then capped with a plastic stopper and stirred, at room temperature, for 14 days. A white solid was observed so the stirring was stopped and the flask kept overnight at room temperature. Tlc (silica-gel, 2:1 Hexanes/acetone) indicated some starting material remaining in addition to a major new spot slightly below the 8-hydroxyquinaldine spot. The supernatent was decanted and the white solid slurried with 100 ml of Et2O then filtered. The white solid was transferred to a 500 ml Erlenmeyer flask and stirred with 200 ml acetone. Gentle warming, at about 50° C., produced a light yellow clear solution which was treated with 1 g of Darco-G-60 decolorizing charcoal. The charcoal was removed by filtration through Celite with subsequent washing of the Celite with an additional 50 ml of acetone. The acetone solution was then combined with an equal volume (250 ml) of hexanes and allowed to stand at room temperature for 4 h. 1.5 g of the product formed a white crystalline solid and was isolated in essentially pure form (99%) by filtration.

TLC:
2,3-Difluoro-4-methylbenzaldehyde Rf=0.8
8-Hydroxyquinaldine Rf=0.7
Product Rf=0.45
2-Amino-4-picoline Rf=0.2

8-Hydroxyquinaldine and the product both glow bright yellow under long wavelength (366 nM) UV light and the product also glows bright yellow under the short wavelength (254 nM) UV light. After standing for several hours in the air tlc spots from both 8-hydroxyquinaldine and the product turn yellow and then brown without any staining.

Preparation of AD4-12902:

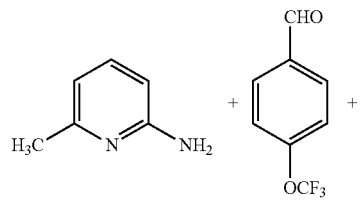

In a manner similar to that described in Example AD4-13022.

2-Amino-6-picoline (1.08 g, 0.01 mol) and 4-trifluoromethoxybenzaldehyde, Acros Organics (1.90 g, 0.01 mol) are combined with 8-hydroxyquinoline, Acros Organics (1.45 g, 0.01 mol) in 50 ml of absolute EtOH to give the desired Betti condensation product as an off-white solid (MP 130-131° C.). The product is isolated by filtration.

Preparation of AD4-12903:

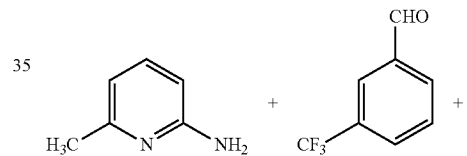

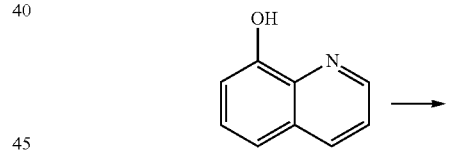

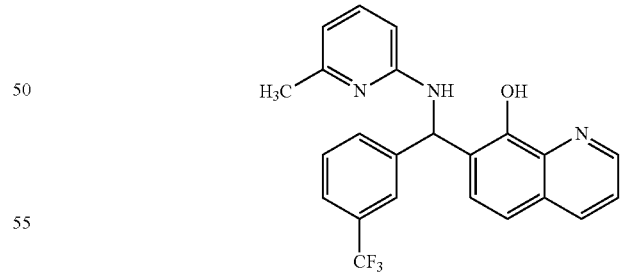

In a manner similar to that described in Example AD4-13021.

2-Amino-6-picoline (1.08 g, 0.01 mol) and 3-(trifluoromethy)benzaldehyde (1.74 g, 0.01 mol) are combined with 8-hydroxyquinoline, Acros Organics (1.45 g, 0.01 mol) in 50 ml of absolute EtOH to give the desired Betti condensation product as an off-white solid (MP 159-160° C.). The product is isolated by filtration.

Preparation of AD4-12904:

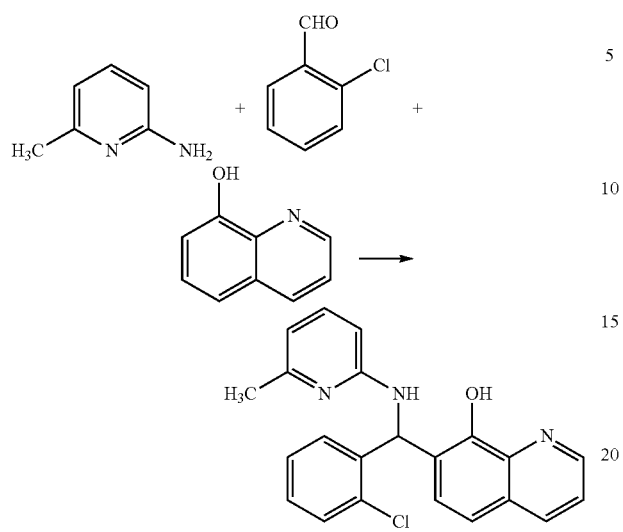

In a manner similar to that described in Example AD4-13022.

2-Amino-6-picoline, Acros Organics (1.08 g, 0.01 mol) and 2-chlorobenzaldehyde, Acros Organics (1.41 g, 0.01 mol) are combined with 8-hydroxyquinoline, Acros Organics (1.45 g, 0.01 mol) in 50 ml of absolute EtOH to give the desired Betti condensation product as a white solid (MP 211-212° C.).

Preparation of AD4-12905:

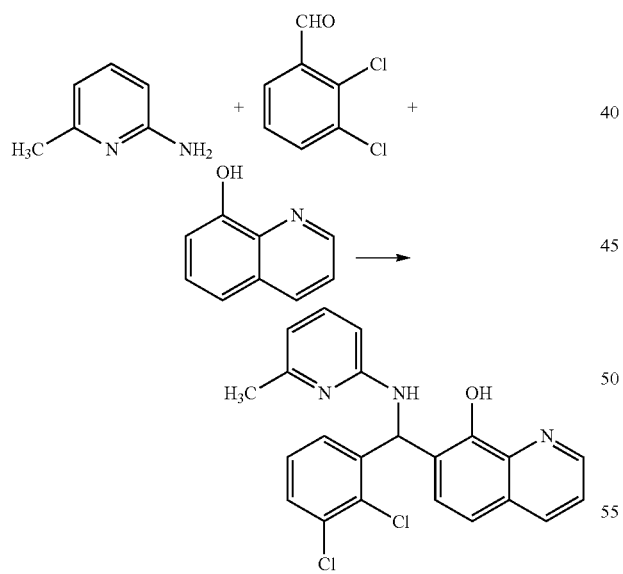

In a manner similar to that described in Example AD4-13022.

2-Amino-6-picoline, Acros Organics (1.08 g, 0.01 mol) and 2,3-dichlorobenzaldehyde, Acros Organics (1.75 g, 0.01 mol) are combined with 8-hydroxyquinoline, Acros Organics (1.45 g, 0.01 mol) in 50 ml of absolute EtOH to give the desired Betti condensation product as a white solid (MP 195-196° C.).

Preparation of AD4-12906:

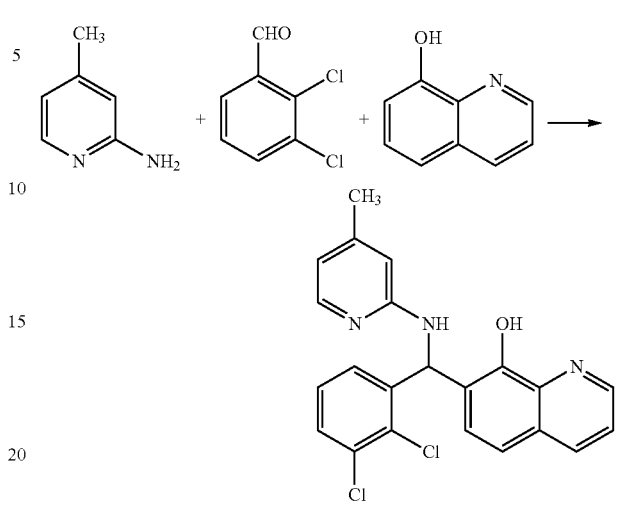

In a manner similar to that described in Example AD4-13022.

2-Amino-4-picoline, Acros Organics (1.08 g, 0.01 mol) and 2,3-dichlorobenzaldehyde, Acros Organics (1.75 g, 0.01 mol) are combined with 8-hydroxyquinoline, Acros Organics (1.45 g, 0.01 mol) in 50 ml of absolute EtOH to give the desired Betti condensation product as an off-white solid (MP 176-177° C.).

Preparation of AD4-12907:

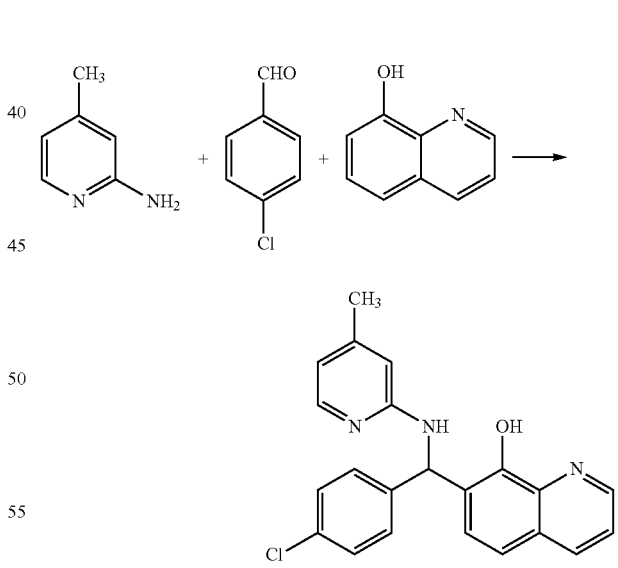

In a manner similar to that described in Example AD4-13022.

2-Amino-4-picoline, Acros Organics (1.08 g, 0.01 mol) and 2-chlorobenzaldehyde, Acros Organics (1.41 g, 0.01 mol) are combined with 8-hydroxyquinoline, Acros Organics (1.45 g, 0.01 mol) in 50 ml of absolute EtOH to give the desired Betti condensation product as a tan solid (MP 176-179° C.).

Preparation of AD4-12908:

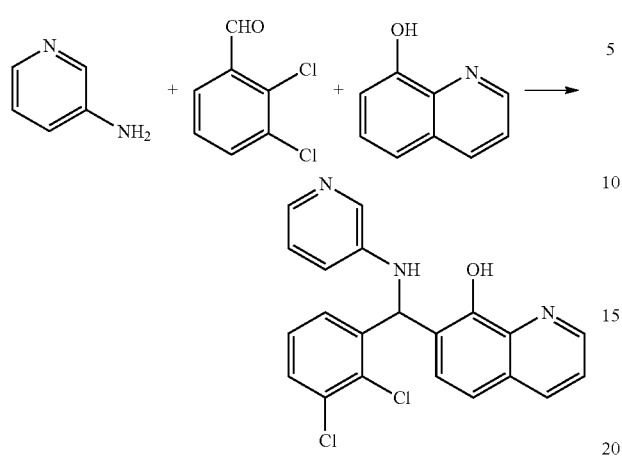

In a manner similar to that described in Example AD4-13021.

3-aminopyridine, Acros Organics (0.94 g, 0.01 mol) and 2,3-dichlorobenzaldehyde, Acros Organics (1.75 g, 0.01 mol) are combined with 8-hydroxyquinoline, Acros Organics (1.45 g, 0.01 mol) in 50 ml of absolute EtOH to give the desired Betti condensation product as a tan solid (MP 119-121° C.).

Preparation of AD4-12909:

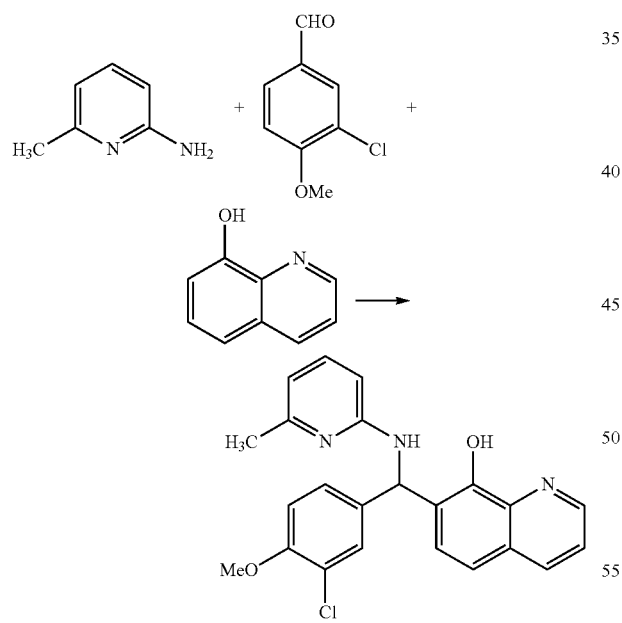

In a manner similar to that described in Example AD4-13021.

2-Amino-6-picoline, Acros Organics (1.08 g, 0.01 mol) and 3-hydroxy-4-methoxybenzaldehyde, Acros Organics (1.52 g, 0.01 mol) are combined with 8-hydroxyquinoline, Acros Organics (1.45 g, 0.01 mol) in 50 ml of absolute EtOH to give the desired Betti condensation product as an off-white solid (MP 179-181° C.).

Preparation of AD4-12910:

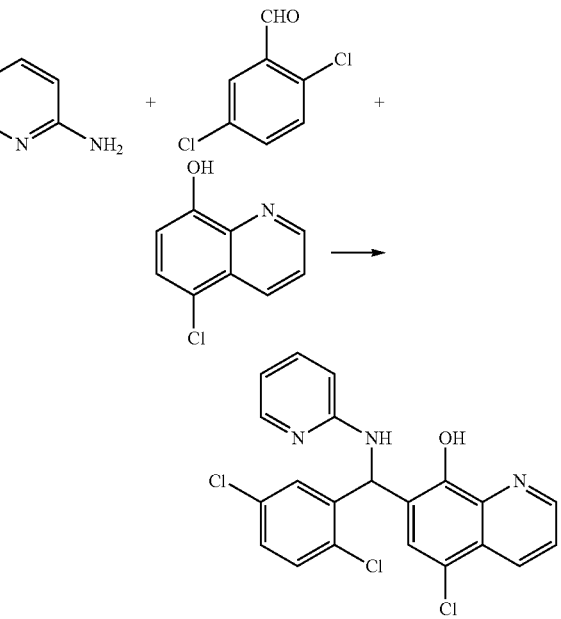

In a manner similar to that described in Example AD4-13022.

2-Aminopyridine, Acros Organics (0.94 g, 0.01 mol) and 2,5-dichlorobenzaldehyde, Acros Organics (1.75 g, 0.01 mol) are combined with 5-chloro-8-hydroxyquinoline, Acros Organics (1.80 g, 0.01 mol) in 50 ml of absolute EtOH to give the desired Betti condensation product as an off-white solid (MP 189-191° C.).

Preparation of AD4-12911:

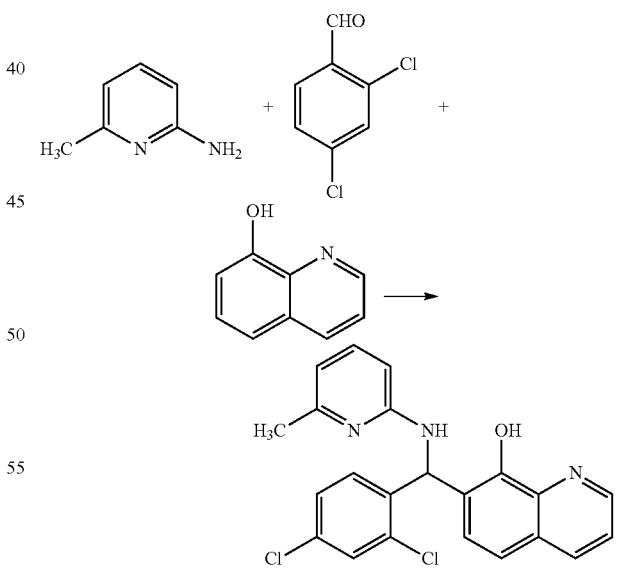

In a manner similar to that described in Example AD4-13022.

2-Amino-6-picoline, Acros Organics (1.08 g, 0.01 mol) and 2,4-dichlorobenzaldehyde, Acros Organics (1.75 g, 0.01 mol) are combined with 8-hydroxyquinoline, Acros Organics (1.45 g, 0.01 mol) in 50 ml of absolute EtOH to give the desired Betti condensation product as a white solid (MP 194-196° C.).

Preparation of AD4-12912:

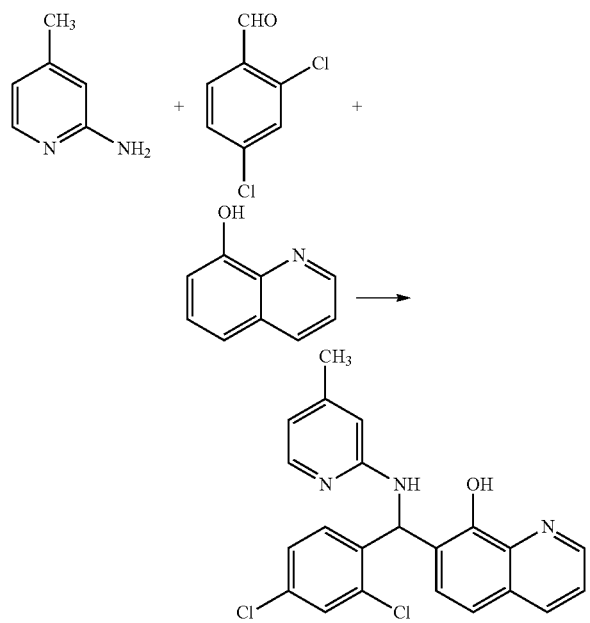

In a manner similar to that described in Example AD4-13022.

2-Amino-4-picoline, Acros Organics (1.08 g, 0.01 mol) and 2,4-dichlorobenzaldehyde, Acros Organics (1.75 g, 0.01 mol) are combined with 8-hydroxyquinoline, Acros Organics (1.45 g, 0.01 mol) in 50 ml of absolute EtOH to give the desired Betti condensation product as an off-white solid (MP 185-187° C.).

Preparation of AD4-12913:

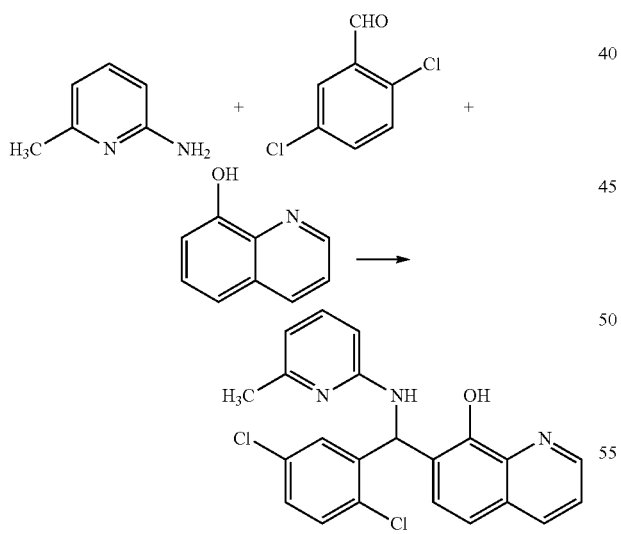

In a manner similar to that described in Example AD4-13022.

2-Amino-6-picoline, Acros Organics (1.08 g, 0.01 mol) and 2,5-dichlorobenzaldehyde, Acros Organics (1.75 g, 0.01 mol) are combined with 8-hydroxyquinoline, Acros Organics (1.45 g, 0.01 mol) in 50 ml of absolute EtOH to give the desired Betti condensation product as a white solid (MP 180-182° C.).

Preparation of AD4-12914:

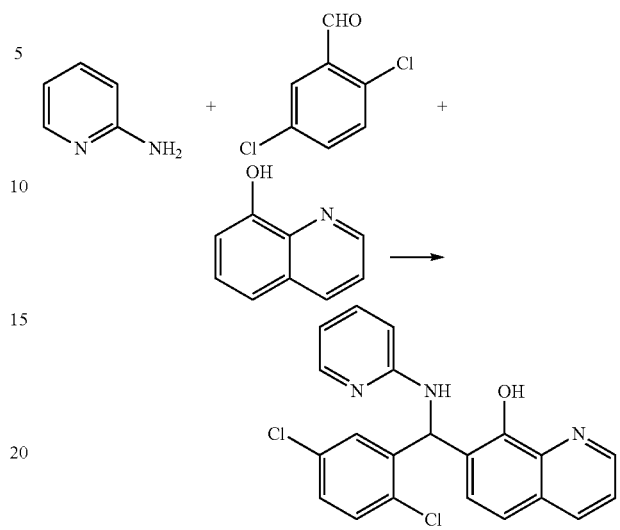

In a manner similar to that described in Example AD4-13022.

2-Aminopyridine, Acros Organics (0.94 g, 0.01 mol) and 2,5-dichlorobenzaldehyde, Acros Organics (1.75 g, 0.01 mol) are combined with 8-hydroxyquinoline, Acros Organics (1.45 g, 0.01 mol) in 50 ml of absolute EtOH to give the desired Betti condensation product as a white solid (MP 141-142° C.).

Preparation of AD4-12915:

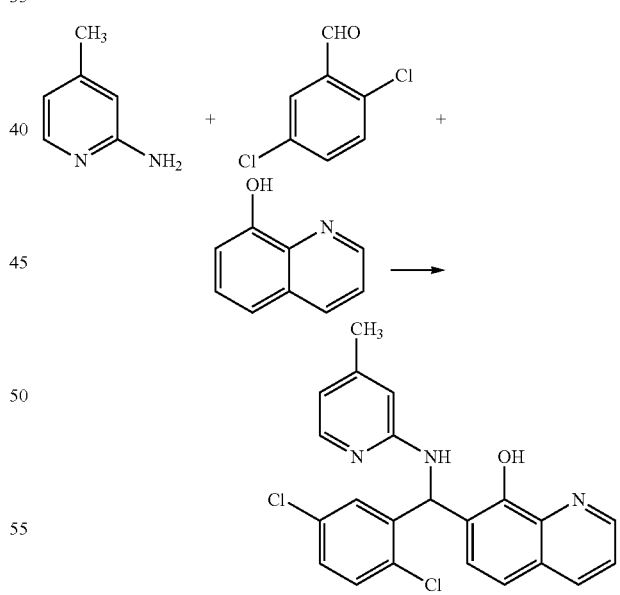

In a manner similar to that described in Example AD4-13022.

2-Amino-4-picoline, Acros Organics (1.08 g, 0.01 mol) and 2,5-dichlorobenzaldehyde, Acros Organics (1.75 g, 0.01 mol) are combined with 8-hydroxyquinoline, Acros Organics (1.45 g, 0.01 mol) in 50 ml of absolute EtOH to give the desired Betti condensation product as a white solid (MP 169-170° C.).

Preparation of AD4-12916:

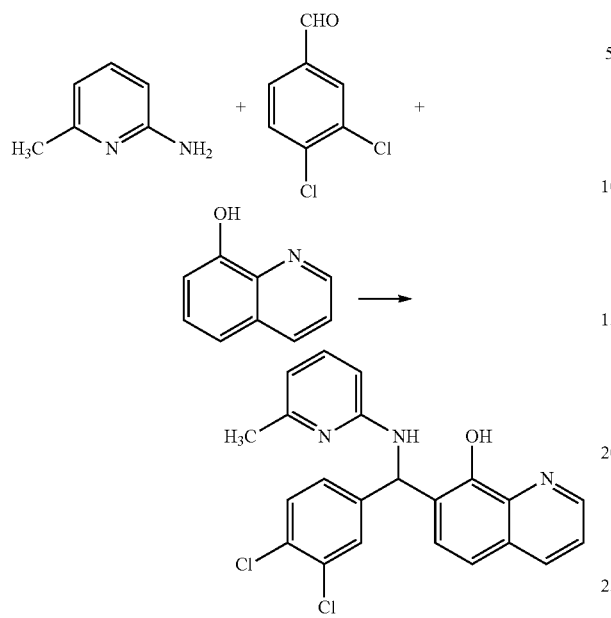

In a manner similar to that described in Example AD4-13022.

2-Amino-6-picoline, Acros Organics (1.08 g, 0.01 mol) and 3,4-dichlorobenzaldehyde, Acros Organics (1.75 g, 0.01 mol) are combined with 8-hydroxyquinoline, Acros Organics (1.45 g, 0.01 mol) in 50 ml of absolute EtOH to give the desired Betti condensation product as a white solid (MP 175-176° C.).

Preparation of AD4-12917:

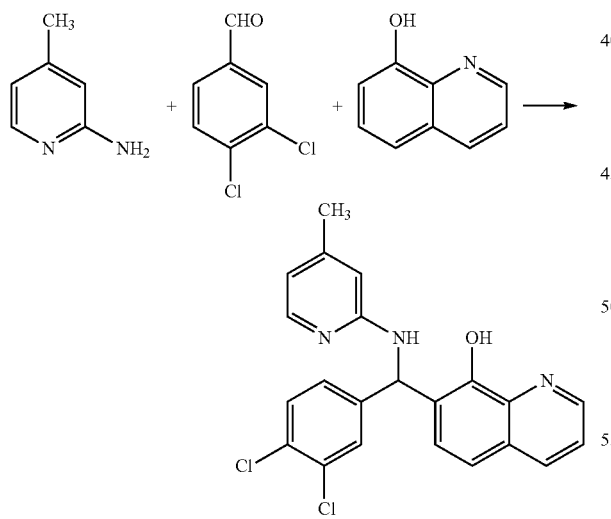

In a manner similar to that described in Example AD4-13022.

2-Amino-4-picoline, Acros Organics (1.08 g, 0.01 mol) and 3,4-dichlorobenzaldehyde, Acros Organics (1.75 g, 0.01 mol) are combined with 8-hydroxyquinoline, Acros Organics (1.45 g, 0.01 mol) in 50 ml of absolute EtOH to give the desired Betti condensation product as a white solid (MP 161-164° C.).

Preparation of AD4-12918:

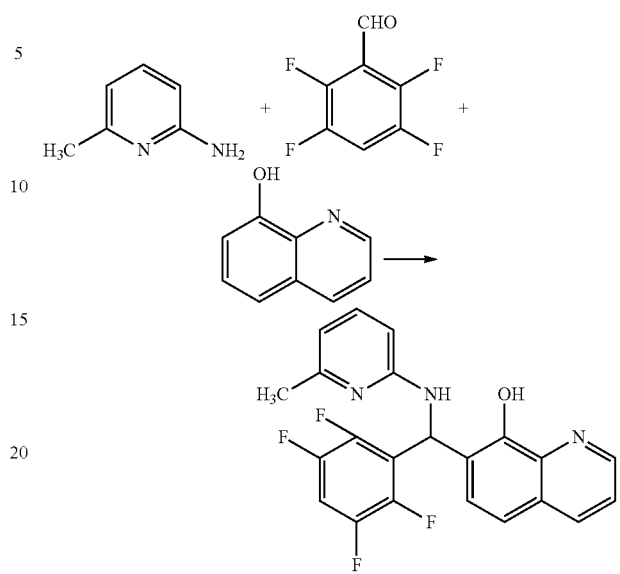

In a manner similar to that described in Example AD4-13021.

2-Amino-6-picoline, Acros Organics (1.08 g, 0.01 mol) and 2,3,5,6-tetrafluorobenzaldehyde, Matrix Scientific (1.78 g, 0.01 mol) are combined with 8-hydroxyquinoline, Acros Organics (1.45 g, 0.01 mol) in 50 ml of absolute EtOH to give the desired Betti condensation product as a white solid (MP 171-173° C.). The product is isolated by filtration.

Preparation of AD4-12954:

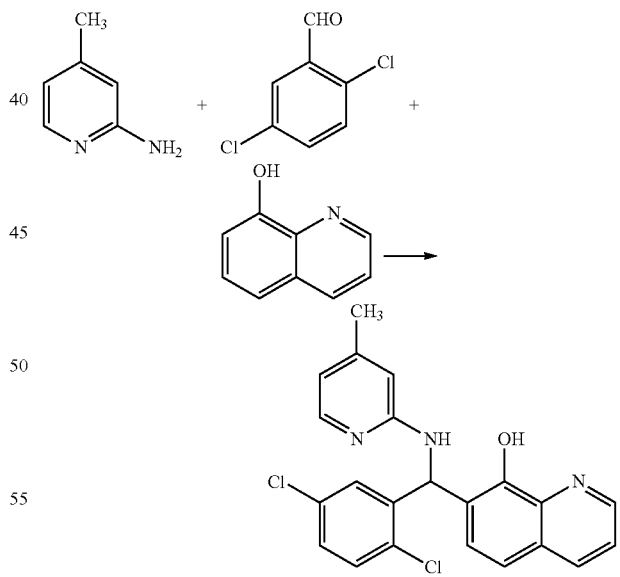

In a manner similar to that described in Example AD4-13021.

2-Amino-4-picoline, Acros Organics (1.08 g, 0.01 mol) and 2,5-dichlorobenzaldehyde, Acros Organics (1.75 g, 0.01 mol) are combined with 8-hydroxyquinoline, Acros Organics (1.45 g, 0.01 mol) in 50 ml of absolute EtOH to give the desired Betti condensation product as an off-white solid (MP 189-191° C.).

Preparation of AD4-12955:

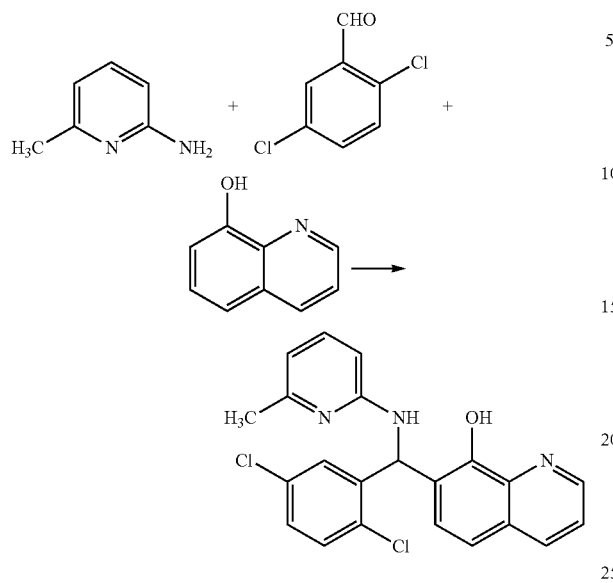

In a manner similar to that described in Example AD4-13021.

2-Amino-6-picoline, Acros Organics (1.08 g, 0.01 mol) and 2,5-dichlorobenzaldehyde, Acros Organics (1.75 g, 0.01 mol) are combined with 8-hydroxyquinoline, Acros Organics (1.45 g, 0.01 mol) in 50 ml of absolute EtOH to give the desired Betti condensation product as an off-white solid (MP 173-174° C.).

Preparation of AD4-12958:

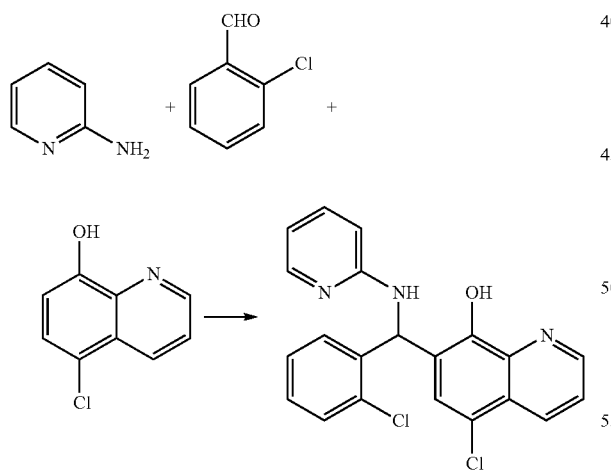

In a manner similar to that described in Example AD4-13021.

2-Aminopyridine, Acros Organics (0.94 g, 0.01 mol) and 2-chlorobenzaldehyde, Acros Organics (1.41 g, 0.01 mol) are combined with 5-chloro-8-hydroxyquinoline, Acros Organics (1.80 g, 0.01 mol) in 50 ml of absolute EtOH to give the desired Betti condensation product as an off-white solid (MP 193-195° C.).

Preparation of AD4-12959:

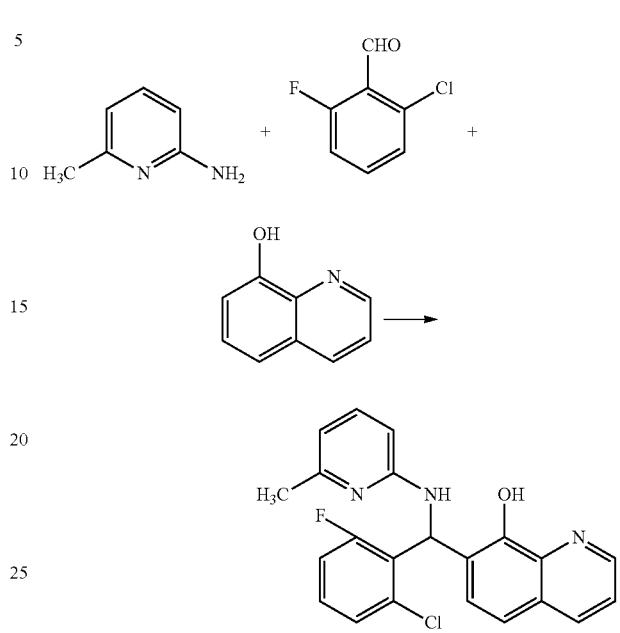

In a manner similar to that described in Example AD4-13021.

2-Amino-6-picoline, Acros Organics (1.08 g, 0.01 mol) and 2-chloro-6-fluorobenzaldehyde, Acros Organics (1.59 g, 0.01 mol) are combined with 8-hydroxyquinoline, Acros Organics (1.45 g, 0.01 mol) in 50 ml of absolute EtOH to give the desired Betti condensation product a white solid (MP 183-184° C.).

Preparation of AD4-13019:

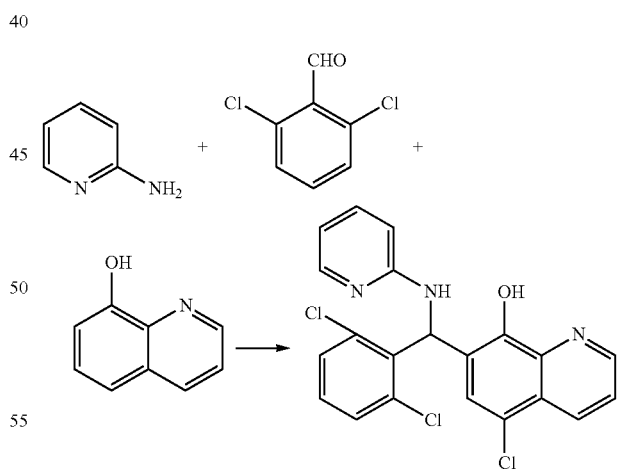

In a manner similar to that described in Example AD4-13022.

2-Aminopyridine, Acros Organics (0.94 g, 0.01 mol) and 2,6-dichlorobenzaldehyde, Acros Organics (1.75 g, 0.01 mol) are combined with 8-hydroxyquinoline, Acros Organics (1.45 g, 0.01 mol) in 50 ml of absolute EtOH to give the desired Betti condensation product an off-white solid (MP 172-175° C.).

Preparation of AD4-13020:

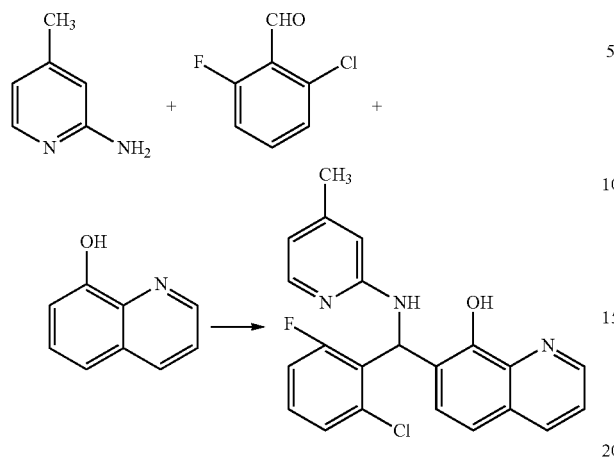

In a manner similar to that described in Example AD4-13022.

2-Amino-4-picoline, Acros Organics (1.08 g, 0.01 mol) and 2-chloro-6-fluorobenzaldehyde, Acros Organics (1.59 g, 0.01 mol) are combined with 8-hydroxyquinoline, Acros Organics (1.45 g, 0.01 mol) in 50 ml of absolute EtOH to give the desired Betti condensation product a white solid (MP 164-166° C.).

Preparation of AD4-13023:

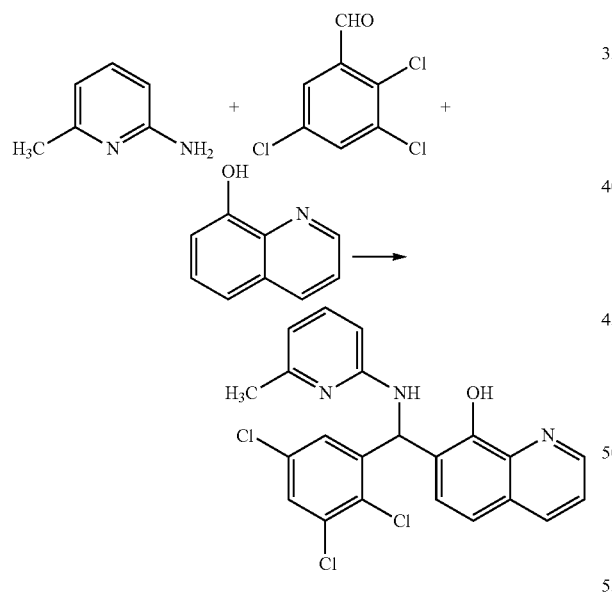

In a manner similar to that described in Example AD4-13022.

2-Amino-6-picoline, Acros Organics (1.08 g, 0.01 mol) and 2,3,5-trichlorobenzaldehyde, Acros Organics (2.09 g, 0.01 mol) are combined with 8-hydroxyquinoline, Acros Organics (1.45 g, 0.01 mol) in 50 ml of absolute EtOH to give the desired Betti condensation product a white solid (MP 184-186° C.).

Preparation of AD4-13024:

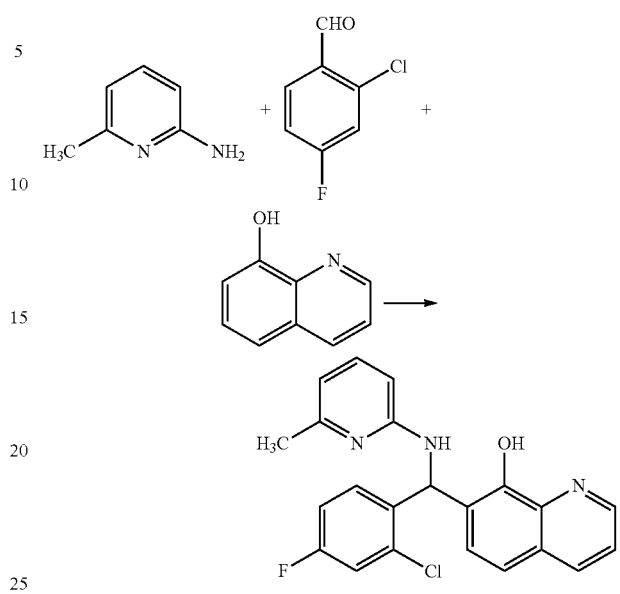

In a manner similar to that described in Example AD4-13022.

2-Amino-6-picoline, Acros Organics (1.08 g, 0.01 mol) and 2-chloro-4-fluorobenzaldehyde, Oakwood Products (1.59 g, 0.01 mol) are combined with 8-hydroxyquinoline, Acros Organics (1.45 g, 0.01 mol) in 50 ml of absolute EtOH to give the desired Betti condensation product a white solid (MP 182-185° C.).

Preparation of AD4-13025:

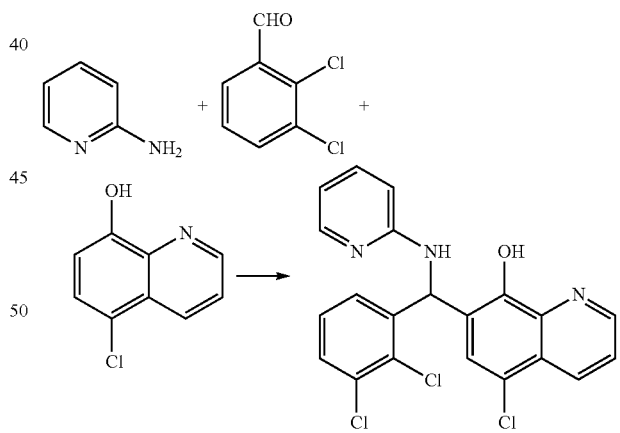

In a manner similar to that described in Example AD4-13022.

2-Aminopyridine, Acros Organics (0.94 g, 0.01 mol) and 2,3-dichlorobenzaldehyde, Acros Organics (1.75 g, 0.01 mol) are combined with 5-chloro-8-hydroxyquinoline, Acros Organics (1.80 g, 0.01 mol) in 50 ml of absolute EtOH to give the desired Betti condensation product a white solid (MP 177-180° C.).

Preparation of AD4-13026:

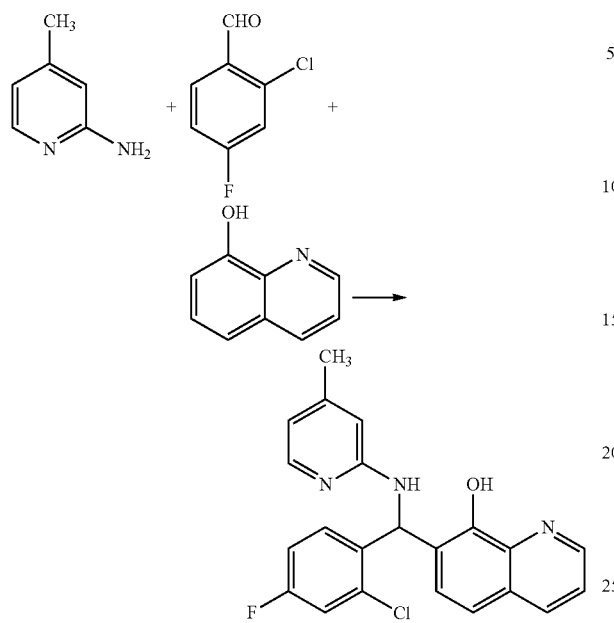

In a manner similar to that described in Example AD4-13022.

2-Amino-4-picoline, Acros Organics (1.08 g, 0.01 mol) and 2-chloro-4-fluorobenzaldehyde, Oakwood Products (1.59 g, 0.01 mol) are combined with 8-hydroxyquinoline, Acros Organics (1.45 g, 0.01 mol) in 50 ml of absolute EtOH to give the desired Betti condensation product an off-white solid (MP 163-165° C.).

Preparation of AD4-13027:

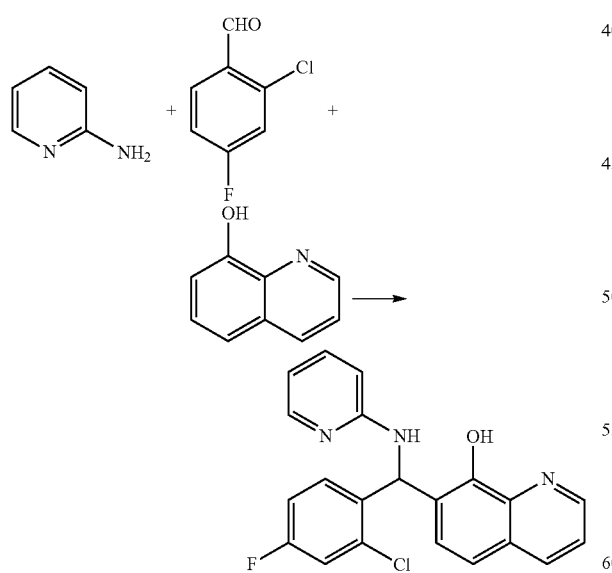

In a manner similar to that described in Example AD4-13022.

2-Aminopyridine, Acros Organics (0.94 g, 0.01 mol) and 2-chloro-4-fluorobenzaldehyde, Oakwood Products (1.59 g, 0.01 mol) are combined with 8-hydroxyquinoline, Acros Organics (1.45 g, 0.01 mol) in 50 ml of absolute EtOH to give the desired Betti condensation product an off-white solid (MP 162-166° C.).

Preparation of AD4-13028:

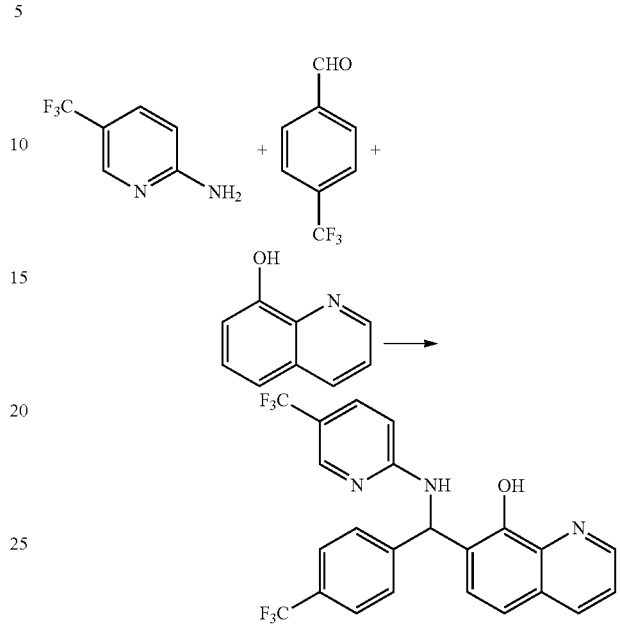

In a manner similar to that described in Example AD4-13021.

2-Amino-5-(trifluoromethyl)pyridine, Acros Organics (1.62 g, 0.01 mol) and 4-(trifluoromethyl)benzaldehyde, Acros Organics (1.74 g, 0.01 mol) are combined with 8-hydroxyquinoline, Acros Organics (1.45 g, 0.01 mol) in 50 ml of absolute EtOH to give the desired Betti condensation product as a green solid (MP 82-94° C.).

Preparation of AD4-13029:

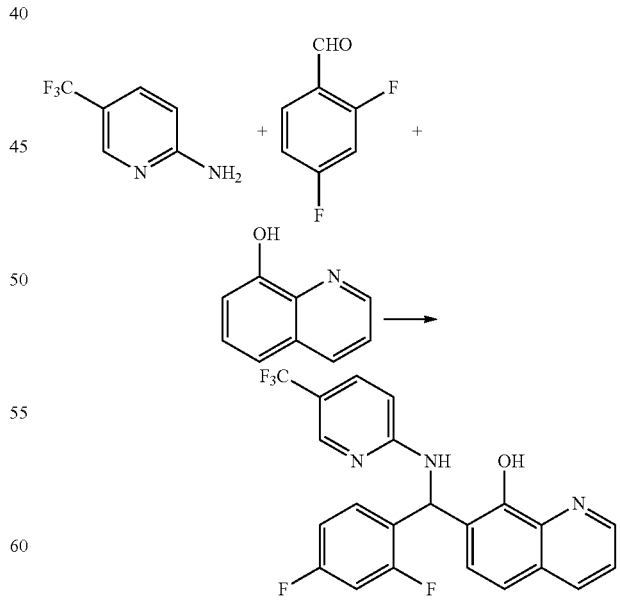

In a manner similar to that described in Example AD4-13021.

2-Amino-5-(trifluoromethyl)pyridine, Acros Organics (1.62 g, 0.01 mol) and 2,4-difluorobenzaldehyde, Acros Organics (1.42 g, 0.01 mol) are combined with 8-hydroxyquinoline, Acros Organics (1.45 g, 0.01 mol) in 50 ml of absolute EtOH to give the desired Betti condensation product as a green solid (MP 124-134° C.).

Preparation of AD4-13030:

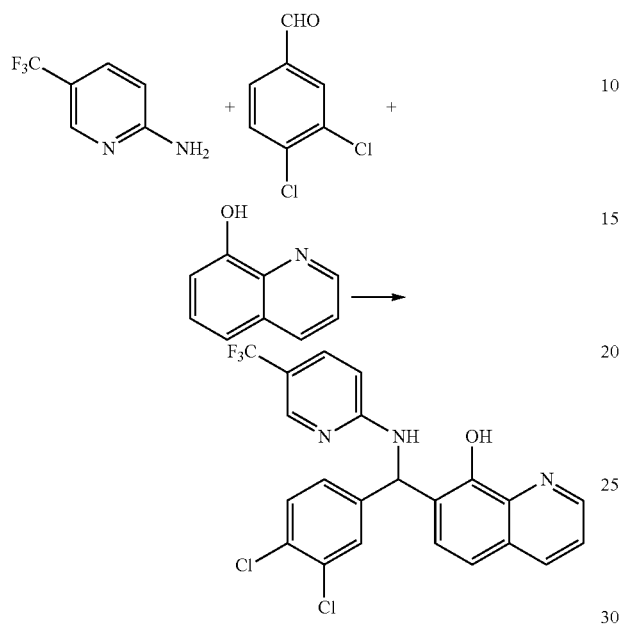

In a manner similar to that described in Example AD4-13021.

2-Amino-5-(trifluoromethyl)pyridine, Acros Organics (1.62 g, 0.01 mol) and 3,4-dichlorobenzaldehyde, Acros Organics (1.75 g, 0.01 mol) are combined with 8-hydroxyquinoline, Acros Organics (1.45 g, 0.01 mol) in 50 ml of absolute EtOH to give the desired Betti condensation product as a green solid (MP 86-87° C.).

Preparation of AD4-13031:

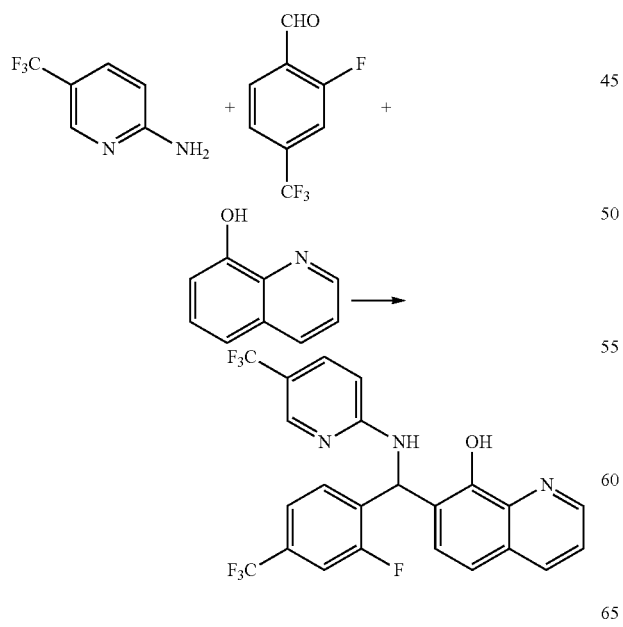

In a manner similar to that described in Example AD4-13021.

2-Amino-5-(trifluoromethyl)pyridine, Acros Organics (1.62 g, 0.01 mol) and 2-fluoro-4-trifluoromethylbenzaldehyde, Oakwood Products (1.92 g, 0.01) are combined with 8-hydroxyquinoline, Acros Organics (1.45 g, 0.01 mol) in 50 ml of absolute EtOH to give the desired Betti condensation product as a green solid (MP 126-132° C.).

Preparation of AD4-13032:

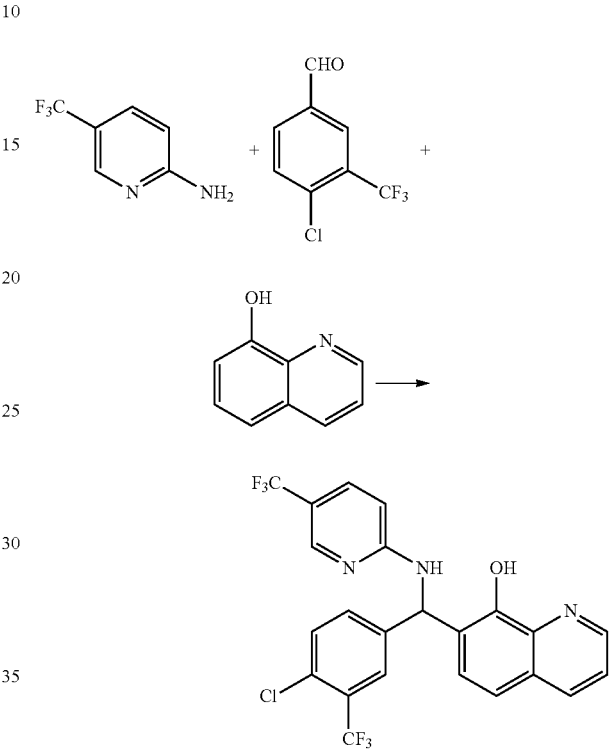

In a manner similar to that described in Example AD4-13021.

2-Amino-5-(trifluoromethyl)pyridine, Acros Organics (1.62 g, 0.01 mol) and 3-(trifluoromethyl)-4-chlorobenzaldehyde, Oakwood Products (2.09 g, 0.01 mol) are combined with 8-hydroxyquinoline, Acros Organics (1.45 g, 0.01 mol) in 50 ml of absolute EtOH to give the desired Betti condensation product as a green solid (MP 81-96° C.).

Preparation of AD4-13033:

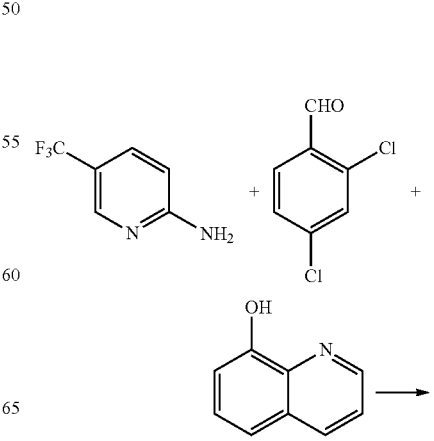

-continued

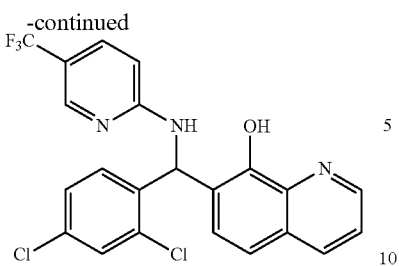

In a manner similar to that described in Example AD4-13021.

2-Amino-5-(trifluoromethyl)pyridine, Acros Organics (1.62 g, 0.01 mol) and 2,4-dichlorobenzaldehyde, Acros Organics (1.75 g, 0.01 mol) are combined with 8-hydroxyquinoline, Acros Organics (1.45 g, 0.01 mol) in 50 ml of absolute EtOH to give the desired Betti condensation product as a green solid (MP 131-143° C.).

Preparation of AD4-13034:

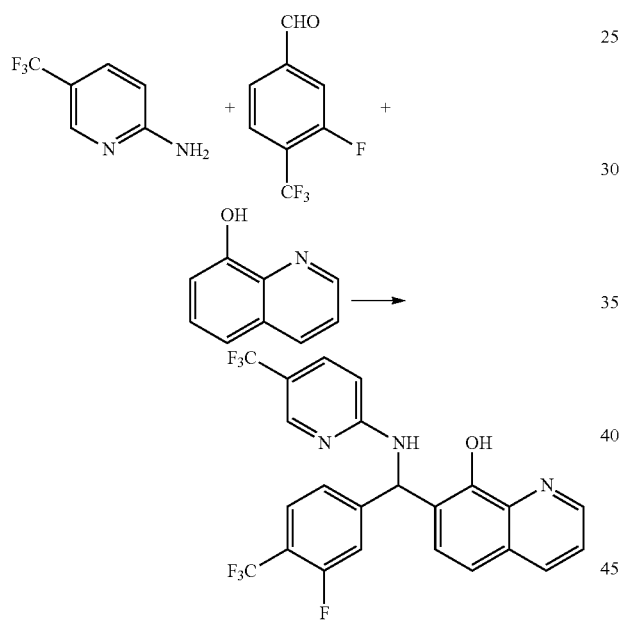

In a manner similar to that described in Example AD4-13021.

2-Amino-5-(trifluoromethyl)pyridine, Acros Organics (1.62 g, 0.01 mol) and 3-fluoro-4-trifluoromethylbenzaldehyde, Oakwood Products (1.92 g, 0.01) are combined with 8-hydroxyquinoline, Acros Organics (1.45 g, 0.01 mol) in 50 ml of absolute EtOH to give the desired Betti condensation product as a green solid (MP 110-117° C.).

Preparation of AD4-13035:

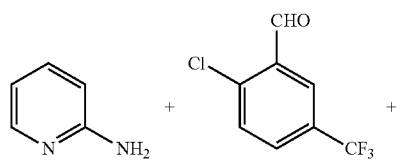

-continued

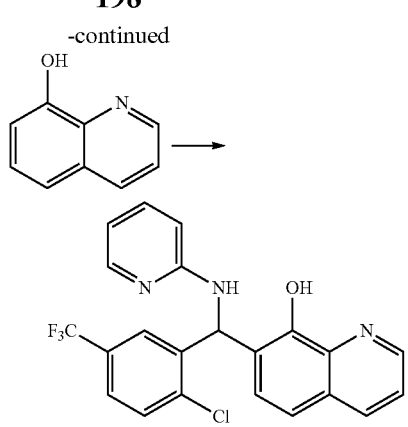

In a manner similar to that described in Example AD4-13021.

2-Aminopyridine, Acros Organics (1.62 g, 0.01 mol) and 2-chloro-5-(trifluoromethyl)benzaldehyde, matrix (2.09 g, 0.01 mol) are combined with 8-hydroxyquinoline, Acros Organics (1.45 g, 0.01 mol) in 50 ml of absolute EtOH to give the desired Betti condensation product as a green solid (MP 137-155° C.).

Preparation of AD4-13036:

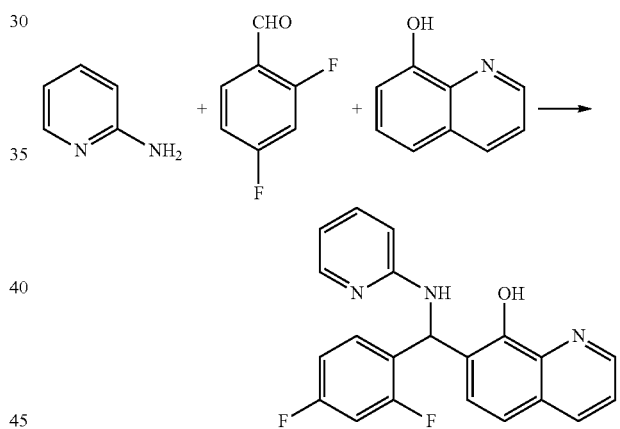

In a manner similar to that described in Example AD4-13021.

2-Aminopyridine, Acros Organics (1.62 g, 0.01 mol) and 2,4-difluorobenzaldehyde, Acros Organics (1.42 g, 0.01 mol) are combined with 8-hydroxyquinoline, Acros Organics (1.45 g, 0.01 mol) in 50 ml of absolute EtOH to give the desired Betti condensation product as a light green solid (MP 136-138° C.).

Preparation of AD4-13037:

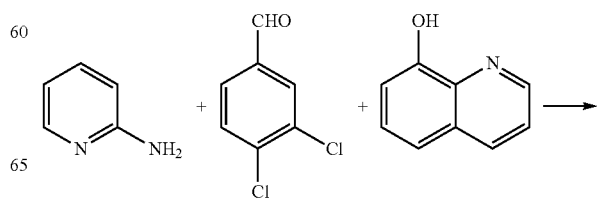

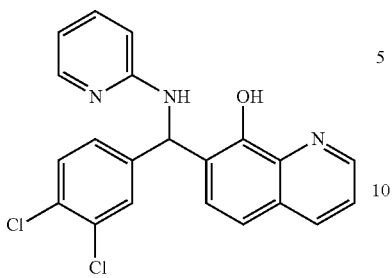

In a manner similar to that described in Example AD4-13021.

2-Aminopyridine, Acros Organics (1.62 g, 0.01 mol) and 3,4-dichlorobenzaldehyde, Acros Organics (1.75 g, 0.01 mol) are combined with 8-hydroxyquinoline, Acros Organics (1.45 g, 0.01 mol) in 50 ml of absolute EtOH to give the desired Betti condensation product as a green solid (MP 117-120° C.).

Preparation of AD4-13038:

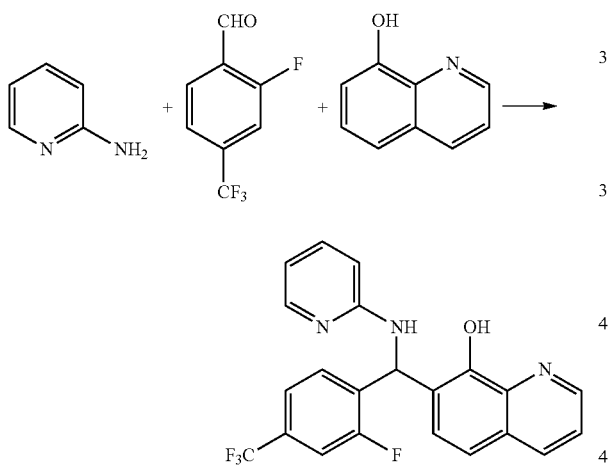

In a manner similar to that described in Example AD4-13021.

2-Aminopyridine, Acros Organics (1.62 g, 0.01 mol) and 2-fluoro-4-trifluoromethylbenzaldehyde, Matrix (1.92 g, 0.01) are combined with 8-hydroxyquinoline, Acros Organics (1.45 g, 0.01 mol) in 50 ml of absolute EtOH to give the desired Betti condensation product as a green solid (MP 126-127° C.).

Preparation of AD4-13039:

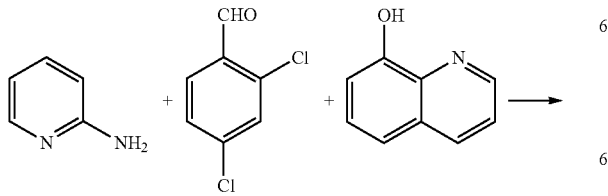

In a manner similar to that described in Example AD4-13021.

2-Aminopyridine, Acros Organics (1.62 g, 0.01 mol) and 2,4-dichlorobenzaldehyde, Acros Organics (1.75 g, 0.01 mol) are combined with 8-hydroxyquinoline, Acros Organics (1.45 g, 0.01 mol) in 50 ml of absolute EtOH to give the desired Betti condensation product as a green solid (MP 99-102° C.).

Preparation of AD4-13040:

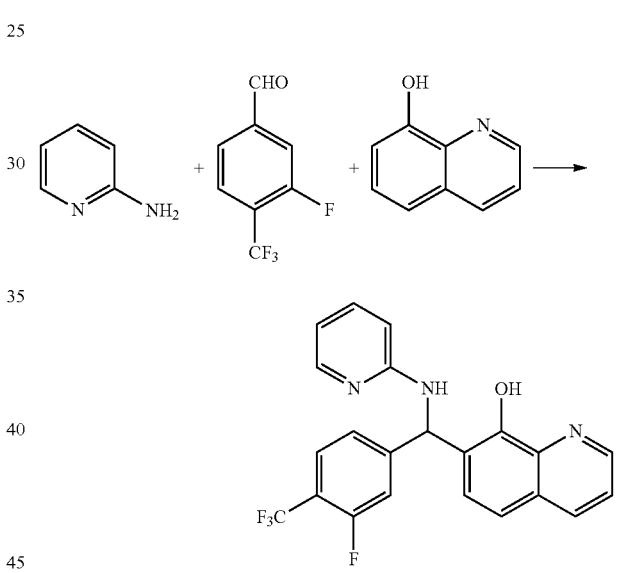

In a manner similar to that described in Example AD4-13021.

2-Aminopyridine, Acros Organics (1.62 g, 0.01 mol) and 3-fluoro-4-trifluoromethylbenzaldehyde, Oakwood Products (1.92 g, 0.01) are combined with 8-hydroxyquinoline, Acros Organics (1.45 g, 0.01 mol) in 50 ml of absolute EtOH to give the desired Betti condensation product as a green solid (MP 82-85° C.).

Preparation of AD4-13041:

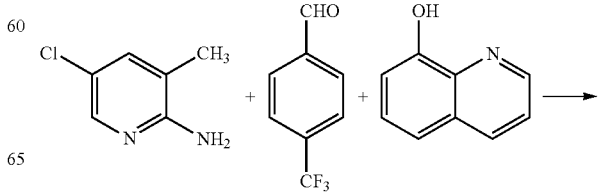

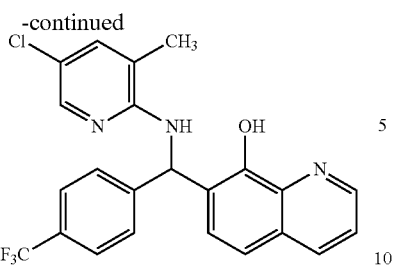

In a manner similar to that described in Example AD4-13021.

2-Amino-5-chloro-3-methylpyridine, Matrix (1.42 g, 0.01 mol) and 4-(trifluoromethyl)benzaldehyde, Acros Organics (1.74 g, 0.01 mol) are combined with 8-hydroxyquinoline, Acros Organics (1.45 g, 0.01 mol) in 50 ml of absolute EtOH to give the desired Betti condensation product as a light green solid (MP 108-110° C.).

Preparation of AD4-13042:

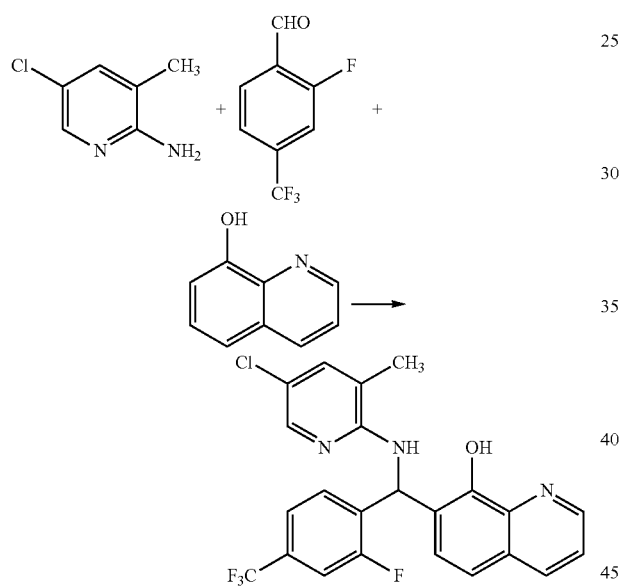

In a manner similar to that described in Example AD4-13021.

2-Amino-5-chloro-3-methylpyridine, Matrix (1.42 g, 0.01 mol) and 2-fluoro-4-trifluoromethylbenzaldehyde, Matrix (1.92 g, 0.01) are combined with 8-hydroxyquinoline, Acros Organics (1.45 g, 0.01 mol) in 50 ml of absolute EtOH to give the desired Betti condensation product as a green solid (MP 106-109° C.).

Preparation of AD4-13043:

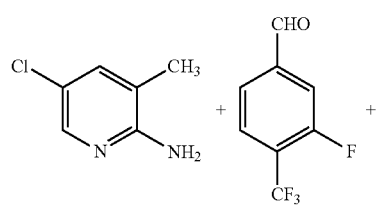

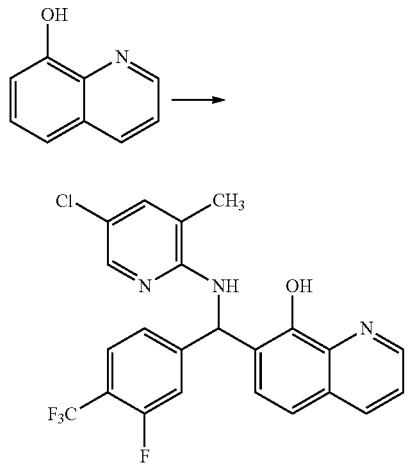

In a manner similar to that described in Example AD4-13021.

2-Amino-5-chloro-3-methylpyridine, Matrix (1.42 g, 0.01 mol) and 3-fluoro-4-trifluoromethylbenzaldehyde, Oakwood Products (1.92 g, 0.01) are combined with 8-hydroxyquinoline, Acros Organics (1.45 g, 0.01 mol) in 50 ml of absolute EtOH to give the desired Betti condensation product as a green solid (MP 128-131° C.).

Preparation of AD4-13044:

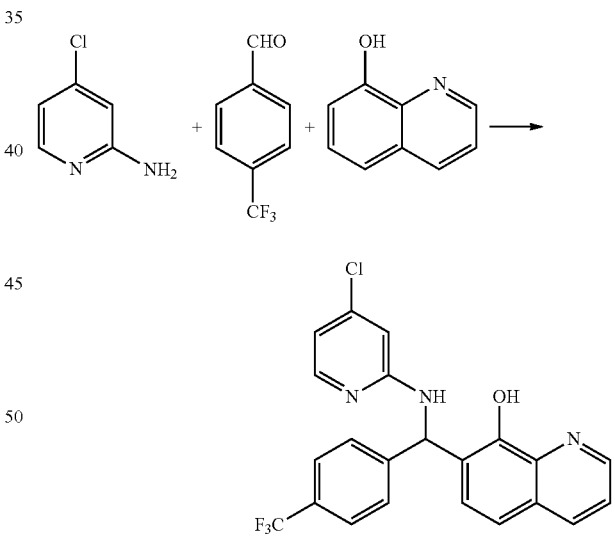

In a manner similar to that described in Example AD4-13021.

2-Amino-4-chloropyridine, Matrix (1.42 g, 0.01 mol) and 4-(trifluoromethyl)benzaldehyde, Acros Organics (1.74 g, 0.01 mol) are combined with 8-hydroxyquinoline, Acros Organics (1.45 g, 0.01 mol) in 50 ml of absolute EtOH to give the desired Betti condensation product as a light green solid (MP 154-155° C.).

Preparation of AD4-13045:

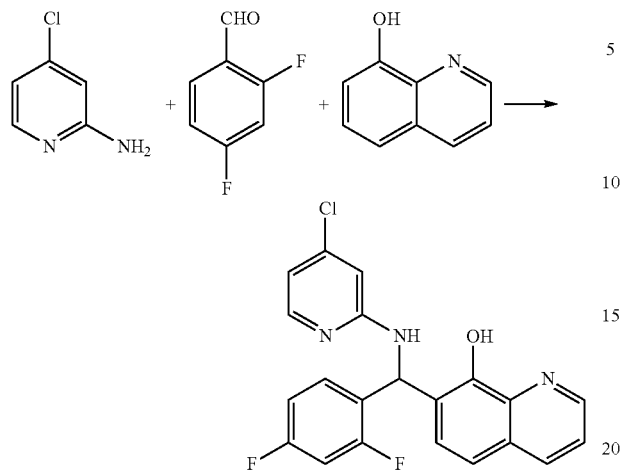

In a manner similar to that described in Example AD4-13021.

2-Amino-4-chloropyridine, Matrix (1.42 g, 0.01 mol) and 2,4-difluorobenzaldehyde, Acros Organics (1.42 g, 0.01 mol) are combined with 8-hydroxyquinoline, Acros Organics (1.45 g, 0.01 mol) in 50 ml of absolute EtOH to give the desired Betti condensation product as a light green solid (MP 171-173° C.).

Preparation of AD4-13046:

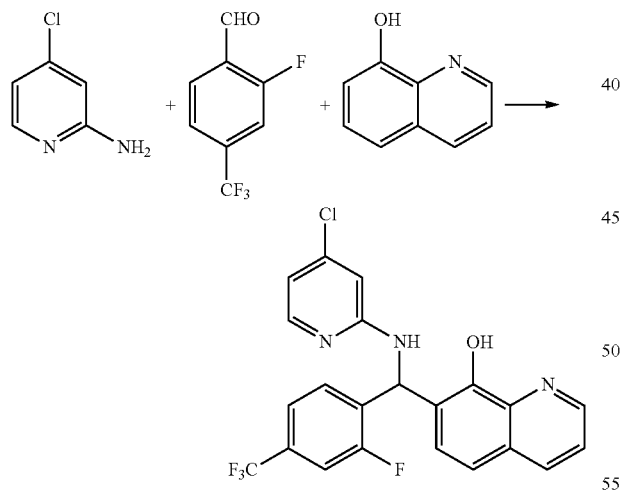

In a manner similar to that described in Example AD4-13021.

2-Amino-4-chloropyridine, Matrix (1.42 g, 0.01 mol) and 2-fluoro-4-trifluoromethylbenzaldehyde, Matrix (1.92 g, 0.01) are combined with 8-hydroxyquinoline, Acros Organics (1.45 g, 0.01 mol) in 50 ml of absolute EtOH to give the desired Betti condensation product as a light green solid (MP 164-165° C.).

Preparation of AD4-13047:

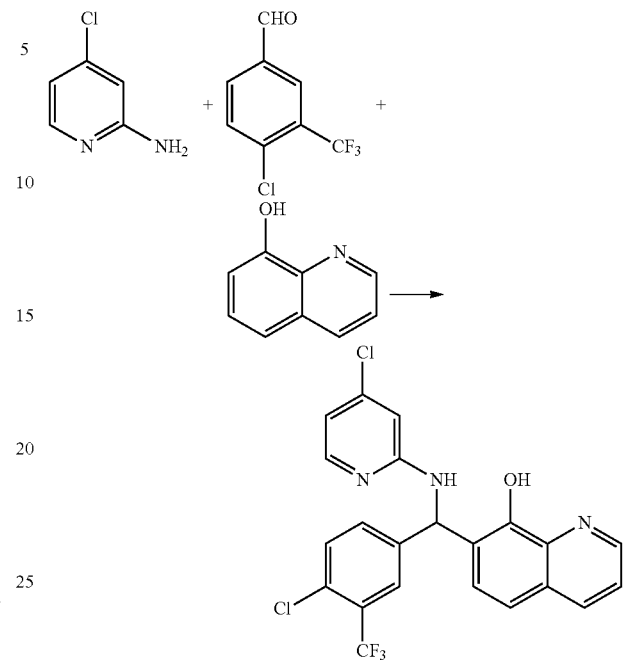

In a manner similar to that described in Example AD4-13021.

2-Amino-4-chloropyridine, Matrix (1.42 g, 0.01 mol) and 3-(trifluoromethyl)-4-chlorobenzaldehyde, Oakwood Products (2.09 g, 0.01 mol) are combined with 8-hydroxyquinoline, Acros Organics (1.45 g, 0.01 mol) in 50 ml of absolute EtOH to give the desired Betti condensation product as a green solid (MP 136-140° C.).

Preparation of AD4-13048:

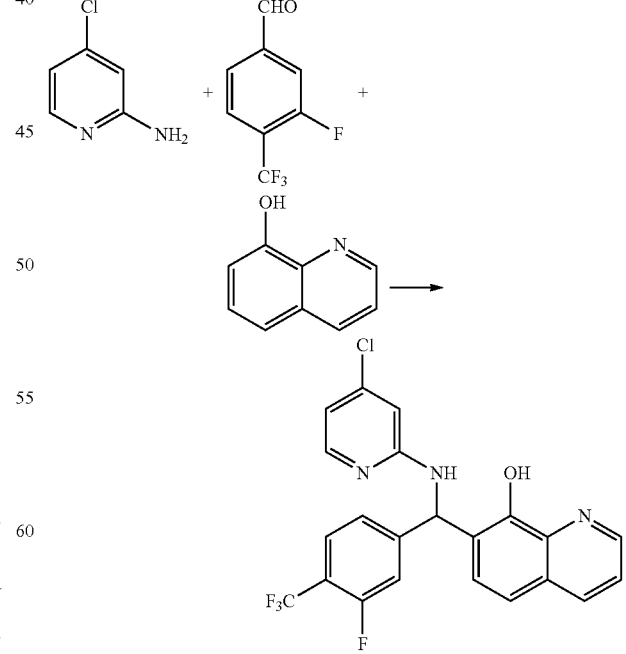

In a manner similar to that described in Example AD4-13021.

2-Amino-4-chloropyridine, Matrix (1.42 g, 0.01 mol) and 3-fluoro-4-trifluoromethylbenzaldehyde, Oakwood Products (1.92 g, 0.01) are combined with 8-hydroxyquinoline, Acros Organics (1.45 g, 0.01 mol) in 50 ml of absolute EtOH to give the desired Betti condensation product as a light green solid (MP 110-134° C.).

Preparation of AD4-13049:

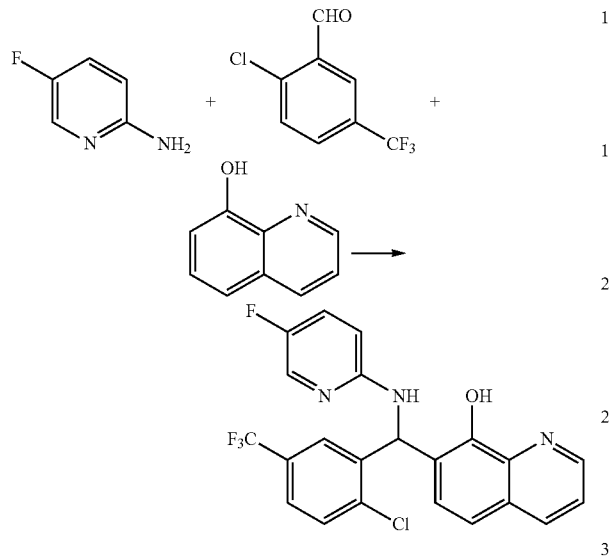

In a manner similar to that described in Example AD4-13021.

2-Amino-5-fluoropyridine, Matrix (1.12 g, 0.01 mol) and 2-chloro-5-(trifluoromethyl)benzaldehyde, matrix (2.09 g, 0.01 mol) are combined with 8-hydroxyquinoline, Acros Organics (1.45 g, 0.01 mol) in 50 ml of absolute EtOH to give the desired Betti condensation product as a light green solid (MP 145-159° C.).

Preparation of AD4-13050:

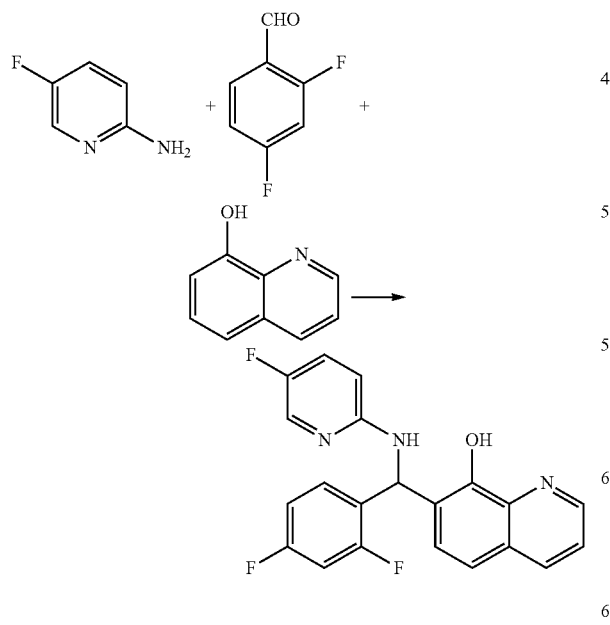

In a manner similar to that described in Example AD4-13021.

2-Amino-5-fluoropyridine, Matrix (1.12 g, 0.01 mol) and 2,4-difluorobenzaldehyde, Acros Organics (1.42 g, 0.01 mol) are combined with 8-hydroxyquinoline, Acros Organics (1.45 g, 0.01 mol) in 50 ml of absolute EtOH to give the desired Betti condensation product as a green solid (MP 88-93° C.).

Preparation of AD4-13051:

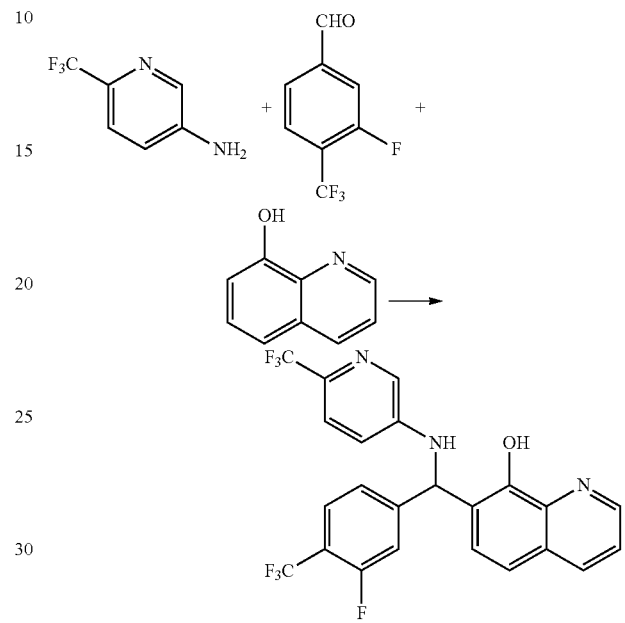

In a manner similar to that described in Example AD4-13021.

3-amino-6-(trifluoromethyl)pyridine, Matrix (1.62 g, 0.01 mol) and 3-fluoro-4-trifluoromethylbenzaldehyde, Oakwood Products (1.92 g, 0.01) are combined with 8-hydroxyquinoline, Acros Organics (1.45 g, 0.01 mol) in 50 ml of absolute EtOH to give the desired Betti condensation product as a brown solid (MP 99-111° C.).

Preparation of AD4-13052:

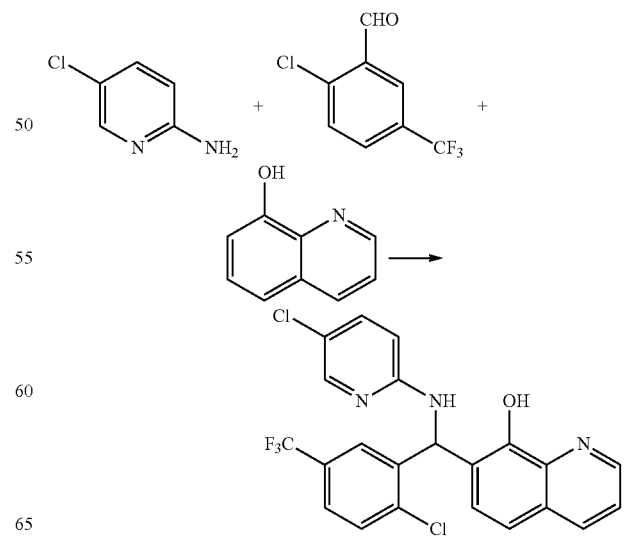

In a manner similar to that described in Example AD4-13021.

2-Amino-5-chloropyridine, Matrix (1.42 g, 0.01 mol) and 2-chloro-5-(trifluoromethyl)benzaldehyde, matrix (2.09 g, 0.01 mol) are combined with 8-hydroxyquinoline, Acros Organics (1.45 g, 0.01 mol) in 50 ml of absolute EtOH to give the desired Betti condensation product as a light green solid (MP 163-165° C.).

Preparation of AD4-13053:

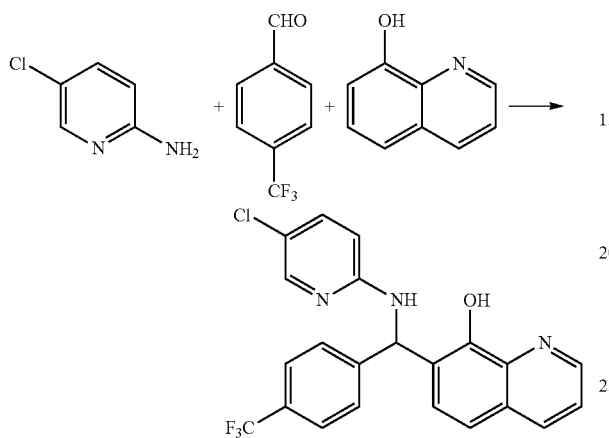

In a manner similar to that described in Example AD4-13021.

2-Amino-5-chloropyridine, Matrix (1.42 g, 0.01 mol) and 4-(trifluoromethyl)benzaldehyde, Acros Organics (1.74 g, 0.01 mol) are combined with 8-hydroxyquinoline, Acros Organics (1.45 g, 0.01 mol) in 50 ml of absolute EtOH to give the desired Betti condensation product as a light green solid (MP 115-130° C.).

Preparation of AD4-13054:

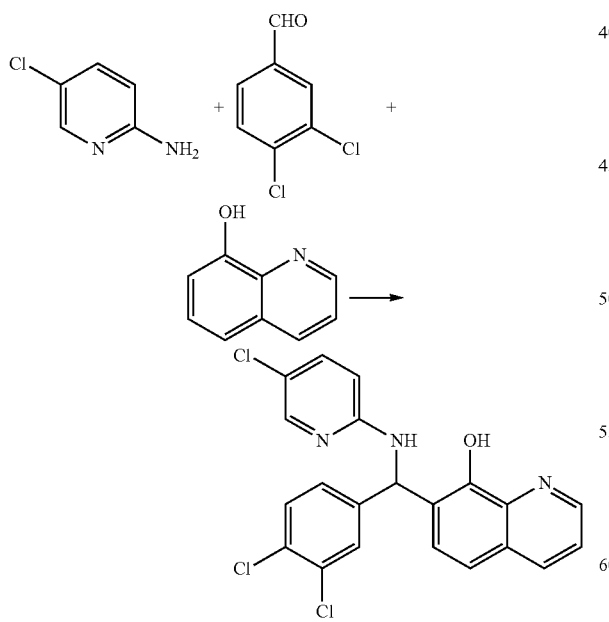

In a manner similar to that described in Example AD4-13021.

2-Amino-5-chloropyridine, Matrix (1.42 g, 0.01 mol) and 3,4-dichlorobenzaldehyde, Acros Organics (1.75 g, 0.01 mol) are combined with 8-hydroxyquinoline, Acros Organics (1.45 g, 0.01 mol) in 50 ml of absolute EtOH to give the desired Betti condensation product as a green solid (MP 96-125° C.).

Preparation of AD4-13055:

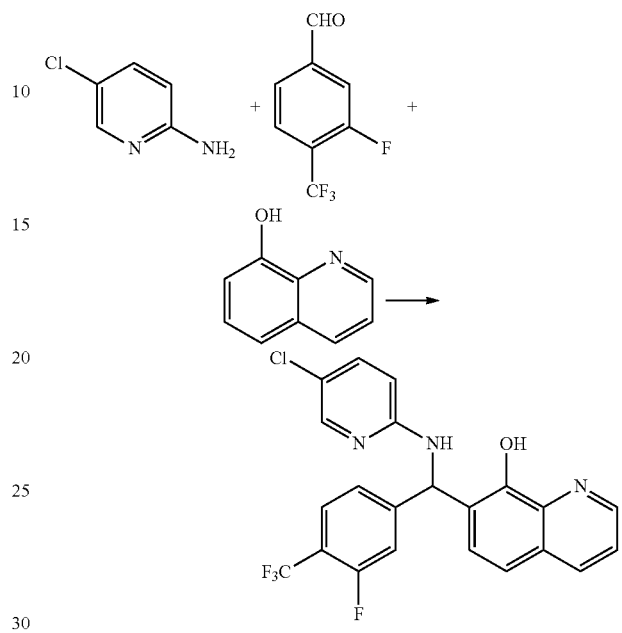

In a manner similar to that described in Example AD4-13021.

2-Amino-5-chloropyridine, Matrix (1.42 g, 0.01 mol) and 3-fluoro-4-trifluoromethylbenzaldehyde, Oakwood Products (1.92 g, 0.01) are combined with 8-hydroxyquinoline, Acros Organics (1.45 g, 0.01 mol) in 50 ml of absolute EtOH to give the desired Betti condensation product as a green solid (MP 133-134° C.).

Preparation of AD4-13056:

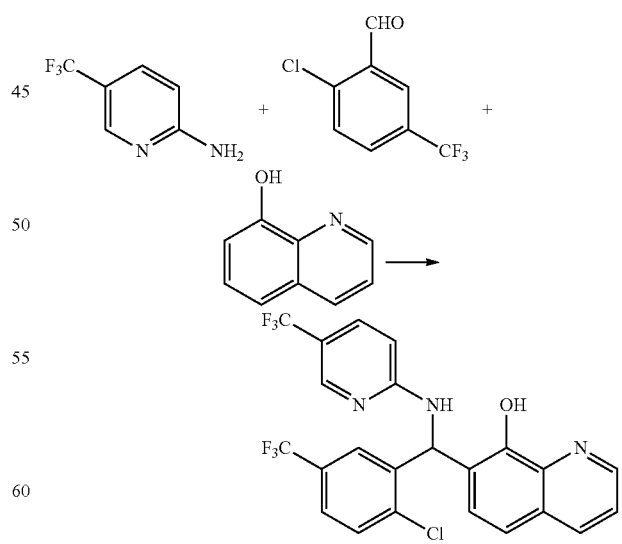

In a manner similar to that described in Example AD4-13021.

2-Amino-5-(trifluoromethyl)pyridine, Acros Organics (1.62 g, 0.01 mol) and 2-chloro-5-(trifluoromethyl)benzaldehyde, Matrix (2.09 g, 0.01 mol) are combined with 8-hydroxyquinoline, Acros Organics (1.45 g, 0.01 mol) in 50 ml of absolute EtOH to give the desired Betti condensation product as a green oil.

Preparation of AD4-13057:

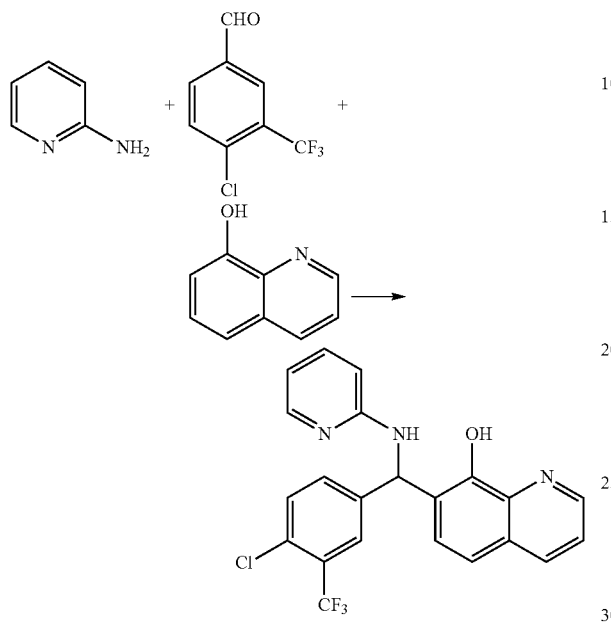

In a manner similar to that described in Example AD4-13021.

2-Aminopyridine, Acros Organics (0.94 g, 0.01 mol) and 3-(trifluoromethyl)-4-chlorobenzaldehyde, Oakwood Products (2.09 g, 0.01 mol) are combined with 8-hydroxyquinoline, Acros Organics (1.45 g, 0.01 mol) in 50 ml of absolute EtOH to give the desired Betti condensation product as a green solid (MP 73-88° C.).

Preparation of AD4-13058:

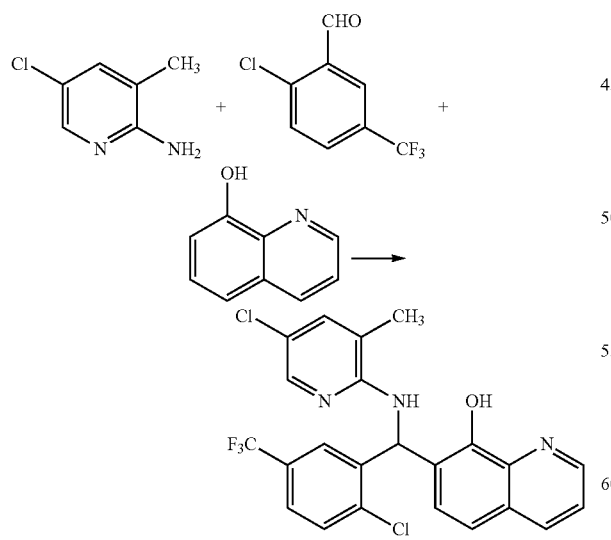

In a manner similar to that described in Example AD4-13021.

2-Amino-5-chloro-3-methylpyridine, Matrix (1.42 g, 0.01 mol) and 2-chloro-5-(trifluoromethyl)benzaldehyde, Matrix (2.09 g, 0.01 mol) are combined with 8-hydroxyquinoline, Acros Organics (1.45 g, 0.01 mol) in 50 ml of absolute EtOH to give the desired Betti condensation product as a green oil.

Preparation of AD4-13059:

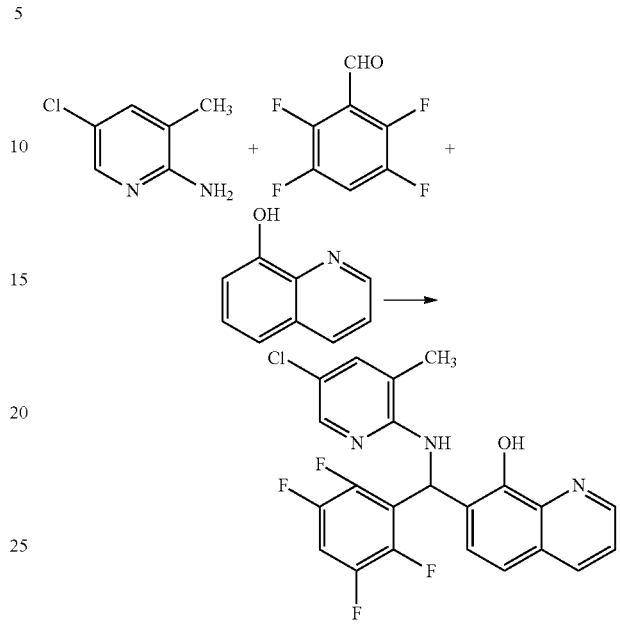

In a manner similar to that described in Example AD4-13021.

2-Amino-5-chloro-3-methylpyridine, Matrix (1.42 g, 0.01 mol) and 2,3,5,6-tetrafluorobenzaldehyde, Matrix Scientific (1.78 g, 0.01 mol) are combined with 8-hydroxyquinoline, Acros Organics (1.45 g, 0.01 mol) in 50 ml of absolute EtOH to give the desired Betti condensation product as a waxy green solid.

Preparation of AD4-13060:

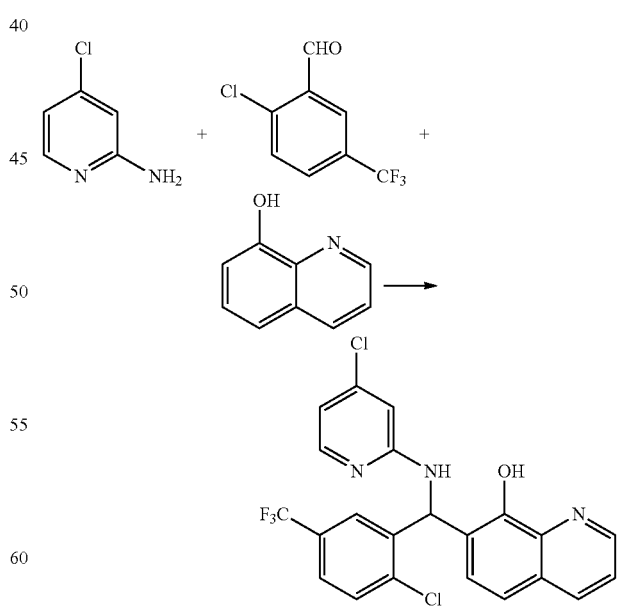

In a manner similar to that described in Example AD4-13021.

2-Amino-4-chloropyridine, Matrix (1.42 g, 0.01 mol) and 2-chloro-5-(trifluoromethyl)benzaldehyde, Matrix (2.09 g, 0.01 mol) are combined with 8-hydroxyquinoline, Acros Organics (1.45 g, 0.01 mol) in 50 ml of absolute EtOH to give the desired Betti condensation product as a waxy green solid.

Preparation of AD4-13061:

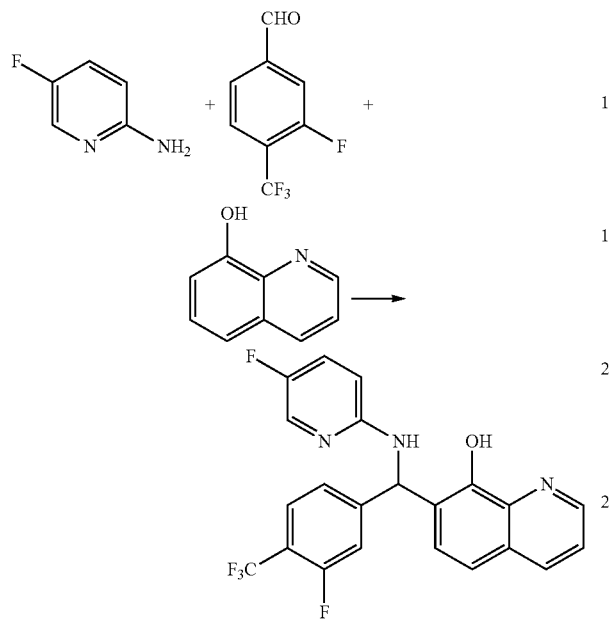

In a manner similar to that described in Example AD4-13021.

2-Amino-5-fluoropyridine, Matrix (1.12 g, 0.01 mol) and 3-fluoro-4-trifluoromethylbenzaldehyde, Oakwood Products (1.92 g, 0.01) are combined with 8-hydroxyquinoline, Acros Organics (1.45 g, 0.01 mol) in 50 ml of absolute EtOH to give the desired Betti condensation product as a green oil.

Preparation of AD4-13062:

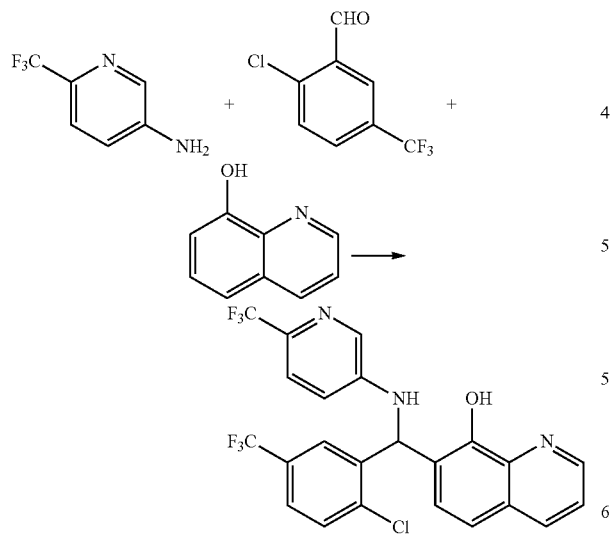

In a manner similar to that described in Example AD4-13021.

3-amino-6-(trifluoromethyl)pyridine, Matrix (1.62 g, 0.01 mol) and 2-chloro-5-(trifluoromethyl)benzaldehyde, Matrix (2.09 g, 0.01 mol) are combined with 8-hydroxyquinoline, Acros Organics (1.45 g, 0.01 mol) in 50 ml of absolute EtOH to give the desired Betti condensation product as a green oil.

Preparation of AD4-13063:

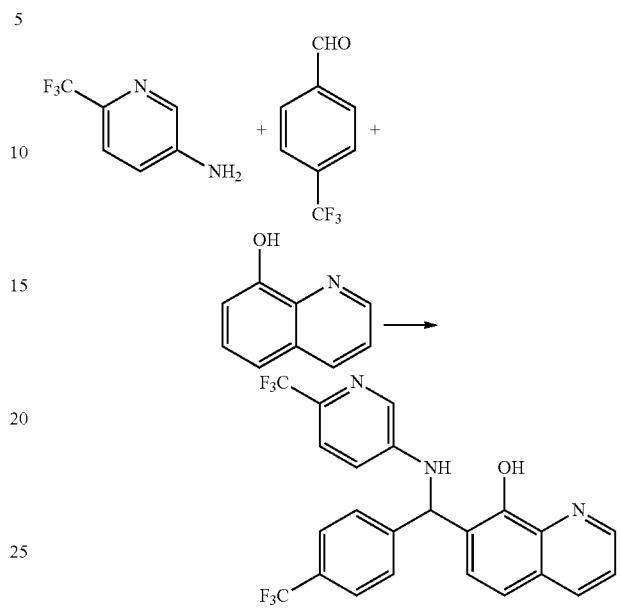

In a manner similar to that described in Example AD4-13021.

3-amino-6-(trifluoromethyl)pyridine, Matrix (1.62 g, 0.01 mol) and 4-(trifluoromethyl)benzaldehyde, Acros Organics (1.74 g, 0.01 mol) are combined with 8-hydroxyquinoline, Acros Organics (1.45 g, 0.01 mol) in 50 ml of absolute EtOH to give the desired Betti condensation product as a green oil.

Preparation of AD4-13064:

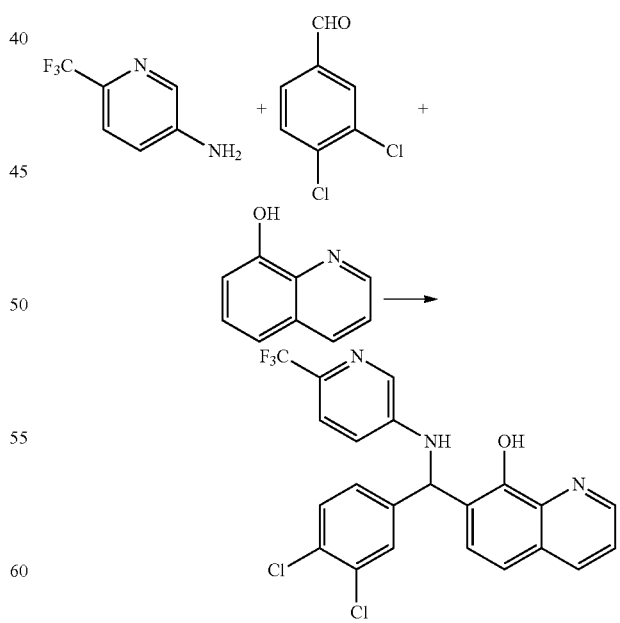

In a manner similar to that described in Example AD4-13021.

3-amino-6-(trifluoromethyl)pyridine, Matrix (1.62 g, 0.01 mol) and 3,4-dichlorobenzaldehyde, Acros Organics (1.75 g, 0.01 mol) are combined with 8-hydroxyquinoline, Acros Organics (1.45 g, 0.01 mol) in 50 ml of absolute EtOH to give the desired Betti condensation product as a green oil.

Preparation of AD4-13065:

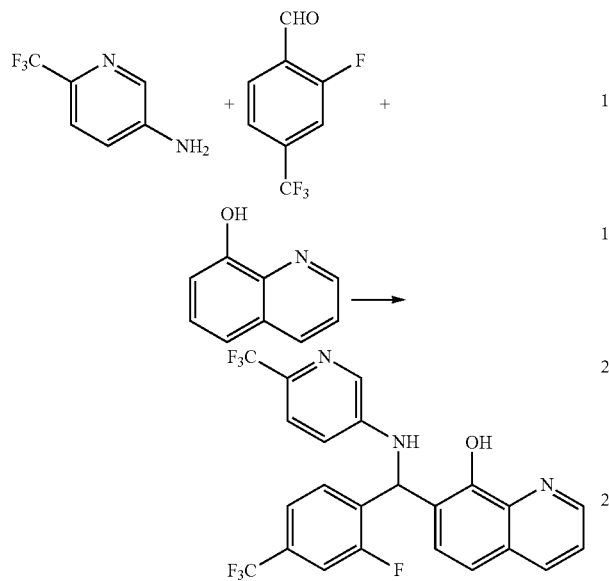

In a manner similar to that described in Example AD4-13021.

3-amino-6-(trifluoromethyl)pyridine, Matrix (1.62 g, 0.01 mol) and 2-fluoro-4-trifluoromethylbenzaldehyde, Matrix (1.92 g, 0.01) are combined with 8-hydroxyquinoline, Acros Organics (1.45 g, 0.01 mol) in 50 ml of absolute EtOH to give the desired Betti condensation product as a green oil.

Preparation of AD4-13066:

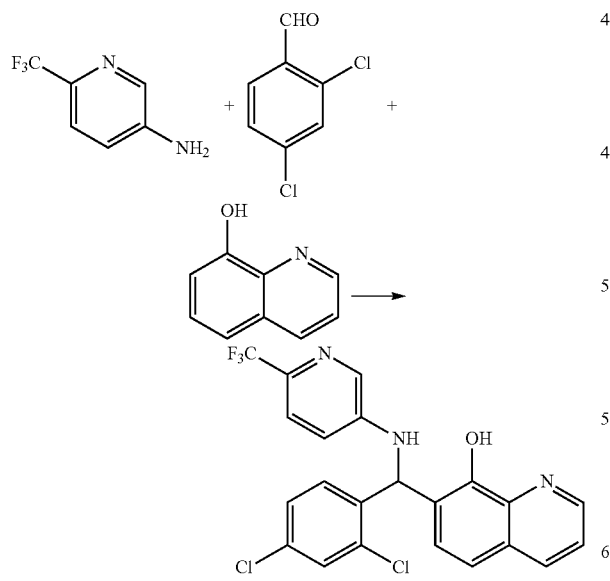

In a manner similar to that described in Example AD4-13021.

3-amino-6-(trifluoromethyl)pyridine, Matrix (1.62 g, 0.01 mol) and 2,4-dichlorobenzaldehyde, Acros Organics (1.75 g, 0.01 mol) are combined with 8-hydroxyquinoline, Acros Organics (1.45 g, 0.01 mol) in 50 ml of absolute EtOH to give the desired Betti condensation product as a green oil.

Preparation of AD4-13067:

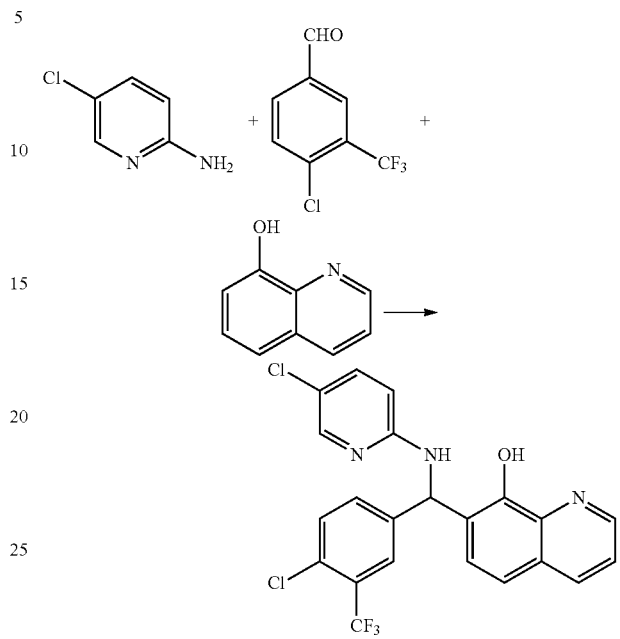

In a manner similar to that described in Example AD4-13021.

2-Amino-5-chloropyridine, Matrix (1.42 g, 0.01 mol) and 3-(trifluoromethyl)-4-chlorobenzaldehyde, Oakwood Products (2.09 g, 0.01 mol) are combined with 8-hydroxyquinoline, Acros Organics (1.45 g, 0.01 mol) in 50 ml of absolute EtOH to give the desired Betti condensation product as a green oil.

Preparation of AD4-13068:

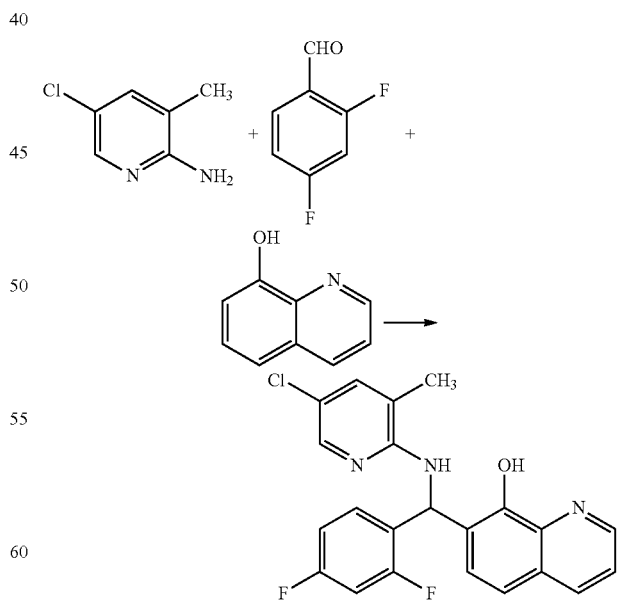

In a manner similar to that described in Example AD4-13021.

2-Amino-5-chloro-3-methylpyridine, Matrix (1.42 g, 0.01 mol) and 2,4-difluorobenzaldehyde, Acros Organics (1.42 g, 0.01 mol) are combined with 8-hydroxyquinoline, Acros Organics (1.45 g, 0.01 mol) in 50 ml of absolute EtOH to give the desired Betti condensation product as a green oil.

Preparation of AD4-13069:

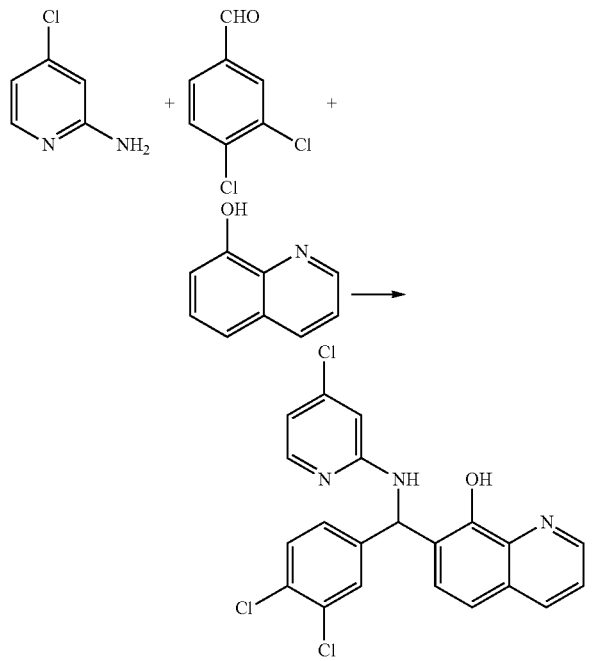

In a manner similar to that described in Example AD4-13021.

2-Amino-4-chloropyridine, Matrix (1.42 g, 0.01 mol) and 3,4-dichlorobenzaldehyde, Acros Organics (1.75 g, 0.01 mol) are combined with 8-hydroxyquinoline, Acros Organics (1.45 g, 0.01 mol) in 50 ml of absolute EtOH to give the desired Betti condensation product as a green solid (MP 118-121° C.).

Preparation of AD4-13070:

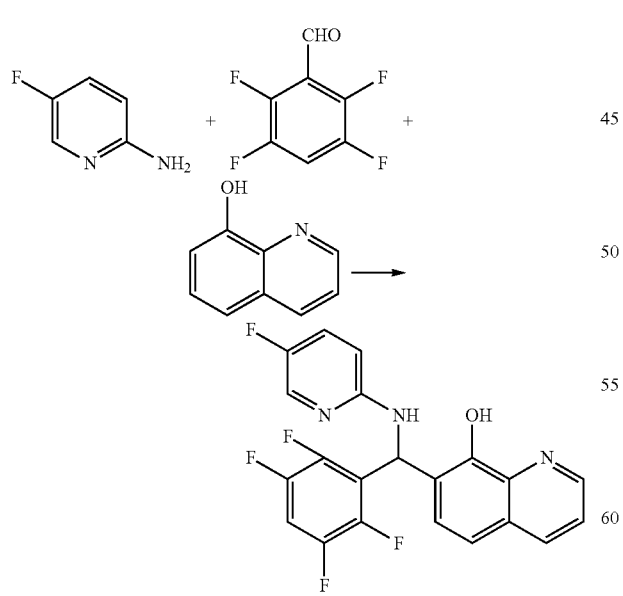

In a manner similar to that described in Example AD4-13021.

2-Amino-5-fluoropyridine, Matrix (1.12 g, 0.01 mol) and 2,3,5,6-tetrafluorobenzaldehyde, Matrix Scientific (1.78 g, 0.01 mol) are combined with 8-hydroxyquinoline, Acros Organics (1.45 g, 0.01 mol) in 50 ml of absolute EtOH to give the desired Betti condensation product as a light green solid (MP 87-90° C.).

Preparation of AD4-13071:

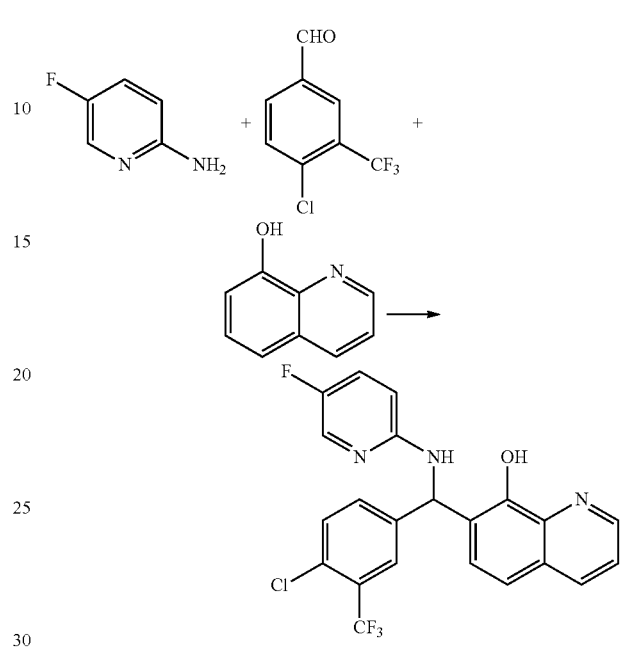

In a manner similar to that described in Example AD4-13021.

2-Amino-5-fluoropyridine, Matrix (1.12 g, 0.01 mol) and 3-(trifluoromethyl)-4-chlorobenzaldehyde, Oakwood Products (2.09 g, 0.01 mol) are combined with 8-hydroxyquinoline, Acros Organics (1.45 g, 0.01 mol) in 50 ml of absolute EtOH to give the desired Betti condensation product as a light green solid (MP 76-86° C.).

Preparation of AD4-13072:

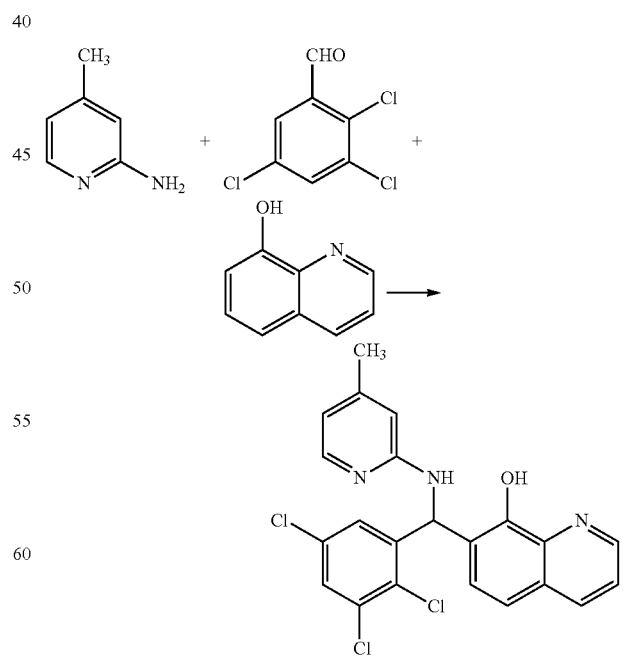

In a manner similar to that described in Example AD4-13022.

2-Amino-4-picoline, Acros Organics (1.08 g, 0.01 mol) and 2,3,5-trichlorobenzaldehyde, Acros Organics (2.09 g, 0.01 mol) are combined with 8-hydroxyquinoline, Acros Organics (1.45 g, 0.01 mol) in 50 ml of absolute EtOH to give the desired Betti condensation product an off-white solid (MP 170-173° C.).

Preparation of AD4-13073:

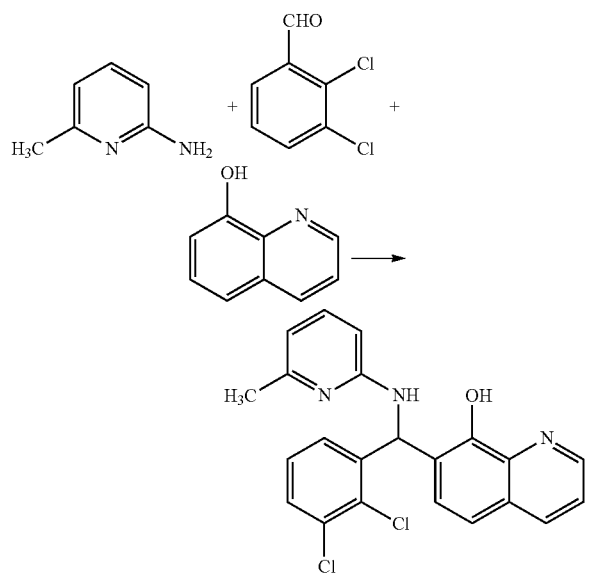

In a manner similar to that described in Example AD4-13022.

2-Amino-6-picoline, Acros Organics (1.08 g, 0.01 mol) and 2,3-dichlorobenzaldehyde, Acros Organics (1.75 g, 0.01 mol) are combined with 8-hydroxyquinoline, Acros Organics (1.45 g, 0.01 mol) in 50 ml of absolute EtOH to give the desired Betti condensation product an off-white solid (MP 165-167° C.).

Preparation of AD4-13074:

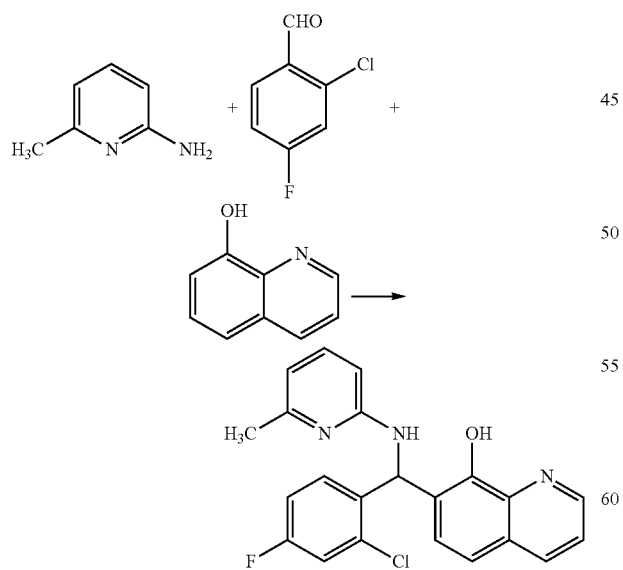

In a manner similar to that described in Example AD4-13022.

2-Amino-6-picoline, Acros Organics (1.08 g, 0.01 mol) and 2-chloro-4-fluorobenzaldehyde, Oakwood Products (1.59 g, 0.01 mol) are combined with 8-hydroxyquinoline, Acros Organics (1.45 g, 0.01 mol) in 50 ml of absolute EtOH to give the desired Betti condensation product an off-white solid (MP 247-250° C.).

Preparation of AD4-13075:

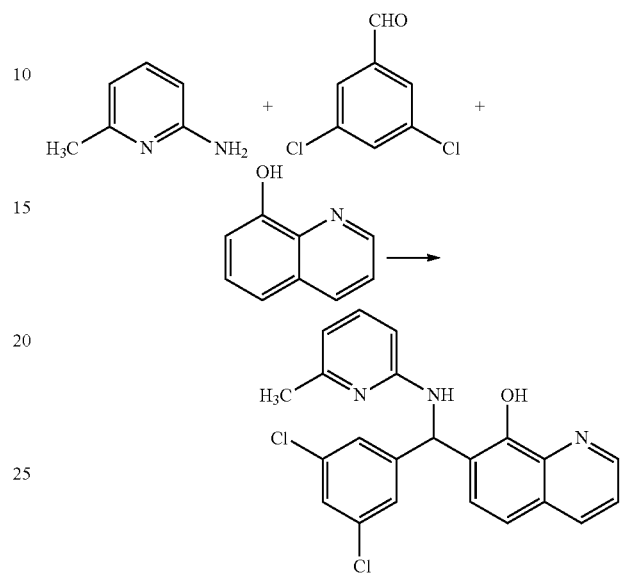

In a manner similar to that described in Example AD4-13022.

2-Amino-6-picoline, Acros Organics (1.08 g, 0.01 mol) and 3,5-dichlorobenzaldehyde, Matrix Scientific (1.75 g, 0.01 mol) are combined with 8-hydroxyquinoline, Acros Organics (1.45 g, 0.01 mol) in 50 ml of absolute EtOH to give the desired Betti condensation product a white solid (MP 126-129° C.).

Preparation of AD4-13076:

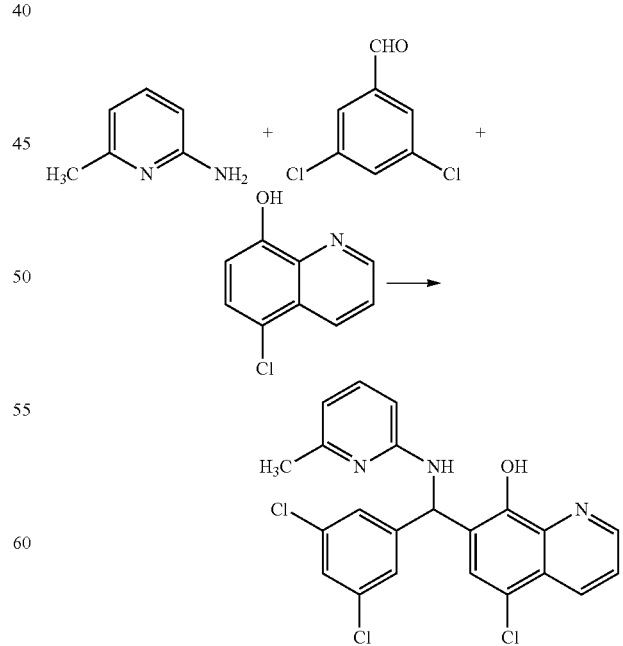

In a manner similar to that described in Example AD4-13022.

2-Amino-6-picoline, Acros Organics (1.08 g, 0.01 mol) and 3,5-dichlorobenzaldehyde, Matrix Scientific (1.75 g, 0.01 mol) are combined with 5-chloro-8-hydroxyquinoline, Acros Organics (1.80 g, 0.01 mol) in 50 ml of absolute EtOH to give the desired Betti condensation product an off-white solid (MP 230-232° C.).

Preparation of AD4-13077:

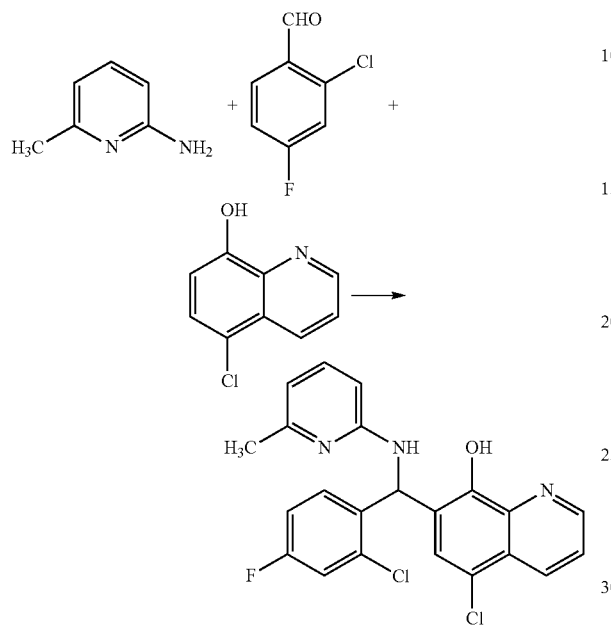

In a manner similar to that described in Example AD4-13022.

2-Amino-6-picoline, Acros Organics (1.08 g, 0.01 mol) and 2-chloro-4-fluorobenzaldehyde, Oakwood Products (1.59 g, 0.01 mol) are combined with 5-chloro-8-hydroxyquinoline, Acros Organics (1.80 g, 0.01 mol) in 50 ml of absolute EtOH to give the desired Betti condensation product an off-white solid (MP 221-223° C.).

Preparation of AD4-13078:

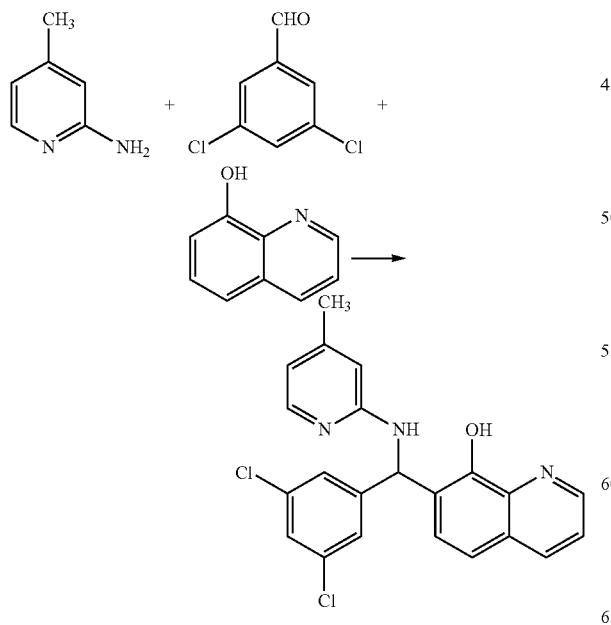

In a manner similar to that described in Example AD4-13022.

2-Amino-4-picoline, Acros Organics (1.08 g, 0.01 mol) and 3,5-dichlorobenzaldehyde, Matrix Scientific (1.75 g, 0.01 mol) are combined with 8-hydroxyquinaldine, Acros Organics (1.59 g, 0.01 mol) in 50 ml of absolute EtOH to give the desired Betti condensation product a white solid (MP 157-159° C.).

Preparation of AD4-13079:

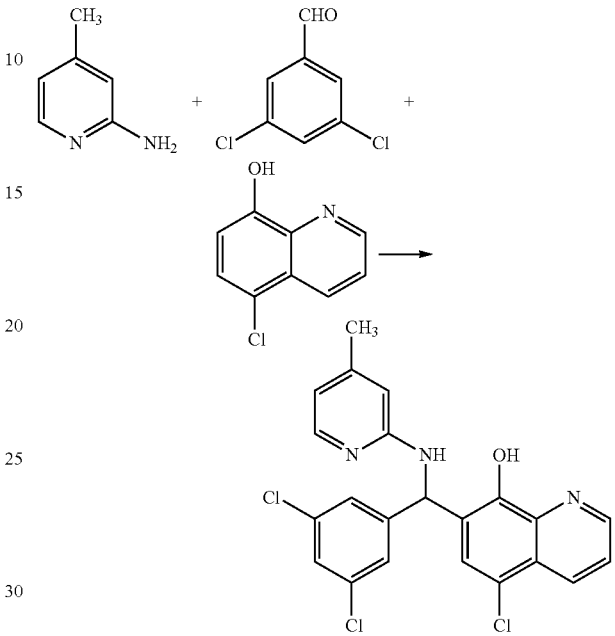

In a manner similar to that described in Example AD4-13022.

2-Amino-4-picoline, Acros Organics (1.08 g, 0.01 mol) and 3,5-dichlorobenzaldehyde, Matrix Scientific (1.75 g, 0.01 mol) are combined with 5-chloro-8-hydroxyquinoline, Acros Organics (1.80 g, 0.01 mol) in 50 ml of absolute EtOH to give the desired Betti condensation product an off-white solid (MP 217-218° C.).

Preparation of AD4-13080:

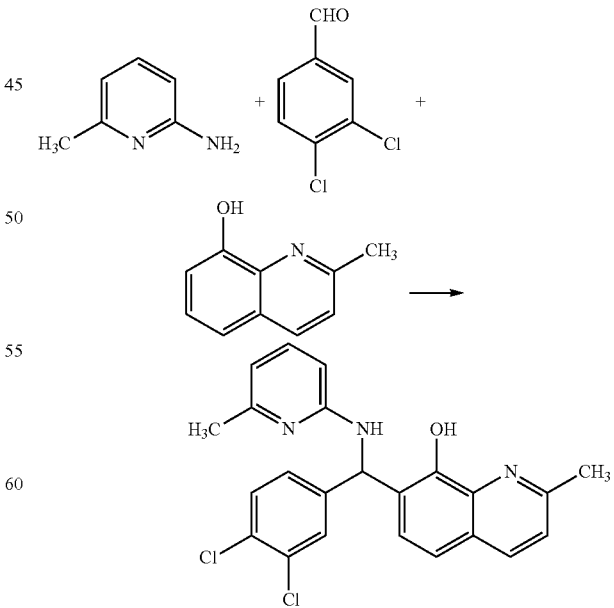

In a manner similar to that described in Example AD4-13022.

2-Amino-6-picoline, Acros Organics (1.08 g, 0.01 mol) and 3,4-dichlorobenzaldehyde, Acros Organics (1.75 g, 0.01 mol) are combined with 8-hydroxyquinaldine, Acros Organics (1.59 g, 0.01 mol) in 50 ml of absolute EtOH to give the desired Betti condensation product a white solid (MP 149-150° C.).

Preparation of AD4-13081:

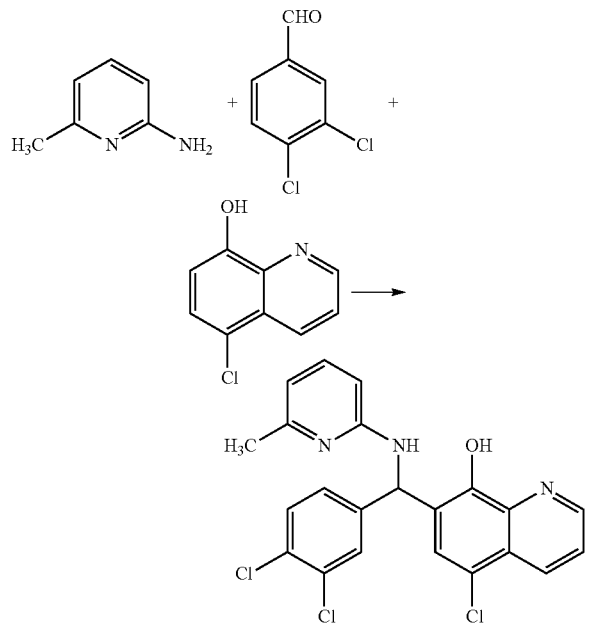

In a manner similar to that described in Example AD4-13022.

2-Amino-6-picoline, Acros Organics (1.08 g, 0.01 mol) and 3,4-dichlorobenzaldehyde, Acros Organics (1.75 g, 0.01 mol) are combined with 5-chloro-8-hydroxyquinoline, Acros Organics (1.80 g, 0.01 mol) in 50 ml of absolute EtOH to give the desired Betti condensation product a white solid (MP 214-216° C.).

Preparation of AD4-13082:

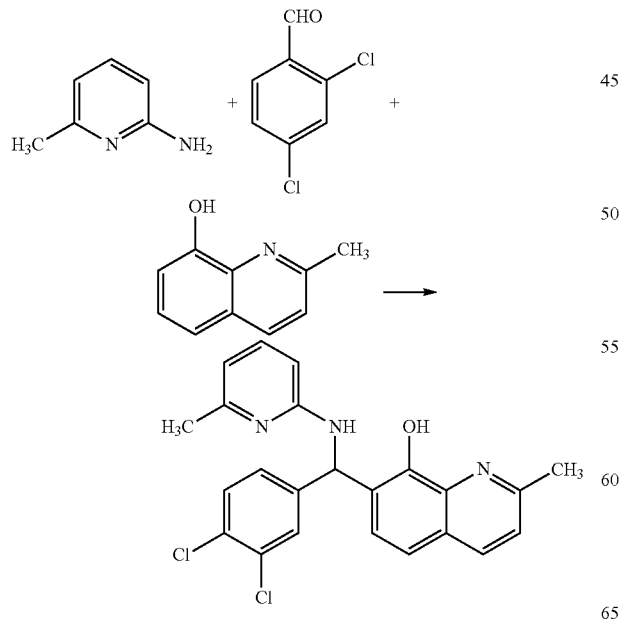

In a manner similar to that described in Example AD4-13022.

2-Amino-6-picoline, Acros Organics (1.08 g, 0.01 mol) and 2,4-dichlorobenzaldehyde, Acros Organics (1.75 g, 0.01 mol) are combined with 8-hydroxyquinaldine, Acros Organics (1.59 g, 0.01 mol) in 50 ml of absolute EtOH to give the desired Betti condensation product a white solid (MP155-159° C.).

Preparation of AD4-13083:

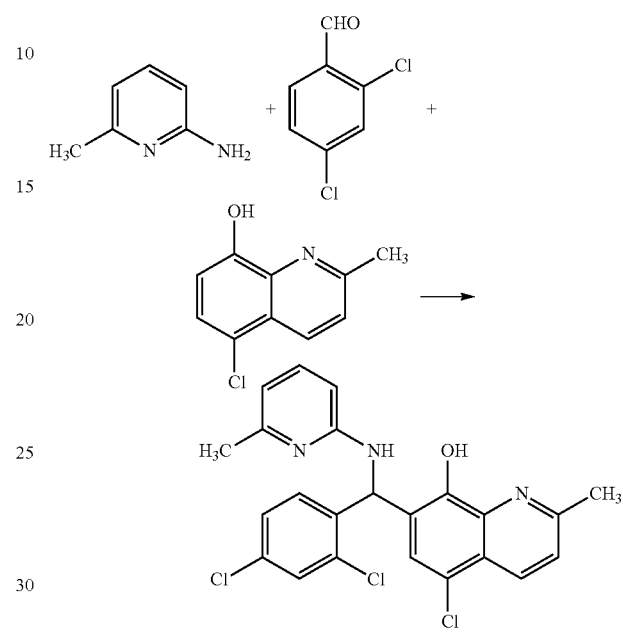

In a manner similar to that described in Example AD4-13022.

2-Amino-6-picoline, Acros Organics (1.08 g, 0.01 mol) and 2,4-dichlorobenzaldehyde, Acros Organics (1.75 g, 0.01 mol) are combined with 5-chloro-8-hydroxyquinoline, Acros Organics (1.80 g, 0.01 mol) in 50 ml of absolute EtOH to give the desired Betti condensation product a white solid (MP 201-202° C.).

Preparation of AD4-13084:

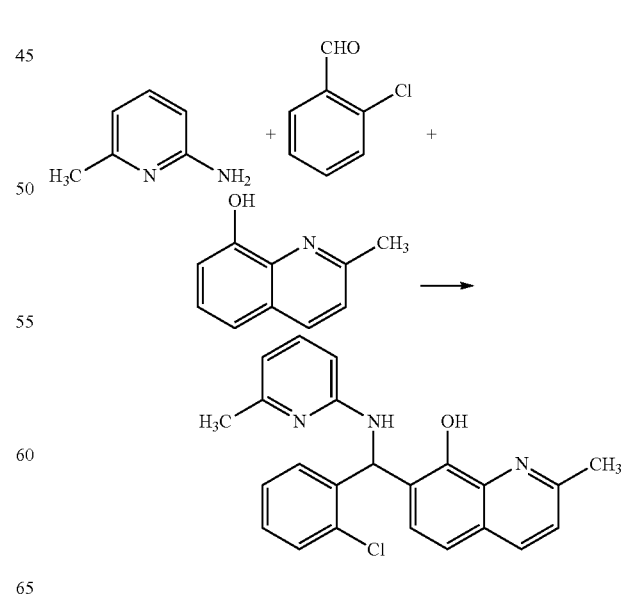

In a manner similar to that described in Example AD4-13022.

2-Amino-6-picoline, Acros Organics (1.08 g, 0.01 mol) and 2-chlorobenzaldehyde, Acros Organics (1.41 g, 0.01 mol) are combined with 8-hydroxyquinaldine, Acros Organics (1.59 g, 0.01 mol) in 50 ml of absolute EtOH to give the desired Betti condensation product a white solid (MP191-197° C.).

Preparation of AD4-13085:

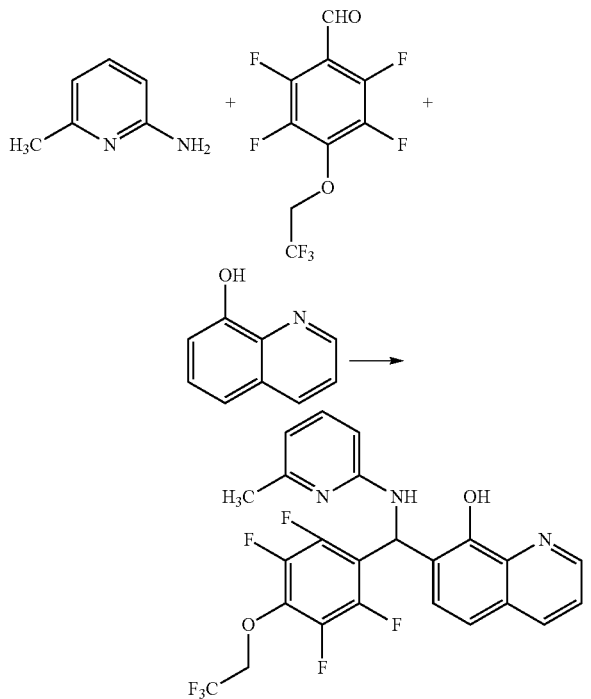

In a manner similar to that described in Example AD4-13022.

2-Amino-6-picoline, Acros Organics (1.08 g, 0.01 mol) and 2,3,5,6-tetrafluoro-4-(2,2,2-trifluoroethoxy)benzaldehyde (BBM-001-009; 2.76 g, 0.01 mol) are combined with 8-hydroxyquinoline, Acros Organics (1.45 g, 0.01 mol) in 50 ml of absolute EtOH to give the desired Betti condensation product as a white solid (MP 131-133° C.).

Preparation of AD4-13086:

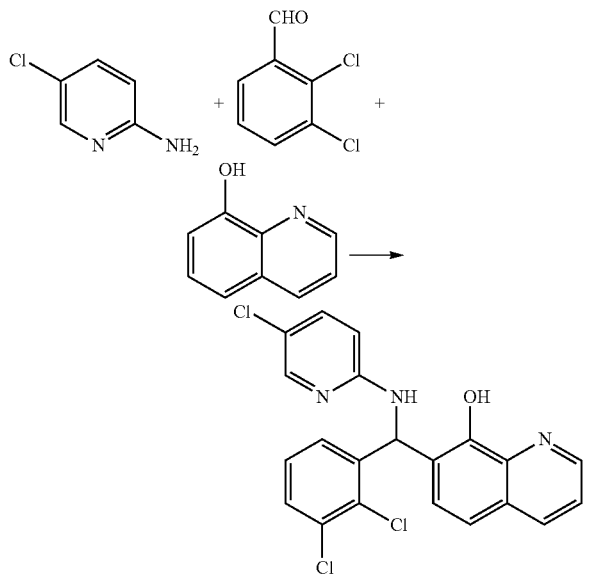

In a manner similar to that described in Example AD4-13021.

2-Amino-5-chloropyridine, Matrix Scientific (1.29 g, 0.01 mol) and 2,3-dichlorobenzaldehyde, Acros Organics (1.75 g, 0.01 mol) are combined with 8-hydroxyquinoline, Acros Organics (1.45 g, 0.01 mol) in 50 ml of absolute EtOH to give the desired Betti condensation product a white solid (MP 155-156° C.).

Preparation of AD4-13087:

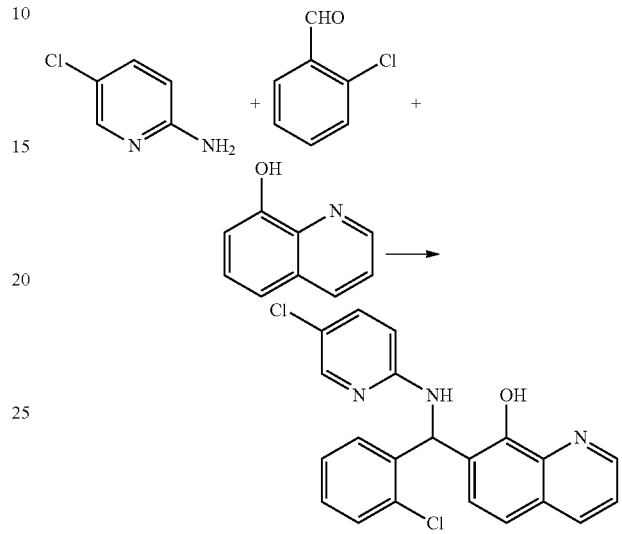

In a manner similar to that described in Example AD4-13021.

2-Amino-5-chloropyridine, Matrix Scientific (1.29 g, 0.01 mol) and 2-chlorobenzaldehyde, Acros Organics (1.41 g, 0.01 mol) are combined with 8-hydroxyquinoline, Acros Organics (1.45 g, 0.01 mol) in 50 ml of absolute EtOH to give the desired Betti condensation product an off-white solid (MP 194-197° C.).

Preparation of AD4-13088:

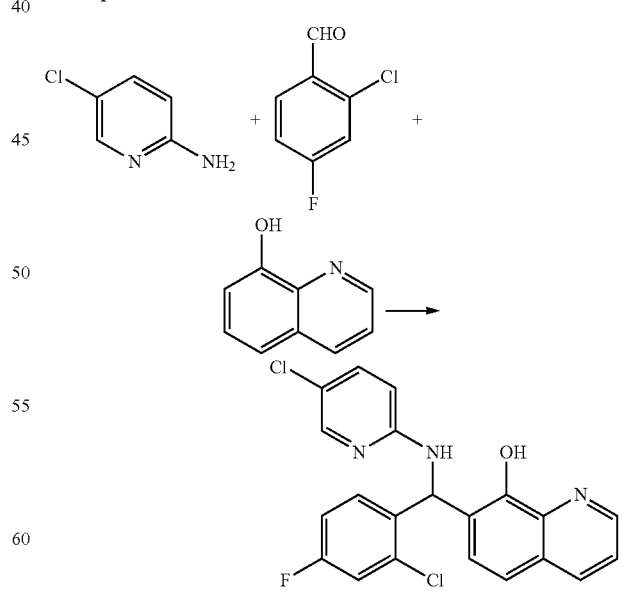

In a manner similar to that described in Example AD4-13021.

2-Amino-5-chloropyridine, Matrix Scientific (1.29 g, 0.01 mol) and 2,chloro-4-fluorobenzaldehyde, Oakwood Products (1.59 g, 0.01 mol) are combined with 8-hydroxyquinoline, Acros Organics (1.45 g, 0.01 mol) in 50 ml of absolute EtOH to give the desired Betti condensation product a white solid (MP 166-169° C.).

Preparation of AD4-13089:

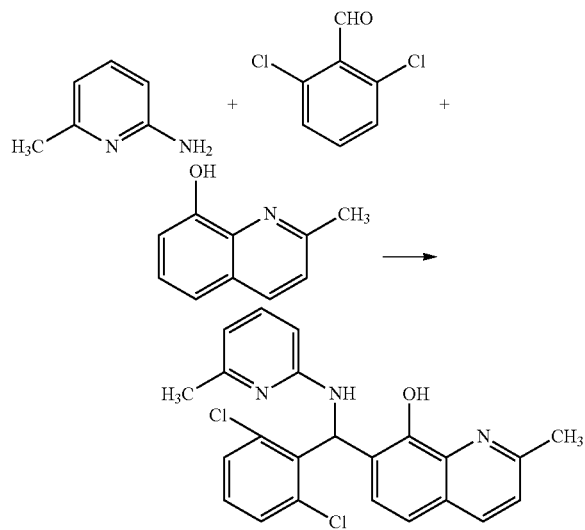

In a manner similar to that described in Example AD4-13022.

2-Amino-6-picoline, Acros Organics (1.08 g, 0.01 mol) and 2,6-dichlorobenzaldehyde, Acros Organics (1.75 g, 0.01 mol) are combined with 8-hydroxyquinaldine, Acros Organics (1.59 g, 0.01 mol) in 50 ml of absolute EtOH to give the desired Betti condensation product an off-white solid (MP 181-183° C.).

Preparation of AD4-13090:

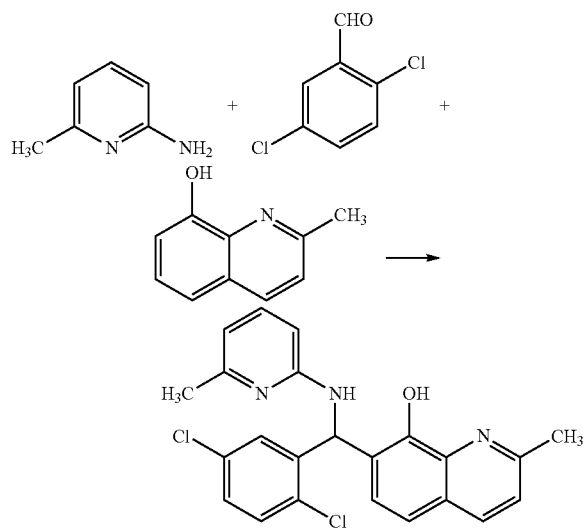

In a manner similar to that described in Example AD4-13022.

2-Amino-6-picoline, Acros Organics (1.08 g, 0.01 mol) and 2,5-dichlorobenzaldehyde, Acros Organics (1.75 g, 0.01 mol) are combined with 8-hydroxyquinaldine, Acros Organics (1.59 g, 0.01 mol) in 50 ml of absolute EtOH to give the desired Betti condensation product as a white solid (MP 159-161° C.).

Preparation of AD4-13091:

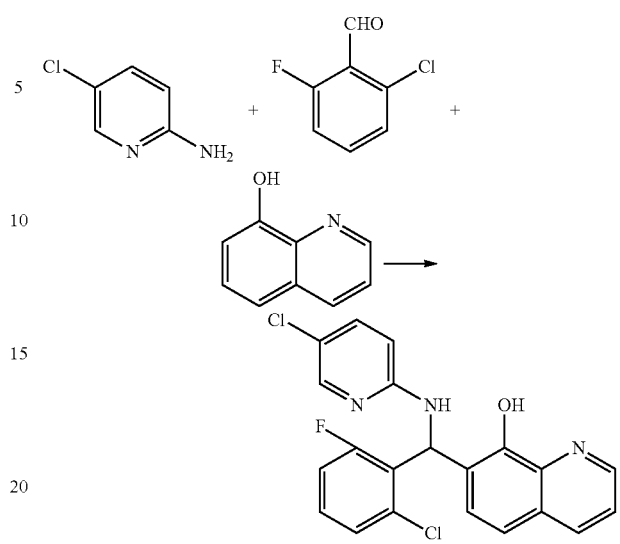

In a manner similar to that described in Example AD4-13021.

2-Amino-5-chloropyridine, Matrix Scientific (1.29 g, 0.01 mol) and 2-chloro-6-fluorobenzaldehyde, Acros Organics (1.59 g, 0.01 mol) are combined with 8-hydroxyquinoline, Acros Organics (1.45 g, 0.01 mol) in 50 ml of absolute EtOH to give the desired Betti condensation product as a white solid (MP 104-108° C.).

Preparation of AD4-13092:

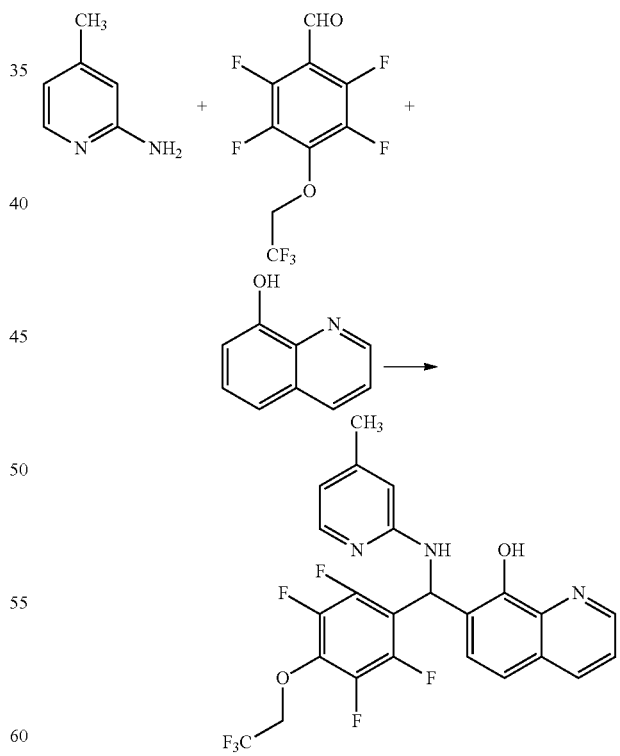

In a manner similar to that described in Example AD4-13021.

2-Amino-4-picoline, Acros Organics (1.08 g, 0.01 mol) and 2,3,5,6-tetrafluoro-4-(2,2,2-trifluoroethoxy)benzaldehyde (BBM-001-009; 2.76 g, 0.01 mol) are combined with 8-hydroxyquinoline, Acros Organics (1.45 g, 0.01 mol) in 50 ml of absolute EtOH to give the desired Betti condensation product as a white solid (MP 145-146° C.).

Preparation of AD4-13093:

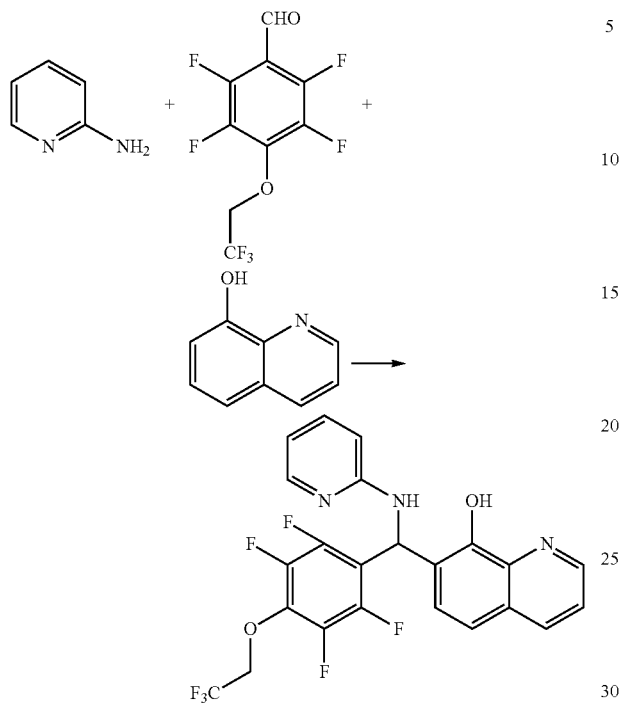

In a manner similar to that described in Example AD4-13021.

2-Aminopyridine, Acros Organics (0.94 g, 0.01 mol) and 2,3,5,6-tetrafluoro-4-(2,2,2-trifluoroethoxy)benzaldehyde (BBM-001-009; 2.76 g, 0.01 mol) are combined with 8-hydroxyquinoline, Acros Organics (1.45 g, 0.01 mol) in 50 ml of absolute EtOH to give the desired Betti condensation product as a white solid (MP 106-109° C.).

Preparation of AD4-13094:

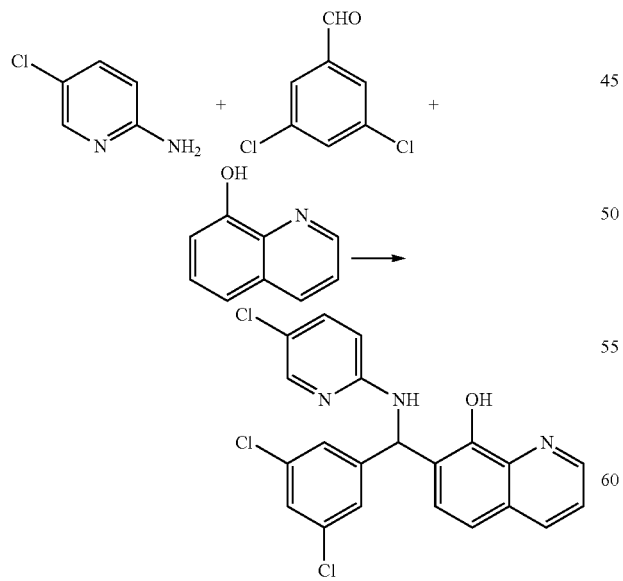

In a manner similar to that described in Example AD4-13021.

2-Amino-5-chloropyridine, Matrix Scientific (1.29 g, 0.01 mol) and 3,5-dichlorobenzaldehyde, Matrix Scientific (1.75 g, 0.01 mol) are combined with 8-hydroxyquinoline, Acros Organics (1.45 g, 0.01 mol) in 50 ml of absolute EtOH to give the desired Betti condensation product as an off-white solid (MP 123-126° C.).

Preparation of AD4-13095:

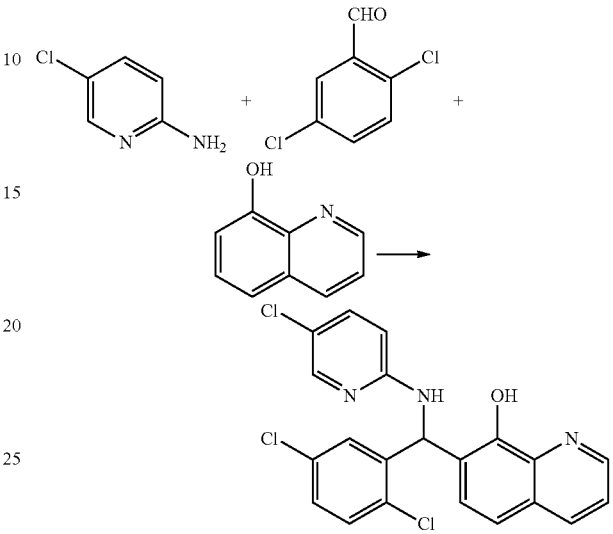

In a manner similar to that described in Example AD4-13021.

2-Amino-5-chloropyridine, Matrix Scientific (1.29 g, 0.01 mol) and 2,5-dichlorobenzaldehyde, Matrix Scientific (1.75 g, 0.01 mol) are combined with 8-hydroxyquinoline, Acros Organics (1.45 g, 0.01 mol) in 50 ml of absolute EtOH to give the desired Betti condensation product as a white solid (MP 197-204° C.).

Preparation of AD4-13096:

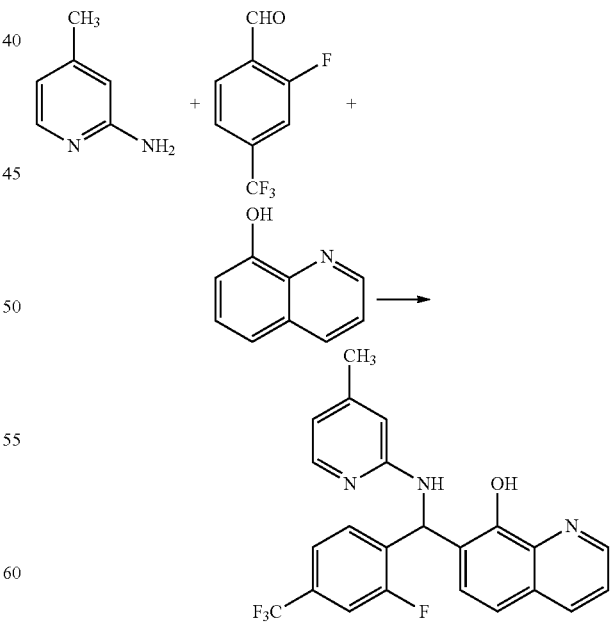

In a manner similar to that described in Example AD4-13021.

2-Amino-4-picoline, Acros Organics (1.08 g, 0.01 mol) and 2-fluoro-4-trifluoromethylbenzaldehyde, Oakwood Products (1.92 g, 0.01) are combined with 8-hydroxyquinoline, Acros Organics (1.45 g, 0.01 mol) in 50 ml of absolute EtOH to give the desired Betti condensation product as a light green solid (MP 160-161° C.).

Preparation of AD4-13097:

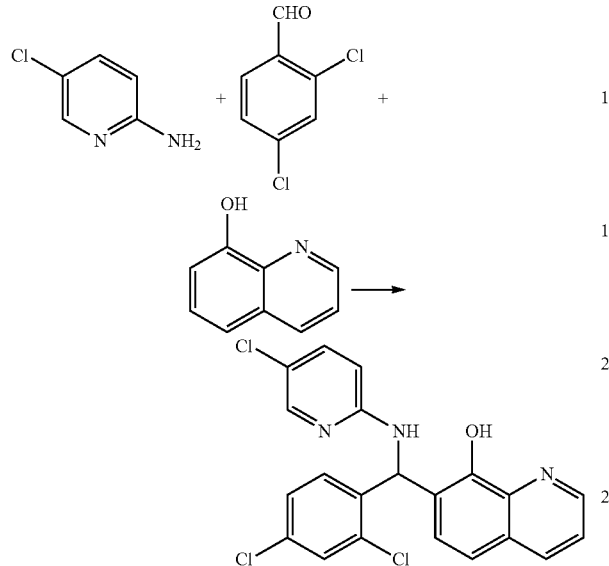

In a manner similar to that described in Example AD4-13021.

2-Amino-5-chloropyridine, Matrix Scientific (1.29 g, 0.01 mol) and 2,4-dichlorobenzaldehyde, Matrix Scientific (1.75 g, 0.01 mol) are combined with 8-hydroxyquinoline, Acros Organics (1.45 g, 0.01 mol) in 50 ml of absolute EtOH to give the desired Betti condensation product as a white solid (MP 155-156° C.).

Preparation of AD4-13098:

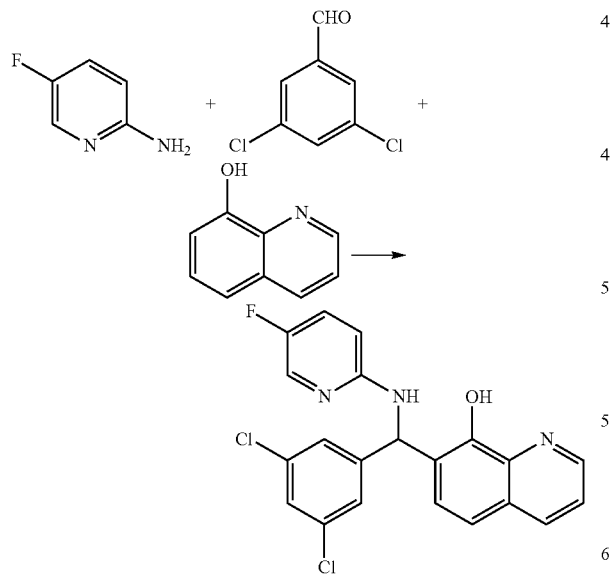

In a manner similar to that described in Example AD4-13021.

2-Amino-5-fluoropyridine, Matrix Scientific (1.12 g, 0.01 mol) and 3,5-dichlorobenzaldehyde, Matrix Scientific (1.75 g, 0.01 mol) are combined with 8-hydroxyquinoline, Acros Organics (1.45 g, 0.01 mol) in 50 ml of absolute EtOH to give the desired Betti condensation product as a white solid (MP 140-141° C.).

Preparation of AD4-13099:

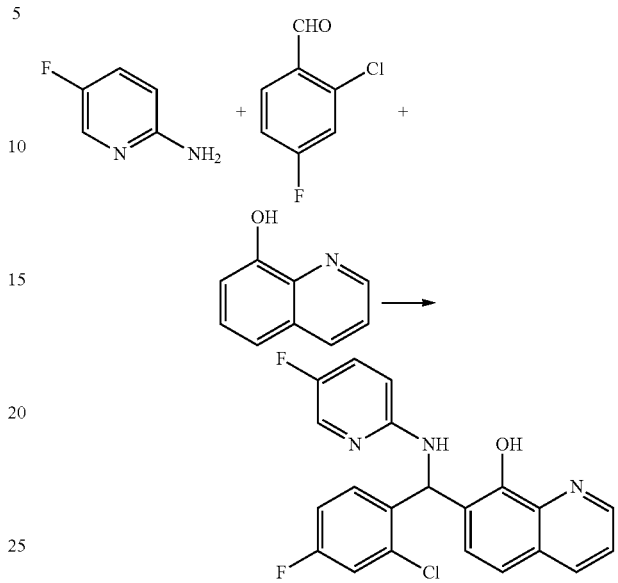

In a manner similar to that described in Example AD4-13021.

2-Amino-5-fluoropyridine, Matrix Scientific (1.12 g, 0.01 mol) and 2-chloro-4-fluorobenzaldehyde, Oakwood Products (1.58 g, 0.01 mol) are combined with 8-hydroxyquinoline, Acros Organics (1.45 g, 0.01 mol) in 50 ml of absolute EtOH to give the desired Betti condensation product as an off-white solid (MP 126-128° C.).

Preparation of AD4-13101:

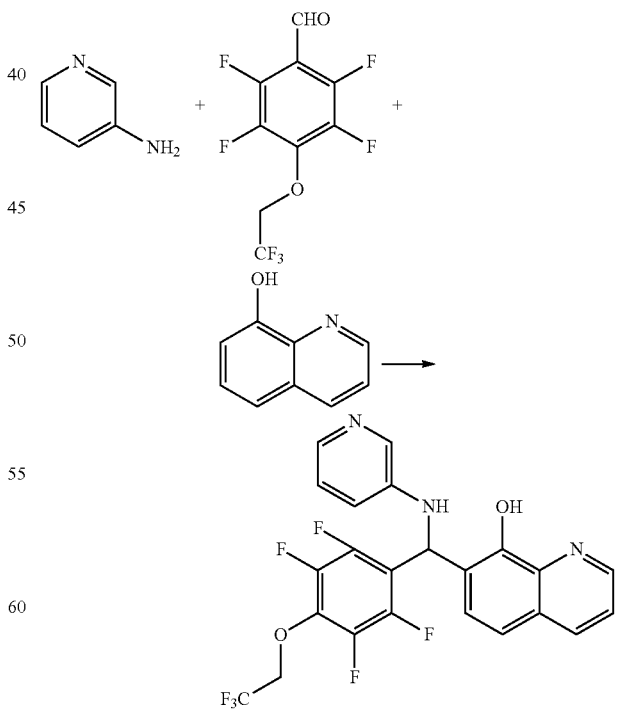

In a manner similar to that described in Example AD4-13021.

3-Aminopyridine, Acros Organics (0.94 g, 0.01 mol) and 2,3,5,6-tetrafluoro-4-(2,2,2-trifluoroethoxy)benzaldehyde (BBM-001-009; 2.76 g, 0.01 mol) are combined with 8-hydroxyquinoline, Acros Organics (1.45 g, 0.01 mol) in 50 ml of absolute EtOH to give the desired Betti condensation product as a brown solid (MP 72-76° C.).

Preparation of AD4-13102:

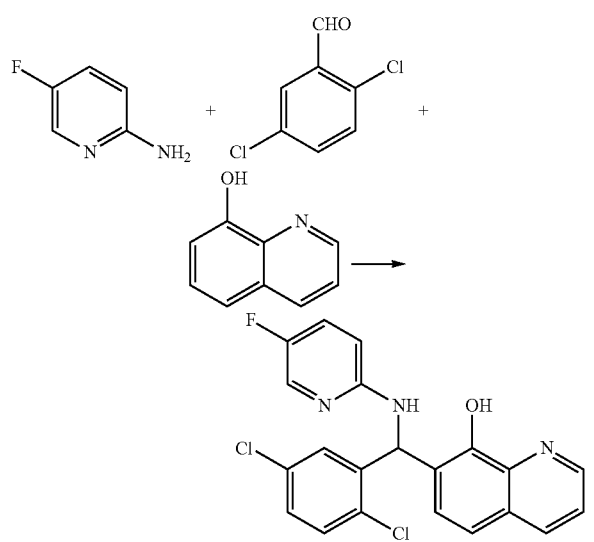

In a manner similar to that described in Example AD4-13022.

2-Amino-5-fluoropyridine, Matrix Scientific (1.12 g, 0.01 mol) and 2,5-dichlorobenzaldehyde, Acros Organics (1.75 g, 0.01 mol) are combined with 8-hydroxyquinoline, Acros Organics (1.45 g, 0.01 mol) in 50 ml of absolute EtOH to give the desired Betti condensation product as a light-yellow solid (MP 14193-195° C.).

Preparation of AD4-13103:

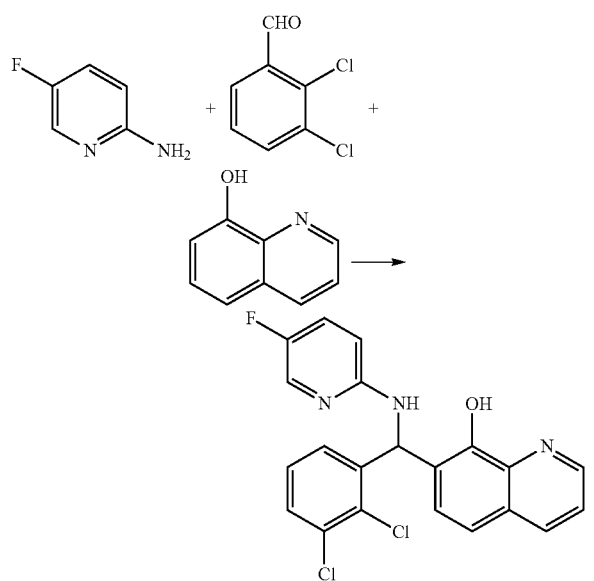

In a manner similar to that described in Example AD4-13021.

2-Amino-5-fluoropyridine, Matrix Scientific (1.12 g, 0.01 mol) and 2,3-dichlorobenzaldehyde, Acros Organics (1.75 g, 0.01 mol) are combined with 8-hydroxyquinoline, Acros Organics (1.45 g, 0.01 mol) in 50 ml of absolute EtOH to give the desired Betti condensation product as an off-white solid (MP 148-150° C.).

Preparation of AD4-13104:

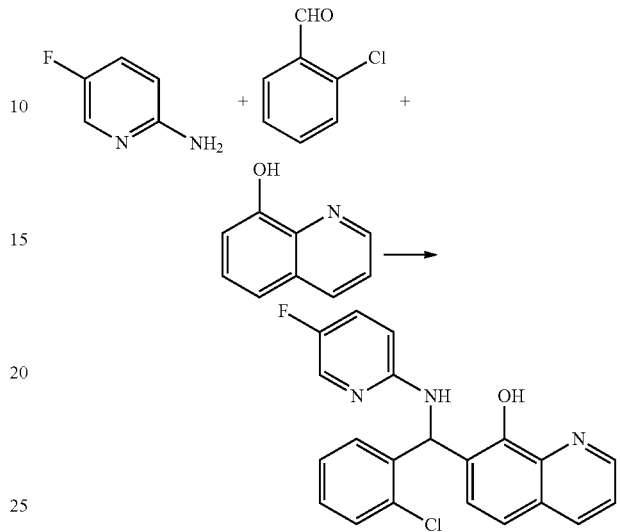

In a manner similar to that described in Example AD4-13021.

2-Amino-5-fluoropyridine, Matrix Scientific (1.12 g, 0.01 mol) and 2-chlorobenzaldehyde, Acros Organics (1.40 g, 0.01 mol) are combined with 8-hydroxyquinoline, Acros Organics (1.45 g, 0.01 mol) in 50 ml of absolute EtOH to give the desired Betti condensation product as a yellow solid (MP 144-145° C.).

Preparation of AD4-13105:

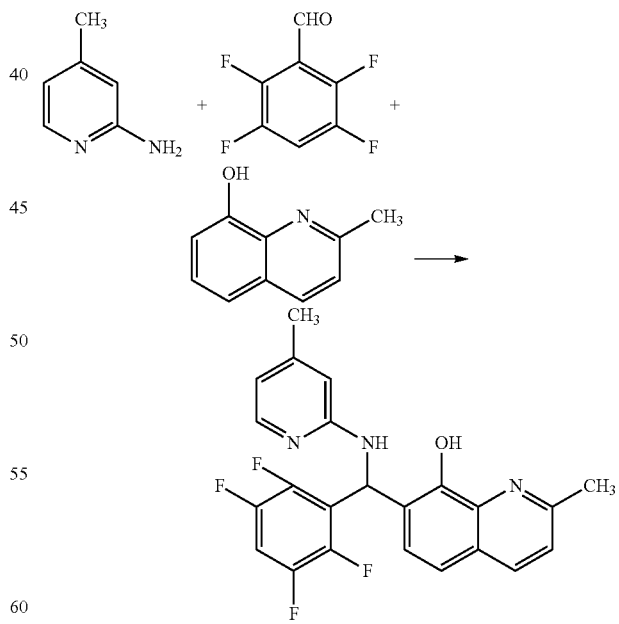

In a manner similar to that described in Example AD4-13021.

2-Amino-4-picoline, Acros Organics (1.08 g, 0.01 mol) and 2,3,5,6-tetrafluorobenzaldehyde, Matrix Scientific (1.78 g, 0.01 mol) are combined with 8-hydroxyquinaldine, Acros Organics (1.59 g, 0.01 mol) in 50 ml of absolute EtOH to give the desired Betti condensation product as a light-orange solid (MP 74-76° C.).

Preparation of AD4-13106:

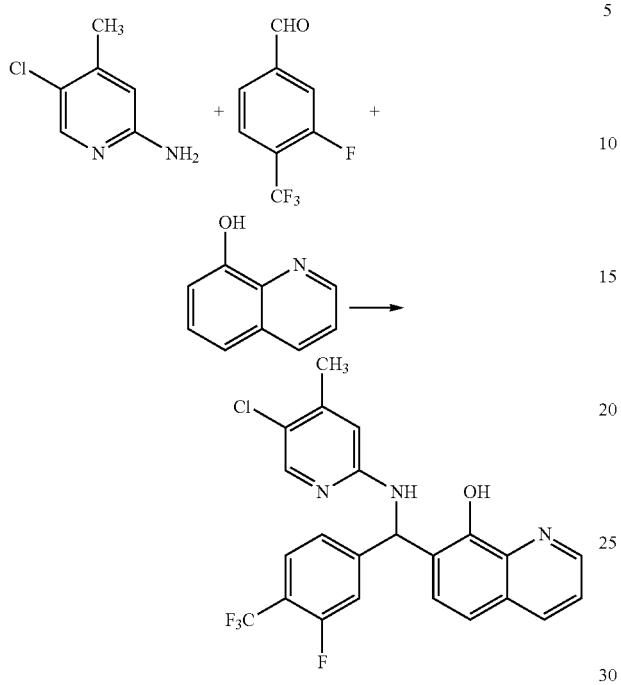

In a manner similar to that described in Example AD4-13021.

2-Amino-4-methyl-5-chloropyridine, Matrix Scientific (1.43 g, 0.01 mol) and 3-fluoro-4-trifluoromethylbenzaldehyde, Matrix Scientific (1.92 g, 0.01) are combined with 8-hydroxyquinoline, Acros Organics (1.45 g, 0.01 mol) in 50 ml of absolute EtOH to give the desired Betti condensation product as a white solid (MP 167-168° C.).

Preparation of AD4-13107:

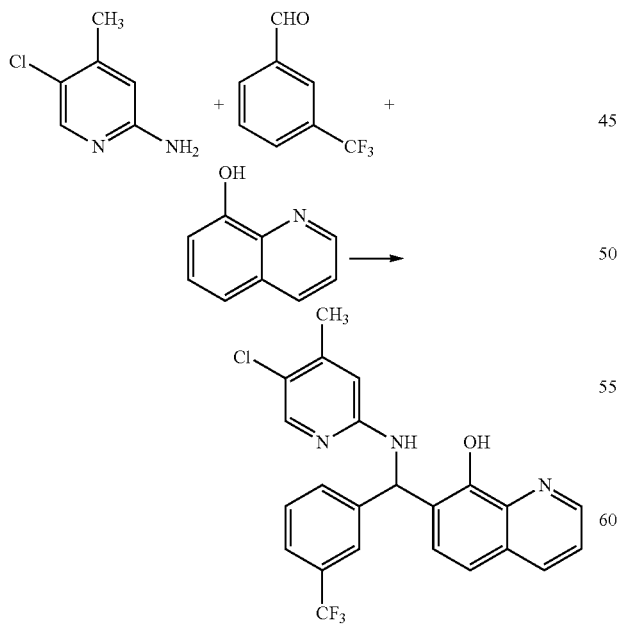

In a manner similar to that described in Example AD4-13021.

2-Amino-4-methyl-5-chloropyridine, Matrix Scientific (1.43 g, 0.01 mol) and 3-trifluoromethylbenzaldehyde, Acros Organics (1.74 g, 0.01 mol) are combined with 8-hydroxyquinoline, Acros Organics (1.45 g, 0.01 mol) in 50 ml of absolute EtOH to give the desired Betti condensation product as a white solid (MP 110-112° C.).

Preparation of AD4-13108:

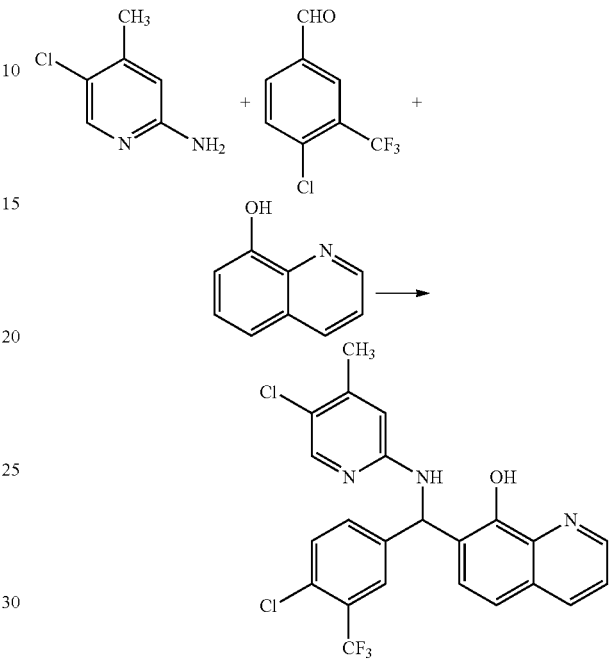

In a manner similar to that described in Example AD4-13021.

2-Amino-4-methyl-5-chloropyridine, Matrix Scientific (1.43 g, 0.01 mol) and 3-trifluoromethyl-4-chlorobenzaldehyde, Oakwood Products (2.08 g, 0.01 mol) are combined with 8-hydroxyquinoline, Acros Organics (1.45 g, 0.01 mol) in 50 ml of absolute EtOH to give the desired Betti condensation product as a white solid (MP 176-177° C.).

Preparation of AD4-13109:

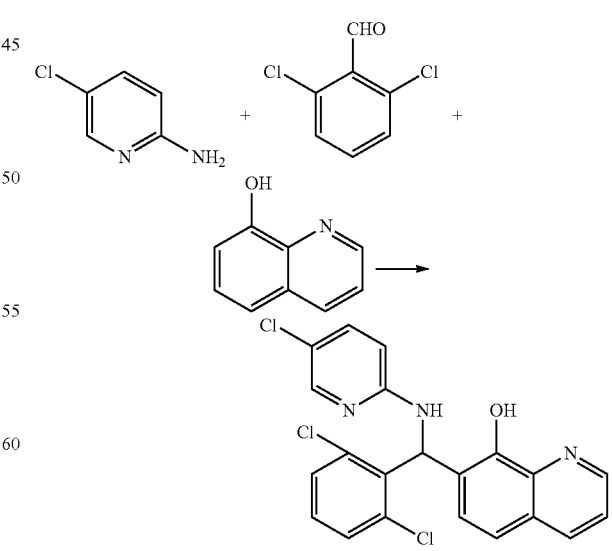

In a manner similar to that described in Example AD4-13021.

2-Amino-5-chloropyridine, Matrix Scientific (1.29 g, 0.01 mol) and 2,6-dichlorobenzaldehyde, Acros Organics (1.75 g, 0.01 mol) are combined with 8-hydroxyquinoline, Acros Organics (1.45 g, 0.01 mol) in 50 ml of absolute EtOH to give the desired Betti condensation product as an off-white solid (MP 202-204° C.).

Preparation of AD4-13110:

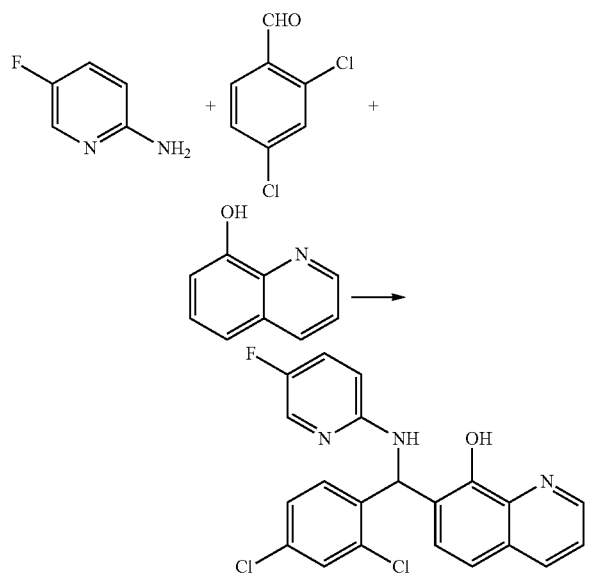

In a manner similar to that described in Example AD4-13022.

2-Amino-5-fluoropyridine, Matrix Scientific (1.12 g, 0.01 mol) and 2,4-dichlorobenzaldehyde, Acros Organics (1.75 g, 0.01 mol) are combined with 8-hydroxyquinoline, Acros Organics (1.45 g, 0.01 mol) in 50 ml of absolute EtOH to give the desired Betti condensation product as an off-white solid (MP 113-114° C.).

Preparation of AD4-13111:

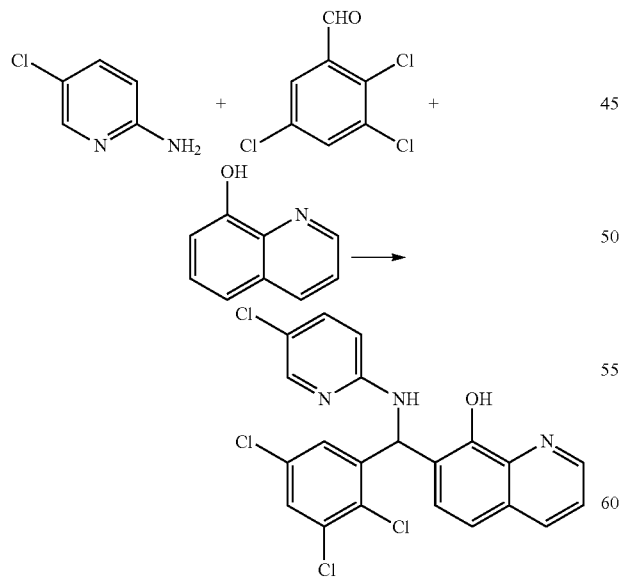

In a manner similar to that described in Example AD4-13021.

2-Amino-5-chloropyridine, Matrix Scientific (1.29 g, 0.01 mol) and 2,3,5-trichlorobenzaldehyde, Acros Organics (2.09 g, 0.01 mol) are combined with 8-hydroxyquinoline, Acros Organics (1.45 g, 0.01 mol) in 50 ml of absolute EtOH to give the desired Betti condensation product as an off-white solid (MP 163-165° C.).

Preparation of AD4-13112:

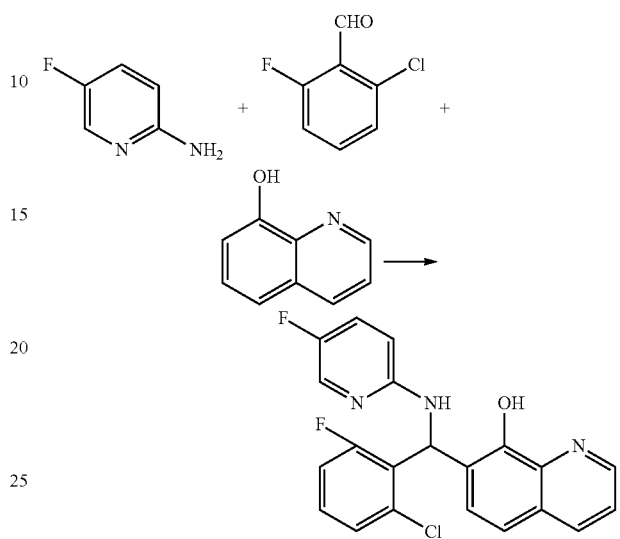

In a manner similar to that described in Example AD4-13022.

2-Amino-5-fluoropyridine, Matrix Scientific (1.12 g, 0.01 mol) and 2-chloro-6-fluorobenzaldehyde, Oakwood Products (1.58 g, 0.01 mol) are combined with 8-hydroxyquinoline, Acros Organics (1.45 g, 0.01 mol) in 50 ml of absolute EtOH to give the desired Betti condensation product as an off-white solid (MP 135-136° C.).

Preparation of AD4-13113:

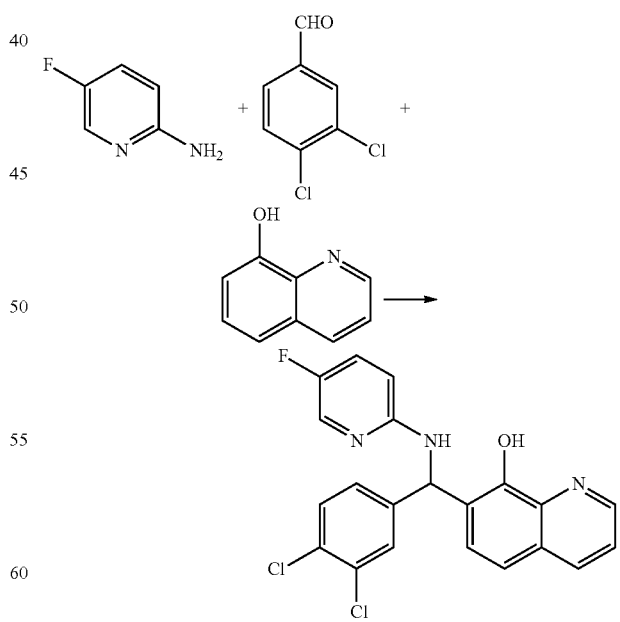

In a manner similar to that described in Example AD4-13022.

2-Amino-5-fluoropyridine, Matrix Scientific (1.12 g, 0.01 mol) and 3,4-dichlorobenzaldehyde, Acros Organics (1.75 g, 0.01 mol) are combined with 8-hydroxyquinoline, Acros Organics (1.45 g, 0.01 mol) in 50 ml of absolute EtOH to give the desired Betti condensation product as a light yellow solid (MP 114-116° C.).

Preparation of AD4-13114:

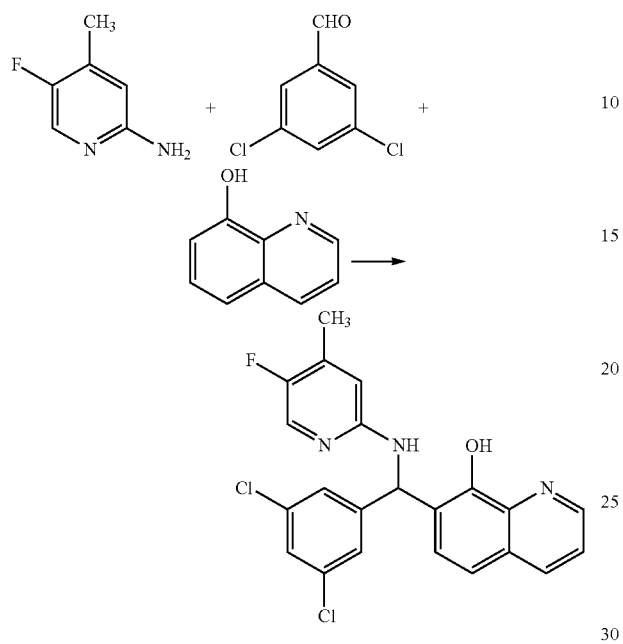

In a manner similar to that described in Example AD4-13021.

2-Amino-4-methyl-5-fluoropyridine, Matrix Scientific (1.26 g, 0.01 mol) and 3,5-dichlorobenzaldehyde, Acros Organics (1.75 g, 0.01 mol) are combined with 8-hydroxyquinoline, Acros Organics (1.45 g, 0.01 mol) in 50 ml of absolute EtOH to give the desired Betti condensation product as a light yellow solid (MP 132-133° C.).

Preparation of AD4-13115:

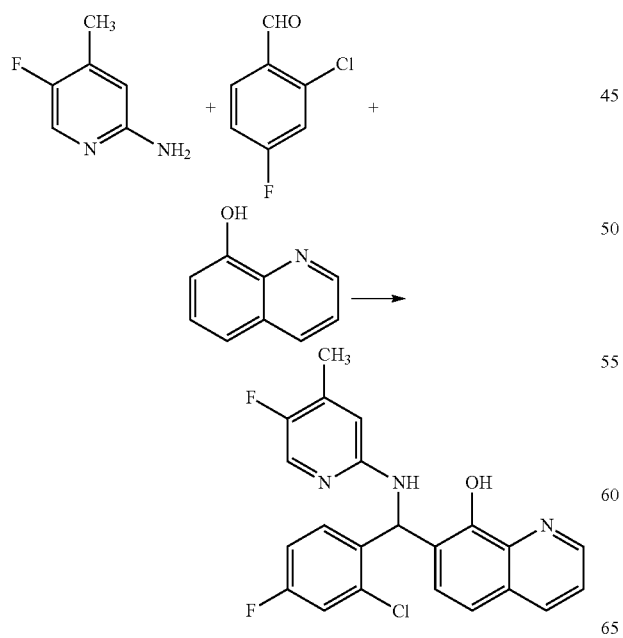

In a manner similar to that described in Example AD4-13021.

2-Amino-4-methyl-5-fluoropyridine, Matrix Scientific (1.26 g, 0.01 mol) and 2-chloro-4-fluorobenzaldehyde, Oakwood Products (1.59 g, 0.01 mol) are combined with 8-hydroxyquinoline, Acros Organics (1.45 g, 0.01 mol) in 50 ml of absolute EtOH to give the desired Betti condensation product as an off-white solid (MP 163-165° C.).

Preparation of AD4-13116:

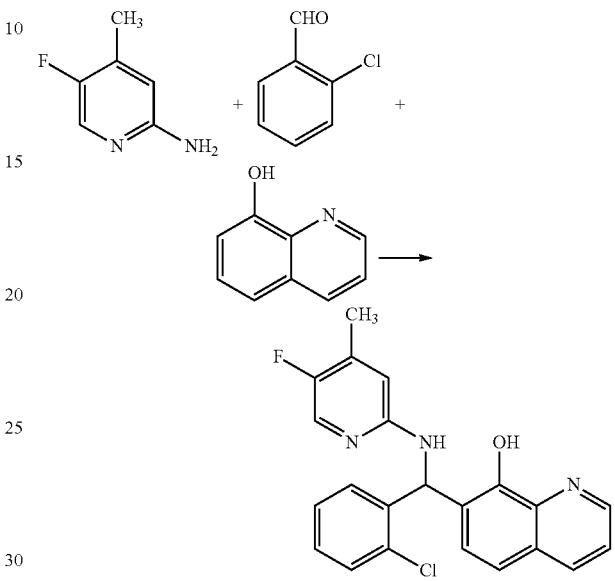

In a manner similar to that described in Example AD4-13021.

2-Amino-4-methyl-5-fluoropyridine, Matrix Scientific (1.26 g, 0.01 mol) and 2-chlorobenzaldehyde, Acros Organics (1.41 g, 0.01 mol) are combined with 8-hydroxyquinoline, Acros Organics (1.45 g, 0.01 mol) in 50 ml of absolute EtOH to give the desired Betti condensation product as an off-white solid (MP 166-168° C.).

Preparation of AD4-13117:

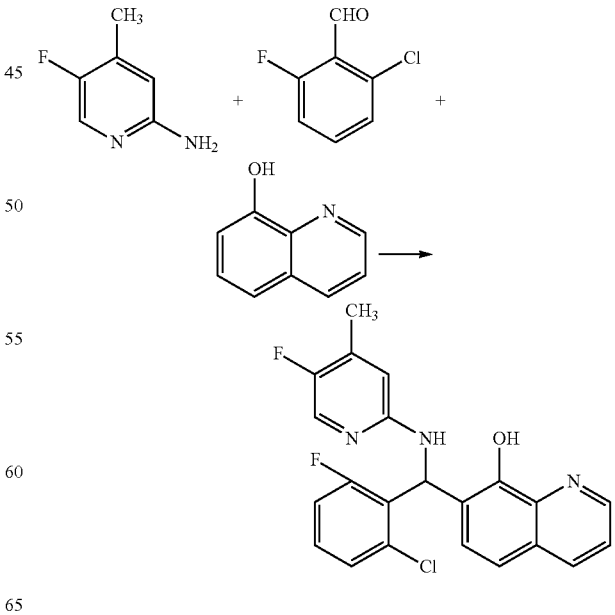

In a manner similar to that described in Example AD4-13021.

2-Amino-4-methyl-5-fluoropyridine, Matrix Scientific (1.26 g, 0.01 mol) and 2-chloro-6-fluorobenzaldehyde, Acros Organics (1.59 g, 0.01 mol) are combined with 8-hydroxyquinoline, Acros Organics (1.45 g, 0.01 mol) in 50 ml of absolute EtOH to give the desired Betti condensation product as a light-yellow solid (MP 166-168° C.).

Preparation of AD4-13118:

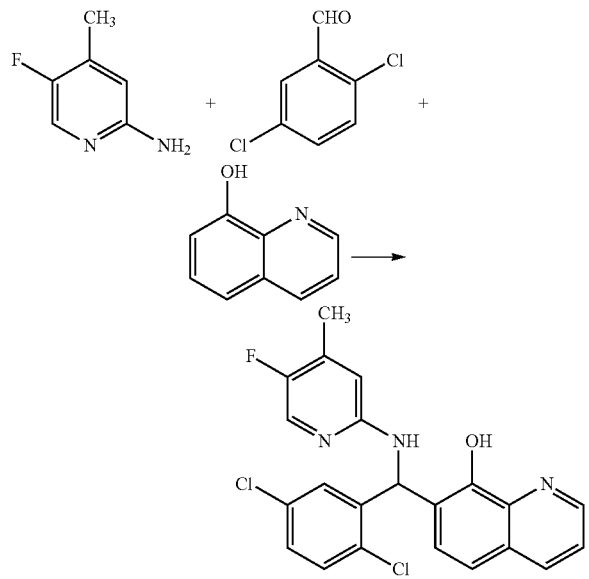

In a manner similar to that described in Example AD4-13021.

2-Amino-4-methyl-5-fluoropyridine, Matrix Scientific (1.26 g, 0.01 mol) and 2,5-dichlorobenzaldehyde, Acros Organics (1.75 g, 0.01 mol) are combined with 8-hydroxyquinoline, Acros Organics (1.45 g, 0.01 mol) in 50 ml of absolute EtOH to give the desired Betti condensation product as a light-yellow solid (MP 209-216° C.).

Preparation of AD4-13119:

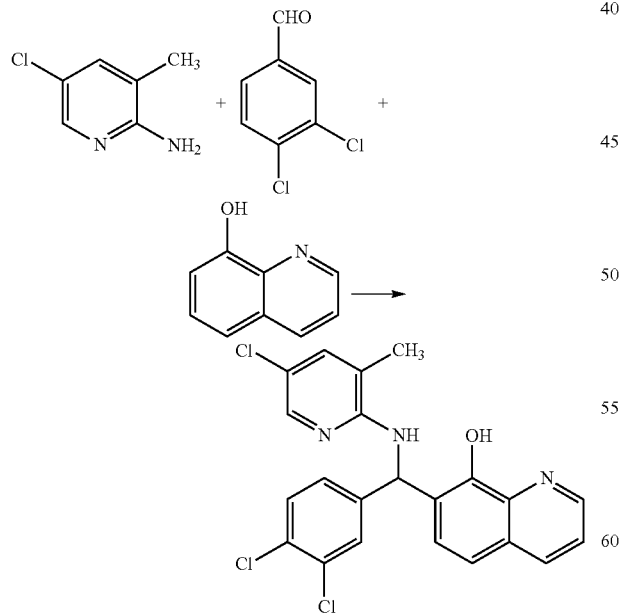

In a manner similar to that described in Example AD4-13021.

2-Amino-3-methyl-5-chloropyridine (BBM-001-071; 1.43 g, 0.01 mol) and 3,4-dichlorobenzaldehyde, Acros Organics (1.75 g, 0.01 mol) are combined with 8-hydroxyquinoline, Acros Organics (1.45 g, 0.01 mol) in 50 ml of absolute EtOH to give the desired Betti condensation product as a white solid (MP 140-141° C.).

Preparation of AD4-13120:

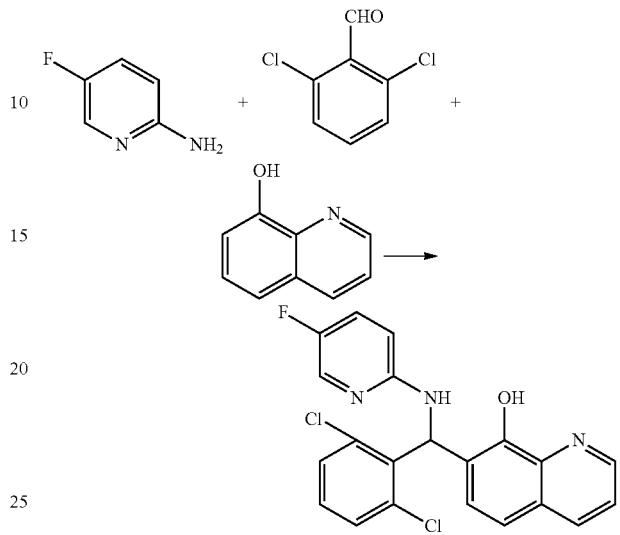

In a manner similar to that described in Example AD4-13022.

2-Amino-5-fluoropyridine, Matrix Scientific (1.12 g, 0.01 mol) and 2,6-dichlorobenzaldehyde, Acros Organics (1.75 g, 0.01 mol) are combined with 8-hydroxyquinoline, Acros Organics (1.45 g, 0.01 mol) in 50 ml of absolute EtOH to give the desired Betti condensation product as an off-white solid (MP 160-161° C.).

Preparation of AD4-13121:

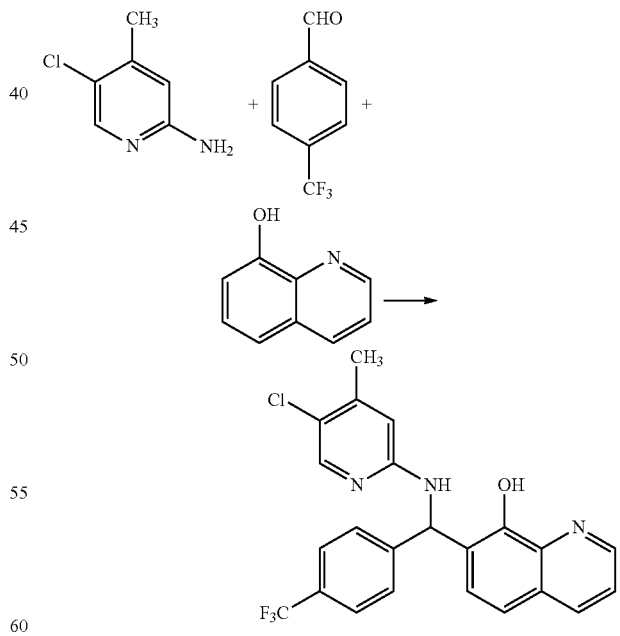

In a manner similar to that described in Example AD4-13021.

2-Amino-4-methyl-5-chloropyridine, Matrix Scientific (1.43 g, 0.01 mol) and 4-trifluoromethylbenzaldehyde, Acros Organics (1.74 g, 0.01 mol) are combined with 8-hydroxyquinoline, Acros Organics (1.45 g, 0.01 mol) in 50 ml of absolute EtOH to give the desired Betti condensation product as an off-white solid (MP 155-158° C.).

Preparation of AD4-13122:

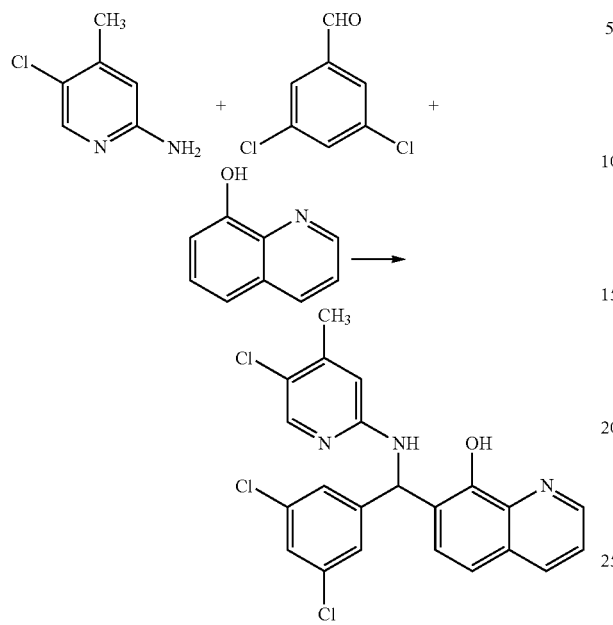

In a manner similar to that described in Example AD4-13021.

2-Amino-4-methyl-5-chloropyridine, Matrix Scientific (1.43 g, 0.01 mol) and 3,5-dichlorobenzaldehyde, Matrix Scientific (1.75 g, 0.01 mol) are combined with 8-hydroxyquinoline, Acros Organics (1.45 g, 0.01 mol) in 50 ml of absolute EtOH to give the desired Betti condensation product as an light-yellow solid (MP 192-194° C.).

Preparation of AD4-13123:

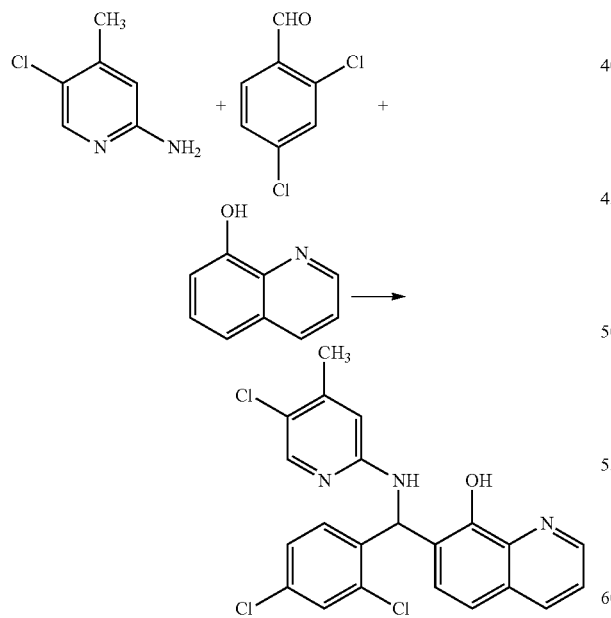

In a manner similar to that described in Example AD4-13021.

2-Amino-4-methyl-5-chloropyridine, Matrix Scientific (1.43 g, 0.01 mol) and 2,4-dichlorobenzaldehyde, Matrix Scientific (1.75 g, 0.01 mol) are combined with 8-hydroxyquinoline, Acros Organics (1.45 g, 0.01 mol) in 50 ml of absolute EtOH to give the desired Betti condensation product as a white solid (MP 147-150° C.).

Preparation of AD4-13124:

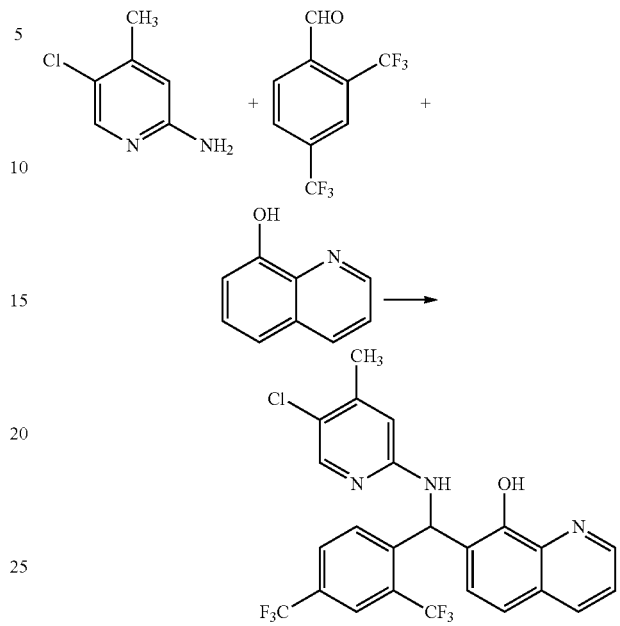

In a manner similar to that described in Example AD4-13021.

2-Amino-4-methyl-5-chloropyridine, Matrix Scientific (1.43 g, 0.01 mol) and 2,4-bistrifluoromethylbenzaldehyde, Oakwood Products (2.42 g, 0.01 mol) are combined with 8-hydroxyquinoline, Acros Organics (1.45 g, 0.01 mol) in 50 ml of absolute EtOH to give the desired Betti condensation product as an white solid (MP 122-127° C.).

Preparation of AD4-13125:

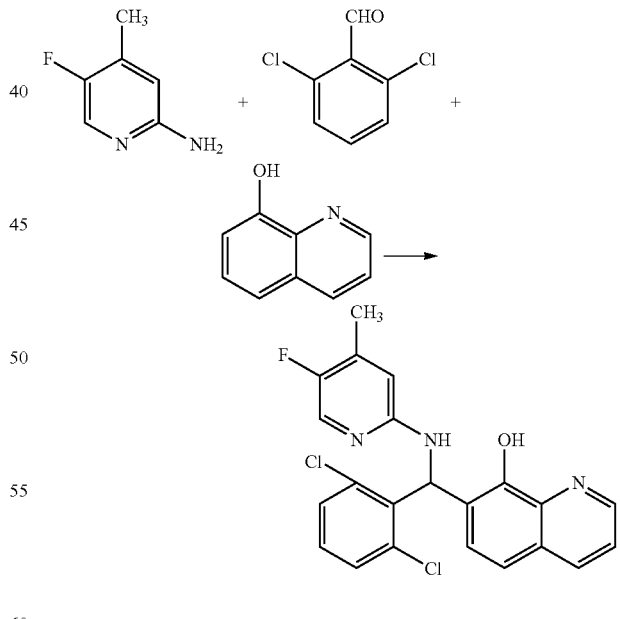

In a manner similar to that described in Example AD4-13021.

2-Amino-4-methyl-5-fluoropyridine, Matrix Scientific (1.26 g, 0.01 mol) and 2,6-dichlorobenzaldehyde, Matrix Scientific (1.75 g, 0.01 mol) are combined with 8-hydroxyquinoline, Acros Organics (1.45 g, 0.01 mol) in 50 ml of absolute EtOH to give the desired Betti condensation product as a light-yellow solid (MP 174-175° C.).

Preparation of AD4-13126:

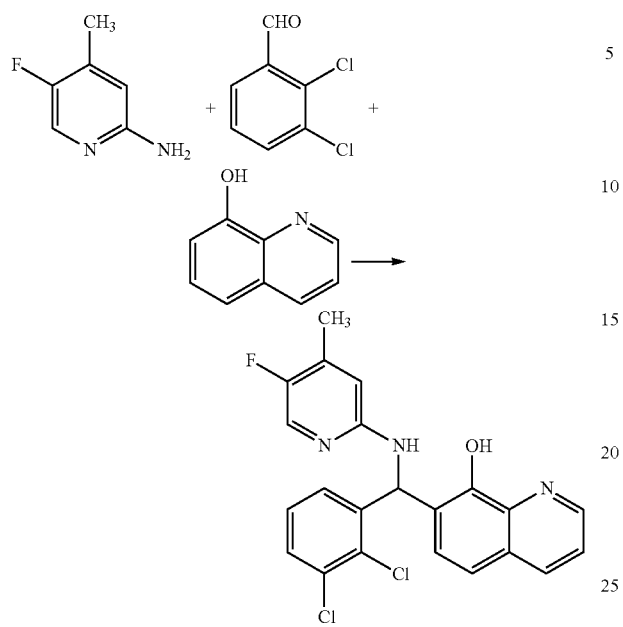

In a manner similar to that described in Example AD4-13021.

2-Amino-4-methyl-5-fluoropyridine, Matrix Scientific (1.26 g, 0.01 mol) and 2,3-dichlorobenzaldehyde, Matrix Scientific (1.75 g, 0.01 mol) are combined with 8-hydroxyquinoline, Acros Organics (1.45 g, 0.01 mol) in 50 ml of absolute EtOH to give the desired Betti condensation product as a light-yellow solid (MP 164-165° C.).

Preparation of AD4-13127:

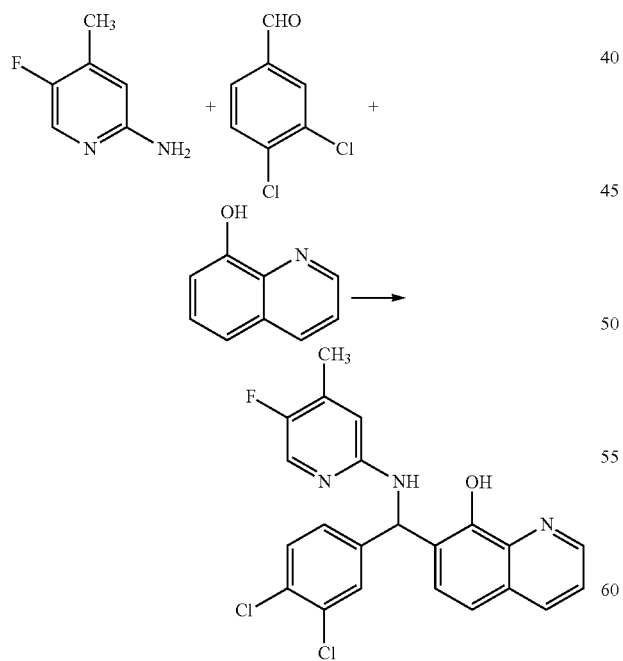

In a manner similar to that described in Example AD4-13021.

2-Amino-4-methyl-5-fluoropyridine, Matrix Scientific (1.26 g, 0.01 mol) and 3,4-dichlorobenzaldehyde, Matrix Scientific (1.75 g, 0.01 mol) are combined with 8-hydroxyquinoline, Acros Organics (1.45 g, 0.01 mol) in 50 ml of absolute EtOH to give the desired Betti condensation product as a white solid (MP 141-142° C.).

Preparation of AD4-13128:

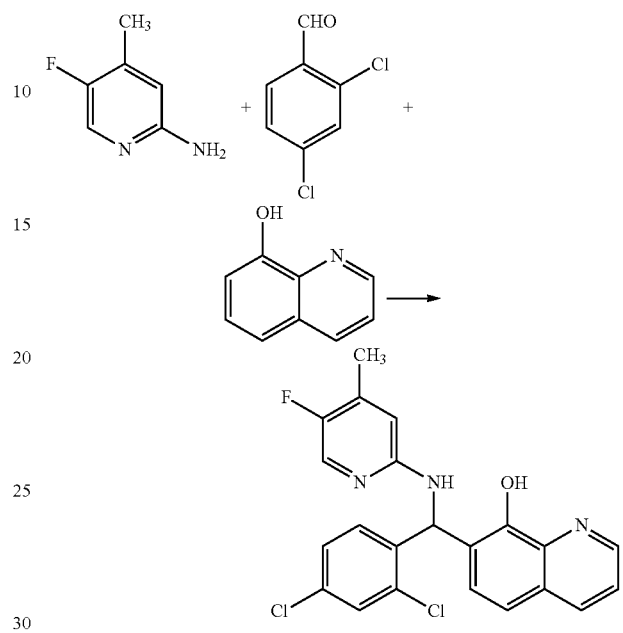

In a manner similar to that described in Example AD4-13021.

2-Amino-4-methyl-5-fluoropyridine, Matrix Scientific (1.26 g, 0.01 mol) and 2,4-dichlorobenzaldehyde, Matrix Scientific (1.75 g, 0.01 mol) are combined with 8-hydroxyquinoline, Acros Organics (1.45 g, 0.01 mol) in 50 ml of absolute EtOH to give the desired Betti condensation product as an off-white solid (MP 87-94° C.).

Preparation of AD4-13129:

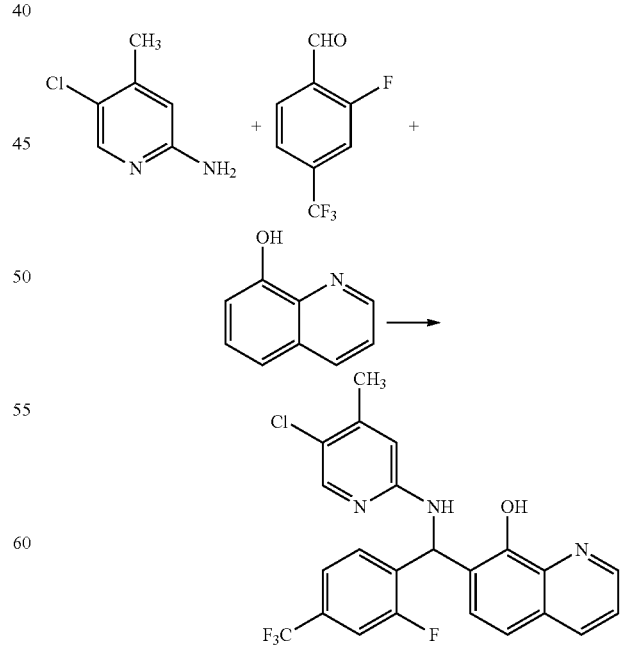

In a manner similar to that described in Example AD4-13021.

2-Amino-4-methyl-5-chloropyridine, Matrix Scientific (1.43 g, 0.01 mol) and 2-fluoro-4-trifluoromethylbenzaldehyde, Oakwood Products (1.92 g, 0.01) are combined with 8-hydroxyquinoline, Acros Organics (1.45 g, 0.01 mol) in 50 ml of absolute EtOH to give the desired Betti condensation product as an light-green solid (MP 161-162° C.).

Preparation of AD4-13130:

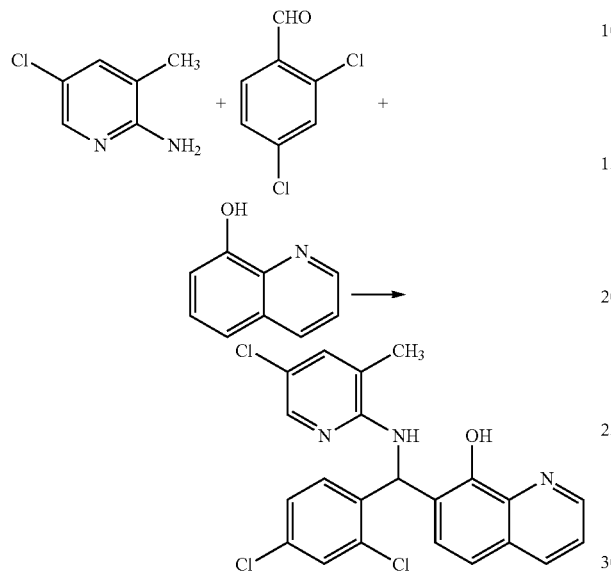

In a manner similar to that described in Example AD4-13021.

2-Amino-3-methyl-5-chloropyridine (BBM-001-071; 1.43 g, 0.01 mol) and 2,4-dichlorobenzaldehyde, Acros Organics (1.75 g, 0.01 mol) are combined with 8-hydroxyquinoline, Acros Organics (1.45 g, 0.01 mol) in 50 ml of absolute EtOH to give the desired Betti condensation product as an light-green solid (MP 158-160° C.).

Preparation of AD4-13131:

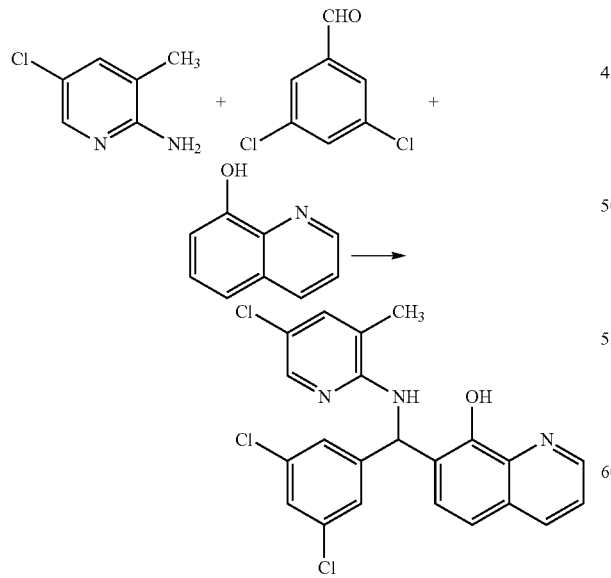

In a manner similar to that described in Example AD4-13021.

2-Amino-3-methyl-5-chloropyridine (BBM-001-071; 1.43 g, 0.01 mol) and 3,5-dichlorobenzaldehyde, Acros Organics (1.75 g, 0.01 mol) are combined with 8-hydroxyquinoline, Acros Organics (1.45 g, 0.01 mol) in 50 ml of absolute EtOH to give the desired Betti condensation product as a light-green solid (MP 146-148° C.).

Preparation of AD4-13132:

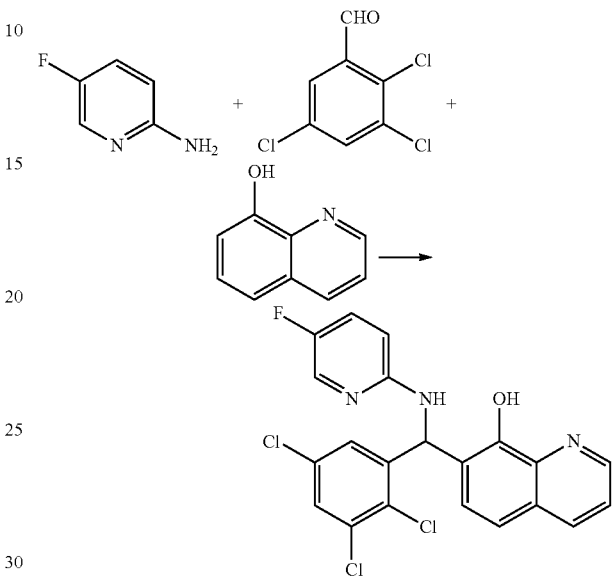

In a manner similar to that described in Example AD4-13022.

2-Amino-5-fluoropyridine, Matrix Scientific (1.12 g, 0.01 mol) and 2,3,5-trichlorobenzaldehyde, Acros Organics (2.10 g, 0.01 mol) are combined with 8-hydroxyquinoline, Acros Organics (1.45 g, 0.01 mol) in 50 ml of absolute EtOH to give the desired Betti condensation product as an off-white solid (MP 96-104° C.).

Preparation of AD4-13133:

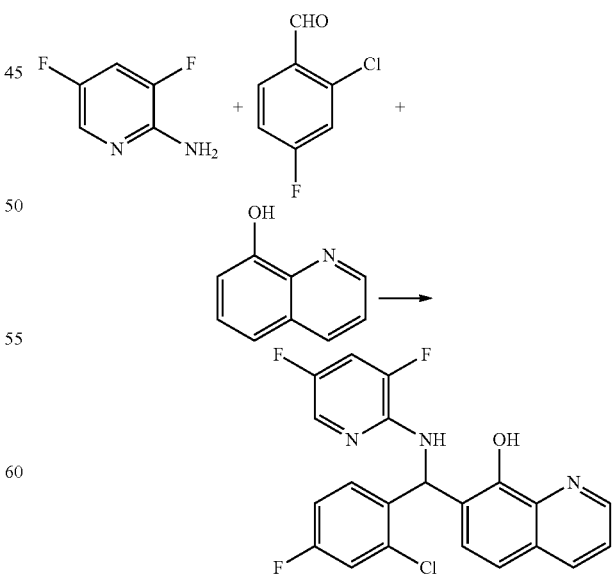

In a manner similar to that described in Example AD4-13022.

2-Amino-3,5-difluoropyridine, Matrix Scientific (1.30 g, 0.01 mol) and 2-chloro-6-fluorobenzaldehyde, Acros Organics (1.59 g, 0.01 mol) are combined with 8-hydroxyquinoline, Acros Organics (1.45 g, 0.01 mol) in 50 ml of absolute EtOH to give the desired Betti condensation product as an off-white solid (MP 159-161° C.).

Preparation of AD4-13134:

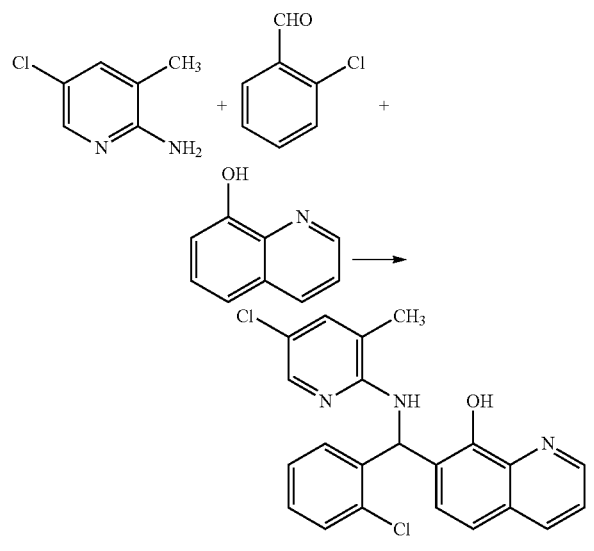

In a manner similar to that described in Example AD4-13021.

2-Amino-3-methyl-5-chloropyridine (BBM-001-071; 1.43 g, 0.01 mol) and 2-chlorobenzaldehyde, Acros Organics (1.41 g, 0.01 mol) are combined with 8-hydroxyquinoline, Acros Organics (1.45 g, 0.01 mol) in 50 ml of absolute EtOH to give the desired Betti condensation product as a white solid (MP 138-139° C.).

Preparation of AD4-13135:

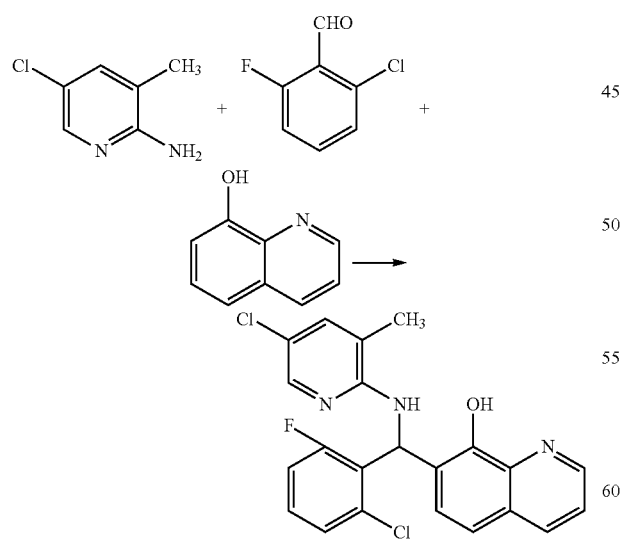

In a manner similar to that described in Example AD4-13021.

2-Amino-3-methyl-5-chloropyridine (BBM-001-071; 1.43 g, 0.01 mol) and 2-chloro-6-fluorobenzaldehyde, Acros Organics (1.59 g, 0.01 mol) are combined with 8-hydroxyquinoline, Acros Organics (1.45 g, 0.01 mol) in 50 ml of absolute EtOH to give the desired Betti condensation product as a light-yellow solid (MP 181-182° C.).

Preparation of AD4-13136:

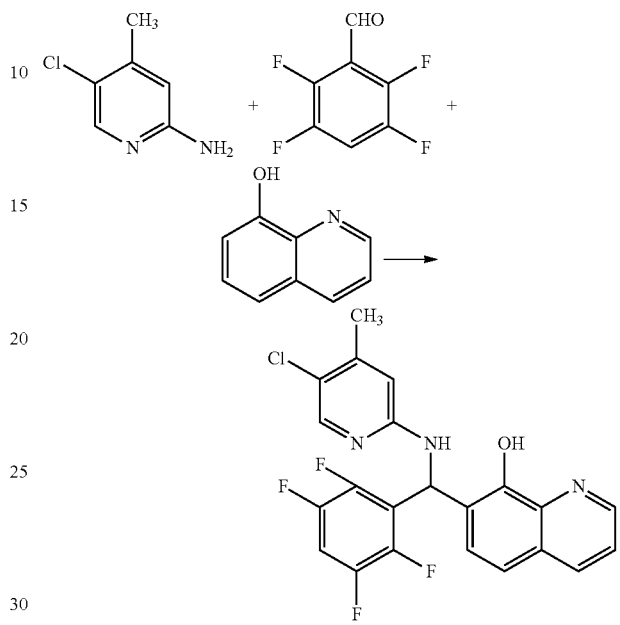

In a manner similar to that described in Example AD4-13021.

2-Amino-4-methyl-5-chloropyridine, Matrix Scientific (1.43 g, 0.01 mol) and 2,3,5,6-tetrafluorobenzaldehyde, Matrix Scientific (1.78 g, 0.01 mol) are combined with 8-hydroxyquinoline, Acros Organics (1.45 g, 0.01 mol) in 50 ml of absolute EtOH to give the desired Betti condensation product as a white solid (MP 180-182° C.).

Preparation of AD4-13137:

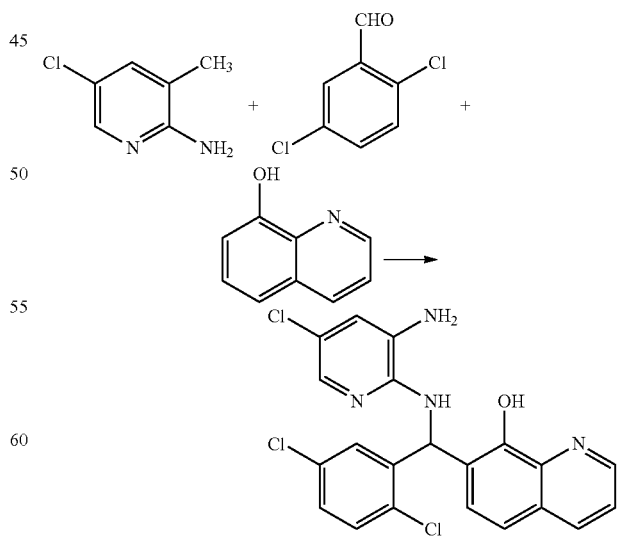

In a manner similar to that described in Example AD4-13021.

2-Amino-3-methyl-5-chloropyridine (BBM-001-071; 1.43 g, 0.01 mol) and 2,5-dichlorobenzaldehyde, Acros Organics (0.58 g, 0.0033 mol) are combined with 8-hydroxyquinoline, Acros Organics (1.45 g, 0.01 mol) in 50 ml of absolute EtOH to give the desired Betti condensation product as an off-white solid (MP 148-150° C.).

Preparation of AD4-13138:

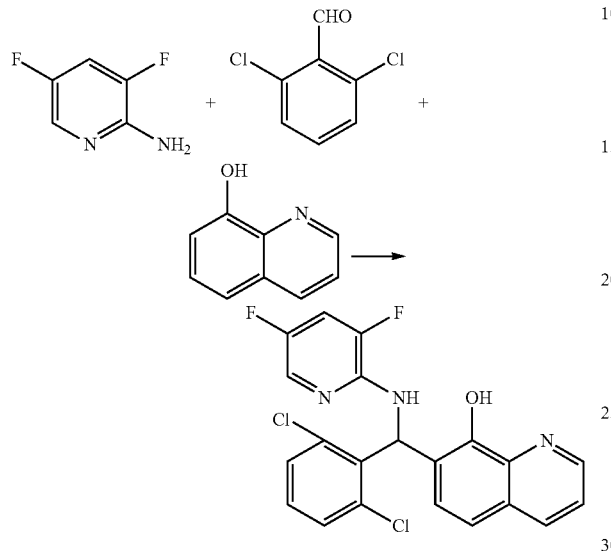

In a manner similar to that described in Example AD4-13022.

2-Amino-3,5-difluoropyridine, Matrix Scientific (1.30 g, 0.01 mol) and 2,6-dichlorobenzaldehyde, Acros Organics (1.75 g, 0.01 mol) are combined with 8-hydroxyquinoline, Acros Organics (1.45 g, 0.01 mol) in 50 ml of absolute EtOH to give the desired Betti condensation product as an off-white solid (MP 174-176° C.).

Preparation of AD4-13139:

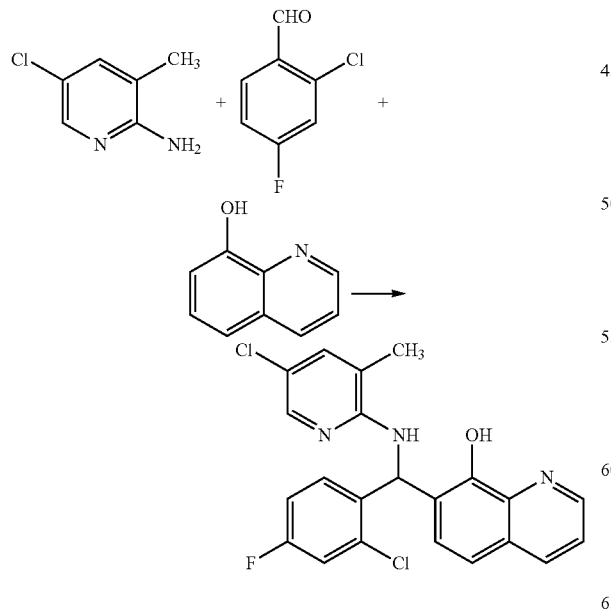

In a manner similar to that described in Example AD4-13021.

2-Amino-3-methyl-5-chloropyridine (BBM-001-071; 1.43 g, 0.01 mol) and 2-chloro-4-fluorobenzaldehyde, Oakwood Products (1.59 g, 0.01 mol) are combined with 8-hydroxyquinoline, Acros Organics (1.45 g, 0.01 mol) in 50 ml of absolute EtOH to give the desired Betti condensation product as a light-yellow solid (MP 162-163° C.).

Preparation of AD4-13140:

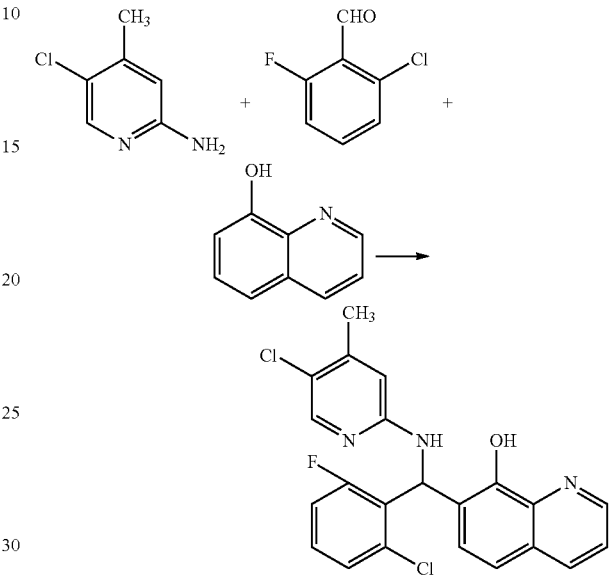

In a manner similar to that described in Example AD4-13021.

2-Amino-4-methyl-5-chloropyridine, Matrix Scientific (1.43 g, 0.01 mol) and 2-chloro-6-fluorobenzaldehyde, Acros Organics (1.59 g, 0.01 mol) are combined with 8-hydroxyquinoline, Acros Organics (1.45 g, 0.01 mol) in 50 ml of absolute EtOH to give the desired Betti condensation product as a light-yellow solid (MP 183-186° C.).

Preparation of AD4-13141:

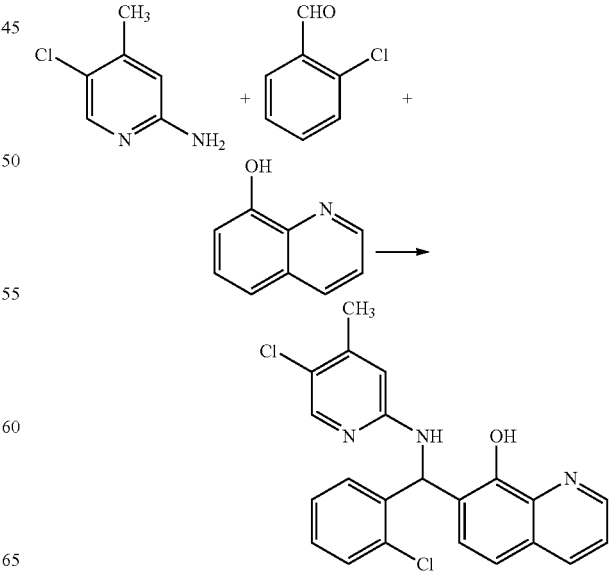

In a manner similar to that described in Example AD4-13021.

2-Amino-4-methyl-5-chloropyridine, Matrix Scientific (1.43 g, 0.01 mol) and 2-chlorobenzaldehyde, Acros Organics (1.41 g, 0.01 mol) are combined with 8-hydroxyquinoline, Acros Organics (1.45 g, 0.01 mol) in 50 ml of absolute EtOH to give the desired Betti condensation product as an off-white solid (MP 169-173° C.).

Preparation of AD4-13142:

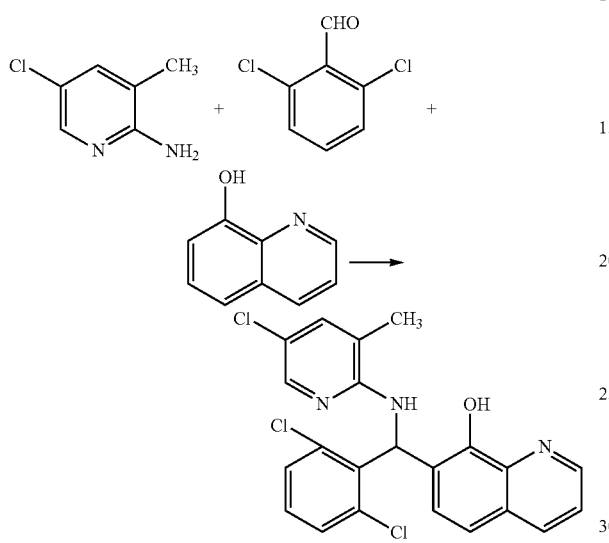

In a manner similar to that described in Example AD4-13021.

2-Amino-3-methyl-5-chloropyridine, BBM-001-071 (1.43 g, 0.01 mol) and 2,6-dichlorobenzaldehyde, Acros Organics (1.75 g, 0.01 mol) are combined with 8-hydroxyquinoline, Acros Organics (1.45 g, 0.01 mol) in 50 ml of absolute EtOH to give the desired Betti condensation product as an off-white solid (MP 221-223° C.).

Preparation of AD4-13143:

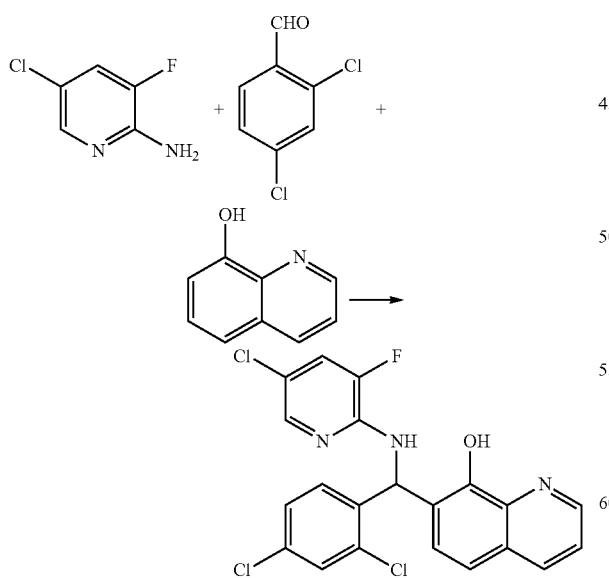

In a manner similar to that described in Example AD4-130212

2-Amino-3-fluoro-5-chloropyridine, Matrix Scientific (1.47 g, 0.01 mol) and 2,4-dichlorobenzaldehyde, Acros Organics (1.75 g, 0.01 mol) are combined with 8-hydroxyquinoline, Acros Organics (1.45 g, 0.01 mol) in 50 ml of absolute EtOH to give the desired Betti condensation product as a white solid (MP 127-128° C.).

Preparation of AD4-13144:

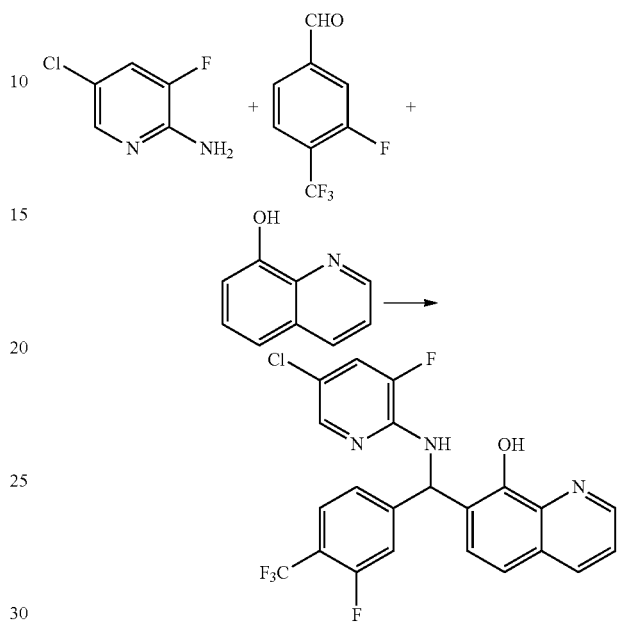

In a manner similar to that described in Example AD4-13021.

2-Amino-3-fluoro-5-chloropyridine, Matrix Scientific (1.47 g, 0.01 mol) and 3-fluoro-4-trifluoromethylbenzaldehyde, Matrix Scientific (1.92 g, 0.01) are combined with 8-hydroxyquinoline, Acros Organics (1.45 g, 0.01 mol) in 50 ml of absolute EtOH to give the desired Betti condensation product as a white solid (MP 101-108° C.).

Preparation of AD4-13145:

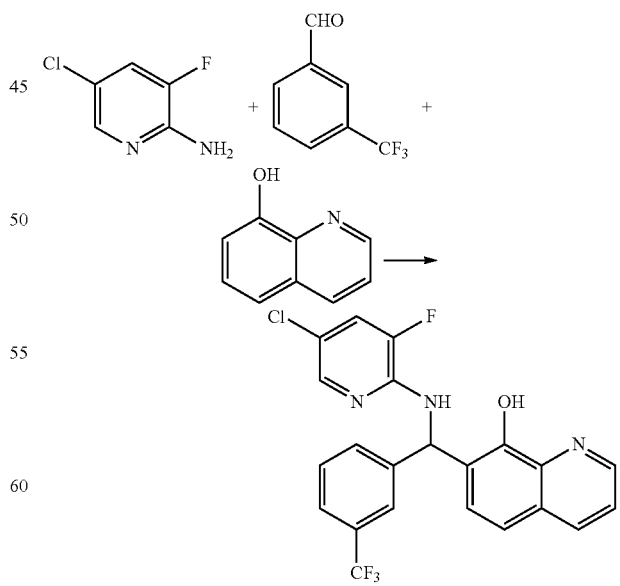

In a manner similar to that described in Example AD4-13021.

2-Amino-3-fluoro-5-chloropyridine, Matrix Scientific (1.47 g, 0.01 mol) and 3-trifluoromethylbenzaldehyde, Acros Organics (1.74 g, 0.01 mol) are combined with 8-hydroxyquinoline, Acros Organics (1.45 g, 0.01 mol) in 50 ml of absolute EtOH to give the desired Betti condensation product as a white solid (MP 93-96° C.).

Preparation of AD4-13146:

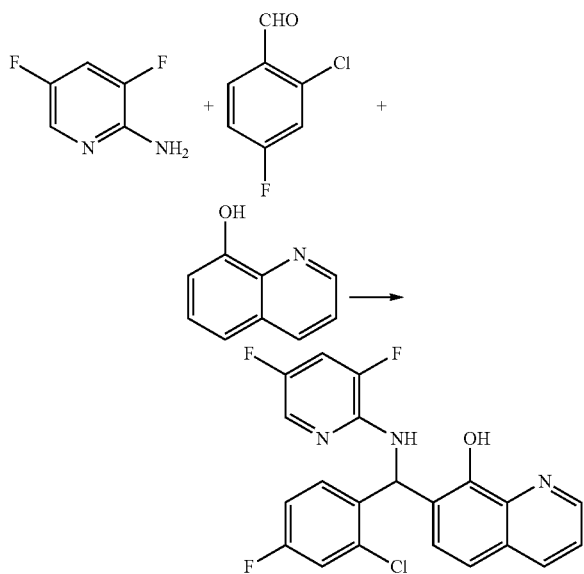

In a manner similar to that described in Example AD4-13021.

2-Amino-3,5-difluoropyridine, Matrix Scientific (1.30 g, 0.01 mol) and 2-chloro-4-fluorobenzaldehyde, Oakwood Products (1.59 g, 0.01 mol) are combined with 8-hydroxyquinoline, Acros Organics (1.45 g, 0.01 mol) in 50 ml of absolute EtOH to give the desired Betti condensation product as a light-green solid (MP 120-124° C.).

Preparation of AD4-13147:

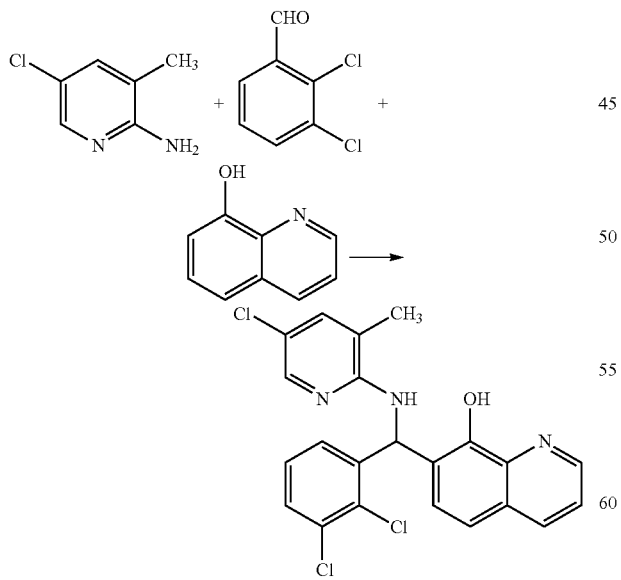

In a manner similar to that described in Example AD4-13021.

2-Amino-3-methyl-5-chloropyridine (BBM-001-071; 1.43 g, 0.01 mol) and 2,3-dichlorobenzaldehyde, Acros Organics (1.75 g, 0.01 mol) are combined with 8-hydroxyquinoline, Acros Organics (1.45 g, 0.01 mol) in 50 ml of absolute EtOH to give the desired Betti condensation product as a light-green solid (MP 88-93° C.).

Preparation of AD4-13148:

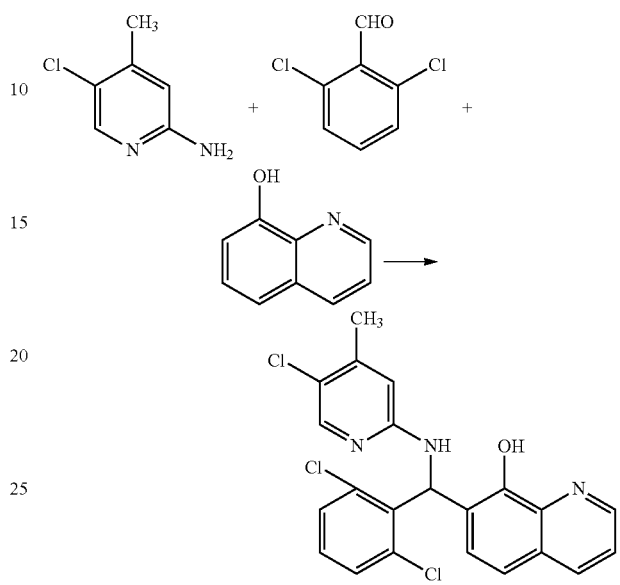

In a manner similar to that described in Example AD4-13021.

2-Amino-4-methyl-5-chloropyridine, Matrix Scientific (1.43 g, 0.01 mol) and 2,6-dichlorobenzaldehyde, Acros Organics (1.75 g, 0.01 mol) are combined with 8-hydroxyquinoline, Acros Organics (1.45 g, 0.01 mol) in 50 ml of absolute EtOH to give the desired Betti condensation product as a light-yellow solid (MP 191-193° C.).

Preparation of AD4-13149:

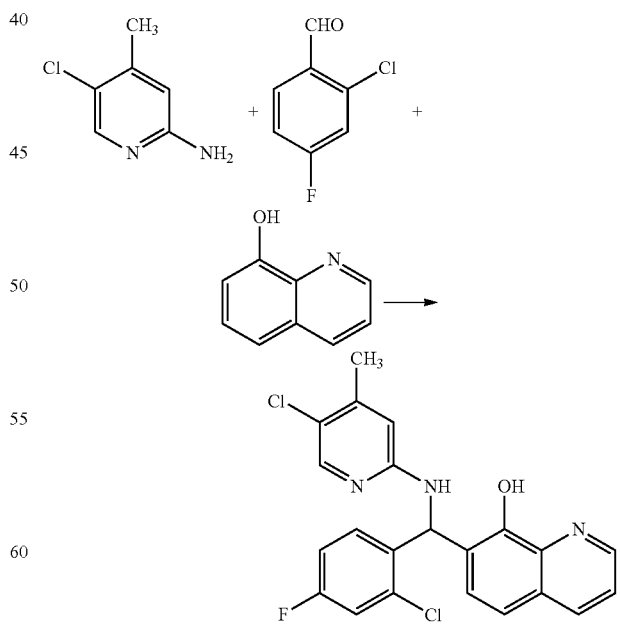

In a manner similar to that described in Example AD4-13022.

2-Amino-4-methyl-5-chloropyridine, Matrix Scientific (1.43 g, 0.01 mol) and 2-chloro-4-fluorobenzaldehyde, Oakwood Products (1.59 g, 0.01 mol) are combined with 8-hydroxyquinoline, Acros Organics (1.45 g, 0.01 mol) in 50 ml of absolute EtOH to give the desired Betti condensation product as an off-white solid (MP 225-227° C.).

Preparation of AD4-13150:

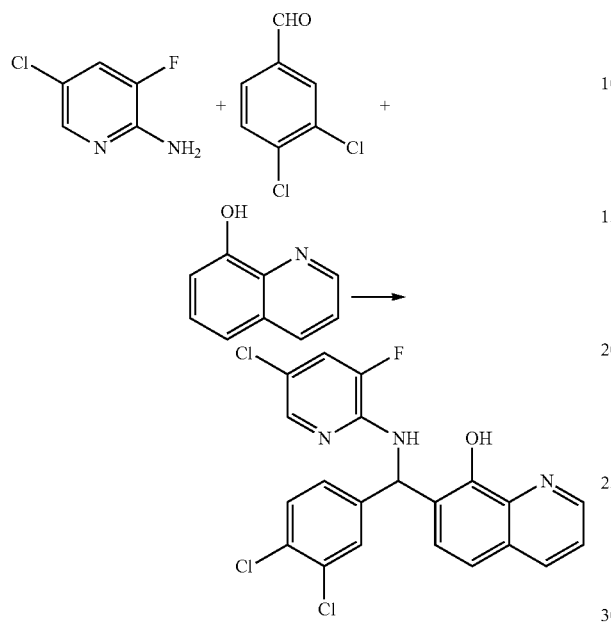

In a manner similar to that described in Example AD4-13021.

2-Amino-3-fluoro-5-chloropyridine, Matrix Scientific (1.47 g, 0.01 mol) and 3,4-dichlorobenzaldehyde, Acros Organics (0.88 g, 0.005 mol) are combined with 8-hydroxyquinoline, Acros Organics (1.45 g, 0.01 mol) in 50 ml of absolute EtOH to give the desired Betti condensation product as a white solid (MP 90-95° C.).

Preparation of AD4-13151:

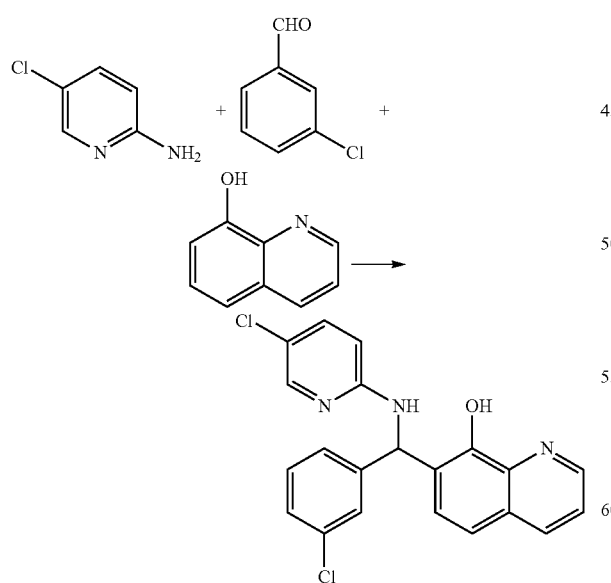

In a manner similar to that described in Example AD4-13021.

2-Amino-5-chloropyridine, Matrix Scientific (1.29 g, 0.01 mol) and 3-chlorobenzaldehyde, Acros Organics (1.41 g, 0.01 mol) are combined with 8-hydroxyquinoline, Acros Organics (1.45 g, 0.01 mol) in 50 ml of absolute EtOH to give the desired Betti condensation product a white solid (MP 148-149° C.).

Preparation of AD4-13152:

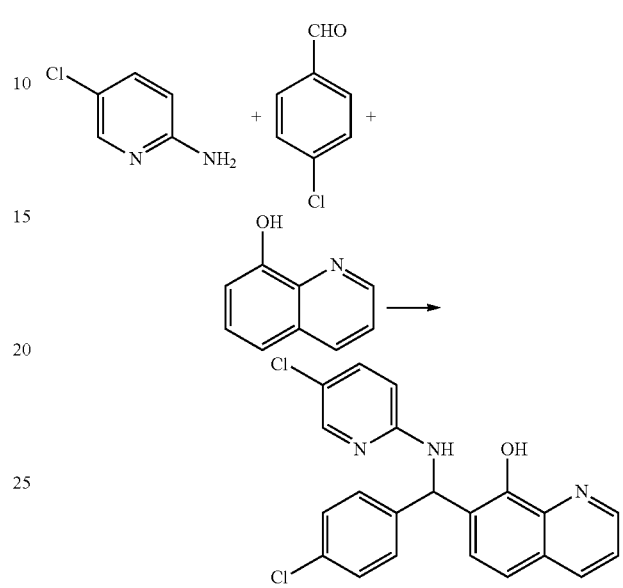

In a manner similar to that described in Example AD4-13022.

2-Amino-5-chloropyridine, Matrix Scientific (1.29 g, 0.01 mol) and 4-chlorobenzaldehyde, Acros Organics (1.41 g, 0.01 mol) are combined with 8-hydroxyquinoline, Acros Organics (1.45 g, 0.01 mol) in 50 ml of absolute EtOH to give the desired Betti condensation product a white solid (MP 144-148° C.).

Preparation of AD4-13153:

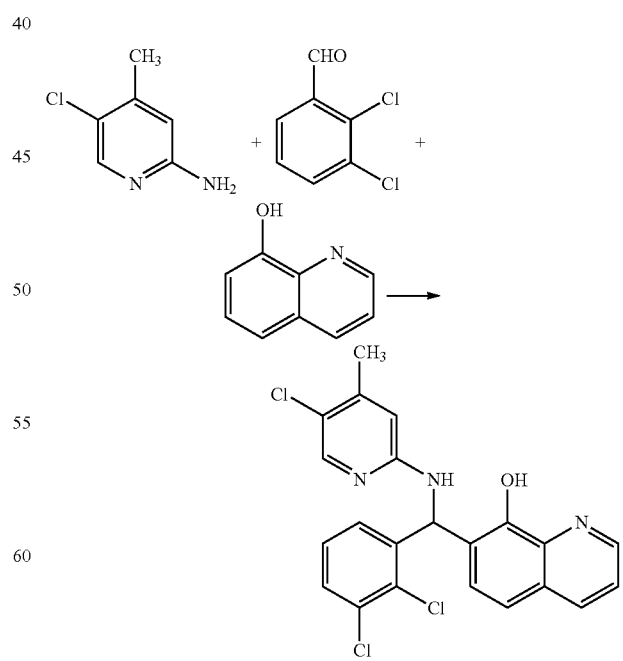

In a manner similar to that described in Example AD4-13021.

2-Amino-4-methyl-5-chloropyridine, Matrix Scientific (1.43 g, 0.01 mol) and 2,3-dichlorobenzaldehyde, Acros Organics (1.75 g, 0.01 mol) are combined with 8-hydroxyquinoline, Acros Organics (1.45 g, 0.01 mol) in 50 ml of absolute EtOH to give the desired Betti condensation product as a white solid (MP 154-156° C.).

Preparation of AD4-13154:

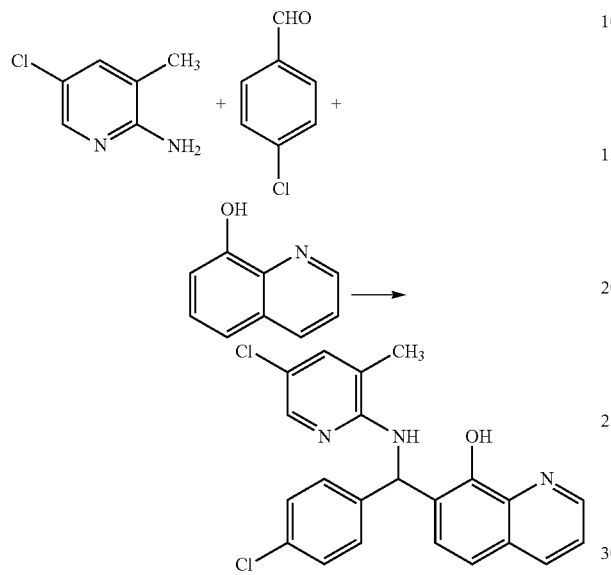

In a manner similar to that described in Example AD4-13021.

2-Amino-3-methyl-5-chloropyridine, BBM-001-071 (1.43 g, 0.01 mol) and 4-chlorobenzaldehyde, Acros Organics (1.41 g, 0.01 mol) are combined with 8-hydroxyquinoline, Acros Organics (1.45 g, 0.01 mol) in 50 ml of absolute EtOH to give the desired Betti condensation product as a light-green solid (MP 136-144° C.).

Preparation of AD4-13155:

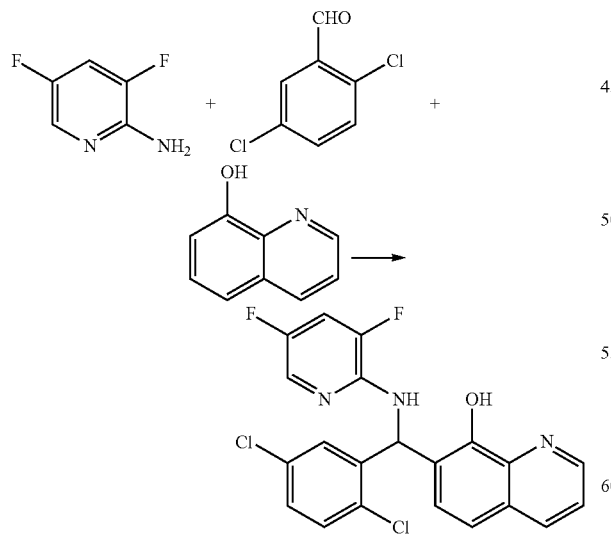

In a manner similar to that described in Example AD4-13022.

2-Amino-3,5-difluoropyridine, Matrix Scientific (0.44 g, 0.0033 mol) and 2,5-dichlorobenzaldehyde, Acros Organics (1.75 g, 0.01 mol) are combined with 8-hydroxyquinoline, Acros Organics (1.45 g, 0.01 mol) in 50 ml of absolute EtOH to give the desired Betti condensation product as an off-white solid (MP 130-131° C.).

Preparation of AD4-13156:

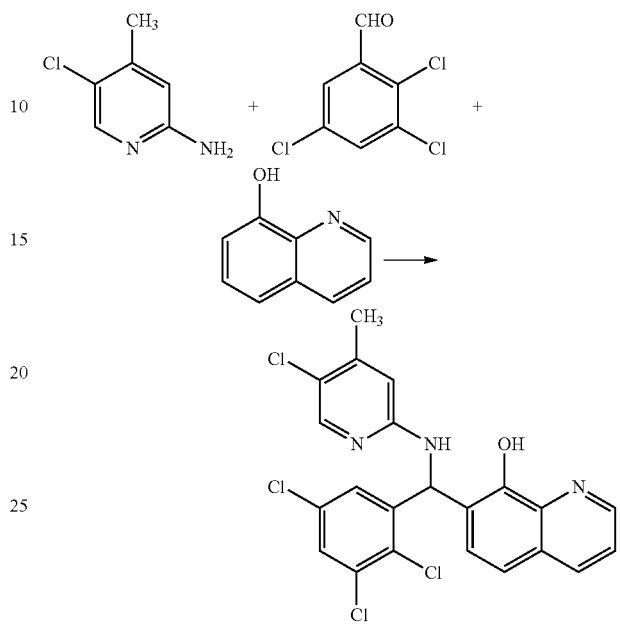

In a manner similar to that described in Example AD4-13022.

2-Amino-4-methyl-5-chloropyridine, Matrix Scientific (1.43 g, 0.01 mol) and 2,3,5-trichlorobenzaldehyde, Acros Organics (2.09 g, 0.01 mol) are combined with 8-hydroxyquinoline, Acros Organics (1.45 g, 0.01 mol) in 50 ml of absolute EtOH to give the desired Betti condensation product as an off-white solid (MP 175-181° C.).

Preparation of AD4-13157:

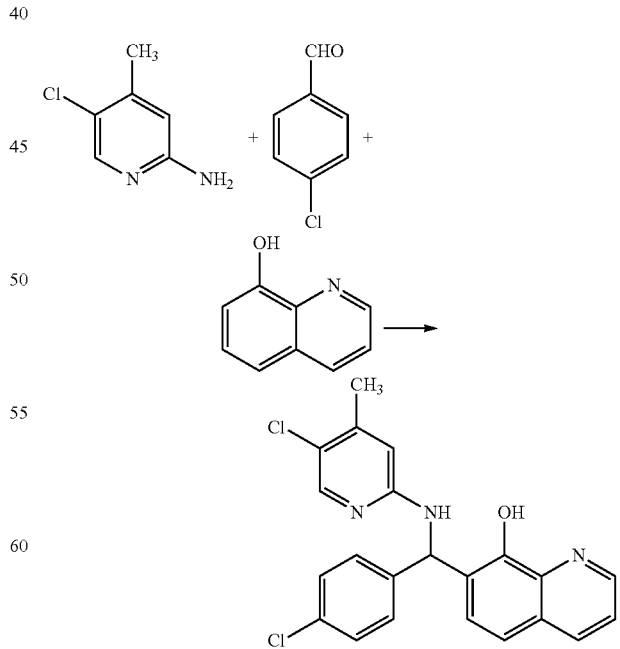

In a manner similar to that described in Example AD4-13021.

2-Amino-4-methyl-5-chloropyridine, Matrix Scientific (1.43 g, 0.01 mol) and 4-chlorobenzaldehyde, Acros Organics (1.41 g, 0.01 mol) are combined with 8-hydroxyquinoline, Acros Organics (1.45 g, 0.01 mol) in 50 ml of absolute EtOH to give the desired Betti condensation product as an off-white solid (MP 159-163° C.).

Preparation of AD4-13158:

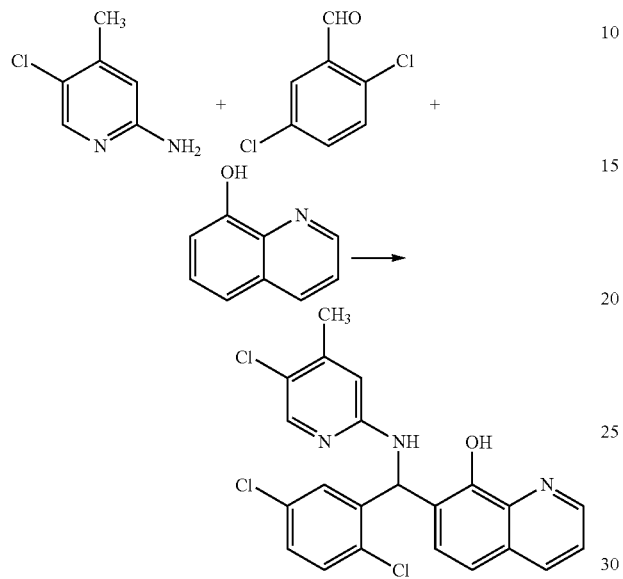

In a manner similar to that described in Example AD4-13021.

2-Amino-4-methyl-5-chloropyridine, Matrix Scientific (1.43 g, 0.01 mol) and 2,5-dichlorobenzaldehyde, Acros Organics (1.75 g, 0.01 mol) are combined with 8-hydroxyquinoline, Acros Organics (1.45 g, 0.01 mol) in 50 ml of absolute EtOH to give the desired Betti condensation product as an off-white solid (MP 195-199° C.).

Preparation of AD4-13159:

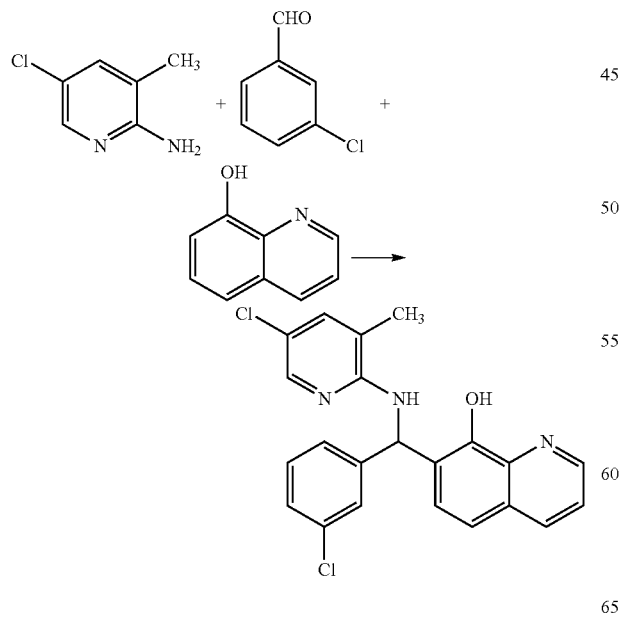

In a manner similar to that described in Example AD4-13021.

2-Amino-3-methyl-5-chloropyridine (BBM-001-071; 1.43 g, 0.01 mol) and 3-chlorobenzaldehyde, Acros Organics (1.41 g, 0.01 mol) are combined with 8-hydroxyquinoline, Acros Organics (1.45 g, 0.01 mol) in 50 ml of absolute EtOH to give the desired Betti condensation product as a white solid (MP 138-141° C.).

Preparation of AD4-13160:

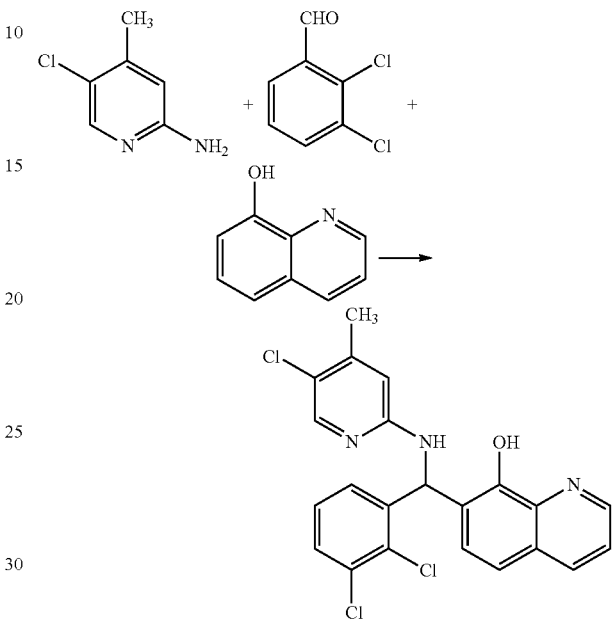

In a manner similar to that described in Example AD4-13021.

2-Amino-4-methyl-5-chloropyridine, Matrix Scientific (1.43 g, 0.01 mol) and 2,3-dichlorobenzaldehyde, Acros Organics (1.75 g, 0.01 mol) are combined with 8-hydroxyquinoline, Acros Organics (1.45 g, 0.01 mol) in 50 ml of absolute EtOH to give the desired Betti condensation product as a white solid (MP 157-164° C.).

Preparation of AD4-13161:

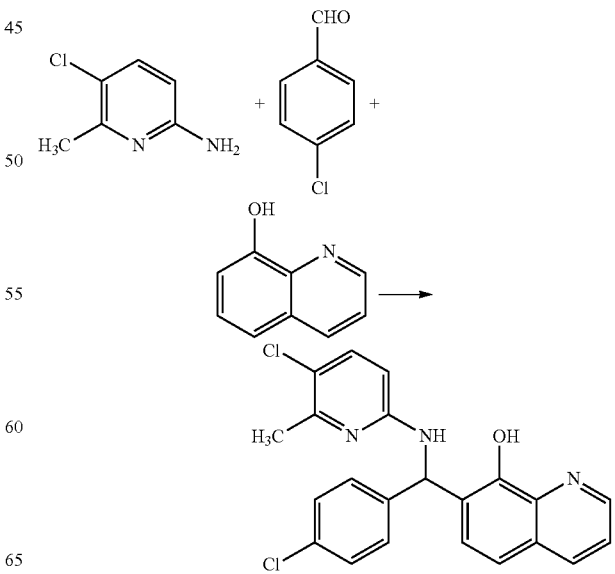

In a manner similar to that described in Example AD4-13022.

2-Amino-5-chloro-6-methylpyridine (IJT-001-090; 1.43 g, 0.01 mol) and 4-chlorobenzaldehyde, Acros Organics (1.41 g, 0.01 mol) are combined with 8-hydroxyquinoline, Acros Organics (1.45 g, 0.01 mol) in 50 ml of absolute EtOH to give the desired Betti condensation product as a white solid (MP 143-146° C.).

Preparation of AD4-13162:

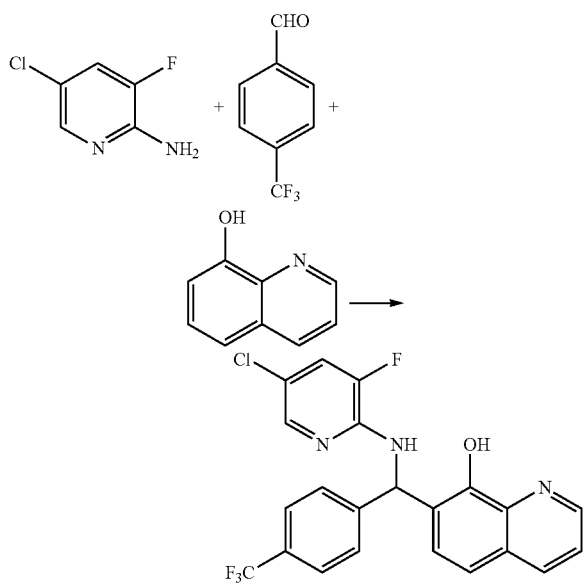

In a manner similar to that described in Example AD4-13021.

2-Amino-3-fluoro-5-chloropyridine, Matrix Scientific (1.47 g, 0.01 mol) and 4-trifluoromethylbenzaldehyde, Acros Organics (1.74 g, 0.01 mol) are combined with 8-hydroxyquinoline, Acros Organics (1.45 g, 0.01 mol) in 50 ml of absolute EtOH to give the desired Betti condensation product as a white solid (MP 106-109° C.).

Preparation of AD4-13163:

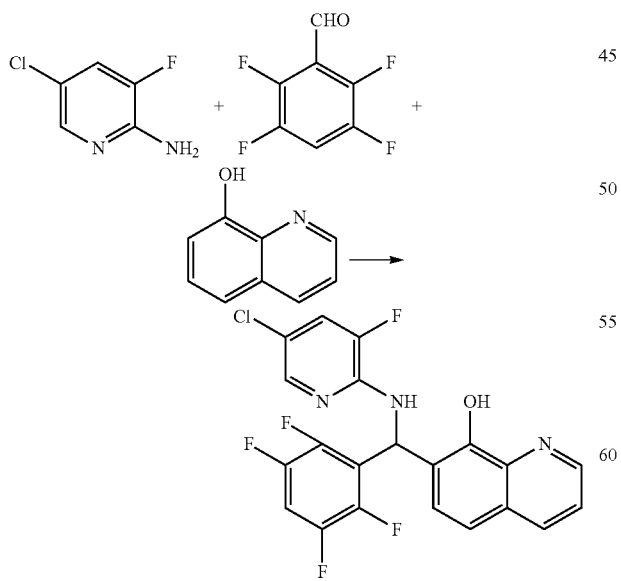

In a manner similar to that described in Example AD4-13021.

2-Amino-3-fluoro-5-chloropyridine, Matrix Scientific (1.47 g, 0.01 mol) and 2,3,5,6-tetrafluorobenzaldehyde, Matrix Scientific (1.78 g, 0.01 mol) are combined with 8-hydroxyquinoline, Acros Organics (1.45 g, 0.01 mol) in 50 ml of absolute EtOH to give the desired Betti condensation product as a white solid (MP 161-163° C.).

Preparation of AD4-13164:

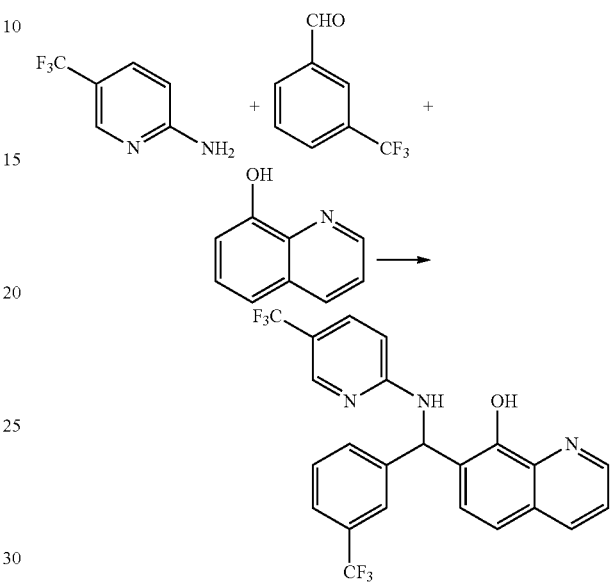

In a manner similar to that described in Example AD4-13021.

2-Amino-5-trifluoromethylpyridine, Matrix Scientific (1.62 g, 0.01 mol) and 3-trifluoromethylbenzaldehyde, Acros Organics (1.74 g, 0.01 mol) are combined with 8-hydroxyquinoline, Acros Organics (1.45 g, 0.01 mol) in 50 ml of absolute EtOH to give the desired Betti condensation product as a white solid (MP 127-128° C.).

Preparation of AD4-13165:

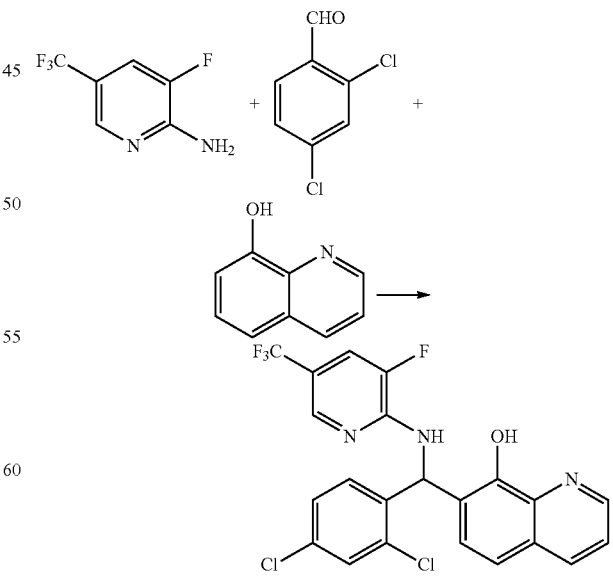

In a manner similar to that described in Example AD4-13021.

2-Amino-3-fluoro-5-trifluoromethylpyridine, Matrix Scientific (1.80 g, 0.01 mol) and 2,4-dichlorobenzaldehyde, Acros Organics (1.75 g, 0.01 mol) are combined with 8-hydroxyquinoline, Acros Organics (1.45 g, 0.01 mol) in 50 ml of absolute EtOH to give the desired Betti condensation product as a light-grey solid (MP 137-139° C.).

Preparation of AD4-13166:

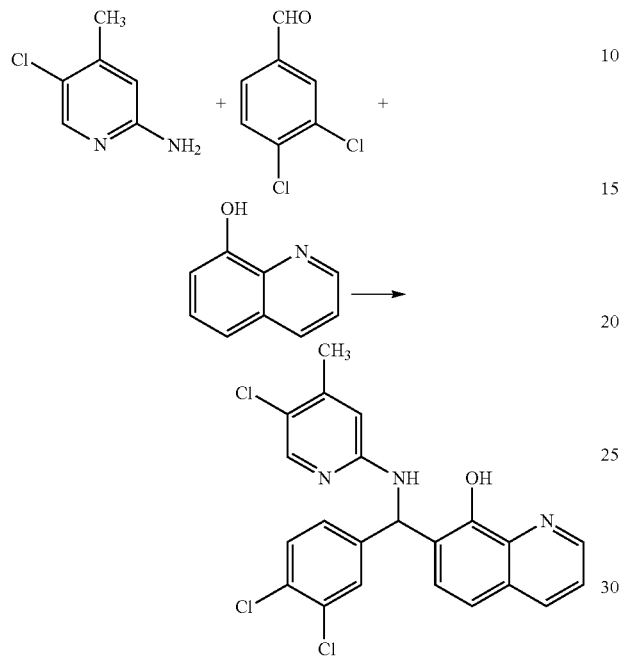

In a manner similar to that described in Example AD4-13021.

2-Amino-4-methyl-5-chloropyridine, Matrix Scientific (1.42 g, 0.01 mol) and 3,4-dichlorobenzaldehyde, Acros Organics (1.75 g, 0.01 mol) are combined with 8-hydroxyquinoline, Acros Organics (1.45 g, 0.01 mol) in 50 ml of absolute EtOH to give the desired Betti condensation product as a white solid (MP 158-160° C.).

Preparation of AD4-13167:

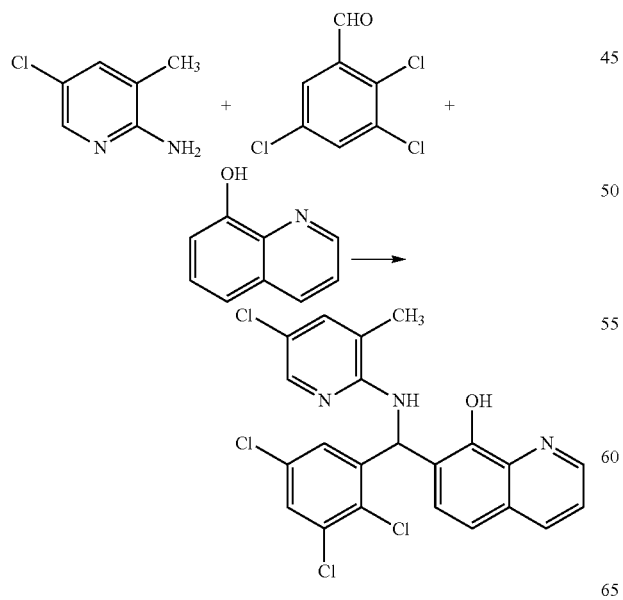

In a manner similar to that described in Example AD4-13021.

2-Amino-3-methyl-5-chloropyridine, BBM-001-071 (1.43 g, 0.01 mol) and 2,3,5-trichlorobenzaldehyde, Acros Organics (2.09 g, 0.01 mol) are combined with 8-hydroxyquinoline, Acros Organics (1.45 g, 0.01 mol) in 50 ml of absolute EtOH to give the desired Betti condensation product as an off-white solid (MP 95-104° C.).

Preparation of AD4-13172:

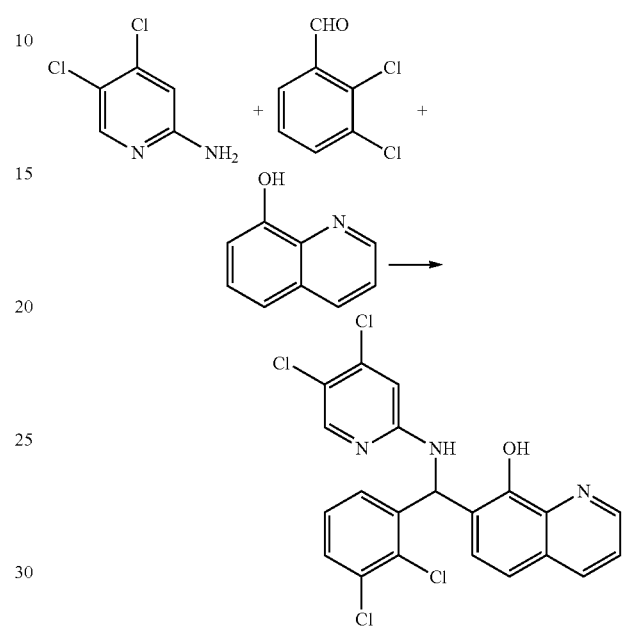

In a manner similar to that described in Example 10.

2-Amino-4,5-dichloropyridine (BBM-001-049; 1.30 g, 0.008 mol) and 2,3-dichlorobenzaldehyde, Acros Organics (1.75 g, 0.01 mol) are combined with 8-hydroxyquinoline, Acros Organics (1.45 g, 0.01 mol) in 50 ml of absolute EtOH to give the desired Betti condensation product as an off-white solid (MP 180-182° C.).

Preparation of AD4-13173:

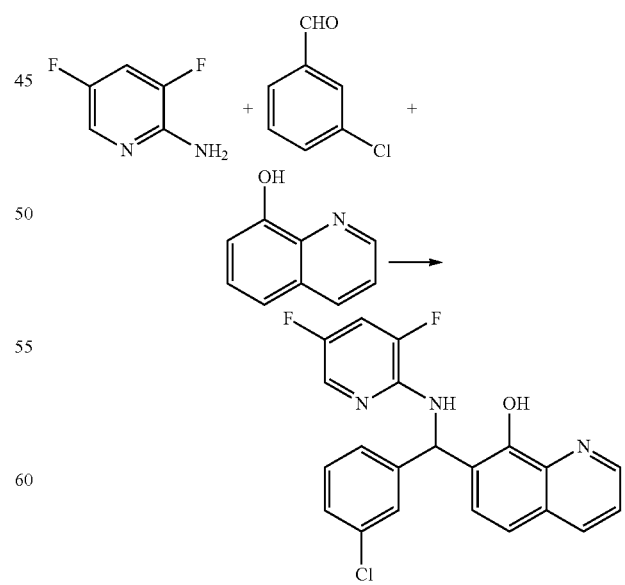

In a manner similar to that described in Example AD4-13021.

2-Amino-3,5-difluoropyridine, Matrix Scientific (1.30 g, 0.01 mol) and 3-chlorobenzaldehyde, Acros Organics (1.41 g, 0.01 mol) are combined with 8-hydroxyquinoline, Acros Organics (1.45 g, 0.01 mol) in 50 ml of absolute EtOH to give the desired Betti condensation product as a tan solid (MP 56-60° C.).

Preparation of AD4-13174:

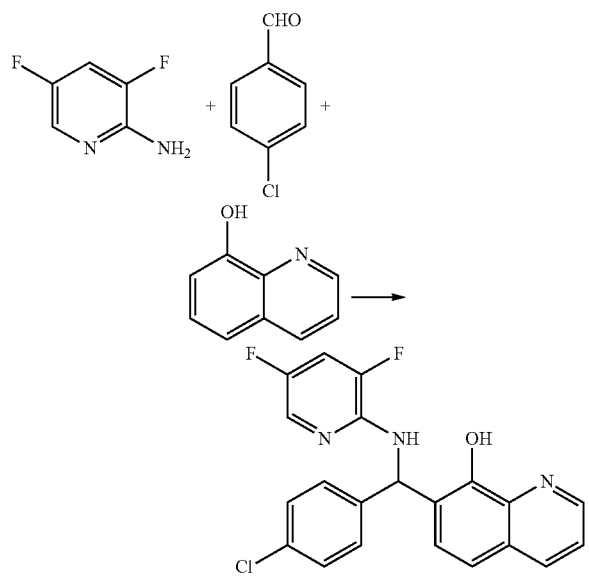

In a manner similar to that described in Example AD4-13022.

2-Amino-3,5-difluoropyridine, Matrix Scientific (1.30 g, 0.01 mol) and 4-chlorobenzaldehyde, Acros Organics (1.41 g, 0.01 mol) are combined with 8-hydroxyquinoline, Acros Organics (1.45 g, 0.01 mol) in 50 ml of absolute EtOH to give the desired Betti condensation product as a tan solid (MP 132-138° C.).

Preparation of AD4-13175:

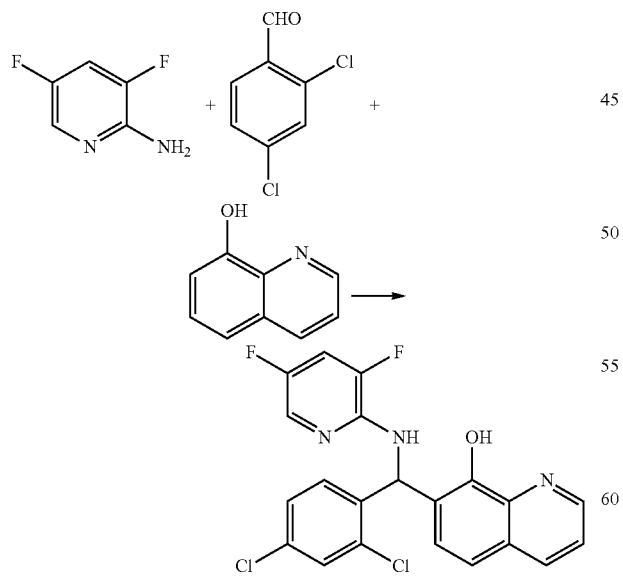

In a manner similar to that described in Example AD4-13021.

2-Amino-3,5-difluoropyridine, Matrix Scientific (1.30 g, 0.01 mol) and 2,4-dichlorobenzaldehyde, Acros Organics (1.75 g, 0.01 mol) are combined with 8-hydroxyquinoline, Acros Organics (1.45 g, 0.01 mol) in 50 ml of absolute EtOH to give the desired Betti condensation product as an off-white solid (MP 88-92° C.).

Preparation of AD4-13176:

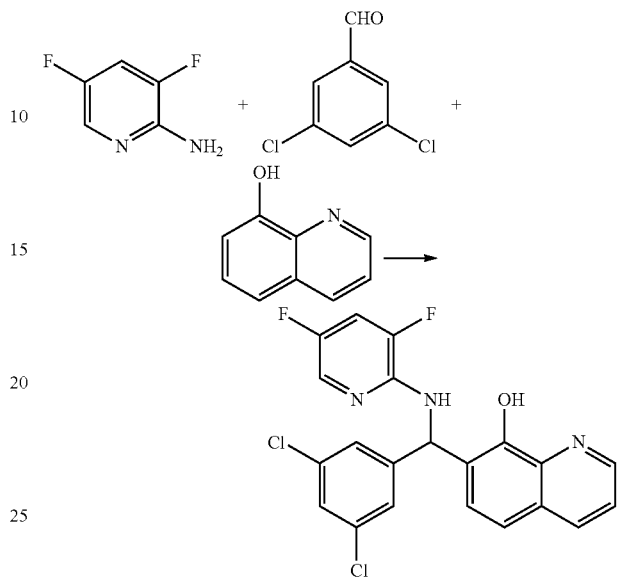

In a manner similar to that described in Example AD4-13022.

2-Amino-3,5-difluoropyridine, Matrix Scientific (1.30 g, 0.01 mol) and 3,5-dichlorobenzaldehyde, Acros Organics (1.75 g, 0.01 mol) are combined with 8-hydroxyquinoline, Acros Organics (1.45 g, 0.01 mol) in 50 ml of absolute EtOH to give the desired Betti condensation product as an off-white solid (MP 68-70° C.).

Preparation of AD4-13177:

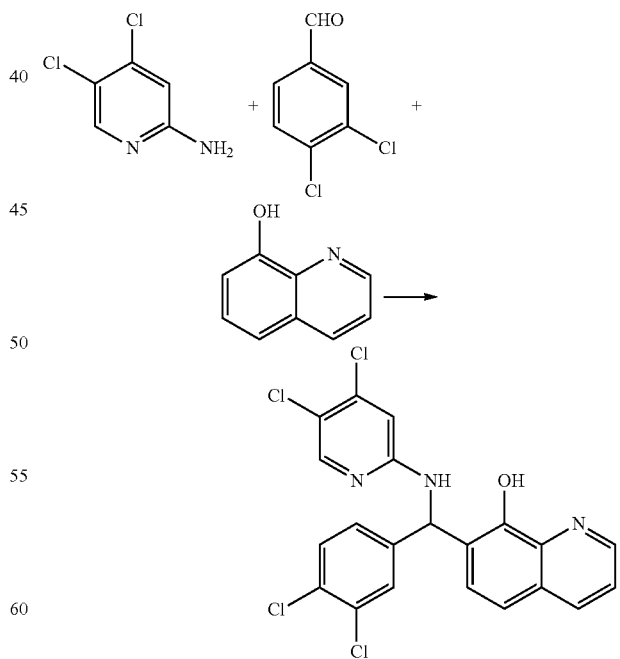

In a manner similar to that described in Example AD4-13021.

2-Amino-4,5-dichloropyridine (BBM-001-049; 1.30 g, 0.008 mol) and 3,4-dichlorobenzaldehyde, Acros Organics (1.75 g, 0.01 mol) are combined with 8-hydroxyquinoline, Acros Organics (1.45 g, 0.01 mol) in 50 ml of absolute EtOH to give the desired Betti condensation product as an off-white solid (MP 145-147° C.).

Preparation of AD4-13178:

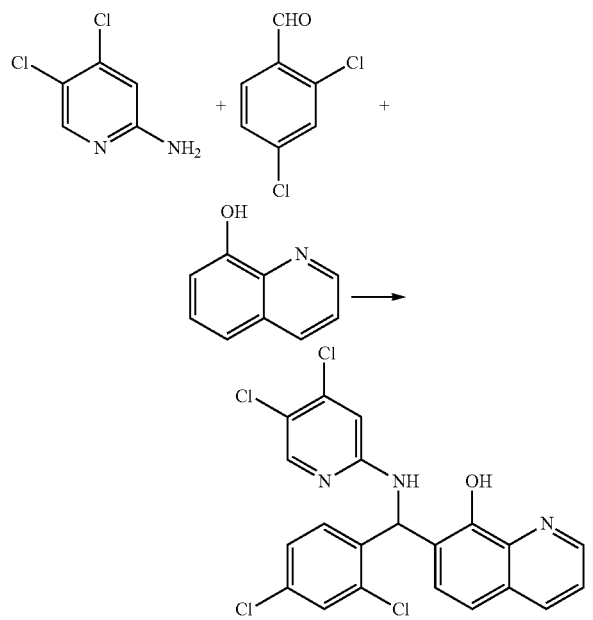

In a manner similar to that described in Example AD4-13021.

2-Amino-4,5-dichloropyridine (BBM-001-049; 1.30 g, 0.008 mol) and 2,4-dichlorobenzaldehyde, Acros Organics (1.75 g, 0.01 mol) are combined with 8-hydroxyquinoline, Acros Organics (1.45 g, 0.01 mol) in 50 ml of absolute EtOH to give the desired Betti condensation product as an off-white solid (MP 153-155° C.).

Preparation of AD4-13179:

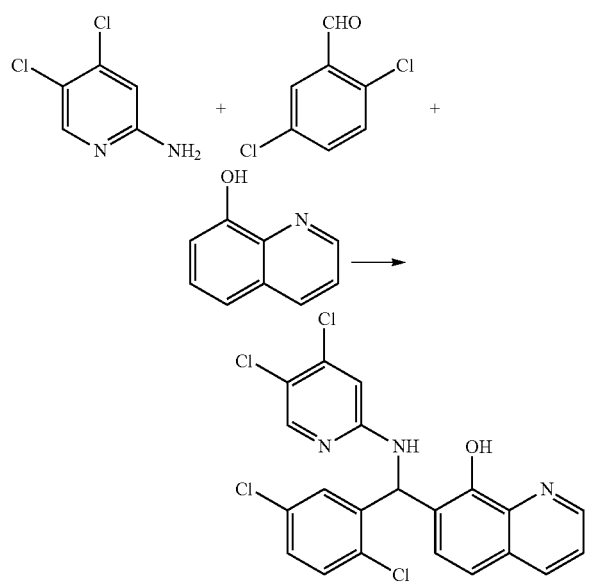

In a manner similar to that described in Example AD4-13021.

2-Amino-4,5-dichloropyridine (BBM-001-049; 1.30 g, 0.008 mol) and 2,5-dichlorobenzaldehyde, Acros Organics (1.75 g, 0.01 mol) are combined with hydroxyquinoline, Acros Organics (1.45 g, 0.01 mol) in 50 ml of absolute EtOH to give the desired Betti condensation product as a white solid (MP 195-197° C.).

Preparation of AD4-13180:

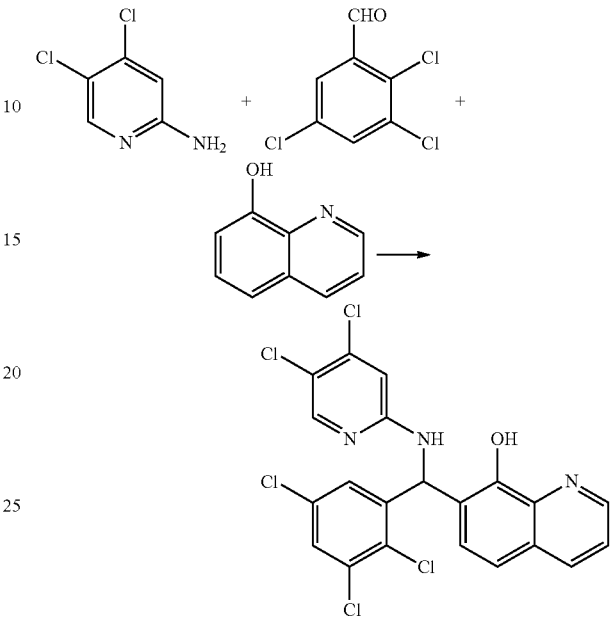

In a manner similar to that described in Example AD4-13021.

2-Amino-4,5-dichloropyridine (BBM-001-049; 1.30 g, 0.008 mol) and 2,3,5-trichlorobenzaldehyde, Acros Organics (2.09 g, 0.01 mol) are combined with 8-hydroxyquinoline, Acros Organics (1.45 g, 0.01 mol) in 50 ml of absolute EtOH to give the desired Betti condensation product as a white solid (MP 192-195° C.).

Preparation of AD4-13181:

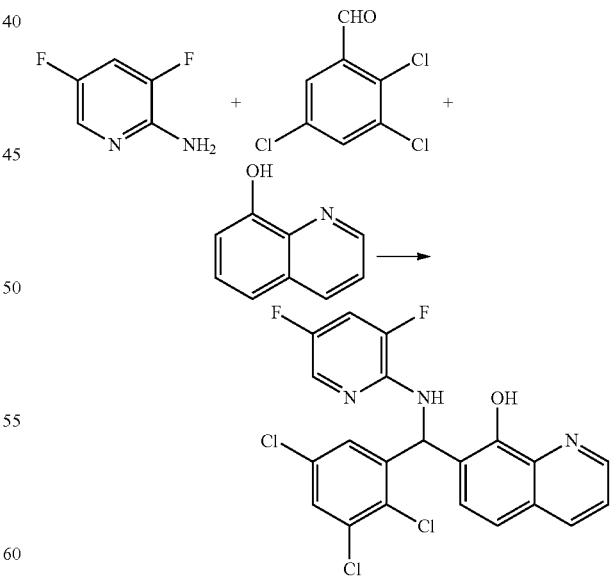

In a manner similar to that described in Example AD4-13021.

2-Amino-3,5-difluoropyridine, Matrix Scientific (1.30 g, 0.01 mol) and 2,3,5-trichlorobenzaldehyde, Acros Organics (2.09 g, 0.01 mol) are combined with 8-hydroxyquinoline, Acros Organics (1.45 g, 0.01 mol) in 50 ml of absolute EtOH to give the desired Betti condensation product as an off-white solid (MP 79-86° C.).

Preparation of AD4-13182:

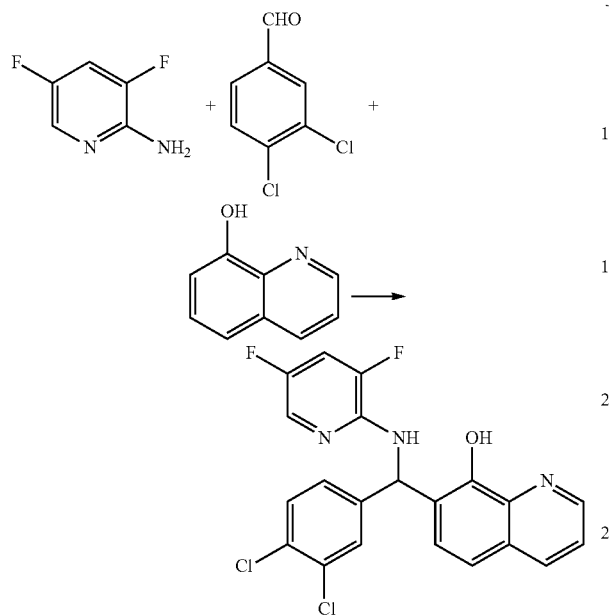

In a manner similar to that described in Example AD4-13021.

2-Amino-3,5-difluoropyridine, Matrix Scientific (1.30 g, 0.01 mol) and 3,4-dichlorobenzaldehyde, Acros Organics (1.75 g, 0.01 mol) are combined with 8-hydroxyquinoline, Acros Organics (1.45 g, 0.01 mol) in 50 ml of absolute EtOH to give the desired Betti condensation product as an off-white solid (MP 60-68° C.).

Preparation of AD4-13183:

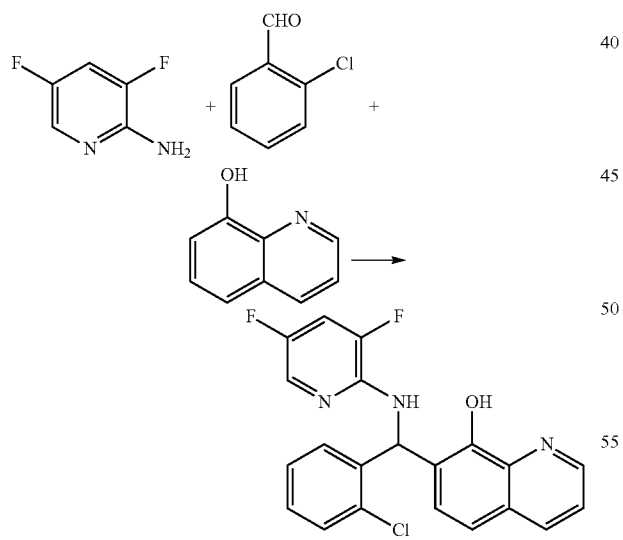

In a manner similar to that described in Example AD4-13021.

2-Amino-3,5-difluoropyridine, Matrix Scientific (1.30 g, 0.01 mol) and 2-chlorobenzaldehyde, Acros Organics (1.41 g, 0.01 mol) are combined with 8-hydroxyquinoline, Acros Organics (1.45 g, 0.01 mol) in 50 ml of absolute EtOH to give the desired Betti condensation product as a light-green solid (MP 140-141° C.).

Preparation of AD4-13184:

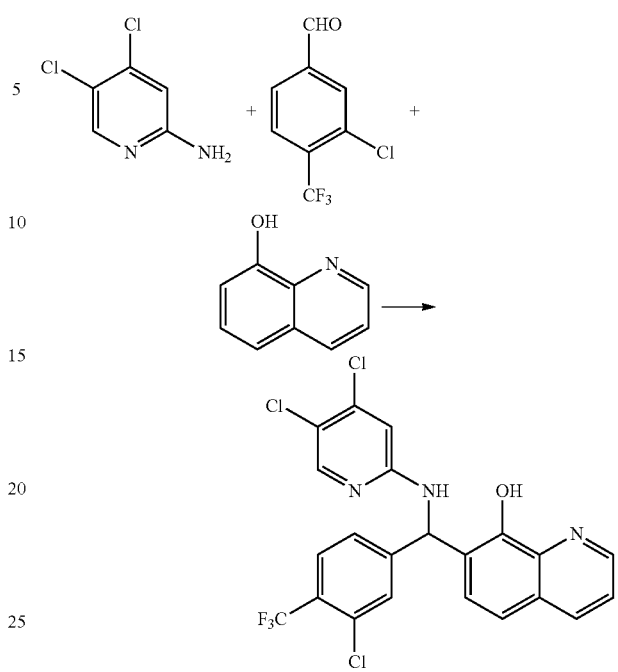

In a manner similar to that described in Example AD4-13021.

2-Amino-4,5-dichloropyridine (BBM-001-049; 1.30 g, 0.008 mol) and 3-trifluoromethyl-4-chlorobenzaldehyde, Oakwood Products, (2.09 g, 0.01 mol) are combined with 8-hydroxyquinoline, Acros Organics (1.45 g, 0.01 mol) in 50 ml of absolute EtOH to give the desired Betti condensation product as a white solid (MP 165-166° C.).

Preparation of AD4-13185:

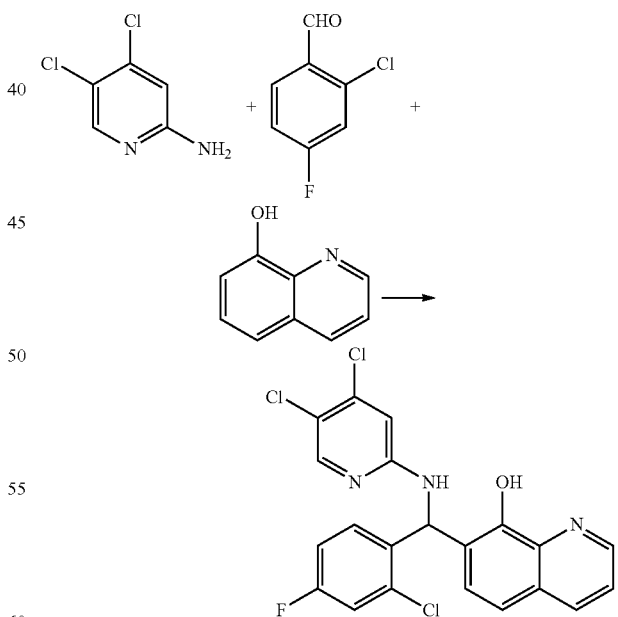

In a manner similar to that described in Example AD4-13021.

2-Amino-4,5-dichloropyridine (BBM-001-049; 1.63 g, 0.01 mol) and 2-chloro-4-fluorobenzaldehyde, Oakwood Products (1.59 g, 0.01 mol) are combined with 8-hydroxyquinoline, Acros Organics (1.45 g, 0.01 mol) in 50 ml of absolute EtOH to give the desired Betti condensation product as a white solid (MP 157-158° C.).

Preparation of AD4-13186:

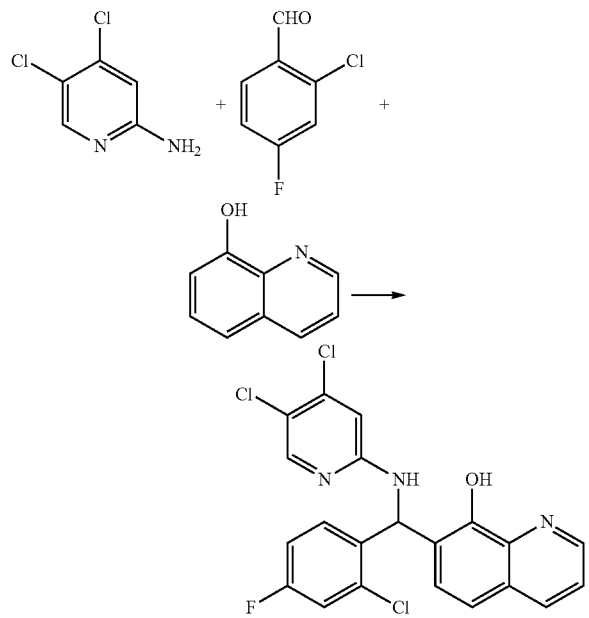

In a manner similar to that described in Example AD4-13021.

2-Amino-4-methyl-5-chloropyridine, Matrix Scientific (01.42 g, 0.01 mol) and 3-hydroxy-4-methoxybenzaldehyde, Acros Organics (1.52 g, 0.01 mol) are combined with 8-hydroxyquinoline, Acros Organics (1.45 g, 0.01 mol) in 50 ml of absolute EtOH to give the desired Betti condensation product as a white solid (MP 103-105° C.).

Preparation of AD4-13187:

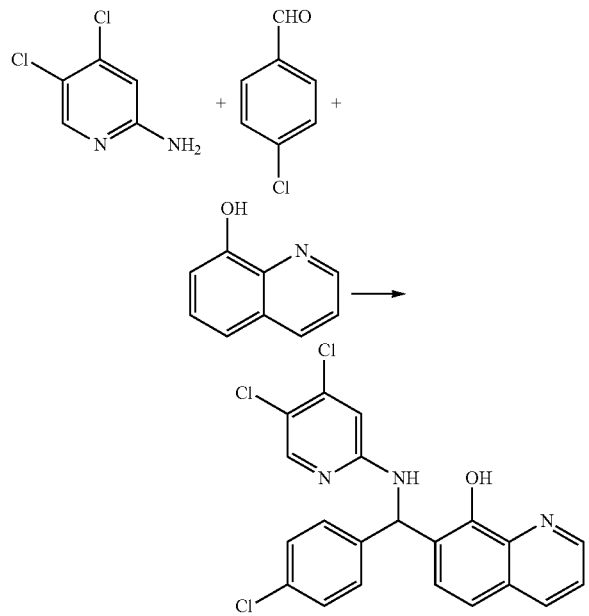

In a manner similar to that described in Example AD4-13022.

2-Amino-4,5-dichloropyridine (BBM-001-049; 1.63 g, 0.01 mol) and 4-chlorobenzaldehyde, Acros Organics (1.41 g, 0.01 mol) are combined with 8-hydroxyquinoline, Acros Organics (1.45 g, 0.01 mol) in 50 ml of absolute EtOH to give the desired Betti condensation product as a white solid (MP 140-141° C.).

Preparation of AD4-13188:

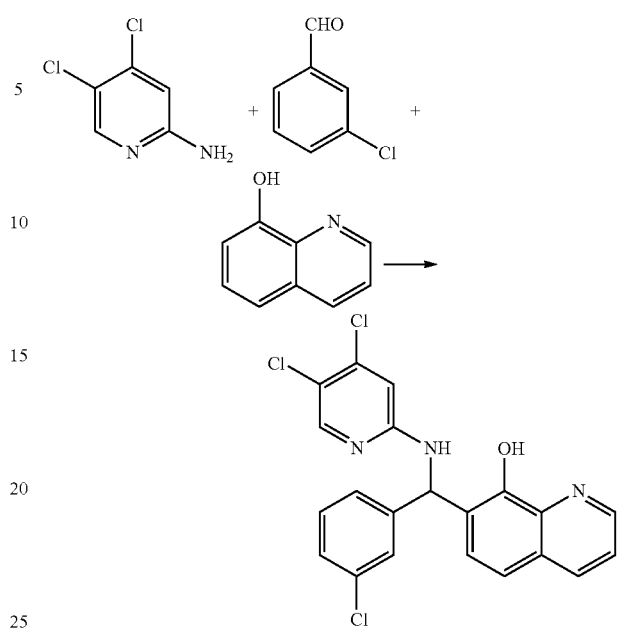

In a manner similar to that described in Example AD4-13021.

2-Amino-4,5-dichloropyridine (BBM-001-049; 1.63 g, 0.01 mol) and 3-chlorobenzaldehyde, Acros Organics (1.41 g, 0.01 mol) are combined with 8-hydroxyquinoline, Acros Organics (1.45 g, 0.01 mol) in 50 ml of absolute EtOH to give the desired Betti condensation product as an off-white solid (MP 116-121° C.).

Preparation of AD4-13189:

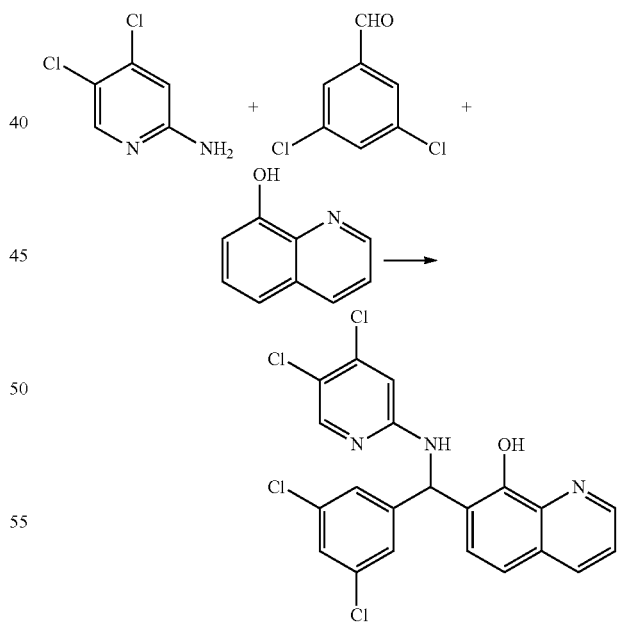

In a manner similar to that described in Example AD4-13021.

2-Amino-4,5-dichloropyridine (BBM-001-049; 1.63 g, 0.01 mol) and 3,5-dichlorobenzaldehyde, Matrix Scientific (1.75 g, 0.01 mol) are combined with 8-hydroxyquinoline, Acros Organics (1.45 g, 0.01 mol) in 50 ml of absolute EtOH to give the desired Betti condensation product as a white solid (MP 155-159° C.).

Preparation of AD4-13190:

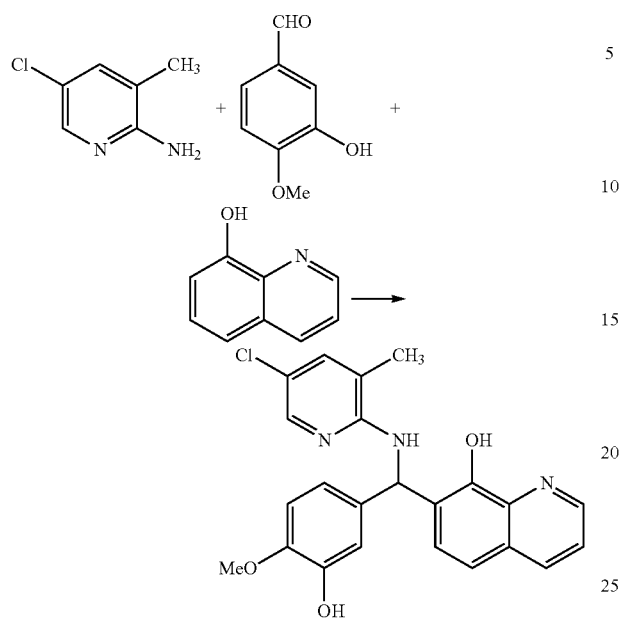

In a manner similar to that described in Example AD4-13021.

2-Amino-3-methyl-5-chloropyridine (BBM-001-071; 1.43 g, 0.01 mol) and 3-hydroxy-4-methoxybenzaldehyde, Acros Organics (1.52 g, 0.01 mol) are combined with 8-hydroxyquinoline, Acros Organics (1.45 g, 0.01 mol) in 50 ml of absolute EtOH to give the desired Betti condensation product as a tan solid (MP 88-92° C.).

Preparation of AD4-13191:

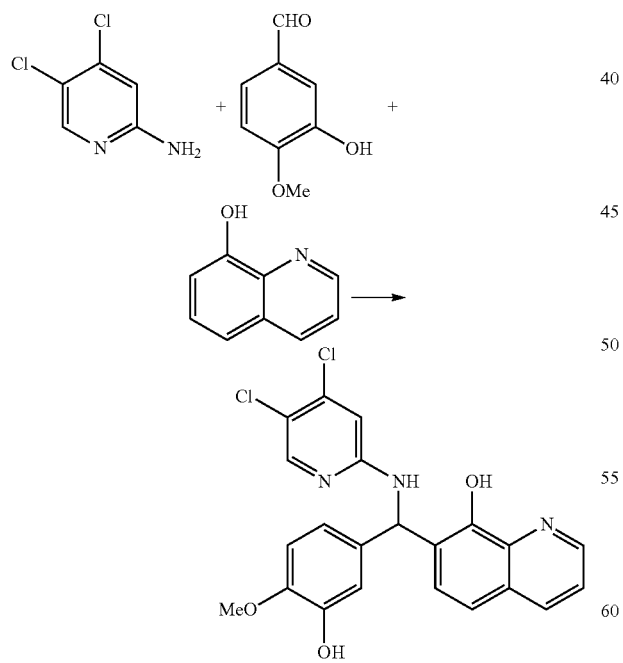

In a manner similar to that described in Example AD4-13021.

2-Amino-4,5-dichloropyridine (BBM-001-049; 1.75 g, 0.01 mol) and 3-hydroxy-4-methoxybenzaldehyde, Acros Organics (1.52 g, 0.01 mol) are combined with 8-hydroxyquinoline, Acros Organics (1.45 g, 0.01 mol) in 50 ml of absolute EtOH to give the desired Betti condensation product as an off-white solid (MP 104-105° C.).

Preparation of AD4-13192:

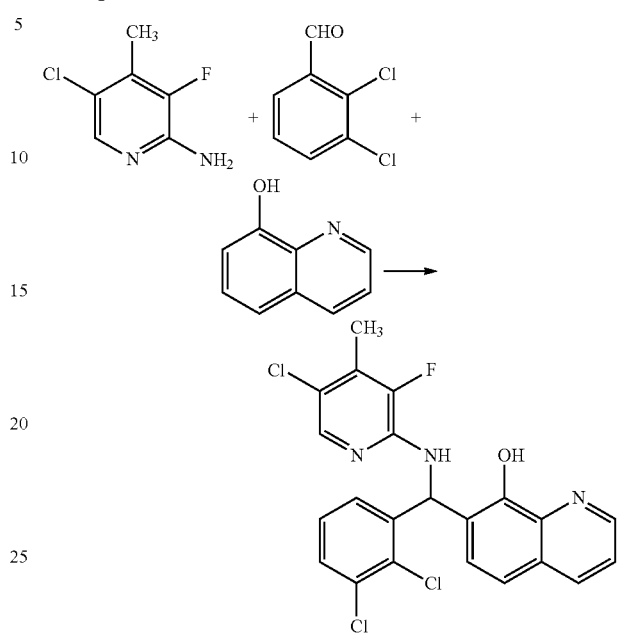

In a manner similar to that described in Example AD4-13021.

2-Amino-3-fluoro-4-methyl-5-chloropyridine (BBM-001-065; 1.61 g 0.01 mol) and 2,3-dichlorobenzaldehyde, Acros Organics (1.75 g, 0.01 mol) are combined with 8-hydroxyquinoline, Acros Organics (1.45 g, 0.01 mol) in 50 ml of absolute EtOH to give the desired Betti condensation product as an off-white solid (MP 179-180° C.).

Preparation of AD4-13193:

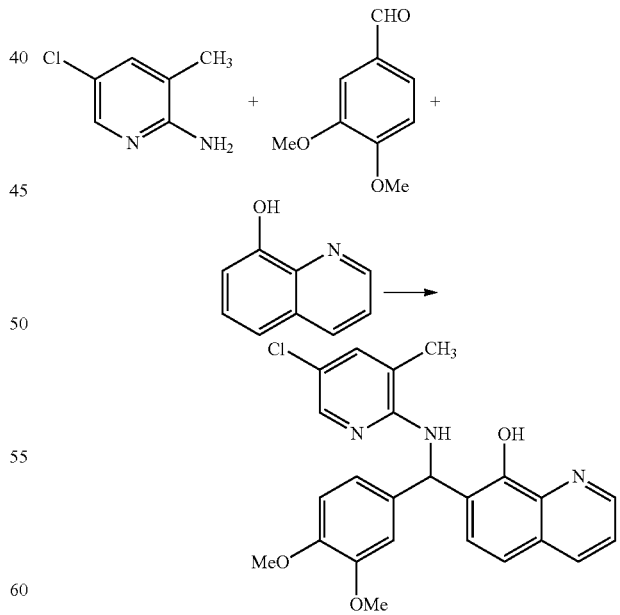

In a manner similar to that described in Example AD4-13021.

2-Amino-3-methyl-5-chloropyridine (BBM-001-071; 1.43 g, 0.01 mol) and 3,4-dimethoxybenzaldehyde, Acros Organics (1.66 g, 0.01 mol) are combined with 8-hydroxyquinoline, Acros Organics (1.45 g, 0.01 mol) in 50 ml of absolute EtOH to give the desired Betti condensation product as an off-white solid (MP 48-53° C.).

Preparation of AD4-13194:

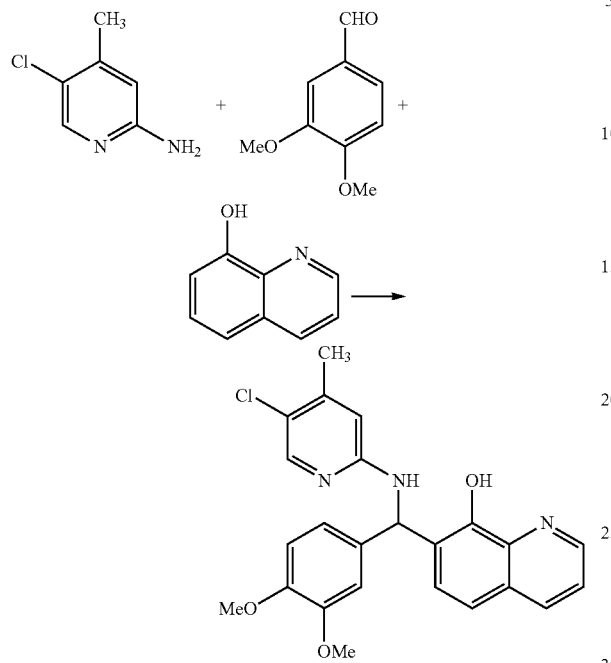

In a manner similar to that described in Example AD4-13021.

2-Amino-4-methyl-5-chloropyridine, Matrix Scientific (1.43 g, 0.01 mol) and 3,4-dimethoxybenzaldehyde, Acros Organics (1.66 g, 0.01 mol) are combined with 8-hydroxyquinoline, Acros Organics (1.45 g, 0.01 mol) in 50 ml of absolute EtOH to give the desired Betti condensation product as a tan oil.

Preparation of AD4-13195:

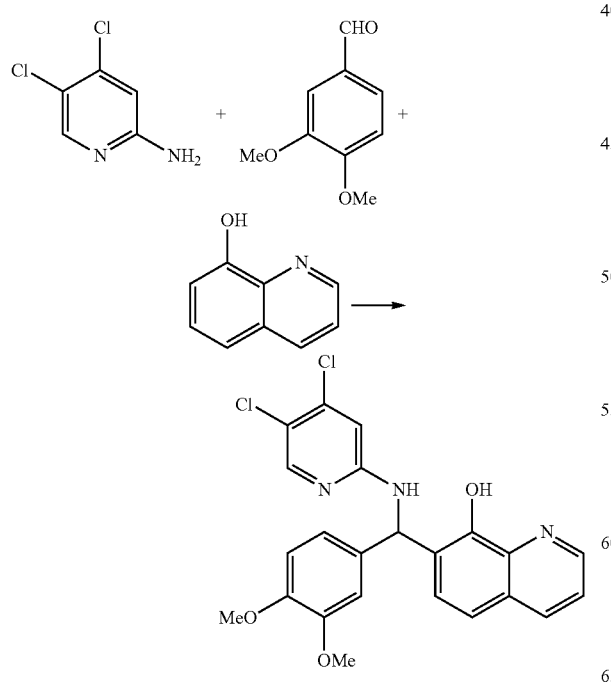

In a manner similar to that described in Example AD4-13021.

2-Amino-4,5-dichloropyridine (BBM-001-049; 1.63 g, 0.01 mol) and 3,4-dimethoxybenzaldehyde, Acros Organics (1.66 g, 0.01 mol) are combined with 8-hydroxyquinoline, Acros Organics (1.45 g, 0.01 mol) in 50 ml of absolute EtOH to give the desired Betti condensation product as a tan oil.

Preparation of AD4-13196:

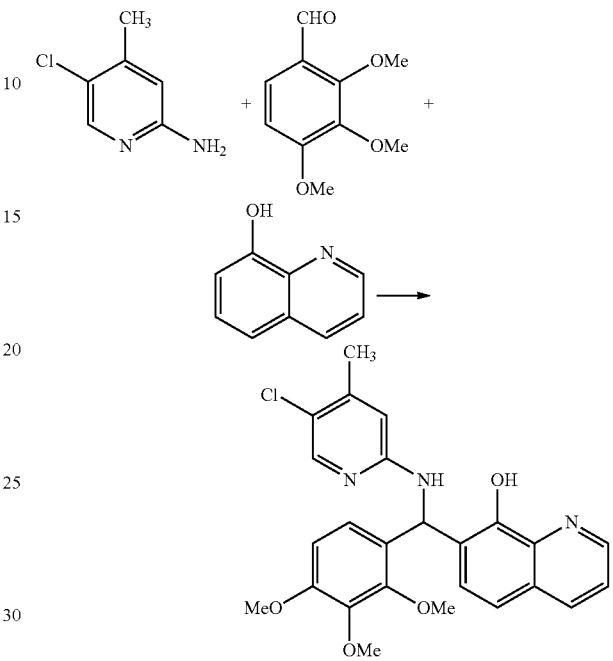

In a manner similar to that described in Example AD4-13021.

2-Amino-4-methyl-5-chloropyridine, Matrix Scientific (1.43 g, 0.01 mol) and 2,3,4-trimethoxybenzaldehyde, Acros Organics (1.96 g, 0.01 mol) are combined with 8-hydroxyquinoline, Acros Organics (1.45 g, 0.01 mol) in 50 ml of absolute EtOH to give the desired Betti condensation product as an off-white solid (MP 165-166° C.).

Preparation of AD4-13197:

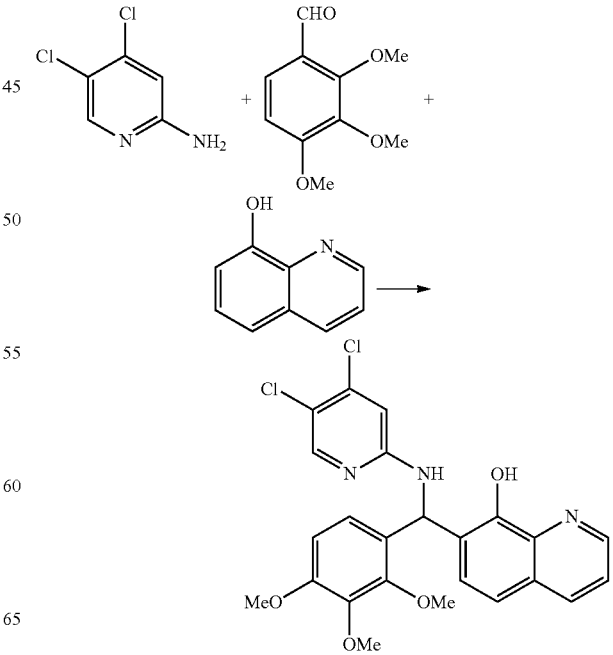

In a manner similar to that described in Example AD4-13021.

2-Amino-4,5-dichloropyridine (BBM-001-049; 1.63 g, 0.01 mol) and 2,3,4-trimethoxybenzaldehyde, Acros Organics (1.96 g, 0.01 mol) are combined with 8-hydroxyquinoline, Acros Organics (1.45 g, 0.01 mol) in 50 ml of absolute EtOH to give the desired Betti condensation product as an off-white solid (MP 187-190° C.).

Preparation of AD4-13199:

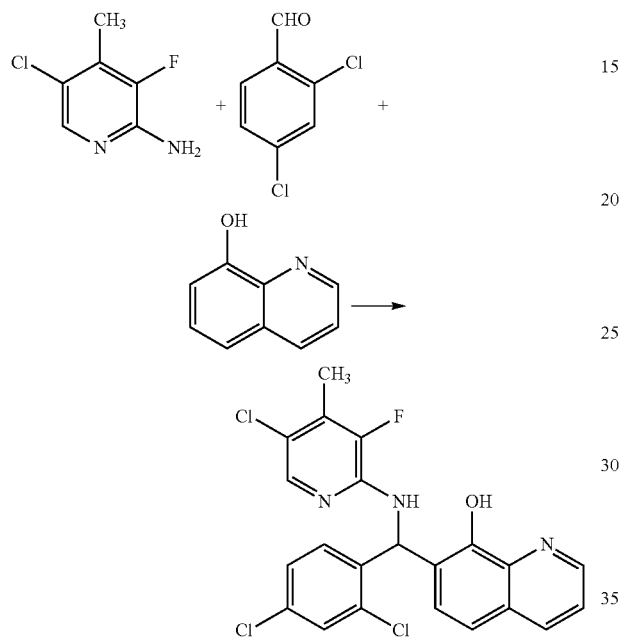

In a manner similar to that described in Example AD4-13021.

2-Amino-3-fluoro-4-methyl-5-chloropyridine (BBM-001-065; 1.61 g 0.01 mol) and 2,4-dichlorobenzaldehyde, Acros Organics (1.75 g, 0.01 mol) are combined with 8-hydroxyquinoline, Acros Organics (1.45 g, 0.01 mol) in 50 ml of absolute EtOH to give the desired Betti condensation product as an off-white solid (MP 164-165° C.).

Preparation of AD4-13200:

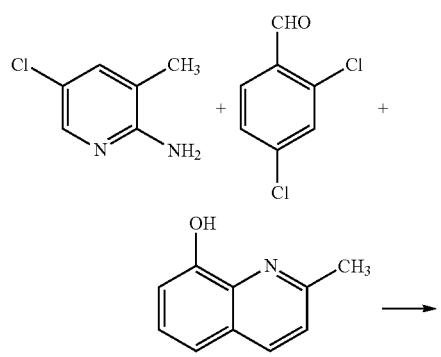

-continued

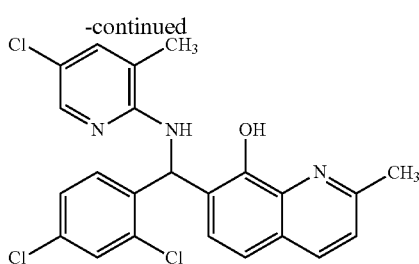

In a manner similar to that described in Example AD4-13021.

2-Amino-3-methyl-5-chloropyridine (BBM-001-071; 1.43 g, 0.01 mol) and 2,4-dichlorobenzaldehyde, Acros Organics (1.75 g, 0.01 mol) are combined with 8-hydroxyquinaldine, Acros Organics (1.59 g, 0.01 mol) in 50 ml of absolute EtOH to give the desired Betti condensation product as a light-green solid (MP 215-217° C.).

Preparation of AD4-13202:

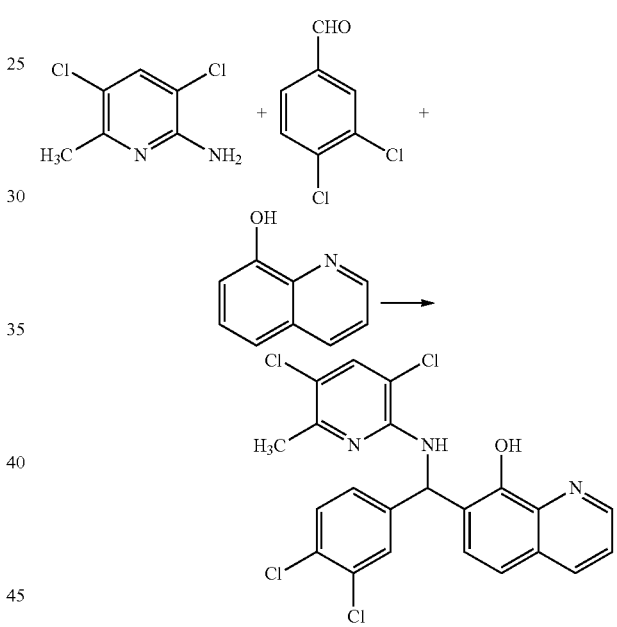

In a manner similar to that described in Example AD4-13021.

2-Amino-3,5-dichloro-6-methylpyridine, Matrix Scientific (1.77 g, 0.01 mol) and 3,4-dichlorobenzaldehyde, Acros Organics (1.75 g, 0.01 mol) are combined with 8-hydroxyquinoline, Acros Organics (1.45 g, 0.01 mol) in 50 ml of absolute EtOH to give the desired Betti condensation product as a white solid (MP 159-160° C.).

Preparation of AD4-13203:

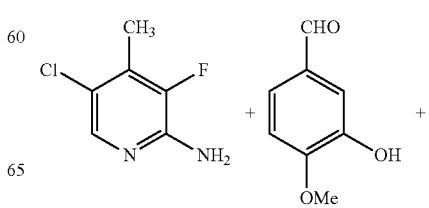

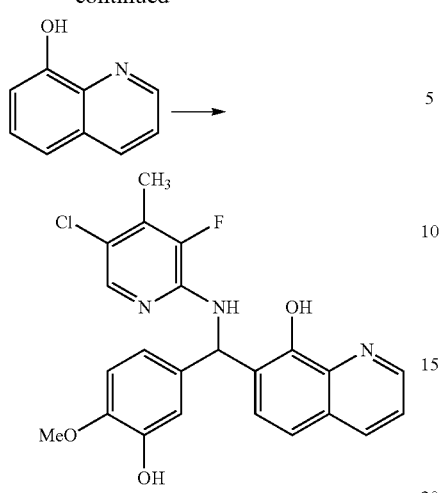

In a manner similar to that described in Example AD4-13021.

2-Amino-3-fluoro-4-methyl-5-chloropyridine (BBM-001-065; 1.61 g 0.01 mol) and 3-hydroxy-4-methoxybenzaldehyde, Acros Organics (1.52 g, 0.01 mol) are combined with 8-hydroxyquinoline, Acros Organics (1.45 g, 0.01 mol) in 50 ml of absolute EtOH to give the desired Betti condensation product as a white solid (MP 87-90° C.).

Preparation of AD4-13206:

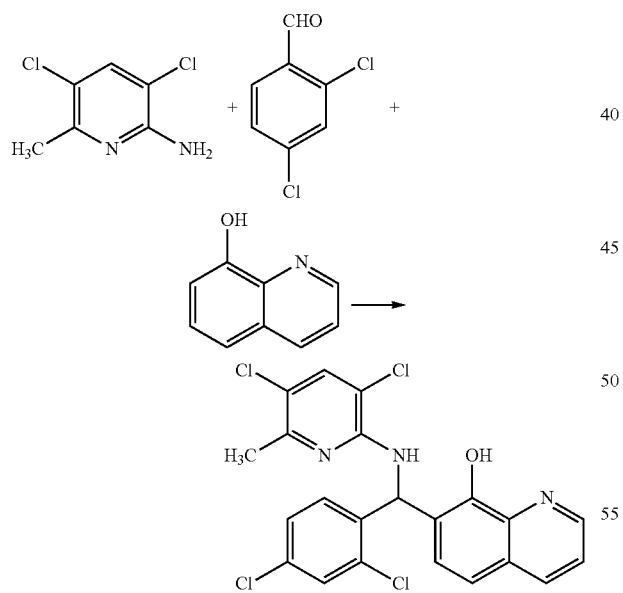

In a manner similar to that described in Example ##.

2-Amino-3,5-dichloro-6-methylpyridine, Matrix Scientific (1.77 g, 0.01 mol) and 2,4-dichlorobenzaldehyde, Acros Organics (1.75 g, 0.01 mol) are combined with 8-hydroxyquinoline, Acros Organics (1.45 g, 0.01 mol) in 50 ml of absolute EtOH to give the desired Betti condensation product as an off-white solid (MP 171-175° C.).

Preparation of AD4-13208:

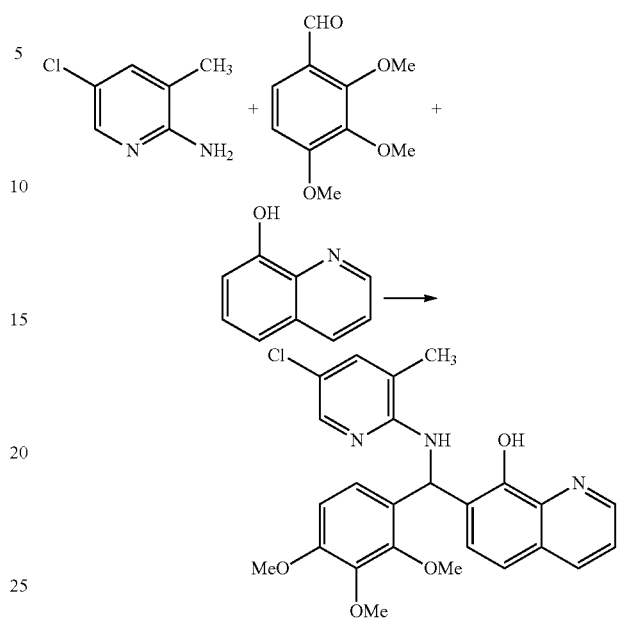

In a manner similar to that described in Example AD4-13021.

2-Amino-3-methyl-5-chloropyridine (BBM-001-071; 1.43 g, 0.01 mol) and 2,3,4-trimethoxybenzaldehyde, Acros Organics (1.96 g, 0.01 mol) are combined with 8-hydroxyquinoline, Acros Organics (1.45 g, 0.01 mol) in 50 ml of absolute EtOH to give the desired Betti condensation product as an off-white solid (MP 178-179° C.).

Preparation of AD4-13209:

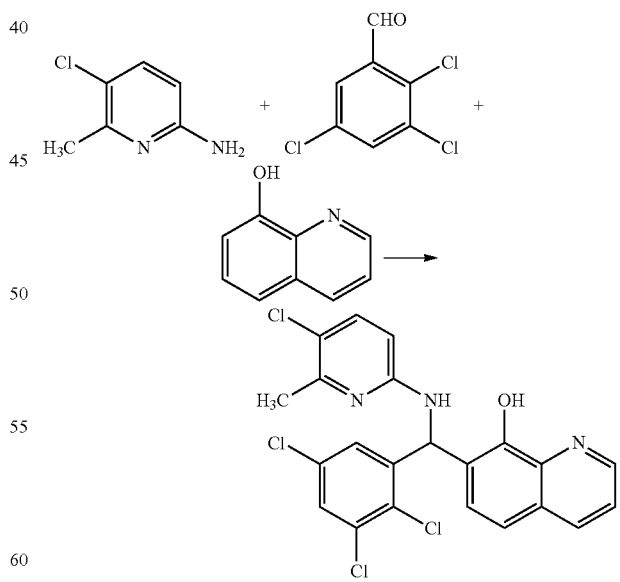

In a manner similar to that described in Example AD4-13021.

2-Amino-5-chloro-6-methylpyridine (IJT-001-090; 1.43 g, 0.01 mol) and 2,3,5-trichlorobenzaldehyde, Acros Organics (2.09 g, 0.01 mol) are combined with 8-hydroxyquinoline, Acros Organics (1.45 g, 0.01 mol) in 50 ml of absolute EtOH to give the desired Betti condensation product as an off-white solid (MP 99-101° C.).

Preparation of AD4-13210:

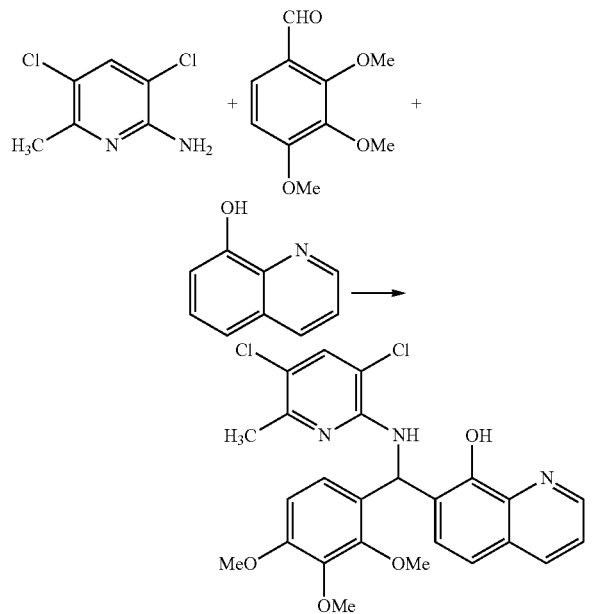

In a manner similar to that described in Example AD4-13021.

2-Amino-3,5-dichloro-6-methylpyridine, Matrix Scientific (1.77 g, 0.01 mol) and 2,3,4-trimethoxybenzaldehyde, Acros Organics (1.96 g, 0.01 mol) are combined with 8-hydroxyquinoline, Acros Organics (1.45 g, 0.01 mol) in 50 ml of absolute EtOH to give the desired Betti condensation product as a light-green solid (MP 135-142° C.).

Preparation of AD4-13211:

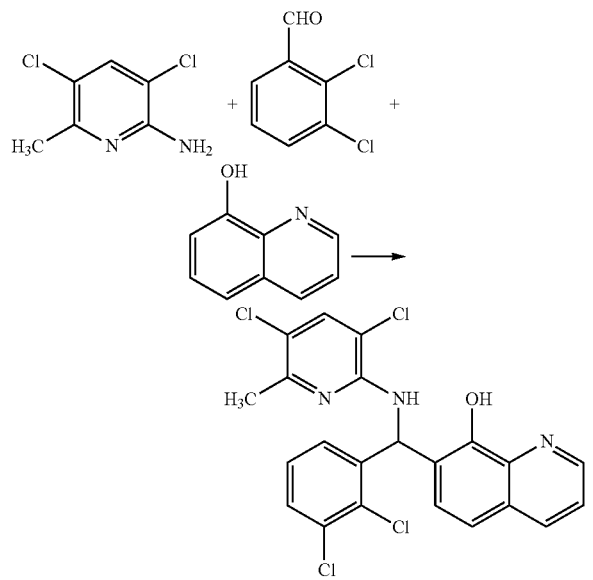

In a manner similar to that described in Example AD4-13021.

2-Amino-3,5-dichloro-6-methylpyridine, Matrix Scientific (1.77 g, 0.01 mol) and 2,3-dichlorobenzaldehyde, Acros Organics (1.75 g, 0.01 mol) are combined with 8-hydroxyquinoline, Acros Organics (1.45 g, 0.01 mol) in 50 ml of absolute EtOH to give the desired Betti condensation product as an off-white solid (MP 211-216° C.).

Preparation of AD4-13212:

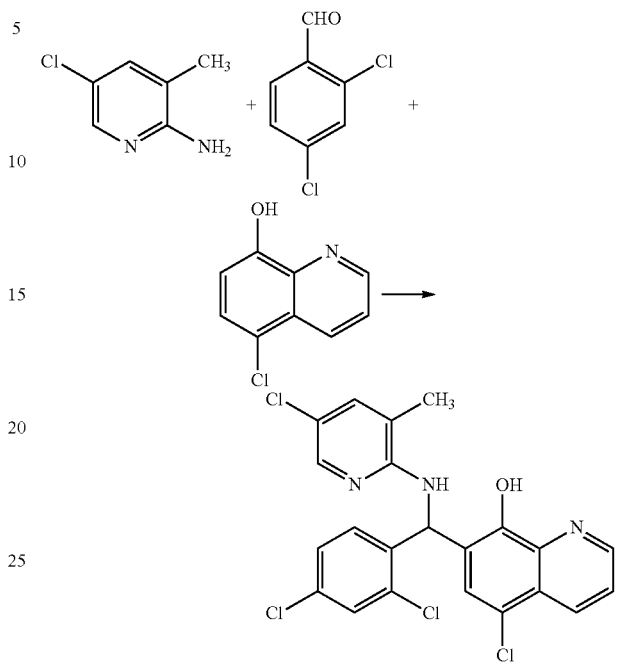

In a manner similar to that described in Example AD4-13021.

2-Amino-3-methyl-5-chloropyridine (BBM-001-071; 1.43 g, 0.01 mol) and 2,4-dichlorobenzaldehyde, Acros Organics (1.75 g, 0.01 mol) are combined with 5-chloro-8-hydroxyquinoline, Acros Organics (1.80 g, 0.01 mol) in 50 ml of absolute EtOH to give the desired Betti condensation product as a light-tan solid (MP 156-158° C.).

Preparation of AD4-13213:

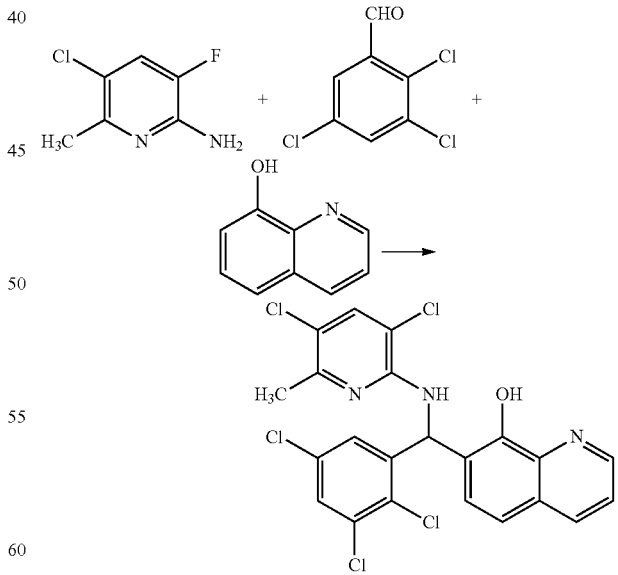

In a manner similar to that described in Example AD4-13021.

2-Amino-3,5-dichloro-6-methylpyridine, Matrix Scientific (1.77 g, 0.01 mol) and 2,3,5-trichlorobenzaldehyde, Acros Organics (2.09 g, 0.01 mol) are combined with 8-hydroxyquinoline, Acros Organics (1.45 g, 0.01 mol) in 50 ml of absolute EtOH to give the desired Betti condensation product as an off-white solid (MP 200-202° C.).

Preparation of AD4-13214:

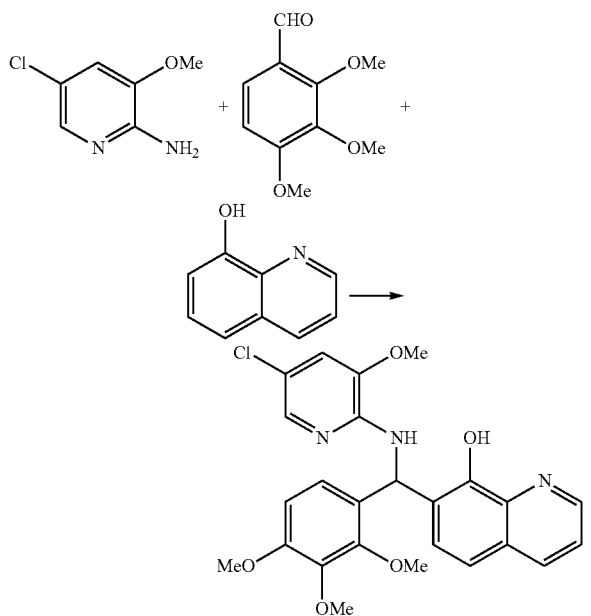

In a manner similar to that described in Example AD4-13021.

2-Amino-3-methoxy-5-chloropyridine (BBM-001-011; 1.59 g, 0.01 mol) and 2,3,4-trimethoxybenzaldehyde, Acros Organics (1.96 g, 0.01 mol) are combined with 8-hydroxyquinoline, Acros Organics (1.45 g, 0.01 mol) in 50 ml of absolute EtOH to give the desired Betti condensation product as a light-yellow solid (MP 82-86° C.).

Preparation of AD4-13215:

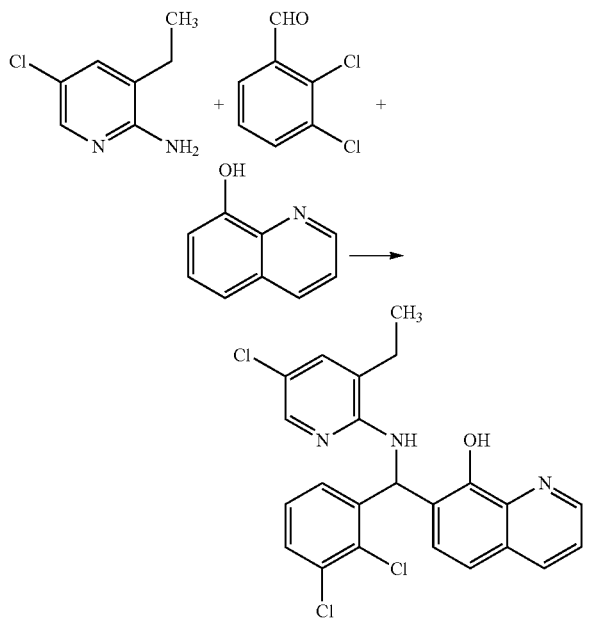

In a manner similar to that described in Example AD4-13021.

2-Amino-3-ethyl-5-chloropyridine (BBM-001-072; 1.57 g, 0.01 mol) and 2,3-dichlorobenzaldehyde, Acros Organics (1.75 g, 0.01 mol) are combined with 8-hydroxyquinoline, Acros Organics (1.45 g, 0.01 mol) in 50 ml of absolute EtOH to give the desired Betti condensation product as an off-white solid (MP 160-163° C.).

Preparation of AD4-13216:

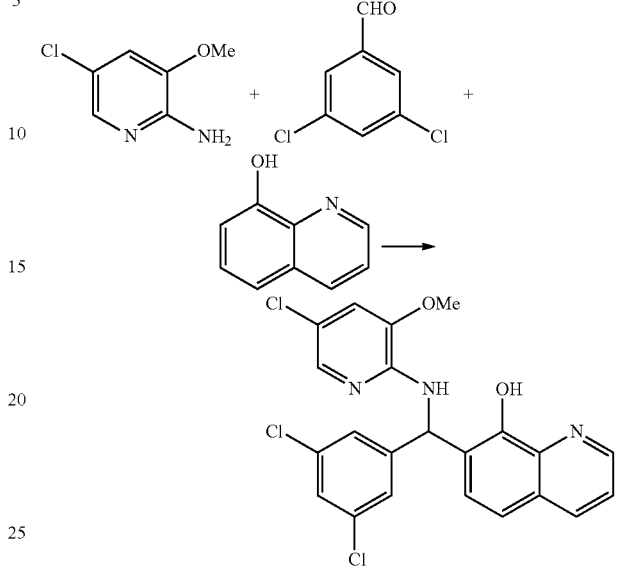

In a manner similar to that described in Example AD4-13021.

2-Amino-3-methoxy-5-chloropyridine (BBM-001-011; 1.59 g, 0.01 mol) and 3,5-dichlorobenzaldehyde, Matrix Scientific (1.75 g, 0.01 mol) are combined with 8-hydroxyquinoline, Acros Organics (1.45 g, 0.01 mol) in 50 ml of absolute EtOH to give the desired Betti condensation product as a light-yellow solid (MP 180-183° C.).

Preparation of AD4-13217:

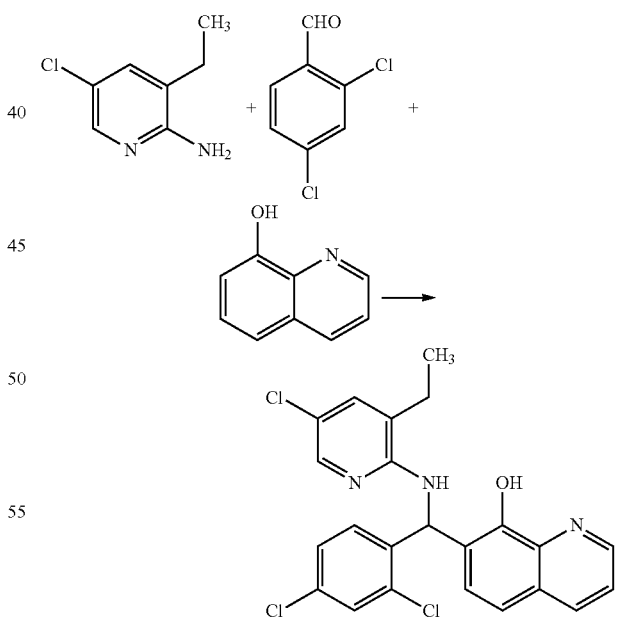

In a manner similar to that described in Example AD4-13021.

2-Amino-3-ethyl-5-chloropyridine (BBM-001-072; 1.57 g, 0.01 mol) and 2,4-dichlorobenzaldehyde, Acros Organics (1.75 g, 0.01 mol) are combined with 8-hydroxyquinoline, Acros Organics (1.45 g, 0.01 mol) in 50 ml of absolute EtOH to give the desired Betti condensation product as a light-green solid (MP 170-171° C.).

Preparation of AD4-13218:

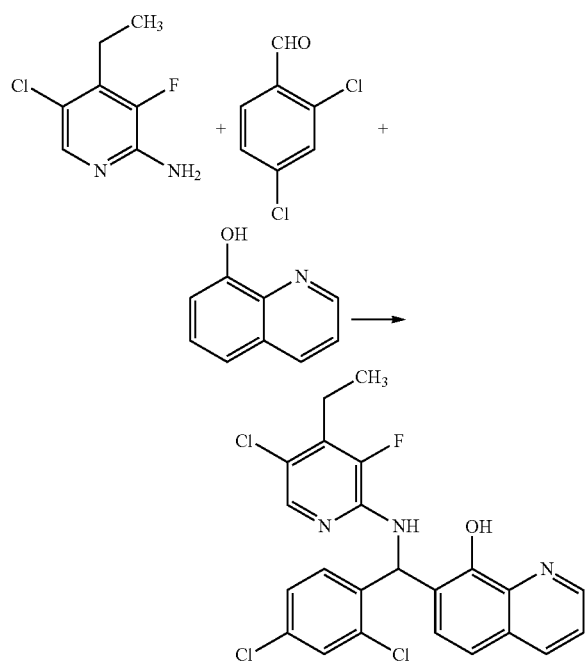

In a manner similar to that described in Example AD4-13021.

2-Amino-3-fluoro-4-ethyl-5-chloropyridine (BBM-001-074; 1.75 g 0.01 mol) and 2,4-dichlorobenzaldehyde, Acros Organics (1.75 g, 0.01 mol) are combined with 8-hydroxyquinoline, Acros Organics (1.45 g, 0.01 mol) in 50 ml of absolute EtOH to give the desired Betti condensation product as a light-yellow solid (MP 62-70° C.).

Preparation of AD4-13219:

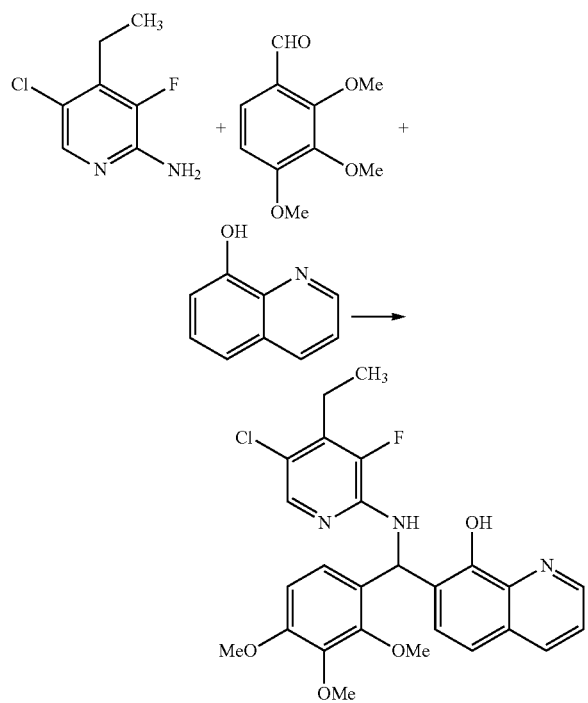

In a manner similar to that described in Example AD4-13021.

2-Amino-3-fluoro-4-ethyl-5-chloropyridine (BBM-001-074; 1.75 g 0.01 mol) and 2,3,4-trimethoxybenzaldehyde, Acros Organics (1.96 g, 0.01 mol) are combined with 8-hydroxyquinoline, Acros Organics (1.45 g, 0.01 mol) in 50 ml of absolute EtOH to give the desired Betti condensation product as a green oil.

Preparation of AD4-13220:

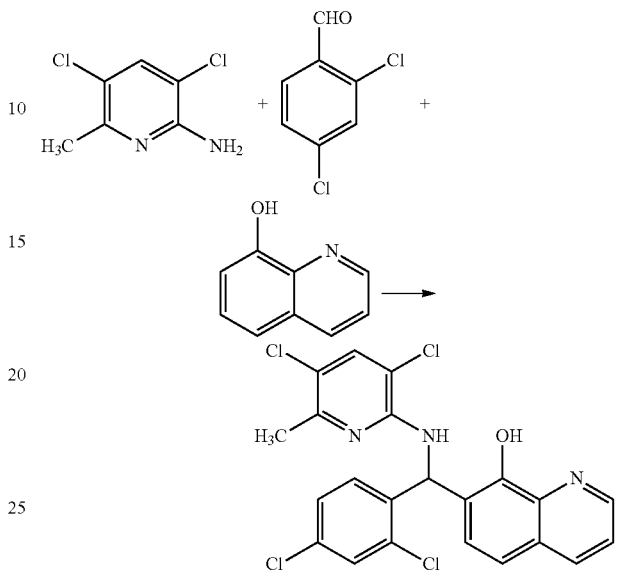

In a manner similar to that described in Example AD4-13021.

2-Amino-3,5-dichloro-6-methylpyridine, Matrix Scientific (1.77 g, 0.01 mol) and 2,5-dichlorobenzaldehyde, Acros Organics (1.75 g, 0.01 mol) are combined with 8-hydroxyquinoline, Acros Organics (1.45 g, 0.01 mol) in 50 ml of absolute EtOH to give the desired Betti condensation product as an off-white solid (MP 58-62° C.).

Preparation of AD4-13221:

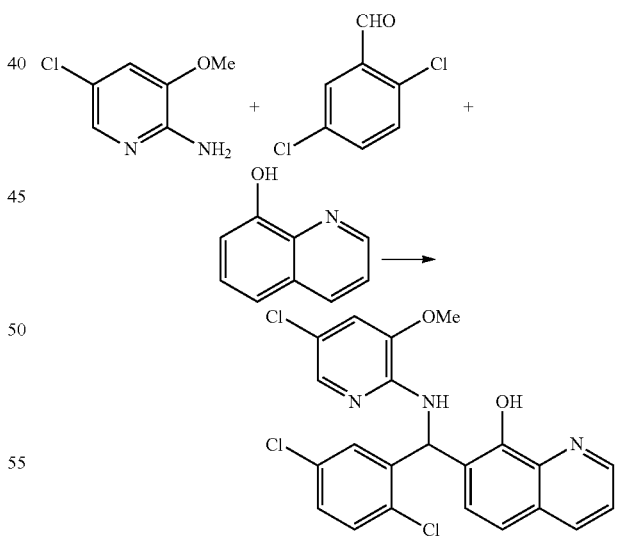

In a manner similar to that described in Example AD4-13021.

2-Amino-3-methoxy-5-chloropyridine (BBM-001-011; 1.59 g, 0.01 mol) and 2,5-dichlorobenzaldehyde, Matrix Scientific (1.75 g, 0.01 mol) are combined with 8-hydroxyquinoline, Acros Organics (1.45 g, 0.01 mol) in 50 ml of absolute EtOH to give the desired Betti condensation product as a light-tan solid (MP 250-267° C.).

Preparation of AD4-13222:

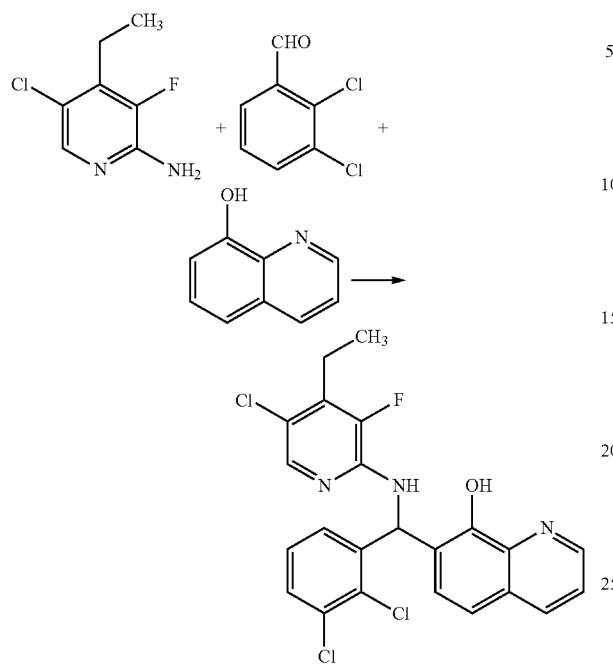

In a manner similar to that described in Example AD4-13021.

2-Amino-3-fluoro-4-ethyl-5-chloropyridine (BBM-001-074; 1.75 g 0.01 mol) and 2,3-dichlorobenzaldehyde, Acros Organics (1.75 g, 0.01 mol) are combined with 8-hydroxyquinoline, Acros Organics (1.45 g, 0.01 mol) in 50 ml of absolute EtOH to give the desired Betti condensation product as a light-tan solid (MP 73-79° C.).

Preparation of AD4-13223:

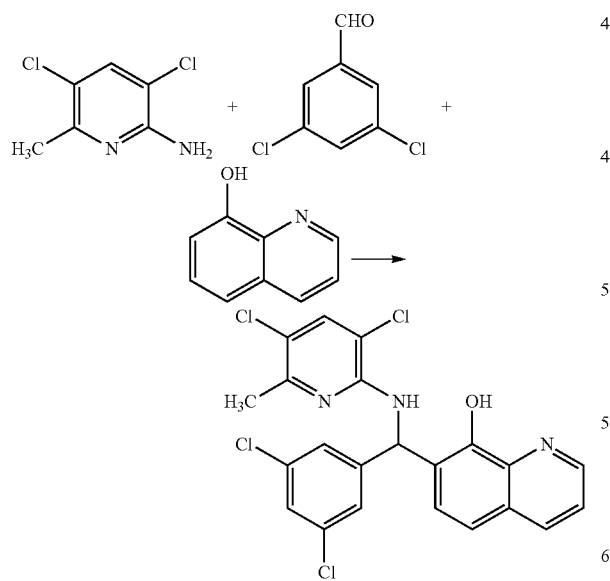

In a manner similar to that described in Example AD4-13021.

2-Amino-3,5-dichloro-6-methylpyridine, Matrix Scientific (1.77 g, 0.01 mol) and 3,5-dichlorobenzaldehyde, Acros Organics (1.75 g, 0.01 mol) are combined with 8-hydroxyquinoline, Acros Organics (1.45 g, 0.01 mol) in 50 ml of absolute EtOH to give the desired Betti condensation product as an off-white solid (MP 128-130° C.).

Preparation of AD4-13224:

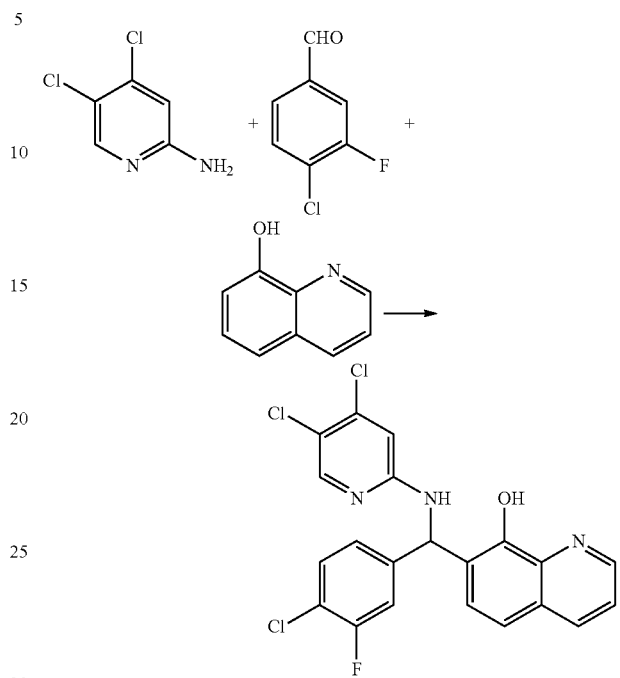

In a manner similar to that described in Example AD4-13021.

2-Amino-4,5-dichloropyridine (BBM-001-049; 1.63 g, 0.01 mol) and 3-fluoro-4-chlorobenzaldehyde, Oakwood Products, (1.59 g 0.01 mol) are combined with 8-hydroxyquinoline, Acros Organics (1.45 g, 0.01 mol) in 50 ml of absolute EtOH to give the desired Betti condensation product as a light-grey solid (MP 106-110° C.).

Preparation of AD4-13225:

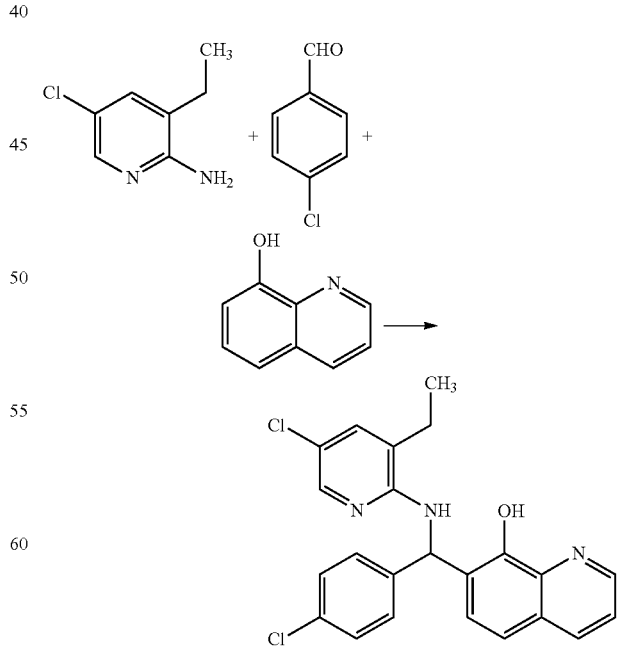

In a manner similar to that described in Example AD4-13021.

2-Amino-3-ethyl-5-chloropyridine (BBM-001-072; 1.57 g, 0.01 mol) and 4-chlorobenzaldehyde, Acros Organics (1.41 g, 0.01 mol) are combined with 8-hydroxyquinoline, Acros Organics (1.45 g, 0.01 mol) in 50 ml of absolute EtOH to give the desired Betti condensation product as a light-gray solid (MP 108-111° C.).

Preparation of AD4-13226:

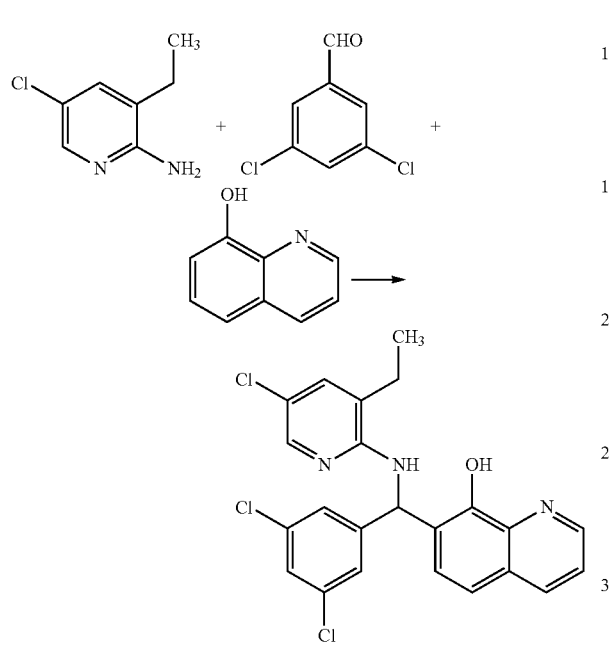

In a manner similar to that described in Example AD4-13021.

2-Amino-3-ethyl-5-chloropyridine (BBM-001-072; 1.57 g, 0.01 mol) and 3,5-dichlorobenzaldehyde, Matrix Scientific (1.75 g, 0.01 mol) are combined with 8-hydroxyquinoline, Acros Organics (1.45 g, 0.01 mol) in 50 ml of absolute EtOH to give the desired Betti condensation product as an off-white solid (MP 145-147° C.).

Preparation of AD4-13227:

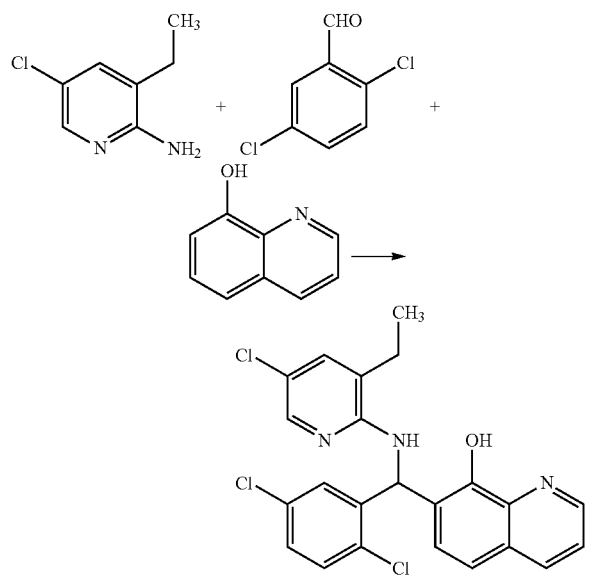

In a manner similar to that described in Example AD4-13021.

2-Amino-3-ethyl-5-chloropyridine (BBM-001-072; 1.57 g, 0.01 mol) and 2,5-dichlorobenzaldehyde, Matrix Scientific (1.75 g, 0.01 mol) are combined with 8-hydroxyquinoline, Acros Organics (1.45 g, 0.01 mol) in 50 ml of absolute EtOH to give the desired Betti condensation product as a light-grey solid (MP 65-69° C.).

Preparation of AD4-13228:

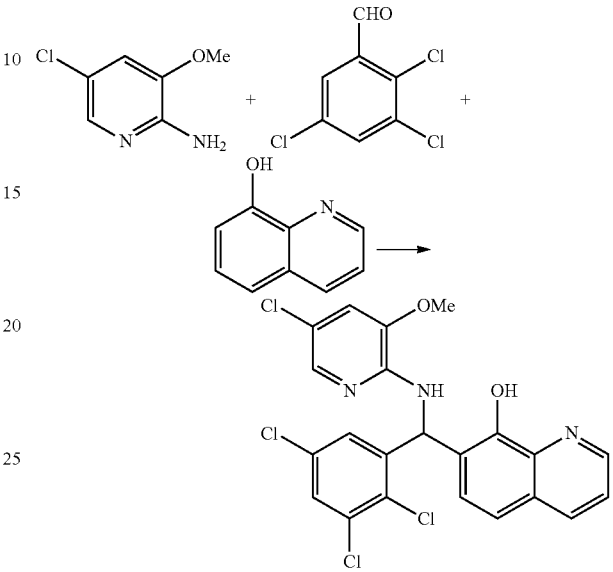

In a manner similar to that described in Example AD4-13021.

2-Amino-3-methoxy-5-chloropyridine, (BBM-001-011; 1.59 g, 0.01 mol) and 2,3,5-trichlorobenzaldehyde, Acros Organics (2.09 g, 0.01 mol) are combined with 8-hydroxyquinoline, Acros Organics (1.45 g, 0.01 mol) in 50 ml of absolute EtOH to give the desired Betti condensation product as a tan (MP 187-190° C.).

Preparation of AD4-13229:

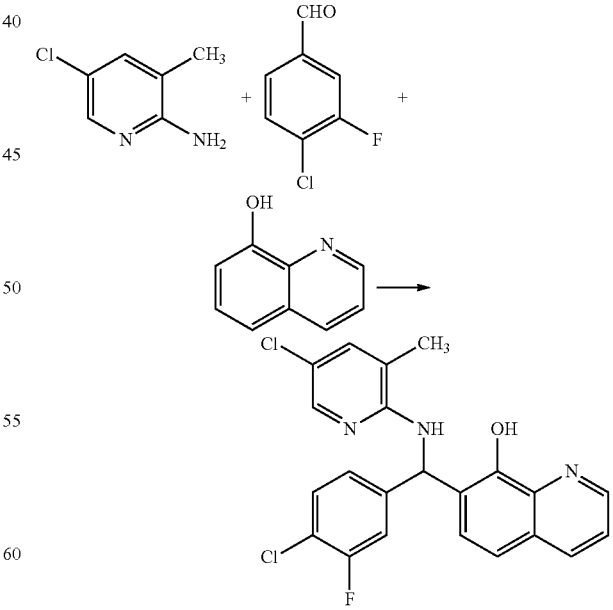

In a manner similar to that described in Example AD4-13021.

2-Amino-3-methyl-5-chloropyridine (BBM-001-071; 1.43 g, 0.01 mol) and 3-fluoro-4-chlorobenzaldehyde, Oakwood Products, (1.59 g 0.01 mol) are combined with 8-hydroxyquinoline, Acros Organics (1.45 g, 0.01 mol) in 50 ml of absolute EtOH to give the desired Betti condensation product as a tan (MP 79-85° C.).

Preparation of AD4-13230:

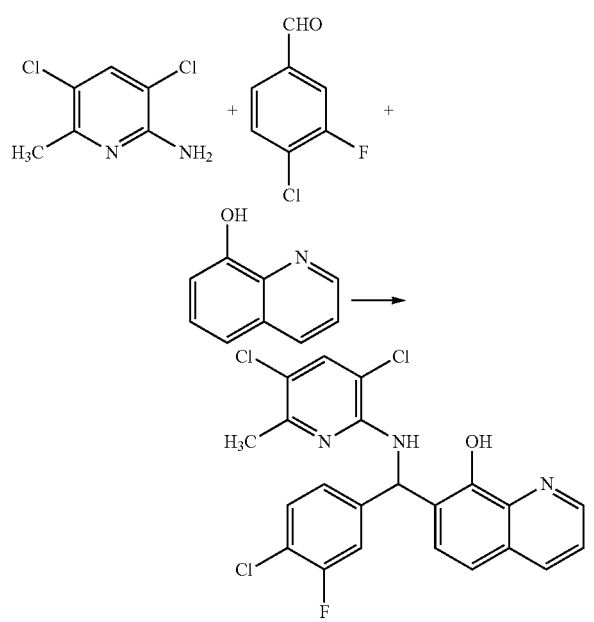

In a manner similar to that described in Example AD4-13021.

2-Amino-3,5-dichloro-6-methylpyridine, Matrix Scientific (1.77 g, 0.01 mol) and 3-fluoro-4-chlorobenzaldehyde, Oakwood Products, (1.59 g 0.01 mol) are combined with 8-hydroxyquinoline, Acros Organics (1.45 g, 0.01 mol) in 50 ml of absolute EtOH to give the desired Betti condensation product as a white solid (MP 101-108° C.).

Preparation of AD4-13231:

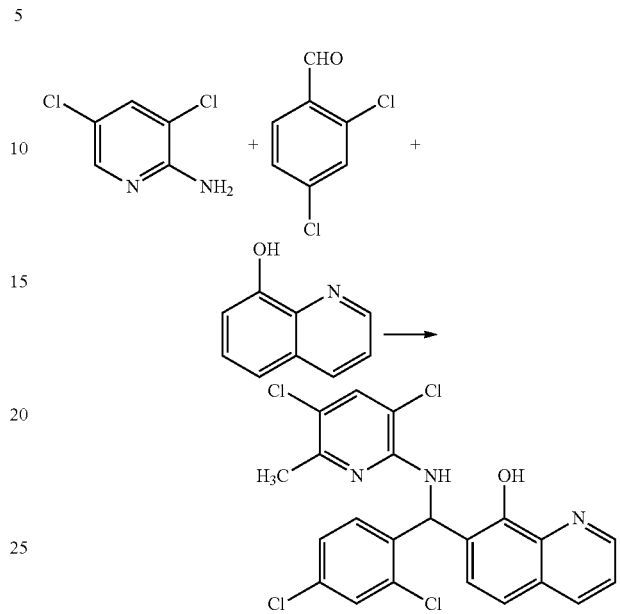

In a manner similar to that described in Example AD4-13021.

2-Amino-3,5-dichloropyridine, Wonda Science (1.63 g, 0.01 mol) and 2,4-dichlorobenzaldehyde, Acros Organics (1.75 g, 0.01 mol) are combined with 8-hydroxyquinoline, Acros Organics (1.45 g, 0.01 mol) in 50 ml of absolute EtOH to give the desired Betti condensation product as a white solid (MP 126-127° C.).

---

What is claimed is:

1. A compound having a formula of:

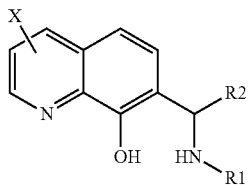

Formula (2)

or a stereoisomer or pharmaceutically acceptable salt thereof;

wherein,

X is selected from the group consisting of: hydrogen, 2-Methyl, 5-Chloro, 5-Nitro, and 6-Hydroxyl;

$R^1$ is selected from the group consisting of:

(i) a 2-Pyridyl ring of Formula (3)

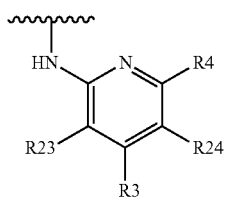

Formula (3)

wherein $R^{23}$ is selected from the group consisting of hydrogen; fluoro; chloro; trifluoromethyl; methyl; ethyl; and methoxy;

$R^3$ is selected from the group consisting of hydrogen; fluoro; chloro; methyl; ethyl; methoxy; a straight chain or branched C-1 to C-4 lower alkyl optionally containing unsaturation; a C-2 to C-6 cycloalkyl optionally containing unsaturation or one oxygen or nitrogen atom; aryl comprising a phenyl or heteroaryl five or six membered ring containing from 1 to 4 N, O, or S atoms; and alkoxy —$OR^{10}$ where $R^{10}$ is a straight chain or branched C-1 to C-4 lower alkyl optionally containing unsaturation or a C-2 to C-6 cycloalkyl optionally containing unsaturation or one oxygen or nitrogen atom;

$R^{24}$ is selected from the group consisting of: hydrogen; fluoro; chloro; and trifluoromethyl; and $R^4$ is selected from the group consisting of hydrogen; methyl; a straight chain or branched C-1 to C-4 lower alkyl optionally containing unsaturation; a C-2 to C-6 cycloalkyl optionally containing unsaturation or one oxygen or nitrogen atom; aryl comprising a phenyl or heteroaryl five or six membered ring containing from 1 to 4 N, O, or S atoms; and alkoxy —$OR^{10}$ where $R^{10}$ is a straight chain or branched C-1 to C-4 lower alkyl optionally containing unsaturation or a C-2 to C-6 cycloalkyl optionally containing unsaturation or one oxygen or nitrogen atom;

(ii) a 3-Pyridyl ring of Formula (4)

Formula (4)

wherein $R^5$, $R^6$, and $R^7$ are independently selected from the group consisting of: hydrogen, a straight chain or branched C-1 to C-4 lower alkyl optionally containing unsaturation; a C-2 to C-6 cycloalkyl optionally containing unsaturation or one oxygen or nitrogen atom; Aryl comprising a phenyl or heteroaryl containing from 1 to 4 N, O, or S atoms; and alkoxy —$OR^{10}$ where $R^{10}$ is a straight chain or branched C-1 to C-4 lower alkyl optionally containing unsaturation or a C-2 to C-6 cycloalkyl optionally containing unsaturation or one oxygen or nitrogen atom; and (iii) a 4-Pyridyl ring of Formula (5)

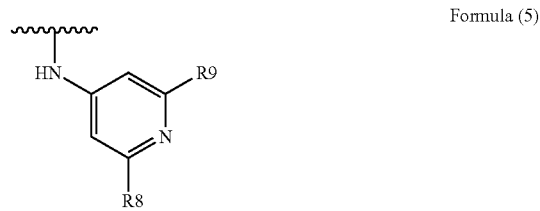

Formula (5)

wherein $R^8$ and $R^9$ are independently selected from the group consisting of: a straight chain or branched C-1 to C-4 lower alkyl optionally containing unsaturation; a C-2 to C-6 cycloalkyl optionally containing unsaturation or one oxygen or nitrogen atom; aryl comprising a phenyl or heteroaryl containing from 1 to 4 N, O, or S atoms; and alkoxy —$OR^{10}$ where $R^{10}$ is a straight chain or branched C-1 to C-4 lower alkyl optionally containing unsaturation or a C-2 to C-6 cycloalkyl optionally containing unsaturation or one oxygen or nitrogen atom; and $R^2$ is selected from the group consisting of:
(i) an unsubstituted phenyl ring or a phenyl ring substituted at the 2-, 3-, 4-, 5- or 6-position with one or more groups independently selected from the group consisting of: straight chain or branched C-1 to C-4 lower alkyl optionally containing unsaturation; C-2 to C-6 cycloalkyl optionally containing unsaturation or one oxygen or nitrogen atom; aryl comprising a phenyl or heteroaryl five or six membered ring containing from 1 to 4 N, O, or S atoms; alkoxy —$OR^{10}$ where $R^{10}$ is a straight chain or branched C-1 to C-4 lower alkyl optionally containing unsaturation or a C-2 to C-6 cycloalkyl optionally containing unsaturation or one oxygen or nitrogen atom; 2,3-methylenedioxy; 3,4-methylenedioxy; dialkylamino having formula —$NR_{13}R_{14}$ wherein $R_{13}$ and $R_{14}$ are independently selected from hydrogen or a straight chain or branched C-1 to C-4 lower alkyl optionally containing unsaturation; trifluoromethyl; trifluoromethoxy; difluoromethoxy; 3,4-methylenedioxy; 2,3-methylenedioxy; nitro; and halogen;
wherein if $R^1$ is a 3-Pyridyl ring of Formula (4) where each of $R^5$, $R^6$, and $R^7$ are hydrogen, and $R^2$ is a phenyl ring, the phenyl ring is substituted with one or more groups independently selected from the group consisting of: a straight chain or branched C-1 to C-4 lower alkyl optionally containing unsaturation; C-2 to C-6 cycloalkyl optionally containing unsaturation or one oxygen or nitrogen atom; a heteroaryl five or six membered ring containing from 1 to 4 N, O, or S atoms; alkoxy —$OR^{10}$ where $R^{10}$ is a straight chain or branched C-1 to C-4 lower alkyl optionally containing unsaturation or a C-2 to C-6 cycloalkyl optionally containing unsaturation or one oxygen or nitrogen atom; 2,3-methylenedioxy; 3,4-methylenedioxy; dialkylamino having formula —$NR_{13}R_{14}$ wherein $R_{13}$ and $R_{14}$ are independently selected from hydrogen or a straight chain or branched C-1 to C-4 lower alkyl optionally containing unsaturation; trifluoromethoxy; difluoromethoxy; 3,4-methylenedioxy; 2,3-methylenedioxy; and nitro;
(ii) a 2-Pyridyl ring substituted at 4- or 6-position of the pyridine ring with one or more groups independently selected from the group consisting of: straight chain or branched C-1 to C-4 lower alkyl optionally containing unsaturation and C-2 to C-6 cycloalkyl optionally containing unsaturation or one oxygen or nitrogen atom;
(iii) an unsubstituted 3-Pyridyl ring or a 3-Pyridyl ring substituted at the 2-, 4- or 6-position of the pyridine ring with one or more groups independently selected from the group consisting of: straight chain or branched C-1 to C-4 lower alkyl optionally containing unsaturation and C-2 to C-6 cycloalkyl optionally containing unsaturation or one oxygen or nitrogen atom; and
(iv) an unsubstituted 4-Pyridyl ring or a 4-Pyridyl ring substituted at the 2- or 6-position of the pyridine ring with one or more groups independently selected from the group consisting of: straight chain or branched C-1 to C-4 lower alkyl optionally containing unsaturation and C-2 to C-6 cycloalkyl optionally containing unsaturation or one oxygen or nitrogen atom;
wherein if each of $R^3$, $R^4$, $R^{23}$, and $R^{24}$ is hydrogen, then $R^2$ is a substituted pyridyl ring or a phenyl substituted with straight chain or branched C-3 to C-4 lower alkyl optionally containing unsaturation; C-2 to C-6 cycloalkyl optionally containing unsaturation or one oxygen or nitrogen atom; aryl comprising a phenyl or heteroaryl five or six membered ring containing from 1 to 4 N, O, or S atoms; alkoxy —$OR^{10}$ where $R^{10}$ is a straight chain or branched C-3 to C-4 lower alkyl optionally containing unsaturation or a C-2 to C-6 cycloalkyl optionally containing unsaturation or one oxygen or nitrogen atom; 2,3-methylenedioxy; 3,4-methylenedioxy; dialkylamino having formula —$NR_{13}R_{14}$ wherein $R_{13}$ and $R_{14}$ are independently selected from hydrogen or a straight chain or branched C-1 to C-4 lower alkyl optionally containing unsaturation; trifluoromethoxy; difluoromethoxy; 3,4-methylenedioxy; 2,3-methylenedioxy; or nitro;
wherein if one of $R^3$, $R^4$, $R^{23}$, or $R^{24}$ is methyl and the other three of $R^3$, $R^4$, $R^{23}$, or $R^{24}$ are hydrogen, then $R^2$ is a substituted pyridyl ring or a phenyl substituted with straight chain or branched C-3 to C-4 lower alkyl optionally containing unsaturation; C-2 to C-6 cycloalkyl optionally containing unsaturation or one oxygen or nitrogen atom; aryl comprising a phenyl or heteroaryl five or six membered ring containing from 1 to 4 N, O, or S atoms; 2,3-methylenedioxy; 3,4-methylenedioxy; dialkylamino having formula —$NR_{13}R_{14}$ wherein $R_{13}$ and $R_{14}$ are independently selected from hydrogen or a straight chain or branched C-1 to C-4 lower alkyl optionally containing unsaturation; trifluoromethyl; trifluoromethoxy; difluoromethoxy; 3,4-methylenedioxy; or 2,3-methylenedioxy; or a stereoisomer or pharmaceutically acceptable salt thereof; and Formula (2) excludes the compound of Formula (1):

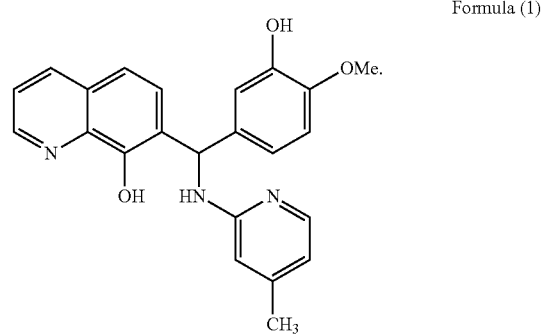 [SMILES: COc1ccc(C(Nc2cc(C)ccn2)c2ccc3cccnc3c2O)cc1O]

Formula (1)

2. The compound of claim 1 wherein $R^1$ is a 2-pyridyl ring of Formula (3) and:
$R^{24}$ is chloro; or
$R^{23}$ is methyl.

3. The compound of claim 1 wherein $R^1$ is a 2-pyridyl ring of Formula (3) and:
  $R^4$ is hydrogen, $R^{24}$ is fluoro, $R^3$ is hydrogen, and $R^{23}$ is fluoro;
  $R^4$ is methyl, $R^{24}$ is chloro, $R^3$ is hydrogen, and $R^{23}$ is fluoro;
  $R^4$ is hydrogen, $R^{24}$ is chloro, $R^3$ is ethyl, and $R^{23}$ is fluoro;
  $R^4$ is hydrogen, $R^{24}$ is fluoro, $R^3$ is methyl, and $R^{23}$ is fluoro;
  $R^4$ is hydrogen, $R^{24}$ is chloro, $R^3$ is hydrogen, and $R^{23}$ is ethyl;
  $R^4$ is methyl, $R^{24}$ is chloro, $R^3$ is hydrogen, and $R^{23}$ is chloro;
  $R^4$ is hydrogen, $R^{24}$ is chloro, $R^3$ is methyl, and $R^{23}$ is fluoro;
  $R^4$ is hydrogen, $R^{24}$ is trifluoromethyl, $R^3$ is hydrogen, and $R^{23}$ is hydrogen;
  $R^4$ is hydrogen, $R^{24}$ is chloro, $R^3$ is hydrogen, and $R^{23}$ is methyl;
  $R^4$ is hydrogen, $R^{24}$ is chloro, $R^3$ is hydrogen, and $R^{23}$ is chloro;
  $R^4$ is hydrogen, $R^{24}$ is chloro, $R^3$ is methyl, and $R^{23}$ is hydrogen; or
  $R^4$ is hydrogen, $R^{24}$ is chloro, $R^3$ is chloro, and $R^{23}$ is hydrogen.

4. The compound of claim 1, wherein $R^1$ is a 2-pyridyl ring of Formula (3) and:
  $R^{24}$ is chloro and $R^3$ is chloro or methyl or $R^{23}$ is chloro or methyl;
  $R^{24}$ is chloro, $R^3$ is hydrogen, and $R^{23}$ is methyl;
  $R^{24}$ is chloro, $R^3$ is methyl, and $R^{23}$ is fluoro;
  $R^{24}$ is chloro, $R^3$ is chloro, and $R^{23}$ is hydrogen;
  $R^{24}$ is chloro, $R^3$ is hydrogen, and $R^{23}$ is chloro.

5. The compound of claim 1 wherein $R^2$ is selected from the group consisting of:
  a phenyl ring substituted at the 2- and 4-positions;
  4-trifluoromethylphenyl;
  2-fluoro,4-trifluoromethylphenyl; and
  2,4-dichlorophenyl.

6. The compound of claim 1 wherein $R^2$ is selected from the group consisting of: 4-chlorophenyl; 2-fluoro,4-trifluoromethylphenyl; 3-fluoro,4-chlorophenyl; 2-fluoro,4-chlorophenyl; 2,3-dichlorophenyl; 2,3,5-trichlorophenyl; 2,4-dichlorophenyl; 3,4-dichlorophenyl; and 3,5-dichlorophenyl.

7. The compound of claim 1 wherein $R^2$ is selected from the group consisting:
  a phenyl ring substituted at the 4 position with chloro and substituted at the 2- or 3-position with chloro or fluoro;
  2,4-dichlorophenyl; and
  2-chloro,4-fluorophenyl.

8. The compound of claim 1 wherein Formula (2) is not one or more of the following compounds:

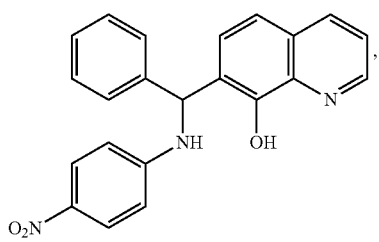

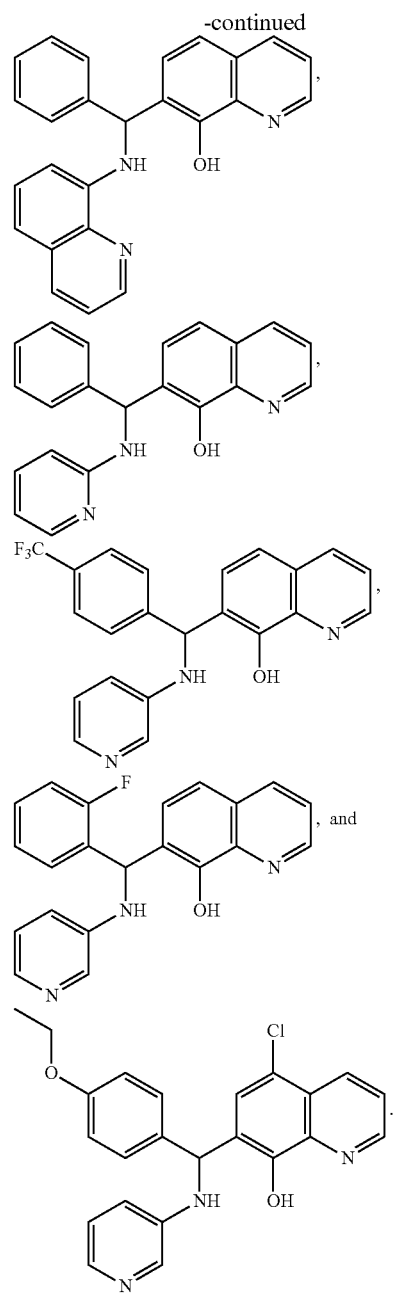

9. The compound of claim 1 that inhibits EGFR activity comprising:
  six or more of functional groups F(I)1, F(I)2, F(I)3, F(I)4, F(I)5, F(I)6, F(I)7, F(I)8, and F(I)9 of a Scheme 11505-like pharmacophore;
  wherein
    functional group F(I)1 donates an H-bond or forms a salt bridge to a carboxylate side chain of receptor Asp553 of SEQ ID NO: 1 and has coordinates of r=56.363, θ (theta)=94.368, and φ (phi)=−17.752 and a spherical radius of about 1.2 Å;
    functional group F(I)2 donates an H-bond to backbone carbonyl of receptor Thr570 of SEQ ID NO: 1 and has coordinates of r=53.290, θ (theta)=101.494, and φ (phi)=−23.244 and a spherical radius of about 1.0 Å;
    functional group F(I)3 forms a hydrophobic contact with a side chain of receptor Val568, an imidazole side chain of receptor His566, and an imidazolidine ring of receptor Pro552 of SEQ ID NO: 1 and has coordinates of r=53.726, θ (theta)=97.830, and φ (phi)=−18.378 and a spherical radius of about 1.7 Å;

functional group F(I)4 donates an H-bond or forms a salt bridge to the side chain carboxylate of receptor Asp563 of SEQ ID NO: 1 and has coordinates of r=56.103, θ (theta)=99.536, and φ (phi)=−21.080 and a spherical radius of about 1.2 Å;

functional group F(I)5 forms a hydrophobic contact with an imidazoline ring of receptor Pro572 and a side chain of Met253 of SEQ ID NO: 1 and has coordinates of r=53.647, θ (theta)=103.844, and φ (phi)=−20.990 and a spherical radius of about 1.4 Å;

functional group F(I)6 donates an H-bond to a backbone carbonyl of receptor Cys571 of SEQ ID NO: 1 and has coordinates of r=51.088, θ (theta)=104.241, and φ (phi)=−25.552 and a spherical radius of about 1.2 Å;

functional group F(I)7 donates an H-bond to a backbone carbonyl of receptor Cys571 of SEQ ID NO: 1 and has coordinates of r=52.340, θ (theta)=103.980, and φ (phi)=−27.461 and a spherical radius of about 1.5 Å;

functional group F(I)8 accepts an H-bond from receptor backbone NH of Ala573 of SEQ ID NO: 1 and has coordinates of r=51.383, θ (theta)=106.455, and φ (phi)=−24.319 and a spherical radius of about 1.2 Å;

functional group F(I)9 accepts an H-bond from receptor backbone NH of Ala573 of SEQ ID NO: 1 and has coordinates of r=52.861, θ (theta)=107.692, and φ (phi)=−25.447 and a spherical radius of about 1.5 Å; and the compound substantially maintains a non-extended tether inactive configuration of EGFR or substantially prevents stabilization of an extended tether active configuration of EGFR.

10. A method for forming a compound of claim 1, comprising:
combining an amino pyridine intermediate compound, an aldehyde intermediate compound, and a hydroxyquinoline intermediate compound in ethanol under conditions sufficient to form a compound of claim 1;
wherein,
the amino pyridine intermediate compound comprises $R^2$—CHO, where $R^2$ is as defined in claim 1;
the aldehyde intermediate compound comprises $R^1$—NH$_2$, where $R^1$ is as defined in claim 1; and
the hydroxyquinoline intermediate compound comprises 8-hydroxyquinoline, optionally substituted with X, where X is as defined in claim 1.

11. The method of claim 10, wherein the aminopyridine intermediate compound is selected from the group consisting of 2-Amino-3-methoxy-5-chloropyridine; 2-Amino-4,5-dichloropyridine; 2-Amino-5-chloro-6-methylpyridine; 2-Amino-5-chloro-3-methylpyridine; 2-Amino-3,5-dichloro-4-methylpyridine; 2-Amino-3,5-dichloro-4,6-dimethylpyridine; 2-Amino-3-fluoro-4-methyl-5-chloropyridine; 2-Amino-3-ethyl-5-chloropyridine; 2-Amino-3-fluoro-4-ethyl-5-chloropyridine; and 2-Amino-4-methyl-3,5-difluoropyridine, or an aminopyridine compound formed according to claim 18.

12. The method of claim 10, wherein the aminopyridine intermediate compound is formed by a method comprising:
(i) combining a substituted or unsubstituted 2-aminopyridine and N-chlorosuccinimide in a solvent comprising ethylacetate or dimethylformamide under conditions sufficient to form a 2-amino-5-chloropyridine derivative; or (ii) combining acetic anhydride in glacial acetic acid and a 2-aminopyridine substituted at 3-position and 5-position with fluoro, chloro, or bromo to form a corresponding acetamide derivative; combining the acetamide derivative and diisopropyl amine and butyllithium in tetrahydrofuran at about −70° C. to deprotonate the acetamide derivative; combining the deprotonated acetamide derivative and a lower alkyl halide to alkylate the 4-position of the acetamide derivative; combining the alkylated acetamide derivative and a concentrated hydrochloric acid in a methanol solvent at about 50° C. to remove the acetamide group and form a 2-amino-3,5-dihalo-4-alkylaminopridine.

13. The method of claim 12, wherein
(i) the 2-aminopyridine of reaction (i) comprises Formula (12), wherein $R^{23}$, $R^3$, and $R^4$ are as defined in claim 1 and $R^{24}$ is hydrogen; and the 2-amino-5-chloropyridine derivative comprises Formula (12), wherein $R^{23}$, $R^3$, and $R^4$ are the same as for the 2-aminopyridine and $R^{24}$ is chloro; or
(ii) the substituted 2-aminopyridine comprises Formula (12), wherein $R^{23}$ is fluoro, chloro, or bromo; $R^3$ is hydrogen; $R^4$ is as defined in claim 1; and $R^{24}$ is fluoro, chloro, or bromo;

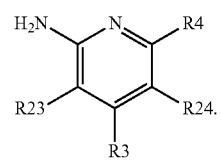

Formula (12)

14. The method of claim 12, wherein the amino pyridine compound is selected from the group consisting of:
2-Amino-3-fluoro-4-methyl-5-chloropyridine;
2-Amino-3-ethyl-5-chloropyridine;
2-Amino-3-fluoro-4-ethyl-5-chloropyridine; and
2-Amino-4-methyl-3,5-difluoropyridine.

15. The compound of claim 1, wherein $R^1$ is a 2-Pyridyl ring of Formula (3) and at least one of $R^3$, $R^{23}$, or $R^{24}$ is fluoro or chloro.

16. The compound of claim 1, wherein $R^1$ is a 2-Pyridyl ring of Formula (3) and at least two of $R^3$, $R^{23}$, or $R^{24}$ is fluoro or chloro.

17. The compound of claim 16, wherein $R^1$ is a 2-Pyridyl ring of Formula (3) and at least one of $R^{23}$ or $R^{24}$ is fluoro or chloro.

18. The compound of claim 16, wherein $R^{24}$ is chloro.

19. The compound of claim 1, wherein $R^1$ is a 2-Pyridyl ring of Formula (3) and one of $R^3$, $R^4$, $R^{23}$, or $R^{24}$ is methyl or ethyl and at least one of $R^3$, $R^4$, $R^{23}$, or $R^{24}$ is halogen.

20. The compound of claim 19, $R^{24}$ is chloro and $R^3$, $R^4$, or $R^{23}$ is methyl or ethyl.

21. The compound of claim 1, wherein $R^1$ is a 2-Pyridyl ring of Formula (3) and none of $R^3$, $R^4$, $R^{23}$, or $R^{24}$ is methyl.

22. The compound of claim 1, wherein $R^1$ is a 3-Pyridyl ring of Formula (4), each of $R^5$, $R^6$, and $R^7$ are hydrogen, and $R^2$ is a 2,4-dimethyl substituted phenyl ring.

23. The compound of claim 1, wherein $R^1$ is a 3-Pyridyl ring of Formula (4) and at least one of $R^5$, $R^6$, or $R^7$ is not hydrogen.

24. The compound of claim 1, wherein $R^2$ is
a 2-chloro substituted phenyl ring;
a 2,3-dichloro substituted phenyl ring;
a 2,4-dichloro substituted phenyl ring;

a 2,5-dichloro substituted phenyl ring;

a 3,4-dichloro substituted phenyl ring;

a 2-chlor, 4-fluoro substituted phenyl ring;

a 4-trifluoromethyl substituted phenyl ring;

a 2-fluoro, 4-trifluoromethyl substituted phenyl ring;

a 2,4-dimethyl substituted phenyl ring; or a 2,3,4-trimethoxy substituted phenyl ring.

25. The compound of claim 1, wherein X is hydrogen.

26. The compound of claim 1, selected from the group consisting of:

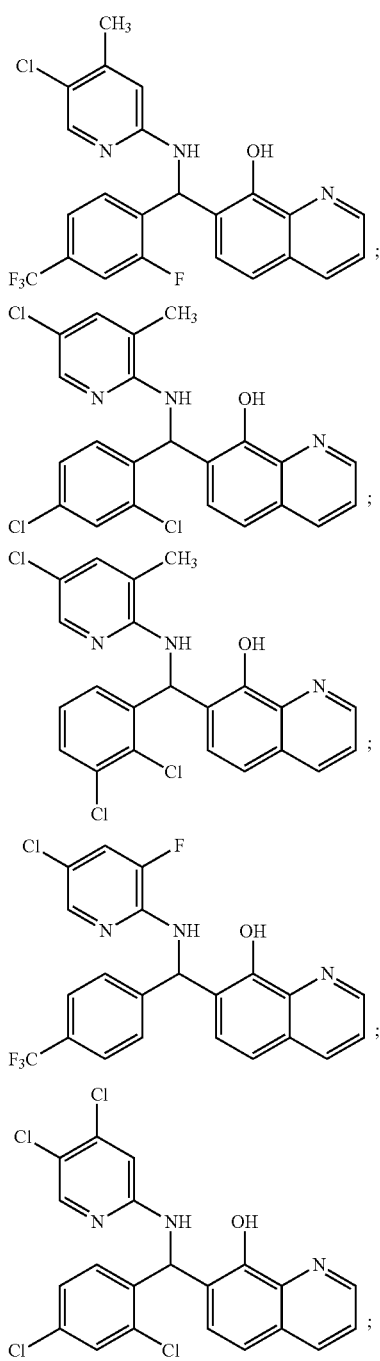

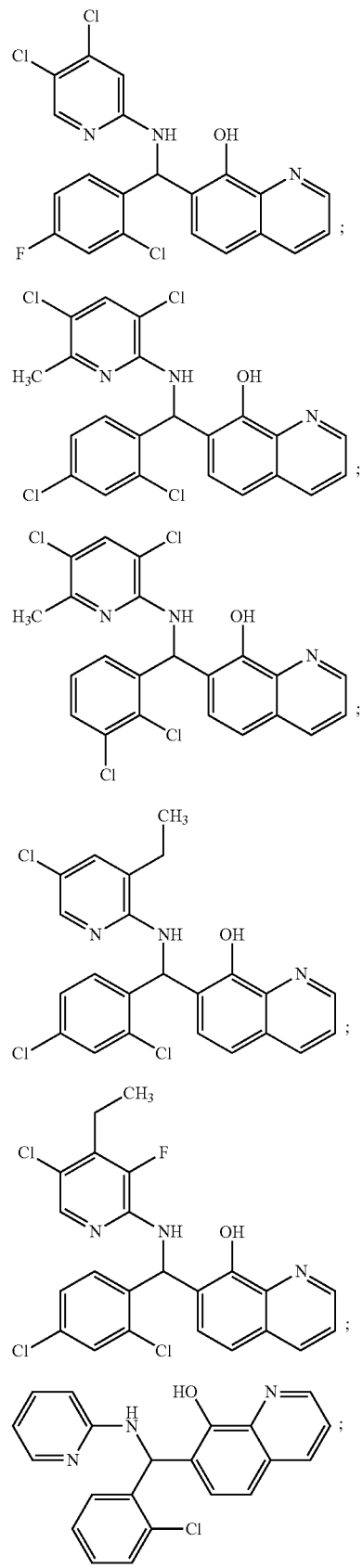

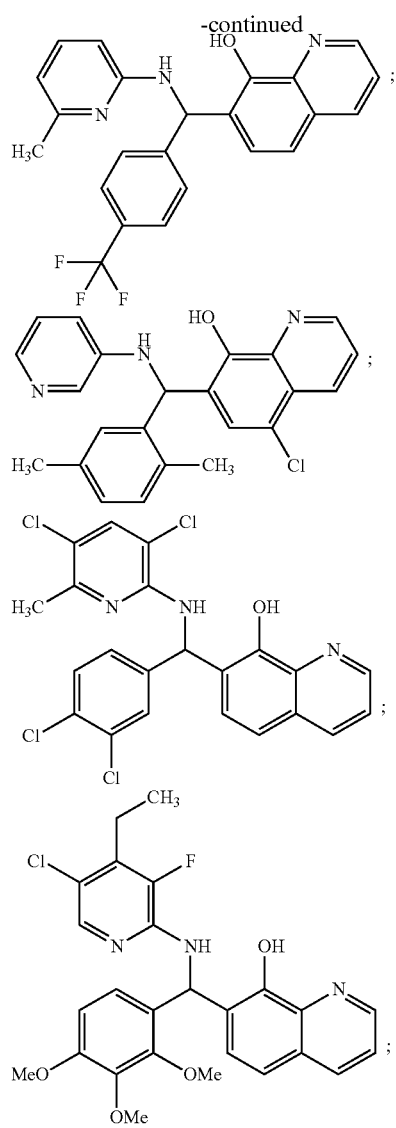
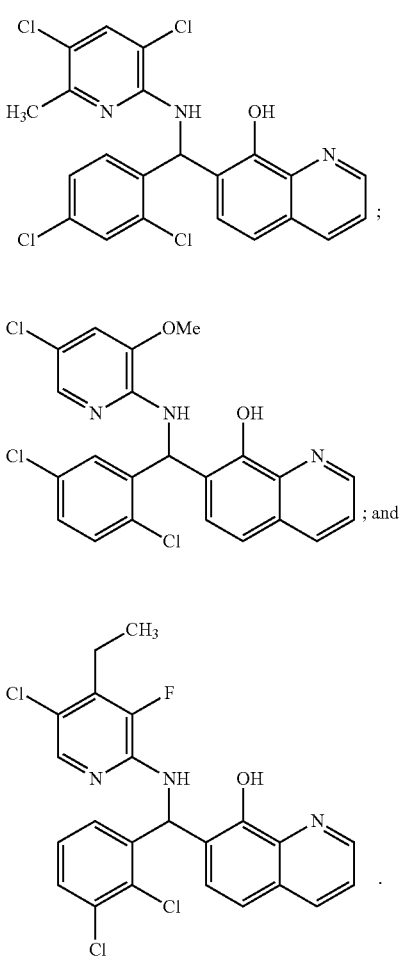
* * * * *

UNITED STATES PATENT AND TRADEMARK OFFICE
CERTIFICATE OF CORRECTION

| | | |
|---|---|---|
| PATENT NO. | : 8,618,302 B2 | Page 1 of 2 |
| APPLICATION NO. | : 12/986146 | |
| DATED | : December 31, 2013 | |
| INVENTOR(S) | : Errico et al. | |

It is certified that error appears in the above-identified patent and that said Letters Patent is hereby corrected as shown below:

In the Claims

Claim 1, Column 295, lines 37-47 (delete):
"(i) a 2-Pyridyl ring of Formula (3)

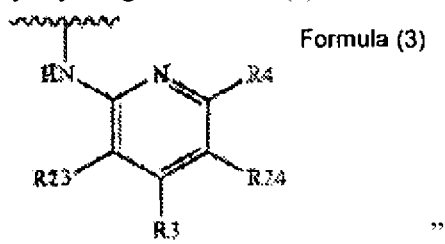

"

Claim 1, Column 295, lines 37-47 (should read):
--(i) a 2-Pyridyl ring of Formula (3)

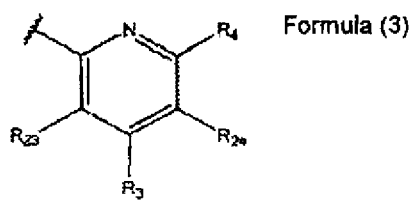

--

Claim 1, Column 296, lines 31-40 (delete):
"(ii) a 3-Pyridyl ring of Formula (4)

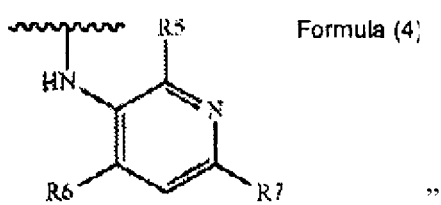

"

Signed and Sealed this
Tenth Day of June, 2014

Michelle K. Lee
*Deputy Director of the United States Patent and Trademark Office*

CERTIFICATE OF CORRECTION (continued)
U.S. Pat. No. 8,618,302 B2

Claim 1, Column 296, lines 31-40 (should read):
--(ii) a 3-Pyridyl ring of Formula (4)

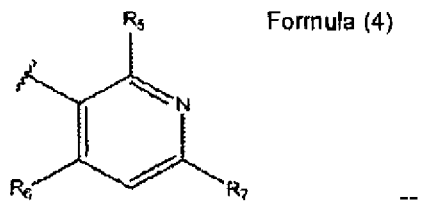

--

Claim 1, Column 296, lines 54-65 (delete):
"(iii) a 4-Pyridyl ring of Formula (5)

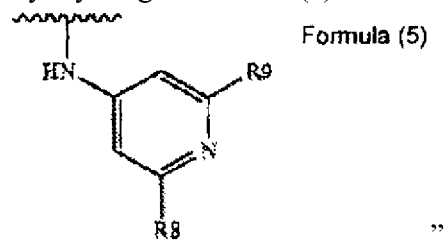

"

Claim 1, Column 296, lines 54-65 (should read):
--(iii) a 4-Pyridyl ring of Formula (5)

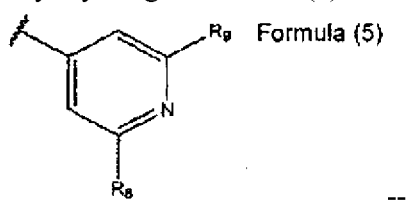

--

UNITED STATES PATENT AND TRADEMARK OFFICE
CERTIFICATE OF CORRECTION

PATENT NO.         : 8,618,302 B2                       Page 1 of 1
APPLICATION NO.    : 12/986146
DATED              : December 31, 2013
INVENTOR(S)        : Joseph P. Errico et al.

It is certified that error appears in the above-identified patent and that said Letters Patent is hereby corrected as shown below:

In the Claims

Claim 11, Column 301, lines 59-60 (shown as):
"...or an aminopyridine compound formed according to claim 18."

Claim 11, Column 301, lines 59-60 (should be):
"...or an aminopyridine compound formed according to claim 12."

Signed and Sealed this
Second Day of December, 2014

Michelle K. Lee
*Deputy Director of the United States Patent and Trademark Office*

SEQUENCE LISTING

```
<160> NUMBER OF SEQ ID NOS: 1

<210> SEQ ID NO 1
<211> LENGTH: 613
<212> TYPE: PRT
<213> ORGANISM: Homo sapiens
<220> FEATURE:
<223> OTHER INFORMATION: Epidermal Growth Factor Receptor

<400> SEQUENCE: 1

Glu Glu Lys Lys Val Cys Gln Gly Thr Ser Asn Lys Leu Thr Gln Leu
1               5                   10                  15

Gly Thr Phe Glu Asp His Phe Leu Ser Leu Gln Arg Met Phe Asn Asn
            20                  25                  30

Cys Glu Val Val Leu Gly Asn Leu Glu Ile Thr Tyr Val Gln Arg Asn
        35                  40                  45

Tyr Asp Leu Ser Phe Leu Lys Thr Ile Gln Glu Val Ala Gly Tyr Val
    50                  55                  60

Leu Ile Ala Leu Asn Thr Val Glu Arg Ile Pro Leu Glu Asn Leu Gln
65                  70                  75                  80

Ile Ile Arg Gly Asn Met Tyr Tyr Glu Asn Ser Tyr Ala Leu Ala Val
                85                  90                  95

Leu Ser Asn Tyr Asp Ala Asn Lys Thr Gly Leu Lys Glu Leu Pro Met
```

```
                100             105             110
Arg Asn Leu Gln Glu Ile Leu His Gly Ala Val Arg Phe Ser Asn Asn
            115                 120                 125
Pro Ala Leu Cys Asn Val Glu Ser Ile Gln Trp Arg Asp Ile Val Ser
        130                 135                 140
Ser Asp Phe Leu Ser Asn Met Ser Met Asp Phe Gln Asn His Leu Gly
145                 150                 155                 160
Ser Cys Gln Lys Cys Asp Pro Ser Cys Pro Asn Gly Ser Cys Trp Gly
                165                 170                 175
Ala Gly Glu Glu Asn Cys Gln Lys Leu Thr Lys Ile Ile Cys Ala Gln
            180                 185                 190
Gln Cys Ser Gly Arg Cys Arg Gly Lys Ser Pro Ser Asp Cys Cys His
        195                 200                 205
Asn Gln Cys Ala Ala Gly Cys Thr Gly Pro Arg Glu Ser Asp Cys Leu
210                 215                 220
Val Cys Arg Lys Phe Arg Asp Glu Ala Thr Cys Lys Asp Thr Cys Pro
225                 230                 235                 240
Pro Leu Met Leu Tyr Asn Pro Thr Thr Tyr Gln Met Asp Val Asn Pro
                245                 250                 255
Glu Gly Lys Tyr Ser Phe Gly Ala Thr Cys Val Lys Cys Pro Arg
            260                 265                 270
Asn Tyr Val Val Thr Asp His Gly Ser Cys Val Arg Ala Cys Gly Ala
        275                 280                 285
Asp Ser Tyr Glu Met Glu Glu Asp Gly Val Arg Lys Cys Lys Lys Cys
        290                 295                 300
Glu Gly Pro Cys Arg Lys Val Cys Asn Gly Ile Gly Ile Gly Glu Phe
305                 310                 315                 320
Lys Asp Ser Leu Ser Ile Asn Ala Thr Asn Ile Lys His Phe Lys Asn
                325                 330                 335
Cys Thr Ser Ile Ser Gly Asp Leu His Ile Leu Pro Val Ala Phe Arg
            340                 345                 350
Gly Asp Ser Phe Thr His Thr Pro Pro Leu Asp Pro Gln Glu Leu Asp
        355                 360                 365
Ile Leu Lys Thr Val Lys Glu Ile Thr Gly Phe Leu Leu Ile Gln Ala
370                 375                 380
Trp Pro Glu Asn Arg Thr Asp Leu His Ala Phe Glu Asn Leu Glu Ile
385                 390                 395                 400
Ile Arg Gly Arg Thr Lys Gln His Gly Gln Phe Ser Leu Ala Val Val
                405                 410                 415
Ser Leu Asn Ile Thr Ser Leu Gly Leu Arg Ser Leu Lys Glu Ile Ser
            420                 425                 430
Asp Gly Asp Val Ile Ile Ser Gly Asn Lys Asn Leu Cys Tyr Ala Asn
        435                 440                 445
Thr Ile Asn Trp Lys Lys Leu Phe Gly Thr Ser Gly Gln Lys Thr Lys
        450                 455                 460
Ile Ile Ser Asn Arg Gly Glu Asn Lys Cys Lys Ala Thr Gly Gln Val
465                 470                 475                 480
Cys His Ala Leu Cys Ser Pro Glu Gly Cys Trp Gly Pro Glu Pro Arg
                485                 490                 495
Asp Cys Val Ser Cys Arg Asn Val Ser Arg Gly Arg Glu Cys Val Asp
            500                 505                 510
Lys Cys Lys Leu Leu Glu Gly Glu Pro Arg Glu Phe Val Glu Asn Ser
        515                 520                 525
```

-continued

```
Glu Cys Ile Gln Cys His Pro Glu Cys Leu Pro Gln Ala Met Asn Ile
        530             535             540

Thr Cys Thr Gly Arg Gly Pro Asp Asn Cys Ile Gln Cys Ala His Tyr
545             550             555             560

Ile Asp Gly Pro His Cys Val Lys Thr Cys Pro Ala Gly Val Met Gly
            565             570             575

Glu Asn Asn Thr Leu Val Trp Lys Tyr Ala Asp Ala Gly His Val Cys
        580             585             590

His Leu Cys His Pro Asn Cys Thr Tyr Gly Cys Thr Gly Pro Gly Leu
        595             600             605

Arg Gly Cys Pro Thr
610
```